US007300942B2

(12) United States Patent
Gregory et al.

(10) Patent No.: US 7,300,942 B2
(45) Date of Patent: Nov. 27, 2007

(54) PRODUCTION OF POLYKETIDES AND OTHER NATURAL PRODUCTS

(75) Inventors: Matthew Alan Gregory, Cambridge (GB); Sabine Gaisser, Cambridge (GB); Hrvoje Petkovic, Cambridge (GB); Steven Moss, Cambridge (GB)

(73) Assignee: Biotica Technology Limited, Essex (GB)

( * ) Notice: Subject to any disclaimer, the term of this patent is extended or adjusted under 35 U.S.C. 154(b) by 0 days.

(21) Appl. No.: 10/497,135

(22) PCT Filed: Jul. 16, 2003

(86) PCT No.: PCT/GB03/03230

§ 371 (c)(1),
(2), (4) Date: Mar. 23, 2005

(87) PCT Pub. No.: WO2004/007709

PCT Pub. Date: Jan. 22, 2004

(65) Prior Publication Data

US 2005/0272132 A1 Dec. 8, 2005

(30) Foreign Application Priority Data

Jul. 16, 2002 (GB) ................... 0216509.0
Oct. 25, 2002 (GB) ................... 0224922.5

(51) Int. Cl.
*C07D 498/18* (2006.01)
*A61P 31/00* (2006.01)
(52) U.S. Cl. ................ 514/291; 514/411; 540/456
(58) Field of Classification Search ............... 540/546; 514/291, 411
See application file for complete search history.

(56) References Cited

FOREIGN PATENT DOCUMENTS

| EP | 0627009 B1 | | 11/1996 |
|---|---|---|---|
| WO | WO 94/09010 | | 4/1994 |
| WO | WO 98/09972 | * | 3/1998 |
| WO | WO 98/54308 | | 12/1998 |
| WO | WO 01/34816 A1 | | 5/2001 |
| WO | WO 01/79520 A1 | | 10/2001 |
| WO | WO 03/048375 A1 | | 6/2003 |

OTHER PUBLICATIONS

Aparicio, J.F., et al., "Organization of the biosynthetic gene cluster for rapamycin in Streptomyces hygroscopicus: analysis of the enzymatic domains in the modular polyketide synthase", Gene 169: 9-16 (1996).
Box, SJ., et al., "27-O-Demethylrapamycin, an Immunosuppressant Compound Produced by a New Strain of Streptomyces hygroscopicus", The J. Of Antibiotics, 48: 1347-1349 (1995).
Chung, L., et al., "Deletion of rapQONML from the Rapamycin Gene Cluster of Streptomyces hygroscopicus", J. Of Antibiotics, 54: 250-256 (2001).
Gaisser, S., et al., "Parallel pathways for oxidation of 14-membered polyketide macrolactones in *Saccharopolyspora erythraea*", Molecular Microbiology, 44: 771-781 (2002).
Gregory, M.A., et al., "Isolation and characterization of pre-rapamycin, the first macrocyclic intermediate in the biosynthesis of the immunosuppressant rapamycin by S. Hygroscopicus", Angew. Chem. Int. Ed. 43: 2551-2553 (2004).
Khaw, L.E., et al., "Mutational biosynthesis of novel rapamycins by a strain of Streptomyces hygroscopicus NRRL 5491 Disrupted in rapL, encoding a putative lysine cyclodeaminase", J. Of Bacteriology, 180: 809-814 (1998).
König, A., et al., "The pipecolate-incorporating enzyme for the biosynthesis of the immunosuppressant rapamycin: Nucleotide sequence analysis, disruption and heterologous expression of rapP from Streptomyces hygroscopicus", Eur. J. Biochem., 247: 526-534 (1997).
Lhoëst, G.J.J., et al., "15-Desmethyl FK-506 and 15, 31-Desmethyl FK-506 from Human Liver Microsomes: Isolation, Identification (by Fast Atom Bombardment Mass Spectrometry and NMR), and Evaluation of in Vitro Immunosuppressive Activity", Clin. Chem., 40: 740-744 (1994).
Lomovskaya, N., et al., "Gene disruption and replacement in the rapamycin-producing Streptomyces hygroscopicus strain ATCC 29253," Microbiology-UK, 143: 875-883 (1997).
Lowden, P.A.S., et al., "The Nature of the Starter Unit for the Rapamycin Polyketide Synthase", Angew. Chem. Int. Ed. Engl. 35: 2249-2251 (1996).
Lowden, P.A.S., "Studies on the Biosynthesis of Rapamycin", Ph.D. Thesis, Chapters 2 and 3 ("On the origin of the starter acid for the rapamycin PKS" and "New rapamycin derivatives by precursor directed biosynthesis") (pp. 22-62, 160-169, plus title page, table of contents and figures) University of Cambridge (1997).
Lowden, P.A.S., "New rapamycin derivatives by precursor-directed biosynthesis", ChemBioChem 5: 535-538 (2004).
Lowden, P.A.S., "Origin and true nature of the starter unit for the rapamycin polyketide synthase", Angew. Chem. Int. Ed. 40: 777-779 (2001).
Molnár, I., et al., "Organisation of the biosynthetic gene cluster for rapamycin in Streptomyces hygroscopicus: analysis of genes flanking the polyketide synthase", Gene, 169: 1-7 (1996).

(Continued)

*Primary Examiner*—Bruck Kifle
(74) *Attorney, Agent, or Firm*—Dann, Dorfman, Herrell & Skillman, P.C.; Robert C. Netter

(57) ABSTRACT

The present invention relates to production of polyketides and other natural products and to libraries of compounds and individual novel compounds. One important area is the isolation and potential use of novel FKBP-ligand analogues and host cells that produce these compounds. The invention is particularly concerned with methods for the efficient transformation of strains that produce FKBP analogues and recombinant cells in which cloned genes or gene cassettes are expressed to generate novel compounds such as polyketide (especially rapamycin) FKBP-ligand analogues, and to processes for their preparation, and to means employed therein (e.g. nucleic acids, vectors, gene cassettes and genetically modified strains).

9 Claims, 36 Drawing Sheets

OTHER PUBLICATIONS

Motamedi, H., et al., "Integrative vectors for heterologous gene expression in Streptomyces spp.", Gene 160:25-31 (1995).

Motamedi, H., et al., "Characterization of Methyltransferase and Hydroxylase Genes Involved in the Biosynthesis of the Immunosuppressants FK506 and FK520", J. Of Bacteriology, 178: 5243-5248 (1996).

Nishida, H., et al., "Generation of Novel Rapamycin Structures by Microbial Manipulations", J. Of Antibiotics, 48: 657-666 (1996).

Paiva, N.L., et al., "Incorporation of acetate, propionate, and methionine into rapamycin by Streptomyces hygroscopicus", J. Of Natural Products, 54: 167-177 (1991).

Paiva, N.L., et al., "The immediate precursor of the nitrogen-containing ring of rapamycin is free pipecolic acid", Enzyme Microb. Technol. 15: 581-585 (1993).

Reather, J.A., "Late steps in the biosynthesis of macrocyclic lactones", Ph.D. thesis, University of Cambridge (title p., ii-x, 1-158) (2000).

Schwecke, T., et al., "The biosynthetic gene cluster for the polyketide immunosuppressant rapamycin", Proc. Natl. Acad. Sci. USA, 92: 7839-7843 (1995).

Shafiee, A., et al., "Chemical and Biological Characterization of Two FK506 Analogs Produced by Targeted Gene Disruption in Streptomyces sp. MA6548", J. Of Antibiotics, 50: 418-423 (1997).

Wong, G.K., et al., "Antifungal Activities of Rapamycin and Its Derivatives, Prolylrapamycin, 32-Desmethylrapamycin, and 32-Desmethoxyrapamycin", J. Of Antibiotics, 51: 487-491 (1998).

Shafiee, A., et al., "Chemical and biological characterization of two FK506 analogs produced by targeted gene . . . ," J. Antibiotics, 50:418-423, (1997).

Motamedi, H., et al., "Characterization of methyltransferse and hydroxylase genes involved in the biosynthesis . . . ," J. Bacteriology, 178:5243-5248, (1996).

Gregory, M.A., et al., "Isolation and characterization of pre-rapamycin, the first macrocyclic . . . ," Angew. Chem. Int. Ed., 43:2551-2553, (2004).

Wong, G.K., et al., "Antifungal activities of rapamycin and its derivatives, prolylrapamycin . . . ," J. Antibiotics, 51:487-491, (1998).

Chung, L., et al., "Deletion of rapQONML from the rapamycin gene cluster of Streptomyces hygroscopicus . . . ," J. Antibiotics, 54:250-256, (2001).

Lhoest, G.J., et al., "15-Desmethyl FK-506 and 15,31-desmethyl FK-506 from human liver . . . ," Clinical Chemistry, 40:740-744, (1994), (Medline Abstract).

* cited by examiner 9-deoxo-16-O-desmethyl-27-desmethoxy-39-O-desmethyl rapamycin 8-deoxo-15-O-desmethyl-26-desmethoxy-38-O-desmethyl prolylrapamycin 9-deoxo-16-O-desmethyl-27-desmethoxy-39-desmethoxy rapamycin 16-O-desmethyl-27-desmethoxy rapamycin

Figure 10

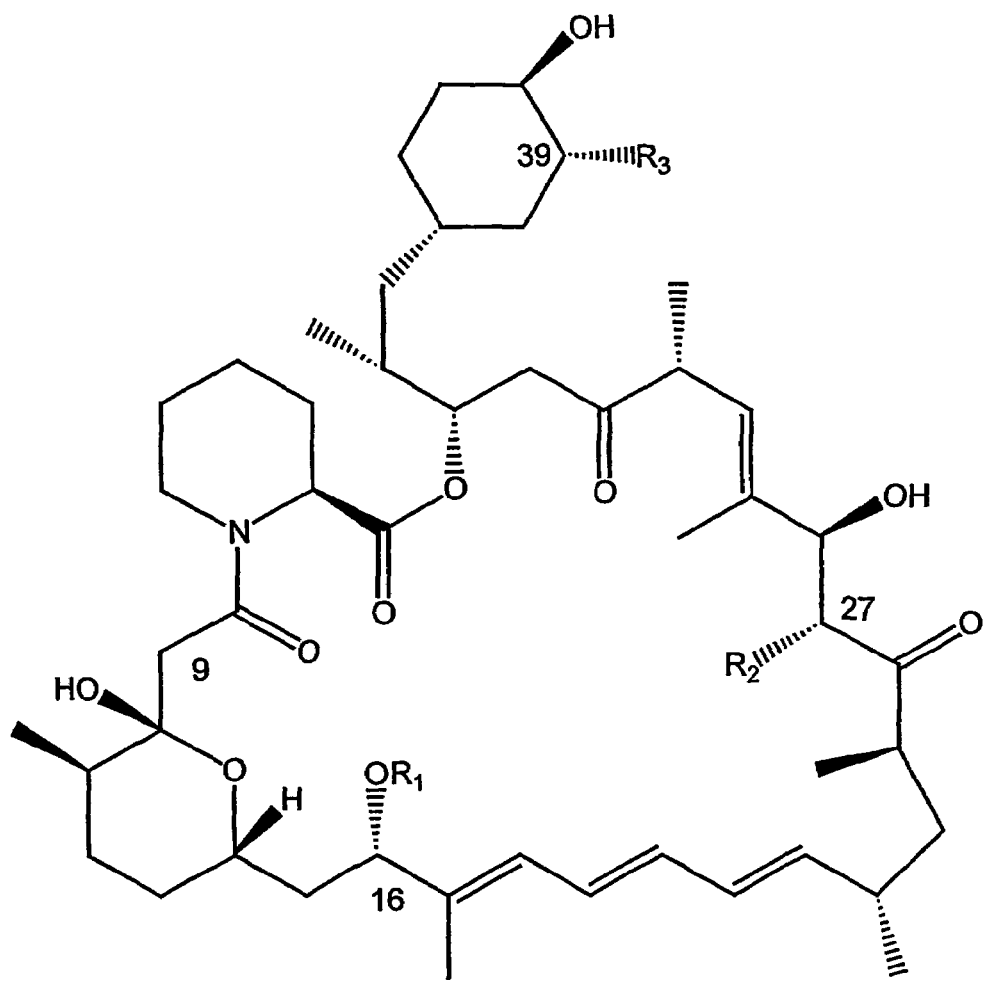

| | | | |
|---|---|---|---|
| $R_1$= H | $R_2$= H | $R_3$= OH | compound 1 |
| $R_1$= H | $R_2$= OH | $R_3$= OH | compound 2 |
| $R_1$= CH$_3$ | $R_2$= H | $R_3$= OH | compound 4 |
| $R_1$= H | $R_2$= OCH$_3$ | $R_3$= OH | compound 5 |
| $R_1$= H | $R_2$= H | $R_3$= OCH$_3$ | compound 6 |
| $R_1$= CH$_3$ | $R_2$= OH | $R_3$= OH | compound 8 |
| $R_1$= H | $R_2$= OH | $R_3$= OCH$_3$ | compound 9 |
| $R_1$= H | $R_2$= OCH$_3$ | $R_3$= OCH$_3$ | compound 15 |
| $R_1$= CH$_3$ | $R_2$= H | $R_3$= OCH$_3$ | compound 16 |
| $R_1$= CH$_3$ | $R_2$= OH | $R_3$= OCH$_3$ | compound 17 |
| $R_1$= CH$_3$ | $R_2$= OCH$_3$ | $R_3$= OH | compound 18 |
| $R_1$= CH$_3$ | $R_2$= OCH$_3$ | $R_3$= OCH$_3$ | compound 19 |

Figure 11

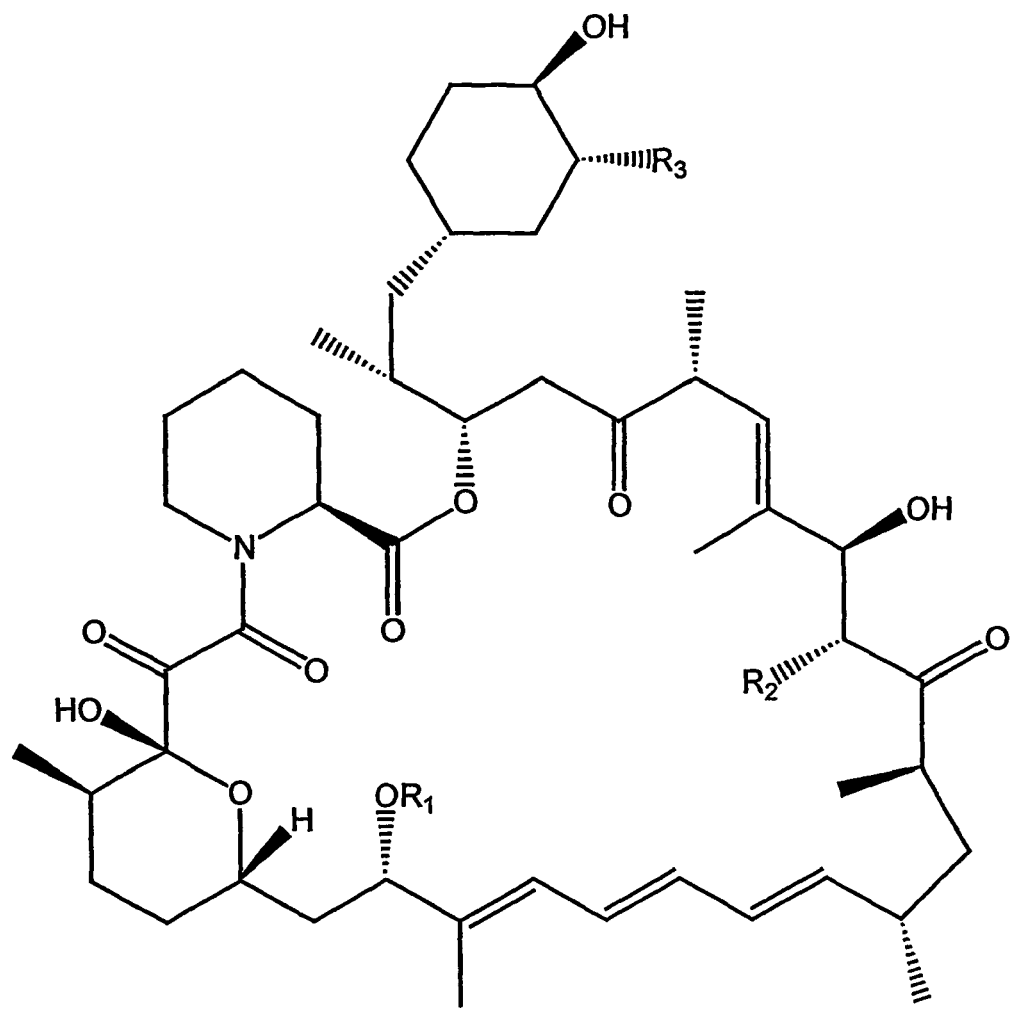

| | | | |
|---|---|---|---|
| $R_1$= H | $R_2$= H | $R_3$= OH | compound 3 |
| $R_1$= H | $R_2$= OH | $R_3$= OH | compound 7 |
| $R_1$= H | $R_2$= OCH$_3$ | $R_3$= OH | compound 10 |
| $R_1$= H | $R_2$= OH | $R_3$= OCH$_3$ | compound 11 |
| $R_1$= H | $R_2$= H | $R_3$= OCH$_3$ | compound 12 |
| $R_1$= CH$_3$ | $R_2$= H | $R_3$= OH | compound 13 |
| $R_1$= CH$_3$ | $R_2$= OH | $R_3$= OH | compound 14 |
| $R_1$= H | $R_2$= OCH$_3$ | $R_3$= OCH$_3$ | compound 20 |
| $R_1$= CH$_3$ | $R_2$= OH | $R_3$= OCH$_3$ | compound 21 |
| $R_1$= CH$_3$ | $R_2$= H | $R_3$= OCH$_3$ | compound 22 |
| $R_1$= CH$_3$ | $R_2$= OCH$_3$ | $R_3$= OH | compound 23 |

Figure 12

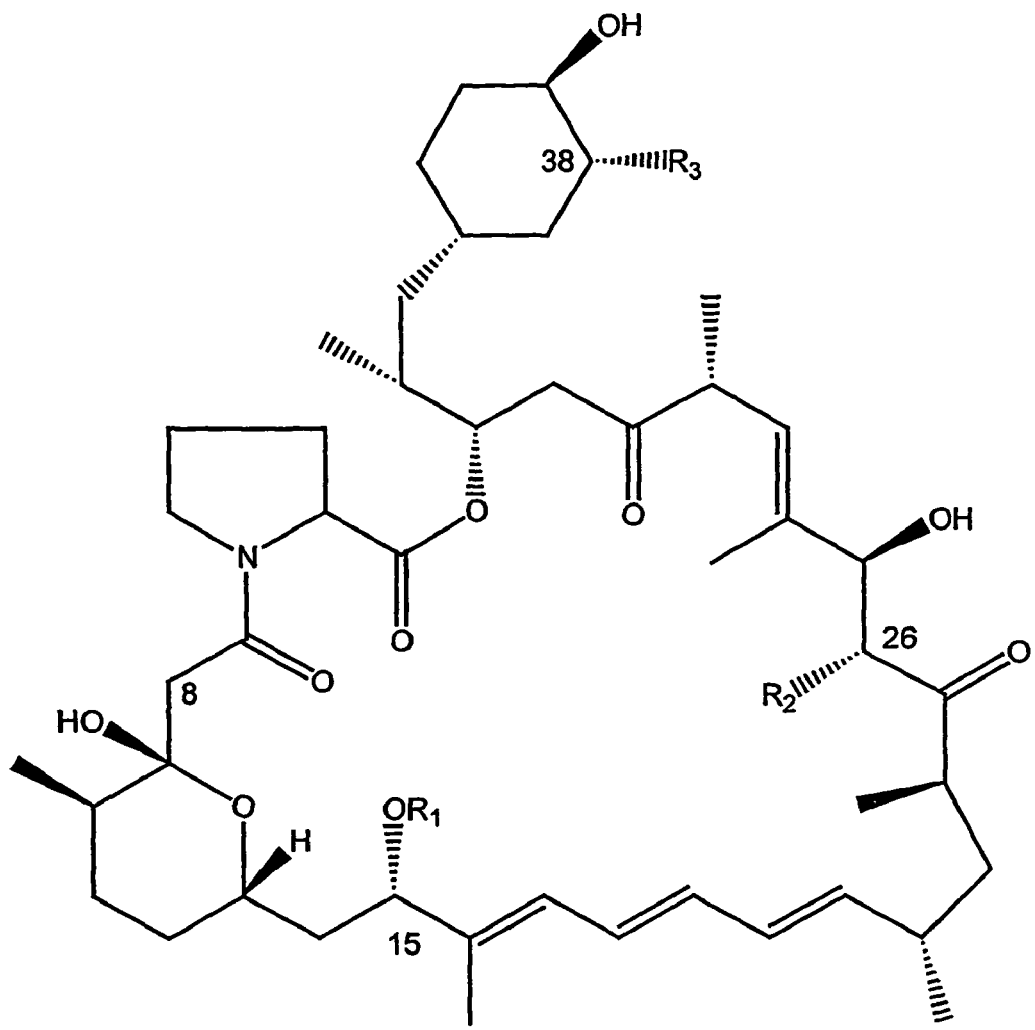

| | | | |
|---|---|---|---|
| $R_1$= H | $R_2$= H | $R_3$= OH | compound 24 |
| $R_1$= H | $R_2$= OH | $R_3$= OH | compound 25 |
| $R_1$= CH$_3$ | $R_2$= H | $R_3$= OH | compound 27 |
| $R_1$= H | $R_2$= OCH$_3$ | $R_3$= OH | compound 28 |
| $R_1$= H | $R_2$= H | $R_3$= OCH$_3$ | compound 29 |
| $R_1$= CH$_3$ | $R_2$= OH | $R_3$= OH | compound 31 |
| $R_1$= H | $R_2$= OH | $R_3$= OCH$_3$ | compound 32 |
| $R_1$= H | $R_2$= OCH$_3$ | $R_3$= OCH$_3$ | compound 38 |
| $R_1$= CH$_3$ | $R_2$= H | $R_3$= OCH$_3$ | compound 39 |
| $R_1$= CH$_3$ | $R_2$= OH | $R_3$= OCH$_3$ | compound 40 |
| $R_1$= CH$_3$ | $R_2$= OCH$_3$ | $R_3$= OH | compound 41 |
| $R_1$= CH$_3$ | $R_2$= OCH$_3$ | $R_3$= OCH$_3$ | compound 42 |

| | | | |
|---|---|---|---|
| $R_1 = H$ | $R_2 = H$ | $R_3 = OH$ | compound 26 |
| $R_1 = H$ | $R_2 = OH$ | $R_3 = OH$ | compound 30 |
| $R_1 = H$ | $R_2 = OCH_3$ | $R_3 = OH$ | compound 33 |
| $R_1 = H$ | $R_2 = OH$ | $R_3 = OCH_3$ | compound 34 |
| $R_1 = H$ | $R_2 = H$ | $R_3 = OCH_3$ | compound 35 |
| $R_1 = CH_3$ | $R_2 = H$ | $R_3 = OH$ | compound 36 |
| $R_1 = CH_3$ | $R_2 = OH$ | $R_3 = OH$ | compound 37 |
| $R_1 = H$ | $R_2 = OCH_3$ | $R_3 = OCH_3$ | compound 43 |
| $R_1 = CH_3$ | $R_2 = OH$ | $R_3 = OCH_3$ | compound 44 |
| $R_1 = CH_3$ | $R_2 = H$ | $R_3 = OCH_3$ | compound 45 |
| $R_1 = CH_3$ | $R_2 = OCH_3$ | $R_3 = OH$ | compound 46 |

| | | |
|---|---|---|
| R₁= H | R₂= H | compound 47 |
| R₁= H | R₂= OH | compound 48 |
| R₁= CH₃ | R₂= H | compound 50 |
| R₁= H | R₂= OCH₃ | compound 51 |
| R₁= CH₃ | R₂= OH | compound 53 |
| R₁= CH₃ | R₂= OCH₃ | compound 57 |

| | | |
|---|---|---|
| $R_1$= H | $R_2$= H | compound 49 |
| $R_1$= H | $R_2$= OH | compound 52 |
| $R_1$= H | $R_2$= OCH$_3$ | compound 54 |
| $R_1$= CH$_3$ | $R_2$= H | compound 55 |
| $R_1$= CH$_3$ | $R_2$= OH | compound 56 |
| $R_1$= CH$_3$ | $R_2$= OCH$_3$ | compound 58 |

| | | |
|---|---|---|
| $R_1 = H$ | $R_2 = H$ | compound 61 |
| $R_1 = H$ | $R_2 = OH$ | compound 64 |
| $R_1 = H$ | $R_2 = OCH_3$ | compound 66 |
| $R_1 = CH_3$ | $R_2 = H$ | compound 67 |
| $R_1 = CH_3$ | $R_2 = OH$ | compound 68 |
| $R_1 = CH_3$ | $R_2 = OCH_3$ | compound 70 |

| | | |
|---|---|---|
| $R_1 = H$ | $R_2 = H$ | compound 59 |
| $R_1 = H$ | $R_2 = OH$ | compound 60 |
| $R_1 = CH_3$ | $R_2 = H$ | compound 62 |
| $R_1 = H$ | $R_2 = OCH_3$ | compound 63 |
| $R_1 = CH_3$ | $R_2 = OH$ | compound 65 |
| $R_1 = CH_3$ | $R_2 = OCH_3$ | compound 69 |

⤴ pre-rapamycin HMBC correlations

↷ pre-rapamycin HMQC correlations

Figure 20
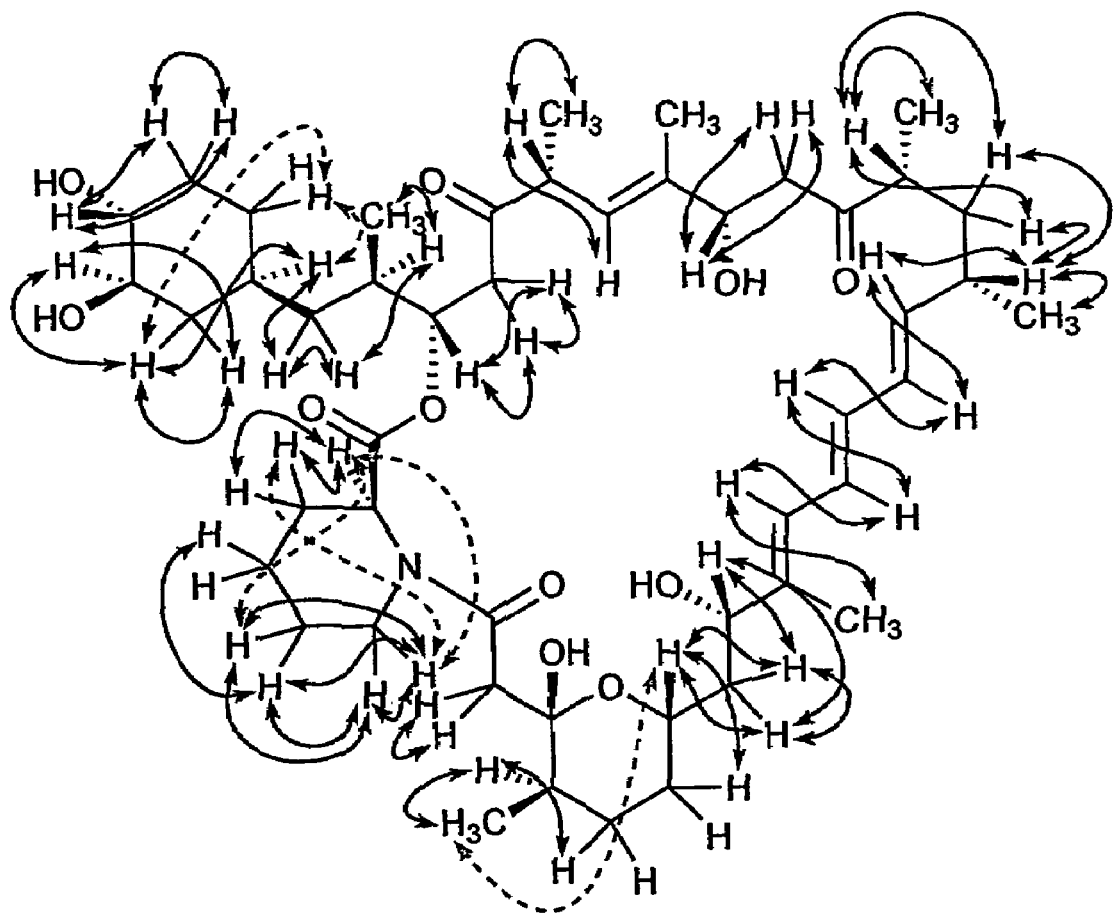
 pre-rapamycin COSY correlations
 selected pre-rapamycin TOCSY correlations

Figure 21

```
  646 GCGACCCGAGCAGATCGTTGGTGTCCTGCTTGCGGCGTTCCGCGATCAGC 597
      |||||||||||||||||||||||||||||||| |||||||||||||||||
92333 GCGACCCGAGCAGATCGTTGGTGTCCTGCTTGCGACGTTCCGCGATCAGC 92382

596 TCGGAGAGGTAGAGGTAGAGCGACTGGCCGGCCGCCATCACGACTTCCTG 547
      ||||||||||||||||||||||||||||||||||||||||||||||||||
92383 TCGGAGAGGTAGAGGTAGAGCGACTGGCCGGCCGCCATCACGACTTCCTG 92432

546 TGAGTAGGCGCCGTTCGAGAGCATCTGGTCCGACCAGGTCCGGAACTTGG 497
      ||||||||||||||||||||||||||||||||||||||||||||||||||
92433 TGAGTAGGCGCCGTTCGAGAGCATCTGGTCCGACCAGGTCCGGAACTTGG 92482

496 TCTGGTCCTCGATCGGCACGCCCAGCAGCTCACAGATCATGATGATCGGC 447
      ||||||||||||||||||||||||||||||||||||||||||||||||||
92483 TCTGGTCCTCGATCGGCACGCCCAGCAGCTCACAGATCATGATGATCGGC 92532

446 AGAGGCAGGGCGAAGTCCTCCATCAGATCGGCGGGGCGCCCTTGGCCAG 397
      ||||||||||||||||||||||||||||||||||||||||||||||||||
92533 AGAGGCAGGGCGAAGTCCTCCATCAGATCGGCGGGGCGCCCTTGGCCAG 92582

396 CATTTTGTCGATCAGATCGTCGGCGACCTCCTGGGTGCGCGGACGCAGGG 347
      ||||||||||||||||||||||||||||||||||||||||||||||||||
92583 CATTTTGTCGATCAGATCGTCGGCGACCTCCTGGGTGCGCGGACGCAGGG 92632

346 CCTCCATCCGGCGGCTGGTCAGCGCCTTGGTCGCCAACCGGCGCAGCCGG 297
      ||||||||||||||||||||||||||||||||||| ||||||||||||||
92633 CCTCCATCCGGCGGCTGGTCAGCGCCTTGGTCGCCACCCGGCGCAGCCGG 92682

296 GTGTGTTCCGGAGGGTCCATCAGCATGATGACGGGCTGGTCCTGGATCGC 247
      ||||||||||||||||||||||||||||||||||||||||||||||||||
92683 GTGTGTTCCGGAGGGTCCATCAGCATGATGACGGGCTGGTCCTGGATCGC 92732

246 CGGGAGGACCCGGGGCACGTCCTTGCCGAGCGTCGCGCTGCGGCTGAACC 197
      ||||||||||||||||||||||||||||||||||||||||||||||||||
92733 CGGGAGGACCCGGGGCACGTCCTTGCCGAGCGTCGCGCTGCGGCTGAACC 92782

196 GCGGGTCCACGAACACCTTGGCGACGTCCTCCCAGCTGGTGGCCAGCCAG 147
      ||||||||||||||||||||||||||||||||||||||| ||||||||||
92783 GCGGGTCCACGAACACCTTGGCGACGTCCTCCCAGCTGGCGGCCAGCCAG 92832

146 GTCTCCCCGCCGTACGGCATCAGGACCCGGCCGAGCTCACCGGCGTCCCG 97
      | |||||| ||||| |||||||||||||||||||||||||||||||||||
92833 GCCTCCCGGCCGTCCAACATCAGGACCCGGCCGAGCTCACCGGCGTCCCG 92882

96 CAGCCGGTTGTACTCGGGGTGGATCTCGAGTCGCTCCATTTCGGCGAAAG 47
      ||||||||||||||||||||||||||||||||||||||||||||||||||
92883 CAGCCGGTTGTACTCGGGGTGGATCTCGAGTCGCTCCATTTCGGCGAAAG 92932

46 GATAAGGGCAGGCCTTTCCGGTCTCACCCTGATCGGTCGTCGACAT 1
      ||||||||||||||||||||||||||||||||||||||||||||||
92933 GATAAGGGCAGGCCTTTCCGGTCTCACCCTGATCGGTCGTCGACAT 92978
```

Figure 22

```
  1 MSTTDQGETGKACPYPFAEMERLEIHPEYNRLRDAGELGRVLMPYGGETW  50
    |||||||||||||||||||||||||||||||||||||||||| | |
  1 MSTTDQGETGKACPYPFAEMERLEIHPEYNRLRDAGELGRVLMLDGREAW  50

51 LATSWEDVAKVFVDPRFSRSATLGKDVPRVLPAIQDQPVIMLMDPPEHTR 100
    || |||||||||||||||||||||||||||||||||||||||||||||||
 51 LAASWEDVAKVFVDPRFSRSATLGKDVPRVLPAIQDQPVIMLMDPPEHTR 100

101 LRRLATKALTSRRMEALRPRTQEVADDLIDKMLAKGAPADLMEDFALPLP 150
    |||·|||||||||||||||||||||||||||||||||||||||||||||
101 LRRVATKALTSRRMEALRPRTQEVADDLIDKMLAKGAPADLMEDFALPLP 150

151 IIMICELLGVPIEDQTKFRTWSDQMLSNGAYSQEVVMAAGQSLYLYLSEL 200
    |||||||||||||||||||||||||||||||||||||||||||||||||
151 IIMICELLGVPIEDQTKFRTWSDQMLSNGAYSQEVVMAAGQSLYLYLSEL 200

201 IAERRKQDTNDLLGSLVRARDKDDRLSETELVGFAVTLLIAGYETTANAI 250
    |||||||||||||||||||||||||||||||||||||||||||||||||
201 IAERRKQDTNDLLGSLVRARDKDDRLSETELVGFAVTLLIAGYETTANAI 250

251 GNSVYTLLTHPEKLAELRKDLSLIPKAVDELLRIIPIAKQASWVRMAVED 300
    |||||||||||||||||||||||||||||||||||||||||||||||||
251 GNSVYTLLTHPEKLAELRKDLSLIPKAVDELLRIIPIAKQASWVRMAVED 300

301 VELSGTIVKAGEAVAIQTHSANTDPKVYDHPEEIDFHRTSNPHMSLGHGA 350
    |||||||||||||||||||||||||||||||||||||||||||||||||
301 VELSGTIVKAGEAVAIQTHSANTDPKVYDHPEEIDFHRTSNPHMSLGHGA 350

351 HHCMGAQLVRVEMQTALGSLISRIPALRFAVPEPRIKFLRGRLVPSLEAL 400
    |||||||||||||||||||||||||||||||||||||||||||||||||
351 HHCMGAQLVRVEMQTALGSLISRIPALRFAVPEPRIKFLRGRLVPSLEAL 400

401 PLTW* 405
    |||||
401 PLTW* 405
```

Figure 23

```
  758 CGGAGGTGACTGTCCGGGGCCATCCGCCGGCGCACCGCGGCACGGACTTG 709
      ||||||||||||||||||| ||||||||||||||||||||||||||||||
93191 CGGAGGTGACTGTCCGGGGGCATCCGCCGGCGCACCGCGGCACGGACTTG 93240

708 ATCGGAGATGTCGTGATCGCTGACCCACTTCAGTTCGGGTATTTCCGTTG 659
      ||||||||||||||||||||||||||||||||||||||||||||||||||
93241 ATCGGAGATGTCGTGATCGCTGACCCACTTCAGTTCGGGTATTTCCGTTG 93290

658 TGATCCGACGCATCGCCTCAAGGCGCTGCCGCGTGAACACGTCGATGTGC 609
      ||||||||||||||||||||||||||||||||||||||||||||||||||
93291 TGATCCGACGCATCGCCTCAAGGCGCTGCCGCGTGAACACGTCGATGTGC 93340

608 GAAAGGGCGCCACCCGGGCGCAGCACGCGCGCGGCCTCCCGCAGGAAACG 559
      ||||||||||||| |||||||| |||||||||||||||||||||||||||
93341 GAAAGGGCGCCACCCCGGCGCAGCGCGCGCGCGGCCTCCCGCAGGAAACG 93390

558 TCCCAGATTGGGGTAGGTGTGCGAGCTCTCGATGTTGACGAGCACATCCA 509
      ||||||||||||||||||||||||||||||||||||||||||||||||||
93391 TCCCAGATTGGGGTAGGTGTGCGAGCTCTCGATGTTGACGAGCACATCCA 93440

508 CCGAGGAGTCCTCGAAGGGCAGTTCCTCGGCGTCGCCCTGGACGAACCGC 459
      ||||||||||||||||||||||||||||||||||||||||||||||||||
93441 CCGAGGAGTCCTCGAAGGGCAGTTCCTCGGCGTCGCCCTGGACGAACCGC 93490

458 AGGGTATCGCCGCGGGACAGCGTGGCGGTGGCGCTGGCGATCGCCTTCGG 409
      ||||||||||||||||||||||||||||||||||||||||||||||||||
93491 AGGGTATCGCCGCGGGACAGCGTGGCGGTGGCGCTGGCGATCGCCTTCGG 93540

408 CGCCAGGTCCAGCCCGGTCATCCGGGCGGTGGGACGAGGCGGGACAGGA 359
      ||||||||||||||||||||||||||||||||||||||||||||||||
93541 CGCCAGGTCCAGCCCGGTCATCCGGGCGGTGGGACGAGGCGGGACAGGA 93590

358 AGTTGAGCCCCTCCCCCATTCCGCAGCCGACCTCCAGGACCGTCCGGCCG 309
      ||||||||||||||||||||||||||||||||||||||||||||||||||
93591 AGTTGAGCCCCTCCCCCATTCCGCAGCCGACCTCCAGGACCGTCCGGCCG 93640

308 TCGCAGCTCTCCAAGCCCTTCGGAAGGTCGCGCAGGGCCAGGTAGTAGAG 259
      ||||||||||||||||||||||||||||||||||||||||||||||||||
93641 TCGCAGCTCTCCAAGCCCTTCGGAAGGTCGCGCAGGGCCAGGTAGTAGAG 93690

258 CTGCTCGCTGAATCCGTCGGTGCCGTACTCGGTGAATCCGGGCAGCCTGG 209
      ||||||||||||||||||||||||||||||||||||||||||||||||||
93691 CTGCTCGCTGAATCCGTCGGTGCCGTACTCGGTGAATCCGGGCAGCCTGG 93740

208 CCTCGATCTCGGCGACGAACTCGGAATCGTGCACACCCCAGTTCCACAGC 159
      ||||||||||||||||||||||||||||||||||||||||||||||||||
93741 CCTCGATCTCGGCGACGAACTCGGAATCGTGCACACCCCAGTTCCACAGC 93790

158 TGGCCCTTTGCCGACATGCTGGCGGCGAGGTCGTAGATGGAGGAGCTGGC 109
      ||||||||||||||||||||||||||||||||||||||||||||||||||
93791 TGGCCCTTTGCCGACATGCTGGCGGCGAGGTCGTAGATGGAGGAGCTGGC 93840

108 GGACTTGAAGGTGGCGGCCTTCGTCTCCGCCTGCGGGGTGCCGGATTCGT 59
      |||||||||||||||||||||||||||||||||||||||||||| |||||
93841 GGACTTGAAGGTGGCGGCCTTCGTCTCCGCCTGCGGGGTGCCGGGTTCGT 93890

58 CGAGATTGATGTCGGCGACACCGCTGGTGAAGGCGGTCACGACGTCGGGT 9
      ||||||||||||| |||| |||||| ||||||||||||||||||||||||
93891 CGAGATTGATGTC.GCGA.ACCGCT.GTGAAGGCGGTCACGACGTCGGGT 93937

8 TGGATCAT 1
      ||||||||
93938 TGGATCAT 93945
```

Figure 24

```
  1 MIQPDVVTAFTSGVADINLDESGTPQAETKAATFKSASSSIYDLAASMSA  50
    |||||||||| . | |||||| |||||||||||||||||||||||||||
  1 MIQPDVVTAFTA.VRDINLDEPGTPQAETKAATFKSASSSIYDLAASMSA  49

51 KGQLWNWGVHDSEFVAEIEARLPGFTEYGTDGFSEQLYYLALRDLPKGLE 100
    |||||||||||||||||||||||||||||||||||||||||||||||||
 50 KGQLWNWGVHDSEFVAEIEARLPGFTEYGTDGFSEQLYYLALRDLPKGLE  99

101 SCDGRTVLEVGCGMGEGLNFLSRLVPTARMTGLDLAPKAIASATATLSRG 150
    |||||||||||||||||||||||||||||||||||||||||||||||||
100 SCDGRTVLEVGCGMGEGLNFLSRLVPTARMTGLDLAPKAIASATATLSRG 149

151 DTLRFVQGDAEELPFEDSSVDVLVNIESSHTYPNLGRFLREAARVLRPGG 200
    |||||||||||||||||||||||||||||||||||||||||||| || ||
150 DTLRFVQGDAEELPFEDSSVDVLVNIESSHTYPNLGRFLREAARALRRGG 199

201 ALSHIDVFTRQRLEAMRRITTEIPELKWVSDHDISDQVRAAVRRRMAPDS 250
    |||||||||||||||||||||||||||||||||||||||||||||| |||
200 ALSHIDVFTRQRLEAMRRITTEIPELKWVSDHDISDQVRAAVRRRMPPDS 249

251 HLRSTLNKQRMNRLARTLALHSQITVFGGTFADYQPPASVKMLSRLGLVP 300
    |||||||||||||||||||||||||||||||||||||||||||||||||
250 HLRSTLNKQRMNRLARTLALHSQITVFGGTFADYQPPASVKMLSRLGLVP 299

301 PMDSLPMETYRHQIAVRV* 319
    ||||||||||||||||||
300 PMDSLPMETYRHQIAVRV* 318
```

Figure 25

```
432 GATCAGGGCGAGGGTGGTGCTCCCCGGCCGGGCGAGCAGCCGGGTGGCGA 383
    ||||||||||||||||||||||||||||||||||||||||||||||| ||
94647 GATCAGGGCGAGGGTGGTGCTCCCCGGCCGGGCGAGCAGCCGGGTGGTGA 94696

382 CGGCCGCGACCGCGCCGGTCCGCATGGCGGTGATGGTGGCCGCGTCGGCG 333
    ||| |||||||||||||||||||||| |||||||||||||||||||||||
94697 CGGACGCGACCGCGCCGGTCCGCATCGCGGTGATGGTGGCCGCGTCGGCG 94746

332 AGCGCGACCATGCTTCCGCTGTCGTCGTCGAGCCGCGACACGGTCCCGAC 283
    |||||||||||||||||||||||||| ||||||||||||||||||||| |
94747 AGCGCGACCATGCTTCCGCTGTCGTCGCCGAGCCGCGACACGGTCCCCAC 94796

282 GATGGTGGGCAGGTTGAAGCGCTCGAAGTTCTGCGGACTGTAGCTGACCG 233
    |||||||||||||||||||||||||||||||| |||||||||||||||||
94797 GATGGTGGGCAGGTTGAAGCGCTCGAAGTTCTCCGGACTGTAGCTGACCG 94846

232 TCTTCATCGTCACACCGATGCCCGACGCGCGGTGCGGCATGAACTCGATG 183
    ||||||||    ||||||||||||||||||||||||||||||||||||||
94847 TCTTCATCGAGCACCCGATGCCCGACGCGCGGTGCGGCATGAACTCGATG 94896

182 ACGCCCGGAACGTCGCCGCCGCGGGCAAAGCCGGTACGCGGTGGCGGCTC 133
    |||||||||||||||||||||||||||||||||| |||||||||||||||
94897 ACGCCCGGAACGTCGCCGCCGCGGGCAAAGCCGGGACGCGGTGGCGGCTC 94946
```

Figure 26

```
  1 MQTKVLCQRDIKRILSVVGRDVMMDRLISEVHAGFARLGRGETDEPPPRT  50
    ||||||||||||||||||||||||||||||||||||||||||||||||
  1 MQTKVLCQRDIKRILSVVGRDVMMDRLISEVHAGFARLGRGETDEPPPRP  50

51 GFARGGDVPGVIEFMPHRASGIGVTMKTVSYSPQNFERFNLPTIVGTVSR 100
    |||||||||||||||||||||||| ||||||||:|||||||||||||||
 51 GFARGGDVPGVIEFMPHRASGIGCSMKTVSYSPENFERFNLPTIVGTVSR 100

101 LDDDSGSMVALADAATITAMRTGAVAAVATRLLARPGSTTLALIGAGAQA 150
    | ||||||||||||||||||||||||  | |||||||||||||||||||
101 LGDDSGSMVALADAATITAMRTGAVASVTTRLLARPGSTTLALIGAGAQA 150

151 VTQAHALSRVLPLERILISDIKAEHAESFAGRVAFLELPVEVTDAATAMA 200
    |||||||||||||||||||||||||||||||||||||||||||||||||
151 VTQAHALSRVLPLERILISDIKAEHAESFAGRVAFLELPVEVTDAATAMA 200

201 TADVLCTVTSVPVGGGPVVPAEPRQAHLHVNGIGADEQGKTELPKALLDD 250
    |||||||||||||||||||||||||||||||||||||||||||||||||
201 TADVLCTVTSVPVGGGPVVPAEPRQAHLHVNGIGADEQGKTELPKALLDD 250

251 AFICVDHPGQARAEGEFQQLPDRELGPSLADLCAAPEIAAPHPERLSVFD 300
    |||||||||||||||||||||||||||||||||||||||||||||||||
251 AFICVDHPGQARAEGEFQQLPDRELGPSLADLCAAPEIAAPHPERLSVFD 300

301 STGSAFADHIALDVLLGFADELGLGHKMSIESTPEDVLDPYSL* 344
    |||||||||||||||||||||||||||||||||||||||||||
301 STGSAFADHIALDVLLGFADELGLGHKMSIESTPEDVLDPYSL* 344
```

Figure 27

```
  201 GCACGCGGAGGGGCCGAAGGAGTCGGGCAGCCATGATGGCGTCGCCTGGG 250
      |||||||||||||||||||||||||  || |||||||||||||||||||
95630 GCACGCGGAGGGGCCGAAGGAGTCGTCGAGGCATGATGGCGTCGCCTGGG 95679

251 CTCGGACACCTGACTACCTCTTCGGTGTCGCGCGGGTGCCCGAGGGCGGC 300
      ||||||||||||||||||||||||||||||||||||||||||||||||||
95680 CTCGGACACCTGACTACCTCTTCGGTGTCGCGCGGGTGCCCGAGGGCGGC 95729

301 CGGTACGCGGCCGGCACCGCGGCCGTCTACACCGGAATCTTCGACCTGAT 350
      ||||||||||||||||||||||||||||||||||||||||||||||||||
95730 CGGTACGCGGCCGGCACCGCGGCCGTCTACACCGGAATCTTCGACCTGAT 95779

351 CGGGACGCTGGGGTACCCCAGTCTGGCCCGCACCTGGAACTACGTCAGCG 400
      ||||||||||||||||||||||||||||||||||||||||||||||||||
95780 CGGGACGCTGGGGTACCCCAGTCTGGCCCGCACCTGGAACTACGTCAGCG 95829

401 GAATCAACACGCCGAACGCCGATGGCCTCGAGGTCTACCGGGACTTCTGT 450
      ||||||||||||||||||||||||||||||||||||||||||||||||||
95830 GAATCAACACGCCGAACGCCGATGGCCTCGAGGTCTACCGGGACTTCTGT 95879

451 GTGGGCCGCGCCGAGGCGCTGGACGCCCGTGGGATCGACCCGGCGACCAT 500
      ||||||||||||||||||||||||||||||||||||||||||||||||||
95880 GTGGGCCGCGCCGAGGCGCTGGACGCCCGTGGGATCGACCCGGCGACCAT 95929

501 GCCGGCGGCGACCGGCATCGGCGCCCACGGCGGCGGCATCACGTGCTACT 550
      |||||||||||||||||||||||||||||||||||   ||||||||||||
95930 GCCGGCGGCGACCGGCATCGGCGCCCACGGCGCGCGCATCACGTGCTACT 95979

551 TCATCGCCGCACGCGCCGGTGACCGGGTCAACATGGAGAACCCGGCCGTG 600
      ||||||||||||||||||||||||||||||||||||||||||||||||||
95980 TCATCGCCGCACGCGCCGGTGACCGGGTCAACATGGAGAACCCGGCCGTG 96029

601 CTCACGGCTCACCGCTACCCGCAGCGGTACGGCCCCCGCCCGCCGGTCTT 650
      ||||||||||||||||||||||||||||||||||||||||||||||||||
96030 CTCACGGCTCACCGCTACCCGCAGCGGTACGGCCCCCGCCCGCCGGTCTT 96079

651 CTCCCGGGCCACCTGGCTCTCGCCGCCGGGGGCGGACGACGGCCGGCTCT 700
      ||||  ||||||||||||||||||||||||||||||       |||||||
96080 CTCC..GGCCACCTGGCTCTCGCCGCCGGGGGCGGA.......CGGCTCT 96120

701 TCGTCTCCGCGACCGCCGGCATCGTCGGTCACGAGACGGTGCACCACGGC 750
      |||||||||||||||||||||||||||||||| |||||||||||||||||
96121 TCGTCTCCGCGACCGCCGGCATCGTCGGTCAGGAGACGGTGCACCACGGC 96170
```

Figure 28

```
  1 VRQLTPPVTAPYCRFEKLGASDLDGDETLLGVIEHRTGHTGVSLAEGCPR  50
    |||||||||||||||||||||||||||||||||||||||||||||||||
  1 VRQLTPPVTAPYCRFEKLGASDLDGDETLLGVIEHRTGHTGVSLAEGCPR  50

51 TAVHTTTREDESFAEAWHAEGPKESGSHDGVAWARTPDYLFGVARVPEGG 100
    |||||||||||||||||||||||||| ||||||||||||||||||||||
 51 TAVHTTTREDESFAEAWHAEGPKESSRHDGVAWARTPDYLFGVARVPEGG 100

101 RYAAGTAAVYTGIFDLIGTLGYPSLARTWNYVSGINTPNADGLEVYRDFC 150
    |||||||||||||||||||||||||||||||||||||||||||||||||
101 RYAAGTAAVYTGIFDLIGTLGYPSLARTWNYVSGINTPNADGLEVYRDFC 150

151 VGRAEALDARGIDPATMPAATGIGAHGGGITCYFIAARAGDRVNMENPAV 200
    |||||||||||||||||||||||||||| ||||||||||||||||||||
151 VGRAEALDARGIDPATMPAATGIGAHGARITCYFIAARAGDRVNMENPAV 200

201 LTAHRYPQRYGPRPPVFSRATWLSPPGADDGRLFVSATAGIVGHETVHHG 250
    ||||||||||||||||||    |. |   |||||||||||| ||||||
201 LTAHRYPQRYGPRPPVFSGHLALAAGG...GRLFVSATAGIVGQETVHHG 247

251 DVAAQCEVSLENIARVIGAENLGRHGLRRGYALADVDHLKVYVRHREDIS 300
    |||||||||||||||||||||||||||||||||||||||||||||||||
248 DVAAQCEVSLENIARVIGAENLGRHGLRRGYALADVDHLKVYVRHREDIS 297

301 TVRRICAERLSREATVAVLHTDIARTDLLVEIEGVVA* 338
    |||||||||||||||||||||||||||||||||||||
298 TVRRICAERLSREATVAVLHTDIARTDLLVEIEGVVA* 335
```

Figure 29

```
 401 AGCGCCTGGCGTCCCTGGCCATCCACGACCTCTACGGCCTGAATGAGGAG  450
     ||||||||||||||||||||||||||||||||||||||||||||   |||
96865 AGCGCCTGGCGTCCCTGGCCATCCACGACCTCTACGGCCTGAAT...GAG 96911

451 GAGGGGCCCGTACTCGAGGGCCAGATGCGGGCCATGGAGGGCGGCACCGA  500
     ||||||||||||||||||||||||||||||||||||||||||||||||||
96912 GAGGGGCCCGTACTCGAGGGCCAGATGCGGGCCATGGAGGGCGGCACCGA 96961

501 CATGGAGAGCATCAAGAGGCTGACCGACGAATTCTTCGGTCACGTCCTGG  550
     |||||||||||||||||||||||||||||||   ||||||||||||||||
96962 CATGGAGAGCATCAAGAGGCTGACCGACGAA...TTCGGTCACGTCCTGG 97008

551 CGCTGGTGCGTGCCAAGCGGGAGCAGGCGGGCGACAGGCTTCTGCACCGG  600
     |||||||||||||||||||||   ||||||||||||||||||||||||||
97009 CGCTGGTGCGTGCCAAGCGGGACGAGGCGGGCGACAGGCTTCTGCACCGG 97058

601 CTGGCCGAGTCCGGCGAGGACGAGATCCTGCTCAGCGACGAGGAGGCGAC  650
     ||||||||||||||||||||||||||||||||||||||||||||||||||
97059 CTGGCCGAGTCCGGCGAGGACGAGATCCTGCTCAGCGACGAGGAGGCGAC 97108

651 CGGGGTGTTCGCCACTCTGCTGTTCGCCGGGCACGACTCGATGCAGCAGA  700
     ||||||||||||||||||||||||||||||||||||||||||||||||||
97109 CGGGGTGTTCGCCACTCTGCTGTTCGCCGGGCACGACTCGATGCAGCAGA 97158

701 TGGTCGGCTACTGTCTGTACGCGCTGCTCTCCCATCCCGAGCAGCGGGCG  750
     ||||||||||| ||||||||||||||||||||||||||||||||||||||
97159 TGGTCGGCTACAGTCTGTACGCGCTGCTCTCCCATCCCGAGCAGCGGGCG 97208

751 GCGCTGCGGGAGAACCCGGACCTGATCGACGGCGCGGTCGAGGAGCTGCT  800
     ||||||||||||||||||||||||||||||||||||||||||||||||||
97209 GCGCTGCGGGAGAACCCGGACCTGATCGACGGCGCGGTCGAGGAGCTGCT 97258

801 GCGCTTCCTGCCGCTCAACCAGCTCGGCGTGCCGCGGGTCTGTGTCGAGG  850
     ||||||||||||||||||||||||||||||||||||||||||||||||||
97259 GCGCTTCCTGCCGCTCAACCAGCTCGGCGTGCCGCGGGTCTGTGTCGAGG 97308

851 ACGTCGAGCTGCACGGCCAGACCATCAGCGCCGGCGACAACGTGATCCCG  900
     ||||||||||||||||||||||||||||||||||||||||||||||||||
97309 ACGTCGAGCTGCACGGCCAGACCATCAGCGCCGGCGACAACGTGATCCCG 97358

901 CTCTACTCGACGGCCAACCGCGACCCCGGCGTCTTCGCCGACCCCGACAC  950
     ||||||||||||||||||||||||||||||||||||||||||||||||||
97359 CTCTACTCGACGGCCAACCGCGACCCCGGCGTCTTCGCCGACCCCGACAC 97408

951 GTTCGACATCACGCGTAAGCCCGAACACAACTTCGCTTTCGGGTACGGCA 1000
     ||||||||||||||||||||||||||||||||||||||||||||||||||
97409 GTTCGACATCACGCGTAAGCCCGAACACAACTTCGCTTTCGGGTACGGCA 97458

1001 TCCACAAGTGCCCGGGGCAGCACCTCGCCCGCGTGTTGATCAAGGTCGCC 1050
     |||||    |||||||||||||||||||||||||||||||||||||||||
97459 TCCACGGCTGCCCGGGGCAGCACCTCGCCCGCGTGTTGATCAAGGTCGCC 97508

1051 ACGCTGCGCCTGTTCGAGCGCTTCCCGGATGTGCGACTGGCGGGCGACGT 1100
     ||  ||||||||||||||||||||||||||||||||||||||||||||||
97509 ACCGTGCGCCTGTTCGAGCGCTTCCCGGATGTGCGACTGGCGGGCGACGT 97558

1101 GCCGATGAACGAGGGTCTGGGCCTGTTCAGCCCGGCCGAGCTCCGGGTCA 1150
     ||||||||||||||||||||||||||||||||||||||||||||||||||
97559 GCCGATGAACGAGGGTCTGGGCCTGTTCAGCCCGGCCGAGCTCCGGGTCA 97608

1151 CCTGGGGAGCGGAGTGA 1167
     |||||||||||||||||
97609 CCTGGGGAGCGGAGTGA 97625
```

Figure 30

```
  1 MSTEAQQESTPTARCPFSIQDGHRTILETGTVGAHELFGVKQWLVAAAED  50
    ||||||||||||||||||||||||||||||||||||||||||||||||||
  1 MSTEAQQESTPTARCPFSIQDGHRTILETGTVGAHELFGVKQWLVAAAED  50

51 VKLVTNDPRFSSAAPSGILGDRRPGWFSGMDSPEHNRYRQKIARDFTLRA 100
    ||||||||||||||||||||||||||||||||||||||||||||||||||
 51 VKLVTNDPRFSSAAPSGILGDRRPGWFSGMDSPEHNRYRQKIARDFTLRA 100

101 ARKQEEFIVRAADSCLDDIEASGPGTDLVPGYAKRLASLAIHDLYGLNEE 150
    |||||||||||||||||||||||||||||||||||||||||||||||| |
101 ARKQEEFIVRAADSCLDDIEASGPGTDLVPGYAKRLASLAIHDLYGLN.E 149

151 EGPVLEGQMRAMEGGTDMESIKRLTDEFFGHVLALVRAKREQAGDRLLHR 200
    ||||||||||||||||||||||||||| |||||||||||::|||||||
150 EGPVLEGQMRAMEGGTDMESIKRLTDE.FGHVLALVRAKRDEAGDRLLHR 198

201 LAESGEDEILLSDEEATGVFATLLFAGHDSMQQMVGYCLYALLSHPEQRA 250
    |||||||||||||||||||||||||||||||||||| |||||||||||
199 LAESGEDEILLSDEEATGVFATLLFAGHDSMQQMVGYSLYALLSHPEQRA 248

251 ALRENPDLIDGAVEELLRFLPLNQLGVPRVCVEDVELHGQTISAGDNVIP 300
    ||||||||||||||||||||||||||||||||||||||||||||||||||
249 ALRENPDLIDGAVEELLRFLPLNQLGVPRVCVEDVELHGQTISAGDNVIP 298

301 LYSTANRDPGVFADPDTFDITRKPEHNFAFGYGIHKCPGQHLARVLIKVA 350
    ||||||||||||||||||||||||||||||||||| |||||||||||||
299 LYSTANRDPGVFADPDTFDITRKPEHNFAFGYGIHGCPGQHLARVLIKVA 348

351 TLRLFERFPDVRLAGDVPMNEGLGLFSPAELRVTWGAE* 389
    |·||||||||||||||||||||||||||||||||||||
349 TVRLFERFPDVRLAGDVPMNEGLGLFSPAELRVTWGAE* 387
```

Figure 31

```
    1 GTGAGCGCGTCCGTGCAGACCATCAAGCTGCCGAACGGCAAGACCGTC.G  49
      ||||||||||||||||||||||||||||||||| ||||| ||||||||| |
97622 GTGAGCGCGTCCGTGCAGACCATCAAGCTGCCGTACGGC.AGACCGTCGG  97670

50 CCCACGTCAACCCGGGCGAGGCGCAGTTCCTCTACCAGGAGATCTTCGCC  99
      ||||||||||||||||||||||||||||||||||||||||||||||||||
97671 CCCACGTCAACCCGGGCGAGGCGCAGTTCCTCTACCAGGAGATCTTCGCC  97720

100 GAGCGGTGCTACTTGCGGCGCGGCCTTGAGCTGCGAGCGGGTGACGTGGT  149
      ||||||||||||||||||||||||||||||||||||||||||||||||||
97721 GAGCGGTGCTACTTGCGGCGCGGCCTTGAGCTGCGAGCGGGTGACGTGGT  97770

150 CTTCGACGTCGGCGCGAACATCGGCATGTTCTCGCTCTTCGCCCACCTGG  199
      ||||||||||||||||||||||||||||||||||||||||||||||||||
97771 CTTCGACGTCGGCGCGAACATCGGCATGTTCTCGCTCTTCGCCCACCTGG  97820

200 AGTGCCCCGATGTCACGGTGCACGCCTTCGAGCCGGCGCCGGTGCCGTAC  249
      ||||||||||||||||||||||||||||||||||||||||||||||||||
97821 AGTGCCCCGATGTCACGGTGCACGCCTTCGAGCCGGCGCCGGTGCCGTAC  97870

250 GCCGCGCTCAGGGCCAATGCCGAGCGGTACGGCATCGCGGGCCGGTTCGA  299
      ||||||||||||||||||||||||||||||||| ||||||||||||||||
97871 GCCGCGCTCAGGGCCAATGCCGAGCGGTACGCCATCGCGGGCCGGTTCGA  97920

300 GCAGTGCGCGGTCTCGGACGTGGCCGGCCGCGGCAAGATGACGTTCTACA  349
      ||||||||||||||||||||||||||||||||||||||||||||||||||
97921 GCAGTGCGCGGTCTCGGACGTGGCCGGCCGCGGCAAGATGACGTTCTACA  97970

350 CGGATACCACGATGATGTCGGGCTTCCACCCGGATCCGGCGACCCGCGCG  399
      ||||||||||||||||||||||||||||||||||||||||||||||||||
97971 CGGATACCACGATGATGTCGGGCTTCCACCCGGATCCGGCGACCCGCGCG  98020

400 GAGCTGCTGCGCAGGCTCGCCATCAACGGCGGGTACAGTGCCGAGGCCGC  449
      ||||||||||||||||||||||||||||||||||||||||||||||||||
98021 GAGCTGCTGCGCAGGCTCGCCATCAACGGCGGGTACAGTGCCGAGGCCGC  98070

450 CGACCGGATGCTGGCCGAGCTGCCGGACACCAGCCAGGTGATCGAGACGT  499
      ||||||||||||||||||||||||||||||||||||||||||||||||||
98071 CGACCGGATGCTGGCCGAGCTGCCGGACACCAGCCAGGTGATCGAGACGT  98120

500 CCGTCGTACGCCTCTCCGACGTCATCGCGGAGCGGGGCATCACCTCGATC  549
      ||||||||||||||||||||||||||||||||||||||||||||||||||
98121 CCGTCGTACGCCTCTCCGACGTCATCGCGGAGCGGGGCATCACCTCGATC  98170

550 GGACTGCTCAAGATCGATGTGGAGAAGAACGAGCGGCATGTGATGGCCGG  599
      ||||||||||||||||||||||||||||||||||||||||||||||||||
98171 GGACTGCTCAAGATCGATGTGGAGAAGAACGAGCGGCATGTGATGGCCGG  98220

600 GATCGACGCGGCCGACTGGCCGCGCATCCGCCAGGTCGTCACCGAGGTGC  649
      |||||||||| |||||||||||||||||||||||||||||||||||||||
98221 GATCGACGCGGGCGACTGGCCGCGCATCCGCCAGGTCGTCACCGAGGTGC  98270
```

Figure 32

```
  1 VSASVQTIKLPNGKTVAHVNPGEAQFLYQEIFAERCYLRRGLELRAGDVV  50
    |||||||||| |: |||||||||||||||||||||||||||||||||||
  1 VSASVQTIKLPYGRPSAHVNPGEAQFLYQEIFAERCYLRRGLELRAGDVV  50

51 FDVGANIGMFSLFAHLECPDVTVHAFEPAPVPYAALRANAERYGIAGRFE 100
    ||||||||||||||||||||||||||||||||||||||||||| |||||
 51 FDVGANIGMFSLFAHLECPDVTVHAFEPAPVPYAALRANAERYAIAGRFE 100

101 QCAVSDVAGRGKMTFYTDTTMMSGFHPDPATRAELLRRLAINGGYSAEAA 150
    |||||||||||||||||||||||||||||||||||||||||||||||||
101 QCAVSDVAGRGKMTFYTDTTMMSGFHPDPATRAELLRRLAINGGYSAEAA 150

151 DRMLAELPDTSQVIETSVVRLSDVIAERGITSIGLLKIDVEKNERHVMAG 200
    |||||||||||||||||||||||||||||||||||||||||||||||||
151 DRMLAELPDTSQVIETSVVRLSDVIAERGITSIGLLKIDVEKNERHVMAG 200

201 IDAADWPRIRQVVTEVHDIDGRLDEVLTLLRGQGFTVLSEQEPLFAGTDI 250
    ||| |||||||||||||||||||||||||||||||||||||||||||||
201 IDAGDWPRIRQVVTEVHDIDGRLDEVLTLLRGQGFTVLSEQEPLFAGTDI 250

251 YQVVARRGDA* 261
    ||||||||||
251 YQVVARRGDA* 261
```

Figure 33

```
201 GGCCACCTCCATCGATCTGTCACCCGAACTGACCGCGGTAGGCCGCCGCA 250
    |||||||||||||||||||||||||||||||||||||||||||| || ||
90998 GGCCACCTCCATCGATCTGTCACCCGAACTGACCGCGGTAGGCCCCCACA 91047

251 AGTTGGCCTCGCGGGGGATCGATAACGTCACCCTGGTCGAGGGTGACGTT 300
    ||||||||||||||||||||||||||||||||||||||||||||||||||
91048 AGTTGGCCTCGCGGGGGATCGATAACGTCACCCTGGTCGAGGGTGACGTT 91097
```

Figure 34

```
  1 MLELGTRLKFRFTGPLLEAVNPRLQGHPYDVLMRLLEGGRIENVLELCGG  50
    ||||||||||||||||||||||||||||||||||||||||||||||||||
  2 MLELGTRLKFRFTGPLLEAVNPRLQGHPYDVLMRLLEGGRIENVLELCGG  51

51 TGFASRMLAERHSKVQATSIDLSPELTAVGRRKLASRGIDNVTLVEGDVS 100
    |||||||||||||||||||||||||||||||  ||||||||||||||||
 52 TGFASRMLAERHSKVQATSIDLSPELTAVGPHKLASRGIDNVTLVEGDVS 101

101 TLPYPDDSFDTVMSAFGLHEVPTAGRLSAIRESVRVLKPGGRFVIVDLDR 150
    |||||||||||||||||||||||||||||||||||||||||||||||||
102 TLPYPDDSFDTVMSAFGLHEVPTAGRLSAIRESVRVLKPGGRFVIVDLDR 151

151 RTKYGWTMDLFMKVMEPKFAPEVFGTGLVDRLKENGFTIDHHESAGPNGW 200
    |||||||||||||||||||||||||||||||||||||||||||||||||
152 RTKYGWTMDLFMKVMEPKFAPEVFGTGLVDRLKENGFTIDHHESAGPNGW 201

201 TQSIVATLEA* 211
    ||||||||||
202 TQSIVATLEA* 212
```

PRODUCTION OF POLYKETIDES AND OTHER NATURAL PRODUCTS

FIELD OF THE INVENTION

The present invention relates to production of polyketides and other natural products and to libraries of compounds and individual novel compounds. One important area is the isolation and potential use of novel FKBP-ligand analogues and host cells that produce these compounds. The invention is particularly concerned with methods for the efficient transformation of strains that produce FKBP analogues and recombinant cells in which cloned genes or gene cassettes are expressed to generate novel compounds such as polyketide (especially rapamycin) FKBP-ligand analogues, and to processes for their preparation, and to means employed therein (e.g. nucleic acids, vectors, gene cassettes and genetically modified strains).

BACKGROUND OF THE INVENTION

Rapamycin (sirolimus) (FIG. 1) is a lipophilic macrolide produced by Streptomyces hygroscopicus NRRL 5491 (Sehgal et al., 1975; Vézina et al., 1975; U.S. Pat. No. 3,929,992; U.S. Pat. No. 3,993,749) with a 1,2,3-tricarbonyl moiety linked to a pipecolic acid lactone (Paiva et al., 1991). Other related macrolides (FIG. 2) include FK506 (tacrolimus) (Schreiber and Crabtree, 1992), FK520 (ascomycin or immunomycin) (Wu et al., 2000), FK525 (Hatanaka H, et al., 1989, FK523 (Hatanaka, H., et al., 1988), antascomicins (Fehr, T., et al., 1996) and meridamycin (Salituro et al., 1995). For the purpose of this invention rapamycin is described by the numbering convention of McAlpine et al. (1991) in preference to the numbering conventions of Findlay et al. (1980) or Chemical Abstracts ($11^{th}$ Cumulative Index, 1982-1986 p60719CS).

The versatile mode of action of rapamycin demonstrates the pharmacological value of the compound and emphasizes the necessity to isolate novel derivatives of the drug. Rapamycin shows moderate antifungal activity, mainly against Candida species but also against filamentous fungi (Baker et al., 1978; Sehgal et al., 1975; Vézina et al., 1975; U.S. Pat. No. 3,929,992; U.S. Pat. No. 3,993,749). Rapamycin inhibits cell proliferation by targeting signal transduction pathways in a variety of cell types, e.g. by inhibiting signalling pathways that allow progression from the $G_1$ to the S-phase of the cell cycle (Kuo et al., 1992). In T cells rapamycin inhibits signalling from the IL-2 receptor and subsequent autoproliferation of the T cells resulting in immunosuppression. The inhibitory effects of rapamycin are not limited to T cells, since rapamycin inhibits the proliferation of many mammalian cell types (Brunn et al, 1996). Rapamycin is, therefore, a potent immunosuppressant with established or predicted therapeutic applications in the prevention of organ allograft rejection and in the treatment of autoimmune diseases (Kahan et at, 1991). It appears to cause fewer side effects than the standard anti-rejection treatments (Navia, 1996). 40-O-(2-hydroxy)ethyl-rapamycin (SDZ RAD, Certican, Everolimus) is a semi-synthetic analogue of rapamycin that shows immunosuppressive pharmacological effects (Sedrani, R. et at, 1998; U.S. Pat. No. 5,665,772). The clinical efficacy of the drug is presently under investigation in Phase III clinical trials (Kirchner et at, 2000). The rapamycin ester CCI-779 (Wyeth-Ayerst) inhibits cell growth in vitro and inhibits tumour growth in vivo (Yu et at, 2001). The drug is currently in Phase III clinical trials. The value of rapamycin in the treatment of chronic plaque psoriasis (Kirby and Griffins, 2001), the potential use of effects such as the stimulation of neurite outgrowth in PC12 cells (Lyons et at, 1994), the block of the proliferative responses to cytokines by vascular and smooth muscle cells after mechanical injury (Gregory et al., 1993) and its role in prevention of allograft fibrosis (Waller and Nicholson, 2001) are areas of intense research (Kahan and Camardo, 2001). Recent reports reveal that rapamycin is associated with lower incidence of cancer in organ allograft patients on long-term immunosuppressive therapy than those on other immunosuppressive regimes, and that this reduced cancer incidence is due to inhibition of angiogenesis (Guba et at, 2002). It has been reported that the neurotrophic activities of immunophilin ligands are independent of their immunosuppressive activity (Steiner et al., 1997) and that nerve growth stimulation is promoted by disruption of the mature steroid receptor complex as outlined in the patent application WO01/03692. Side effects such as hyperlipidemia and thrombocytopenia as well as potential teratogenic effects have been reported (Hentges et at, 2001; Kahan and Camardo, 2001).

The polyketide backbone of rapamycin is synthesised by head-to-tail condensation of a total of seven propionate and seven acetate units to a shikimate derived cyclohexane carboxylic acid starter unit (Paiva et al., 1991). The L-lysine derived imino acid, pipecolic acid, is condensed via an amide linkage onto the last acetate of the polyketide backbone (Paiva et al., 1993) and is followed by lactonisation to form the macrocycle. A 107 kb genomic region containing the biosynthetic gene cluster has been sequenced (Schwecke et at, 1995). Analysis of the open reading frames revealed three large genes encoding the modular polyketide synthase (PKS) (Aparicio et al., 1996; Schwecke et al., 1995). Embedded between the PKS genes lies the rapP gene encoding a protein with sequence similarity to activation domains of nonribosomal peptide synthetases and it is thought to act analogously (König et al., 1997). The region encoding the PKS genes is flanked on both sides by 24 additional open reading frames encoding enzymes believed to be required for the biosynthesis of rapamycin (Molnár et al., 1996). These include the following post-polyketide modification enzymes: two cytochrome P450 monooxygenases, designated as RapJ and RapN, an associated ferredoxin RapO, and three potential SAM-dependent O-methyltransferases RapI, RapM and RapQ. Other adjacent genes have putative roles in the regulation and the export of rapamycin (Molnár et al., 1996). The cluster also contains the gene rapL whose product RapL is proposed to catalyse the formation of the rapamycin precursor L-pipecolic acid through the cyclodeamination of L-lysine (Khaw et al., 1998; Paiva et al., 1993). The introduction of a frameshift mutation into rapL gave rise to a mutant unable to produce significant amounts of rapamycin and feeding of L-pipecolic acid to the growth medium restored wild-type levels of rapamycin production (Khaw et al., 1998). The biosynthetic precursors to the cyclohexane ring of rapamycin originate from the shikimic acid pathway (Lowden et al., 1996; Lowden et al., 2001). Other closely-related macrolides such as FK506 (tacrolimus) (Schreiber and Crabtree, 1992), FK520 (ascomycin or immunomycin) (Wu et al., 2000), antascomicin (Fehr, T., et al., 1996) and meridamycin (Salituro et al., 1995) share a common pharmacophore that interacts with FK506-binding proteins (FKBPs) (FIG. 2). Thus rapamycin and related compounds for example, but without limitation, FK506, FK520, 'hyg', FK523, meridamycin, antascomicin, FK525 and tsukubamydn can be considered "FKBP-ligands". The partial sequence of the FK506 gene cluster (Motamedi et al., 1996; Motamedi et al., 1997; Motamedi and Shafiee, 1998), the 'hyg' cluster (Ruan et al., 1997) and the complete sequence of the FK520 gene cluster have been published (VWu et al., 2000; U.S. Pat. No. 6,150,513). There is significant homology between genes within these clusters and the rapamycin biosynthetic gene cluster and similarity in enzyme function (Motamedi et al., 1996).

The pharmacologic actions of rapamycin characterised to date are believed to be mediated by the interaction with cytosolic receptors termed FKBPs or immunophilins. Immunophilins (this term is used to denote immunosuppressant binding proteins) catalyse the isomerisation of cis and trans peptidyl-proline bonds and belong to a highly conserved family of enzymes found in a wide variety of organisms (Rosen and Schreiber, 1992). Two large groups of enzymes belonging to the family of immunophilins are represented by FKBPs and cyclophilins (Schreiber and Crabtree, 1992). The major intracellular rapamycin receptor in eukaryotic T-cells is FKBP12 (DiLella and Craig, 1991) and the resulting complex interacts specifically with target proteins to inhibit the signal transduction cascade of the cell. FK506, an immunosuppressive agent structurally related to rapamycin, also specifically binds to FKBP12 but it effects immunosuppression through a different mechanism (Chang et al., 1991; Sigal and Dumont, 1992). Rapamycin and FK506 compete for the same binding site, thus FK506 can have an antagonistic effect with rapamycin when the two drugs are used together (Cao et al., 1995). Analysis of the crystal structure of the FKBP12-rapamycin complex has identified a rapamycin-binding pharmacophore termed the 'binding domain' (Van Duyne et al., 1993) (see FIG. 1). The 'binding domain' is required for the interaction with the immunophilin and consists, for both FK506 and rapamycin, of the C-1 to C-14 region including the ester linkage, the pipecolinyl ring, the dicarbonyl and the hemiketal ring (see FIG. 2). The interaction is characterised by many hydrophobic contacts and some hydrogen bonds including one to the hydroxyl group on the cyclohexane ring. The pipecolinyl ring (C2 to N7) makes the deepest penetration into the protein where it is surrounded by highly conserved aromatic amino acid residues lining the hydrophobic binding cavity. Both the C1 and the C8 carbonyl groups are involved in hydrogen bonding and the C9 carbonyl group protrudes into a pocket formed by three completely conserved aromatic amino acid residues (one tyrosine and two phenylalanine acid residues) in FKBP12. The domain of the immunophilin-ligand complex interacting with the target protein projects away from FKBP.

The target of the rapamycin-FKBP12 complex has been identified in yeast as TOR (target of rapamycin) (Alarcon et al., 1999) and the mammalian protein is known as FRAP (FKBP-rapamycin associated protein) or mTOR (mammalian target of rapamycin) (Brown et al., 1994). These proteins show significant similarity to the phosphotransferase domains of phosphatidylinositol 3-kinases and the observation that a point mutation in the FKBP12-rapamycin binding domain (FRB) of mTOR abolishes mTOR kinase activity provides evidence for the involvement of FRB in the function of the kinase domain (Vilella-Bach et al, 1999). The crystal structure of FKBP12-rapamycin with a truncated form of mTOR containing the FRB domain (Chen et al., 1995) has been obtained thus defining the 'effector' domain of rapamycin (Choi et al, 1996; Liang et al, 1999). The analysis of the crystal structure revealed that protein-protein contacts are relatively limited compared to the interaction between rapamycin and each protein. No hydrogen bonds between rapamycin and FRB were identified. Interaction is concentrated in a series of hydrophobic contacts between the triene region of rapamycin and mainly aromatic residues of FRB (Liang et al., 1999). The most deeply buried atom of rapamycin is the methyl attached to C23 (see FIG. 2). The C23 to C34 region and the cyclohexyl ring of rapamycin make superficial hydrophobic contacts with FRB. A small conformational change in rapamycin was evident between the binary and the ternary complexes (Liang et al., 1999).

Divergences between the biological effects of C16 methoxy group rapamycin analogues and their ability to bind FKBP12 were detected and the location of the C16 substituents at the interfacial space between FKBP12 and mTOR was postulated (Luengo et al., 1995). The analysis of the crystal structure of FKBP12 with the non-immunosuppressive 28-O-methyl rapamycin revealed a significant difference in the orientation of the cyclohexyl ring which may result in disruption of mTOR binding (Kallen et al., 1996).

Rapamycin impacts signalling cascades within the cell through the inhibition of the $p70^{S6k}$ kinase, a serine/threonine kinase in higher eukaryotes which phosphorylates the ribosomal protein S6 (Ferrari et al., 1993; Kuo et al., 1992). The S6 protein is located in the ribosomal 40S subunit and it is believed to be an important functional site involved in tRNA and mRNA binding. A regulatory function for mRNA translation through S6 phosphorylation by $p70^{S6k}$ has been postulated (Kawasome et al., 1998). Rapamycin inhibits protein synthesis through its effect on other growth related events, including the activity of cyclin-dependent kinases, phosphorylation of cAMP-responsive element modulator (CREM) and phosphorylation of the elongation factor binding protein 4E-BP-1 (PHAS1) (Hung et al., 1996). The drug induces the accumulation of the dephosphorylated species of 4E-BP1 that binds to the translation initiation factor eIF-4E, thus, suppressing translation initiation of cap-dependent mRNAs (Hara et al., 1997; Raught et al., 2001).

A link between mTOR signalling and localized protein synthesis in neurons; the effect on the phosphorylation state of proteins involved in translational control; the abundance of components of the translation machinery at the transcriptional and translational levels; control of amino acid permease activity and the coordination of the transcription of many enzymes involved in metabolic pathways have been described (Raught et al., 2001). Rapamycin sensitive signalling pathways also appear to play an important role in embryonic brain development, learning and memory formation (Tang et al, 2002). Research on TOR proteins in yeast also revealed their roles in modulating nutrient-sensitive signalling pathways (Hardwick et al, 1999). Similarly, mTOR has been identified as a direct target for the action of protein kinase B and of having a key role in insulin signalling (Shepherd et al., 1998; Nave et al, 1999). Mammalian TOR has also been implicated in the polarization of the actin cytoskeleton and the regulation of translational initiation (Alarcon et at, 1999). Phophatidylinositol 3-kinases, such as mTOR, are functional in several aspects of the pathogenesis of tumours such as cell-cycle progression, adhesion, cell survival and angiogenesis (Roymans and Slegers, 2001).

Most immunophilins do not appear to be directly involved in immunosuppressive activities and relatively little is known concerning their natural ligands although candidates for natural ligands of the FKBPs termed FKBP-associated proteins (FAP) such as FAP48 and FAP1 have been reported. The specific interaction of FAPs with FKBPs during the formation of complexes was prevented by rapamycin in a dose-dependent manner (Chambraud et at, 1996; Kunz et al., 2000). Immunophilins appear to function in a wide range of cellular activities such as protein folding; assembly and trafficking of proteins; co-regulation of molecular complexes including heat shock proteins; steroid receptors; ion channels; cell-to-cell interactions and transcription and translation of genes (Galat 2000; Hamilton and Steiner 1998). All immunophilins possess the protein folding property of peptidyl-prolyl cis-trans isomerisation and several immunophilins are found located in the endoplasmic reticulum, a principal site of protein synthesis in the cell. In addition to FKBP12 (U.S. Pat. No. 5,109,112) other immunophilins include FKBP12.6 (U.S. Pat. No. 5,457,182), FKBP13 (Hendrickson et al., 1993; U.S. Pat. No. 5,498, 597), FKBP25 (Hung and Schreiber, 1992; Jin et al, 1992), FKBP14.6 (U.S. Pat. No. 5,354,845), FKBP52 (U.S. Pat. No. 5,763,590), FKBP60 (Yem et al, 1992) and FKBP65 (Patterson et al., 2000).

The multitude of the FKBP's which are present in different cell types also underline the utility of isolating novel FKBP-ligand analogues with potentially changed binding and/or effector domains.

Pharmacokinetic studies of rapamycin and rapamycin analogues have demonstrated the need for the development of novel rapamycin compounds that may be more stable in solution, more resistant to metabolic attack and have improved bio-availability. Modification using chemically available positions on the molecule has been addressed, however, this approach has limited utility as the sites available for chemical modification are limited and there is less ability to selectively modify a particular position. Biological approaches to producing novel rapamycin analogues have been less successful due to the difficulties encountered in working with the organism (Lomovskaya et al., 1997; Kieser et al., 2000) despite the availability of the sequence of the biosynthetic gene cluster of rapamycin from *S. hygroscopicus* (Schwecke et al., 1995).

A range of synthesised rapamycin analogues using the chemically available sites of the molecule has been reported. The description of the following compounds was adapted to the numbering system of the rapamycin molecule described in FIG. 1. Chemically available sites on the molecule for derivatisation or replacement include C40 and C28 hydroxyl groups (e.g. U.S. Pat. No. 5,665,772; U.S. Pat. No. 5,362, 718), C39 and C16 methoxy groups (e.g. WO96/41807; U.S. Pat. No. 5,728,710), C32, C26 and C9 keto groups (e.g. U.S. Pat. No. 5,378,836; U.S. Pat. No. 5,138,051; U.S. Pat. No. 5,665,772). Hydrogenation at C17, C19 and/or C21, targeting the triene, resulted in retention of antifungal activity but loss of immunosuppression (e.g. U.S. Pat. No. 5,391,730; U.S. Pat. No. 5,023,262). Significant improvements in the stability of the molecule (e.g. formation of oximes at C32, C40 and/or C28, U.S. Pat. No. 5,563,145, U.S. Pat. No. 5,446,048), resistance to metabolic attack (e.g. U.S. Pat. No. 5,912,253), bioavailability (e.g. U.S. Pat. No. 5,221,670; U.S. Pat. No. 5,955,457; WO98/04279) and the production of prodrugs (e.g. U.S. Pat. No. 6,015,815; U.S. Pat. No. 5,432,183) have been achieved through derivatisation. However, chemical modification requires significant quantities of rapamycin template and, as a base and acid labile compound, it is difficult to work with. Where chemical derivatisation can be group selective, it is often difficult to be site selective. Consequently, chemical modification invariably requires multiple protective and deprotecive steps and produces mixed products in variable yields.

The isolation of rapamycin analogues using biological methods such as biotransformation and phage-based genetic modification has also been described. Isolation of minor metabolites from both mutant strains and rapamycin producing strains has provided small quantities of a number of rapamycin analogues. These strains are often low yielding and produce mixtures of rapamycin analogues. The isolation of 27-O-desmethylrapamycin and 27-desmethoxyrapamycin was reported from the culture supernatant of *S. hygroscopicus* NCIMB 40319 (Box et al., 1995). The antifungal activity of 27-O-desmethylrapamycin was lower than that of rapamycin but the inhibition of FKBP12 PPIase activity seemed to be increased. The inhibition of ConA-stimulated proliferation of murine splenic T cells and the inhibition of LPS-stimulated proliferation of murine splenic B cells was decreased when compared to rapamycin (Box et al., 1995). Similarly, antifungal activities of the rapamycin derivatives prolylrapamycin, 27-O-desmethylrapamycin and 27-desmethoxyrapamycin were lower than that of rapamycin (Wong et al., 1998). Rapamycin analogues (16-O-desmethylrapamycin, 27-O-desmethylrapamycin, 39-O-desmethylrapamycin, 16,27-O-bisdesmethylrapamycin, prolylrapamycin, 26-O-desmethylprolylrapamycin, 9-deoxorapamycin, 27-desmethoxyrapamycin, 27-desmethoxy-39-O-desmethylrapamycin, 9-deoxo-27-desmethoxyrapamycin, 28-dehydrorapamycin, 9-deoxo-27-desmethoxy-39-O-desmethylrapamycin) were also isolated from *Actinoplanes* sp N902-109 after the addition of cytochrome P450 inhibitors and/or precursor feeding to the culture or after biotransformation of isolated rapamycin (Nishida et al, 1995). The use of such inhibitors, however, only allows the targeting of a particular enzyme function and is not site selective. Rational production of a single selected analogue is not possible via this method. The resulting production of mixtures of rapamycin analogues rather than a single desired product also impacts yield. The mixed lymphocyte reaction (MLR) inhibitory activity of the compounds was assessed and little effect on the activity was detected after the loss of the methyl group at C27 or/and C16. In addition, 9-deoxorapamycin showed a more significant decrease in activity and the loss of the methoxy group at C27, the hydroxy group at C28 and the substitution of a pipecolinyl group for a prolyl group resulted in a reduction in potency (Nishida et at, 1995). Similarly, biotransformation of rapamycin and the isolation of 16,39-O-bisdesmethylrapamycin have been reported (WO 94/09010). The retention of inhibitory activity in cell proliferation assays with compounds modified in the cyclohexyl ring, e.g. 39-O-desmethylrapamycin and C40 modifications such as SDZ RAD, identify this region of the molecule as a target for the generation of novel rapamycin analogues. Novel rapamycin analogues were reported after feeding cyclohexanecarboxylic acid, cycloheptanecarboxylic acid, cyclohex-1-enecarboxylic acid, 3-methylcyclohexanecarboxylic acid, cyclohex-3enecarboxylic acid, 3-hydroxycyclohex-4-enecarboxylic acid and cyclohept-1-enecarboxylic acid to cultures of *S. hygroscopicus* thus demonstrating the flexibility in the loading module of the rapamycin polyketide synthase (P. A. S. Lowden, PhD dissertation, University of Cambridge, 1997). These novel rapamycin analogues were produced in competition with the natural starter, 4, 5-dihydroxycyclohex-1-enecarboxylic acid, resulting in reduced yields and mixed products.

The isolation of recombinant *S. hygroscopicus* strains producing various rapamycin analogues, using biological methods mediated by phage technology (Lomovskaya et al., 1997), has been reported. In the presence of added proline derivatives, a *S. hygroscopicus* rapL deletion mutant synthesized the novel rapamycin analogues prolylrapamycin, 4-hydroxyprolylrapamycin and 4-hydroxyprolyl-26-desmethoxy-rapamycin (Khaw et al., 1998). Similarly, the novel rapamycins 3-hydroxy-prolyl-rapamycin, 3-hydroxyprolyl-26-desmethoxy-rapamycin, and trans-3aza-bicyclo[3,1,0]hexane-2-carboxylic acid rapamycin have been identified as described in WO98/54308. The activity of prolylrapamycin and 4-hydroxyprolyl-26-desmethoxy-rapamycin was assessed in proliferation assays and the inhibitory activity of the latter compound was significantly less than that of rapamycin (Khaw et at, 1998). The deletion of five contiguous genes, rapQONML (responsible for post-polyketide modifications at C16, C27 and production of L-pipecolic acid) and their replacement with a neomycin resistance marker in *S. hygroscopicus* ATCC29253 using phage-based metholgy resulted in the production of 16-O-desmethyl-27-desmethoxyrapamycin when fed with pipecolic acid (Chung et al, 2001). No complementation of this deletion mutant has been demonstrated using this technology. Furthermore, the site-specific functionality of rapM and rapQ remains unclear; therefore, rational design of rapamycin analogues requiring methylation at C16-H or C27-OH has not been enabled. The phage-based methodology suffers from a number of drawbacks as described in more detail below. It offers a difficult and protracted process of obtaining engineered strains and has a reduced versatility in comparison to the methodology disclosed within this current patent.

Conventional approaches to manipulate rapamycin modifying genes using biological methods comprise the mutation or deletion of individual genes in the chromosome of a host strain or/and the insertion of individual genes as extra copies of homologous or heterologous genes either individually or as gene cassettes (WO01/79520, WO 03/048375). However, the isolation of novel rapamycin analogues using such biological methods has been limited due to the difficulties in transforming the rapamycin-producing organism *S. hygroscopicus*. It has been reported that the commonly used methods of transformation with plasmid DNA or conjugal transfer were unsuccessful with the rapamycin producing strain (Lomovskya et al., 1997, Schweke et al., 1995, Kieser et al., 2000). The current state of the art uses the methodology of Lomovskya et al. (1997), a work intensive phage based method that is severely limited by the size of the cloned DNA fragments transferred into *S. hygroscopicus* (Kieser et al., 2000). This technology is limited to the transfer of a maximum of 6.4 kb of cloned DNA. Thus, when complementing a deletion mutant using this technology the artisan is limited to the inclusion of ~2 functional genes in addition to desired promoter, regions of homology and resistance marker. The genetic information for the rapamycin biosynthetic gene cluster has been available since 1995 (Schwecke et al., 1995), however, limited progress in this area has been made (Khaw et al., 1998; Chung et al., 2001; WO01/34816).

SUMMARY OF THE INVENTION

The present invention provides recombinant methods for the efficient transformation of strains that contain a biosynthetic cluster encoding an FKBP ligand, for example but without limitation *Streptomyces hygroscopicus* subsp. *hygroscopicus* NRRL 5491, *Actinoplanes* sp. N902-109 FERM BP-3832, *Streptomyces* sp. M6554, *Streptomyces hygroscopicus* var. *ascomyceticus* MA 6475 ATCC 14891, *Streptomyces hygroscopicus* var. *ascomyceticus* MA 6678 ATCC 55087, *Streptomyces hygroscopicus* var. *ascomyceticus* MA 6674, *Streptomyces hygroscopicus* var. *ascomyceticus* ATCC 55276, *Streptomyces tsukubaensis* No.9993 FERM BP-927, *Streptomyces hygroscopicus* subsp. *yakushimaensis*, *Streptomyces* sp. DSM 4137, *Streptomyces* sp. DSM 7348, *Micromonospora* n.sp. A92-306401 DSM 8429, *Steptomyces* sp. MA 6858 ATCC 55098, *Steptomyces* sp. MA 6848, said methods comprising:

(a) constructing a conjugative deletion plasmid in an *E. coli* strain that is dam, dcm or dam and dcm.

(b) generation of spores from said strain suitable for conjugation wherein said strain is grown at a humidity of between 10% and 40% and the spores are harvested at between 5 and 30 days;

(c) conjugating the *E. coli* strain of step (a) with the spores from step (b) on a medium that comprises per litre:
   i) 0.5 g to 5 g corn steep powder,
   ii) 0.1 g to 5 g Yeast extract,
   iii) 0.1 g to 10 g calcium carbonate; and
   iv) 0.01 g to 0.5 g iron sulphate;

said media additionally containing BACTO-agar and starch and having been dried to result in 1-20% weight loss; and (d) optionally culturing the strain under conditions suitable for polyketide production.

In a preferred embodiment the methods are used for the transformation of *Streptomyces hygroscopicus* subsp. *hygroscopicus* (e.g. NRRL 5491), *Actinoplanes* sp. N902-109 (e.g. FERM BP-3832), *Streptomyces* sp. AA6554, *Streptomyces hygroscopicus* var *ascomyceticus* (e.g. MA 6475 ATCC 14891), *Streptomyces hygroscopicus* var. *ascomyceticus* (e.g. MA 6678 ATCC 55087), *Streptomyces hygroscopicus* var. *ascomyceticus* (e.g. MA 6674), *Streptomyces hygroscopicus* var. *ascomyceticus* (e.g. ATCC 55276), *Streptomyces tsukubaensis* No.9993 (e.g. FERM BP-927), *Streptomyces hygroscopicus* subsp. *yakushimaensis*, *Streptomyces* sp. (e.g. DSM 4137), *Streptomyces* sp. (e.g. DSM 7348), *Micromonospora* n.sp. A92-306401 (e.g. DSM 8429) or *Streptomyces* sp. (e.g. MA 6858 ATCC 55098). In a more preferred embodiment the methods are used for the transformation of: *S. hygroscopicus* subsp. *hygroscopicus* (e.g. NRRL 5491) or *S. hygroscopicus* var. *ascomycpeticus* (e.g. ATCC 14891). In a still more highly preferred embodiment the methods are used for the transformation of the rapamycin producer *S hygroscopicus* subsp. *hygroscopicus* (e.g. NRRL 5491).

Therefore the present invention also provides a recombinant strain that contains biosynthetic clusters that encode FKBP-ligands where one or more auxiliary genes have been deleted or inactivated using the methods as described herein.

In a further aspect, the present invention provides recombinant methods and materials for expressing combinations of polyketide modification enzymes so as to produce novel polyketide analogues. In a specific embodiment, the present invention provides recombinant methods and materials for expressing the combinations of enzymes responsible for post-PKS modification and/or precursor supply from biosynthetic clusters that encode FKBP-ligands for example but without limitation rapamycin, FK506, FK520, FK523, FK525, antascomicin, meridamycin, tsukubamycin and analogues therof and methods for the production of analogues in recombinant host cells. In a preferred embodiment the recombinant methods and materials are used for expressing the combinations of enzymes responsible for post-PKS modification and/or precursor supply in the biosynthesis of rapamycin, FK520, FK506 and 'hyg' and methods for the production of rapamycini FK520, FK506 and 'hyg' analogues in recombinant host cells. In a more highly preferred embodiment the recombinant methods and materials are used for expressing the combinations of enzymes responsible for post-PKS modification and/or precursor supply in the biosynthesis of rapamycin and methods for the production of rapamycin analogues in recombinant host cells.

Broadly, the present invention is concerned with the alteration of a gene system which has a core portion responsible for the production of a basic product, and a multiplicity of modifying genes responsible for effecting relatively small modifications to the basic product—e.g. effecting glycosylation, oxidation, reduction, alkylation, dealkylation, acylation or cyclisation of the basic product, and a multiplicity of precursor supply genes which are involved in the production of particular precursor compounds (e.g. pipecolate; 4,5 dihydroxycyclohex-1-ene carboxylic acid). Thus the basic product may be a modular polyketide and the modifying genes may be concerned with glycosylation and/or other modifications of a polyketide chain, and the precursor supply genes may be involved in the production and/or incorporation of natural or non-natural precursors (e.g. pipecolate and/or 4,5 dihydroxycyclohex-1-ene carboxylic acid in the rapamycin system).

The core portion may not function properly or even at all in the absence of a precursor supply gene (unless a natural or unnatural precursor compound is supplied or is otherwise available).

In one aspect the invention provides methods for the alteration of a gene system with a core portion that cannot function due to a deletion or inactivation of a precursor supply gene. Suitable gene systems include, but are not limited to, the rapamycin, antascomicin, FK520, FK506, 'hyg', FK523, meridamycin, FK525 and tsukubamycin biosynthetic clusters. In this aspect of the invention, the precursor supply gene lacking is preferably rapK or a homologue of rapK (e.g. fkbO in the FK506 or FK520 gene clusters). The gene system is preferably the rapamycin cluster. The precursor supply gene lacking is more preferably rapK. This aspect of the invention provides methods for the efficient production of a multiplicity of basic products through the incorporation of natural or non-natural precursors (e.g. 4,5-dihydroxycyclohex-1-ene carboxylic acid). Methods may also embody further aspects as set out below.

Another type of system is a non-ribosomal peptide ("NRP") system where the basic product is a peptide and the modifying genes are genes responsible for modifications to a peptide (glycosylation, reduction etc), and the precursor supply genes are genes involved in the production of unusual amino acid residues to be incorporated in the peptide. Systems can also be of mixed type, e.g. having a polyketide part and a part with a different biosynthetic origin, e.g. NRP. Indeed, rapamycin can be regarded as an example of this since the pipecolate residue is an amino acid residue added by an enzyme similar to ones found in NRP systems.

These modifying genes and precursor supply genes may be regarded as "auxiliary genes" for polyketide synthesis and the term "auxiliary genes" as used herein may refer to modifying genes, precursor supply genes or both.

The alteration of the gene system involves the creation of a functioning altered system in which the set of auxiliary genes has been altered. Thus one or more auxiliary genes (and preferably two or more, three or more, four or more, five or more, six or more or seven or more) may have been deleted (or rendered non-functional) and/or replaced by different genes.

This may involve a "deletion system" comprising nucleic acid encoding a gene system lacking a multiplicity of functional auxiliary genes. This deletion system can then be complemented with one or more functional auxiliary genes (which may be the same as or different from the genes they replace). This can be carried out combinatorially, a deletion system being complemented by a multiplicity of different genes and sets of genes.

An altered system which differs from the natural system in lacking one or more modifying functions could be produced (a) by producing a deletion system and restoring by complementation less than all of the deleted genes; or (b) by selectively deleting or inactivating genes of an existing system. In an altered system produced according to (b) genes may be inactivated by site-directed mutagenesis of an active site important in the protein function (active site point mutation), by truncation of the gene through a frameshift mutation, by an in-frame deletion of a section of the gene important to its function, such as an active site; partial deletion or inactivation by point mutation. These could all be carried out by double recombination and selecting for the mutant genotype, or by single recombination. In a preferred embodiment the altered system is produced by method (a). Such methods could also be used in producing a deletion system. The "complementation" approach (a) is preferably homologous, in that the "restored" genes are from the same gene cluster, however, heterologous complementation, wherein the "restored" genes are selected from a different biosynthetic cluster that encodes FKBP-ligands, is also contemplated by the present invention. In a preferred embodiment the "restored" genes are essentially the same as the deleted genes, or are variants thereof, which perform similar functions.

In a further aspect of the invention, an altered system with a deleted (or non-functional) precursor supply gene can be fed with alternative precursors so that it produces variant products.

As applied to a polyketide synthase ("PKS") system, one preferred type of embodiment is a method for producing polyketides comprising: (a) providing a strain of an organism which contains one or more PKS genes expressible to produce a functioning PKS which can generate a polyketide in the organism, for example PKS genes that encode a FKBP-ligand, the organism lacking one or more (and preferably a plurality) of functional auxiliary genes naturally associated with said PKS genes which encode gene products capable of effecting respective modifications of the polyketide; and (b) effecting complementation by causing said organism to express one or more auxiliary genes, the expressed modifying genes constituting an incomplete set of auxiliary genes naturally associated with said PKS genes and/or comprising one or more variant auxiliary genes; and (c) culturing said strain and optionally isolating the polyketide analogues produced.

The step of providing a strain of an organism containing one or more PKS genes may include a step of providing nucleic acid encoding a gene cluster comprising said one or more PKS genes and lacking said one or more auxiliary genes; and introducing said nucleic acid into the organism.

The PKS genes are preferably rapamycin genes. The auxiliary genes which are lacking are preferably one or more of rapK, rapI, rapQ, rapM, the contiguous genes rapN and O (herein designated as rapN/O), rapL and rapJ. In specific embodiments contemplated by the present invention:

i) one auxiliary gene is lacking, for example rapK; rapI; rapQ; rapM; rapL, rapN/O or rapJ is lacking; preferably where one auxiliary gene is lacking it is selected from the group consisting of rapK; rapI; rapQ; rapM; rapN/O and rapJ;

ii) two auxiliary genes are lacking for example: rapKrapI; rapKrapQ; rapKrapM, rapKrapN/O; rapKrapL; rapKrapJ; rapIrapQ; rapIrapM; rapIrapN/O; rapIrapL;

rapIrapJ; rapQrapM; rapQrapN/O; rapQrapL; rapQrapJ; rapMrapN/O; rapMrapL; rapMrapJ; rapN/OrapL; rapN/OrapJ or rapLrapJ are lacking;

iii) three auxiliary genes are lacking for example: rapKrapIrapQ; rapKrapIrapM; rapKrapIrapN/O; rapKrapIrapL; rapKrapIrapJ; rapKrapQrapM; rapKrapQRapN/O; rapKrapQrapL; rapKrapQrapJ; rapKrapMrapN/O; rapKrapMrapL; rapKrapMrapJ; rapKrapN/OrapL, rapKrapN/OrapJ; rapKrapLrapJ; rapIrapQrapM; rapIrapQrapN/O; rapIrapQrapL; rapIrapQrapJ; rapIrapMrapN/O; rapIrapMrapL; rapI rapMrapJ; rapIrapN/OrapL, rapIrapN/OrapJ; rapIrapLrapJ; rapQrapMrapN/O; rapQrapMrapL; rapQrapMrapJ; rapQrapN/OrapL, rapQrapN/OrapJ; rapQrapLrapJ; rapMrapN/OrapL, rapMrapN/OrapJ; rapMrapLrap or rapN/OrapLrapJ are lacking iv) four auxiliary genes are lacking, for example: rapKrapIrapQrapM; rapKrapIrapQrapN/O; rapKrapIrapQrapL, rapKrapIrapQrapJ; rapKrapIrapMrapN/O; rapKrapIrapMrapL; rapKrapIrapMrapJ; rapKrapIrapN/OrapL; rapKrapIrapN/OrapJ; rapKrapIrapLrapJ; rapKrapQrapMrapN/O; rapKrapQrapMrapL; rapKrapQrapMrapJ; rapKrapQrapN/OrapL; rapK, rapQ, rapN/O, rapJ; rapKrapQrapLrapJ; rapKrapMrapN/OrapL; rapKrapMrapN/OrapJ; rapKrapMrapLrapJ; rapKrapN/OrapLrapJ; rapIrapQrapMrapN/O; rapIrapQrapMrapL; rapI rapQrapMrapJ; rapIrapQrapN/OrapL, rapIrapQrapN/OrapJ; rapIrapQrapLrapJ, rapIrapMrapN/OrapL; rapIrapMrapN/OrapJ; rapIrapMrapLrapJ; rapIrapN/OrapLrapJ; rapQrapMrapN/OrapL; rapQrapMrapN/OrapJ; rapQrapMrapLrapJ; rapQrapN/OrapLrapJ or rapMrapN/OrapLrapJ are lacking;

v) five auxiliary genes are lacking, for example: rapKrapIrapQrapMrapN/O; rapKrapIrapQrapMrapL; rapKrapIrapQrapMrapJ; rapKrapIrapQrapN/OrapL; rapKrapIrapQrapN/OrapJ; rapKrapIrapQrapLrapJ; rapKrapIrapMrapN/OrapL; rapKrapIrapMrapN/OrapJ; rapKrapIrapMrapLrapJ; rapKrapIrapN/OrapLrapJ; rapKrapQrapMrapN/OrapL; rapKrapQrapMrapN/OrapJ, rapKrapQrapMrapLrapJ, rapKrapQrapN/OrapLrapJ; rapKrapMrapN/OrapLrapJ; rapIrapQrapMrapN/OrapL; rapIrapQrapMrapN/OrapJ; rapIrapQrapN/OrapLrapJ; rapIrapMrapN/OrapLrapJ; rapQrapMrapN/OrapLrapJ or rapIrapQrapMrapLrapJ are lacking;

vi) six auxiliary genes are lacking for example: rapKrapIrapQrapMrapN/OrapL; rapKrapIrapQrapMrapN/OrapJ; rapKrapIrapQrapMrapLrapJ; rapKrapIrapQrapN/OrapLrapJ, rapKrapIrapMrapN/OrapLrapJ; rapKrapQrapMrapN/OrapLrapJ or rapIrapQrapMrapN/OrapLrapJ are lacking; or vii) seven auxiliary genes are lacking, e.g. rapKrapIrapQrapMrapN/OrapLrapJ are lacking.

The expression "lacking one or more functional auxiliary genes" covers both the lack of a gene and the presence of a gene but in a non-functioning state, e.g. because it has been specifically disabled.

In one aspect, the invention provides a novel and expeditious route to the efficient incorporation of natural or non-natural precursors into FKBP-ligands. These include, but are not limited to, the rapamycin, antascomicin, FK520, FK506, hyg', FK523, meridamycin, FK525 and tsukubamycin polyketide synthase/non-ribosomal peptide synthase systems, the invention thus provides novel analogues of their respective natural products. In specific aspect, the invention provides a novel and expeditious route to the efficient incorporation of natural or non-natural precursors providing novel rapamycin analogues.

Therefore in one aspect the present invention provides a method of generating analogues of FKBP-ligands which incorporate a non-natural starter unit, said method comprising:

(a) generating a recombinant strain in which at least the rapK homologue has been deleted or inactivated; and (b) feeding a non-natural starter unit to said strain In a preferred embodiment the recombinant strain is generated using the methods of the present invention.

In further aspects the invention provides libraries of compounds and individual compounds available using such systems. Thus a typical compound is a variant of a compound naturally produced by a gene system which has a core portion responsible for the production of a basic product, and a multiplicity of auxiliary genes responsible for effecting relatively small modifications to the basic product, the variant being producible by a system altered so that one or more of the auxiliary genes are absent, non-functional, or replaced by functional variants. A preferred class of compounds is rapamycin analogues corresponding to products of a rapamycin system wherein one or more of the genes selected from the group consisting of rapK rapI, rapQ, rapM, rapN, rapO, rapL and rapJ genes are absent, non-functional or variant.

In a further aspect, the present invention provides novel FKBP-analogues, in a preferred embodiment the present invention provides novel rapamycin analogues. Such compounds may have one or more useful properties, for example but without limitation, utility as immunosuppressants, antifungal agents, anticancer agents, neuroregenerative agents, or agents for the treatment of psoriasis, rheumatoid arthritis, fibrosis and other hyperproliferative diseases.

Definitions:

As used herein the term "modifying gene(s)" includes the genes required for post-polyketide synthase riodifications of the polyketide, for example but without limitation cytochrome P450 monooxygenases, ferredoxins and SAM-dependent O-methyltransferases. In the rapamycin system these modifying genes include rapN/O, rapM, rapI, rapQ, and rapJ but a person of skill in the art will appreciate that PKS systems related to rapamycin (for example but without limitation: FK506, FK520, antascomicin, 'hyg', FK523, meridamycin, FK525 and tsukubamycin) will have homologues of at least a subset of these genes, some of which are discussed further below.

As used herein the term "precursor supply gene(s)" includes the genes required for the supply of the natural or non-natural precursors, the genes required for the synthesis of any naturally or non-naturally incorporated precursors and the genes required for the incorporation of any naturally or non-naturally incorporated precursors. For example but without limitation in the rapamycin system these genes include rapL, rapK and rapP but a person of skill in the art will appreciate that PKS systems related to rapamycin (for example but without limitation: FK506, FK520, antascomicin, 'hyg', FK523, meridamycin, FK525 and tsukubamycin) will have homologues of these genes, some of which are discussed further below.

As used herein, the term "auxiliary gene(s)" includes references to modifying genes, precursor supply genes or both modifying genes and precursor supply genes.

As used herein, the term "precursor" includes the natural starter units (i.e. 4,5-dihydroxycyclohex-1-ene carboxylic acid), non-natural starter units, and naturally incorporated amino acids (i.e. pipecolic acid) and non-naturally incorporated amino acids As used herein the term "non-natural starter unit" refers to any compounds which can be incorporated as a starter unit in polyketide synthesis that are not the starter unit usually chosen by that PKS.

As used herein, the term "FKBP-ligands" refers to compounds that bind to the immunophilin FKBP, such compounds preferentially contains an α, β-diketo amide where the β-keto is masked as an hemi-acetal. Such compounds include, without limitation, rapamycin, FK520, FK506, antascomicin, hyg', FK523, meridamycin, FK525 and tsukubamycin, As used herein, the term "biosynthetic clusters that encode FKBP-ligands" includes but is not limited to the gene clusters which direct the synthesis of rapamycin, FK506, FK520, 'hyg', FK523, antascomicin, meridamycin, FK525 and tsukubamycin.

As used herein the term "strains that contain biosynthetic clusters that encode FKBP-ligands" includes but is not limited to: *Streptomyces hygroscopicus* subsp. *hygroscopicus* (e.g. NRRL 5491), *Actinoplanes* sp. N902-109 (e.g. FERM BP-3832), *Streptomyces* sp. M6554, *Streptomyces hygroscopicus* var. *ascomyceticus* MA 6475 (e.g. ATCC 14891), *Streptomyces hygroscopicus* var. *ascomyceticus* MA 6678 (e.g. ATCC 55087), *Streptomyces hygroscopicus* var. *ascomyceticus* MA 6674, *Streptomyces hygroscopicus* var. *ascomyceticus* (e.g. ATCC 55276), *Streptomyces tsukubaensis* No.9993 (e.g. FERM BP-927), *Streptomyces hygroscopicus* subsp. *yakushimaensis, Streptomyces* sp. (e.g. DSM 4137), *Streptomyces* sp. (e.g. DSM 7348), *Micromonospora* n.sp. A92-306401 (e.g. DSM 8429) or *Streptomyces* sp. MA 6858 (e.g. ATCC 55098).

As used herein, the term "rapK homologue" refers to homologues of the rapamycin gene rapK from other biosynthetic clusters that encode FKBP-ligands, for example but without limitation: the fkbO gene from the FK520 cluster, the fkbO gene from the FK506 cluster and the Orf5 in the 'hyg' cluster. Such rapK homologues perform the same function as rapK in the synthesis of these related FKBP-ligands, namely they are essential for the supply of the natural starter unit. Preferably, such rapK homologues have at least 40% sequence identity, preferably at least 60%, at least 70%, at least 80%, at least 90% or at least 95% sequence identity to the sequence of rapK as shown in FIG. 27 (SEQ ID NO: 13).

DETAILED DESCRIPTION OF THE INVENTION

In one aspect, the present invention provides a novel and expeditious method for the transformation of *S. hygroscopicus*. The use of phage technology for the isolation of genetically modified strains of *S. hygroscopicus* has previously been described (Khaw et al., 1998; Lomovskaya et al., 1997). However, no method other than transfection has ever been reported for the introduction of DNA into the rapamycin producing strain *S. hygroscopicus*. Indeed, it has been stated previously that the commonly used methods of transformation with plasmid DNA or conjugal transfer were unsuccessful with the rapamycin-producing strain (Lomovskaya et al., 1997, Kieser et al., 2000; Schweke et al., 1995).

In the present invention, surprisingly a conjugation protocol to successfully transform *S. hygroscopicus* was established as described in Example 1. The methodology was exemplified by the isolation of the deletion mutant in *S. hygroscopicus* MG2-10 (Example 2) and by the expression of genes and gene combinations as described in Examples 3, 5 and 15.

Therefore, in one aspect the present invention provides a method for producing a recombinant strain that contains biosynthetic clusters that encode FKBP-ligands where one or more auxiliary genes have been deleted or inactivated said method comprising:

(a) construction of a conjugative plasmid in an *E. coli* strain that is dam, dcm or dam and dcm;
(b) generation of spores from said strain suitable for conjugation wherein said strain is grown at a humidity of between 10% and 40% and the spores are harvested at between 5 and 30 days;
(c) conjugating the *E. coli* strain of step (a) with the spores from step (b) in a medium that comprises per litre:
  i) 0.5 g to 5 g corn steep powder,
  ii) 0.1 g to 5 g Yeast extract,
  iii) 0.1 g to 10 g calcium carbonate; and
  iv) 0.01 g to 0.5 g iron sulphate;
said media additionally containing BACTO-agar and starch and having been dried to result in 1-20% weight loss; and
(d) optionally culturing the strain under conditions suitable for polyketide production.

Preferably the *E. coli* strain of step (a) is dam⁻ and dcm⁻.

Preferably, in step (b) the spores are harvested at between 10 and 25 days or at between 14 and 21 days. In another embodiment, in step (b) the strain is grown at a humidity of between 10 and 20%.

In a specific embodiment the starch in the media in step (c) used is wheat starch.

In preferred embodiments the media used in step (c) comprises 1 g to 4 g corn steep powder, 1 g to 49 Yeast extract, 1 g to 5 g calcium carbonate; and 0.2 g to 0.4 g iron sulphate per litre. In a more preferred embodiment the media comprises per litre: 2.5 g corn steep powder, 3 g Yeast extract, 3 g calcium carbonate; and 0.3 g iron sulphate;

The complementation strategy disclosed in this invention provides an expeditious method to assess and identify the function of each auxiliary gene i.e. rapK, rapQ, rapN/O, rapM, rapL, rapJ and/or rapI in rapamycin biosynthesis. The gene product RapK has previously been identified as an interesting candidate for a pteridine-dependent dioxygenase that could also catalyse an oxidative step in the biosynthesis of rapamycin (Molnár et al., 1996). The homologous gene fkbO was identified in the biosynthetic gene cluster of FK506 and due to the structural similarity of rapamycin and FK506 a role for rapK in the oxidation of the C9 OH group was postulated (Motamedi et al., 1996). The findings in Examples 3, 4 and 6, describing the rapK-dependent production of pre-rapamycin by *S. hygroscopicus* MG2-10 [pSGsetrapK] suggests that RapK has at least an additional function in rapamycin biosynthesis.

In another aspect, therefore, the methods of the present invention led to the elucidation of the function of RapK, namely that the expression of the rapK gene is essential for the accumulation of any cyclised macrolide product. In a further aspect, the present invention describes the complementation of *S. hygroscopicus* MG2-10 with fkbO, the homologue of rapK from the FK520 cluster, with the surprising observation of fkbO dependent production of pre-rapamycin by *S. hygroscopicus* MG2-10[pMG169-1] (Example 11). It can be seen by one skilled in the art that fkbO fulfils a similar function in the production of FK520 as rapK and fkbO in the production of pre-rapamycin. Further, one skilled in the art wilt appreciate that other homologues of rapK, including but not limited to, fkbO in the FK506 cluster, fkbO in the FK520 cluster and Orf5 in the 'hyg' cluster also fulfil the same function. In a further aspect of the invention, homologues of rapK in biosynthetic clusters that encode FKBP-ligands, including, but not limited to, FK506, FK520, FK525, antascomicin, FK523, tsukubamycin, and 'hyg' can be deleted or inactivated, providing strains unable to make their respective known natural products. Similarly, the complementation strategy outlined above provides an expeditious method to investigate the function, specificity and order for the expressed products of auxiliary genes in the biosynthesis of other polyketides or non-ribosomal peptides.

In a preferred class of embodiment, the present invention provides a method for the production of a recombinant host strain capable of producing rapamycin analogues, further involving the construction of genomic deletions, including but not limited to rapQONMLKJI introduced into S. hygroscopicus and complementation or partial complementation by expressing single genes or combinations of genes, including but not limited to rapK, rapt, rapQ, rapM, the contiguous genes rapN and O (herein designated as rapN/O), rapL and rapJ, in gene cassettes. Further, the invention provides a method of producing said rapamycin analogues by culturing said recombinant host strain, and optionally isolating the rapamycin analogues produced. Thus, the recombinant strain MG2-10[pSGsetrapK], produced by complementation of the genomic deletion strain S. hygroscopicus MG2-10, with rapK, was cultured to produce 9-deoxo-16-O-desmethyl-27-desmethoxy-39-O-desmethyl-rapamycin (pre-rapamycin).

In a further aspect of this class of the invention, the strategy involves the integration of a vector comprising a sub-set of genes including, but not limited to, rapK, rapI, rapQ, rapM, rapN, rapO, rapL and rapJ into the S. hygroscopicus deletion mutant above. Such integration may be performed using a variety of available integration functions including but not limited to: ΦC31-based vectors, vectors based on pSAM2 integrase (e.g. in pPM927 (Smovkina et al., 1990)), R4 integrase (e.g. in pAT98 (Matsuura et al., 1996)), (DVWB integrase (e.g. in pKT02 (Van Mellaert et al., 1998)), ΦBT1 integrase ((e.g. pRT801) Gregory et al., in press) and L5 integrase (e.g. Lee et al., 1991). In some cases this may need alteration of the host strain by addition of the specific attB site for the integrase to enable high efficiency integration. Replicating vectors could also be used, either as replacements to, or in addition to ΦC31-based vectors. These include, but are not limited to, vectors based on pIJ101 (e.g. pIJ487, Kieser et al., 2000), pSG5 (e.g. pKC1139, Bierman et al., 1992) and SCP2* (e.g. pIJ698, Kieser et al., 2000). This methodology has been exemplified herein by the use of the ΦBT1 and ΦC31 site-specific integration functions.

Although the introduction of gene cassettes into S. hygroscopicus has been exemplified in the present invention using the ΦBT1 and the ΦC31 site-specific integration functions, those skilled in the art will appreciate that there are a number of different strategies described in the literature, including those mentioned above that could also be used to introduce such gene cassettes into prokaryotic, or more preferably actinomycete, host strains. These include the use of alternative site-specific integration vectors as described above and in the following articles (Kieser et al., 2000; Van Mellaert et al., 1998; Lee et al., 1991; Smovkina et al., 1990; Matsuura et al., 1996). Alternatively, plasmids containing the gene cassettes may be integrated into a neutral site on the chromosome using homologous recombination sites. Further, for a number of actinomycete host strains, including S. hygroscopicus, the gene cassettes may be introduced on self-replicating plasmids (Kieser et al., 2000; WO98/01571).

In a further aspect of this class, the invention provides gene cassettes for the complementation of the recombinant S. hygroscopicus deletion strains. Methods of constructing gene cassettes and their heterologous use to produce hybrid glycosylated macrolides have been previously described (Gaisser et al., 2002; WO01/79520, WO 03/048375). The cloning method used to isolate the gene cassettes of the present invention differs significantly from the approach previously described in that the gene cassette is assembled directly in an expression vector rather than pre-assembling the genes in pUC18/19-plasmids, thus providing a more rapId cloning procedure. The approach is exemplified as described in Example 3, 4, 5, 9 and 15. As described herein, a suitable vector (for example but without limitation pSGLit1) can be constructed for use in the construction of said gene cassettes, where a suitable restriction site (for example but without limitation XbaI), sensitive to dam methylation is inserted 5' to the gene(s) of interest and a second restriction site (for example XbaI) can be inserted 3' to the genes of interest. The skilled artisan will appreciate that other restriction sites may be used as an alternative to XbaI and that the methylation sensitive site may be 5' or 3' of the gene(s) of interest.

The use of gene cassettes enables the rapid and parallel generation of multiple recombinant strains-deleted in any combination of modifying genes from a single S. hygroscopicus deletion strain. The cloning strategy facilitates the assembly of a library of gene cassettes in either a directed or random manner, and is therefore a poweiful tool for the combinatorial production of novel rapamycin analogues including but not exclusively limited to 9-deoxo-16-O-desmethyl-27-desmethoxy-39-O-desmethyl-rapamycin (pre-rapamycin), 9-deoxo-16-O-desmethyl-27-O-desmethyl-39-O-desmethyl-rapamycin, 16-O-desmethyl-27-desmethoxy-39-O-desmethyl-rapamycin, 9-deoxo-16-O-desmethyl-39-O-desmethyl-rapamycin, 9-deoxo-16-O-desmethyl-27-desmethoxy-rapamycin, 16-O-desmethyl-27-O-desmethyl-39-O-desmethyl-rapamycin, 9-deoxo-27-O-desmethyl-39-O-desmethyl-rapamycin, 9-deoxo-16-O-desmethyl-27-O-desmethyl-rapamycin , 27-O-desmethyl-39-O-desmethyl-rapamycin, 9-deoxo-16-O-desmethyl-rapamycin , 9-deoxo-39-O-desmethyl-rapamycin, 8-deoxo-15-O-desmethyl-26-desmethoxy-38-O-desmethyl-prolylrapamycin (pre-prolylrapamycin), 8-deoxo-15-O-desmethyl-26-O-desmethyl-38-O-desmethyl-prolylrapamycin, 15-O-desmethyl-26-desmethoxy-38-O-desmethyl-prolylrapamycin, 8-deoxo-26-desmethoxy-38-O-desmethyl-prolylrapamycin, 8-deoxo-15-O-desmethyl-38-O-desmethyl-prolylrapamycin, 8-deoxo-15-O-desmethyl-26-desmethoxy-prolylrapamycin, 15-desmethyl-26-O-desmethyl-38-O-desmethyl-prolylrapamycin, 8-deoxo-26-O-desmethyl-38-O-desmethyl-prolylrapamycin, 8-deoxo-15-O-desmethyl-26-O-desmethyl-prolylrapamycin, 15-O-desmethyl-38-O-desmethyl-prolylrapamycin, 15-O-desmethyl-26-O-desmethyl-prolylrapamycin, 15-O-desmethyl-26-desmethoxy-prolylrapamycin, 26-desmethoxy-38-O-desmethyl-prolylrapamycin, 26-O-desmethyl-38-O-desmethyl-prolylrapamycin, 8-deoxo-15-O-desmethyl-prolylrapamycin, 8-deoxo-26-O-desmethyl-prolylrapamycin, 8-deoxo-38-O-desmethyl-prolylrapamycin, 15-O-desmethyl-prolylrapamycin, 38-O-desmethyl-prolylrapamycin, 9-deoxo-16-O-desmethyl-27-desmethoxy-39-desmethoxy-rapamycin, 9-deoxo-16-O-desmethyl-27-O-desmethyl-39-desmethoxy-rapamycin, 16-O-desmethyl-27-desmethoxy-39-desmethoxy-rapamycin, 9-deoxo-27-desmethoxy-39-desmethoxy-rapamycin, 9-deoxo-16-O-desmethyl-39-desmethoxy-rapamycin, 16-O-desmethyl-27-O-desmethyl-39-desmethoxy-rapamycin, 9-deoxo-27-O-desmethyl-39-desmethoxy-rapamycin, 16-O-desmethyl-39-desmethoxy-rapamycin, 27-desmethoxy-39-desmethoxy-rapamycin, 27-O-desmethyl-39-desmethoxy-rapamycin, 9-deoxo-39-desmethoxy-rapamycin, 8-deoxo-15-O-desmethyl-26-desmethoxy-38-desmethoxy-prolylrapamycin, 8-deoxo-15-desmethyl-26-O-desmethyl-38desmethoxy-prolylrapamycin, 15-O-desmethyl-26-desmethoxy-38-desmethoxy-prolylrapamycin, 8-deoxo-26-desmethoxy-38-desmethoxy-prolylrapamycin, 8-deoxo-15-O-desmethyl-38-desmethoxy-prolylrapamycin, 15-O-desmethyl-26-desmethyl-38-desmethoxy-prolylrapamycin, 8-deoxo-26-O-desmethyl-38-desmethoxy-prolylrapamycin, 15-O-desmethyl-38-desmethoxy-prolylrapamycin, 26desmethoxy-38-desmethoxy-prolylrapamycin, 26-O-desmethyl-38-desmethoxy-prolylrapamycin, 8-deoxo-38-desmethoxy-prolylrapamycin, 38-desmethoxy-prolylrapamycin, 9-deoxo-16-O-desmethyl-27-desmethoxy-36-de(3-cis-methoxy-4-trans-hydroxycyclohexyl)-36-(hydroxycyclohexenyl) rapamycin, 9-deoxo-16-O-desmethyl-27-desmethoxy-36-de(3-cis-methoxy-4-trans-hydroxycyclohexyl)-36-(dihydroxy cyclohexyl) rapamycin, 9-deoxo-16-O-desmethyl-27-desmethoxy-36-de(3-cis-methoxy-4-trans-hydroxycyclohexyl)-36-(hydroxynorbornyl) rapamycin, 9-deoxo-16-O-desmethyl-27-desmethoxy-36-de(3-cis-methoxy-4-trans-hydroxycyclohexyl)-36-(3-methyl-4-hydroxycyclohexyl) rapamycin, 9-deoxo-16-O-desmethyl-27-desmethoxy-36-de(3-cis-methoxy-4-trans-hydroxycyclohexyl)-36-(4-methyl hydroxycyclohexyl) rapamycin, 9-deoxo-16-O-desmethyl-27-desmethoxy-36-de(3-cis-methoxy-4-trans-hydroxycyclohexyl)-36-(3-fluoro-4-hydroxycyclohexyl) rapamycin, 9-deoxo-16-O-desmethyl-27-desmethoxy-36-de(3-cis-methoxy-4-trans-hydroxycyclohexyl)-36-(3-hydroxy-4-fluorocyclohexyl) rapamycin, 9-deoxo-16-O-desmethyl-27-desmethoxy-36-de(3-cis-methoxy-4-trans-hydroxycyclohexyl)-36-(3-chloro4-hydroxycyclohexyl) rapamycin, 9-deoxo-16-O-desmethyl-27-desmethoxy-36-de(3-cis-methoxy-4-trans-hydroxycyclohexyl)-36-(3-hydroxy-4-chlorocyclohexyl) rapamycin, 9deoxo-16-O-desmethyl-27-desmethoxy-36de(3-cis-methoxy-4-trans-hydroxycyclohexyl)-36-(3-cis-4-cis-dihydroxycyclohexyl) rapamycin, 9-deoxo-16-O-desmethyl-27-desmethoxy-36-de(3-cis-methoxy-4-trans-hydroxycyclohexyl)-36-(3-tran-strans-dihydroxycyclohexyl) rapamycin, 9-deoxo-16-O-desmethyl-27-O-desmethyl-39-O-desmethyl rapamycin, 9-deoxo-16-O-desmethyl-27 O-desmethyl-36-de(3-cis-methoxy-4-trans-hydroxycyclohexyl)-36-(hydroxycyclohexenyl) rapamycin, 9-deoxo-16-O-desmethyl-27-O-desmethyl-36-de(3-cis-methoxy -trans-hydroxycylohexyl)-36-(hydroxynorbornyl) rapamycin, 9deoxo-16-desmethyl-27-O-desmethyl-36-de(3-cis-methoxy-4-trans-hydroxycyclohexyl)-36-(4-methyl hydroxycyclohexyl) rapamycin.

In a further aspect of this class, the present invention provides a system for the combinatorial production of recombinant host strains capable of producing rapamycin analogues, involving construction of a genomic deletion rapQONMLKJI introduced into *S. hygroscopicus* and its partial complementation by a combinatorial library of gene cassettes comprising one or a plurality of the deleted auxiliary genes rapQ, rapN/O, rapM, rapL, rapK, rapJ, and rapI.

The approach outlined comprises as a part the cloning strategy to combine genes including but not exclusively limited to rapK, rapI, rapQ, rapM, rapN/O, rapL and rapJ, and/or genes with similar gene functions, in any possible gene combination and gene order.

Another aspect of the invention allows the enhancement of gene expression by changing the order of genes in a gene cassette. As applied to the preferred class, the genes may comprise one or more of rapK, rapI, rapQ, rapM, rapN/O, rapL and rapJ and/or genes with similar functions, allowing the arrangement of the genes in a multitude of permutations as outlined in Example 5.

The cloning strategy outlined in this invention also allows the introduction of a histidine tag in combination with a terminator sequence 3' of the gene cassette to enhance gene expression. Those skilled in the art will appreciate other terminator sequences could be used.

Another aspect of the invention describes the multiple uses of promotor sequences in the assembled gene cassette to optimise gene expression.

It will now be obvious to one skilled in the art that *S. hygroscopicus* deletion strains, the deletion comprising, but not limited to, a gene or a sub-set of the genes rapQ, rapN/O, rapM, rapL, rapK, rapJ and rapI could be constructed. In this case, gene cassettes for complementation or partial complementation would generally comprise single genes or a plurality of genes selected from the sub-set of the genes deleted.

It is well known to those skilled in the art that there are homologues to several of the rapamycin modifying and precursor supply genes in the gene clusters of closely related systems including FK506 (Motamedi et al., 1996; Motamedi et al., 1997; Motamedi & Shafiee, 1998) and FK520 (Wu et al, 2000). These include the following as described in Table I below:

TABLE I

| Rapamycin gene | FK506 homologue | FK520 homologue | 'hyg' |
|---|---|---|---|
| rapI (Acc No CAA60470) | fkbM (Acc No AAC44360) | fkbM (Acc No AAF86398) | |
| rapJ (Acc No CAA60469) | fkbD (Acc No AAC44359) | fkbD (Acc No AAF86397) | |
| rapK (Acc No CAA60468) | fkbO (Acc No AAC68817) | fkbO (Acc No AAF86394) | Orf5 (Acc No AAC38060) |
| rapL (Acc No CAA60467) | fkbL (Motamedi & Shafiee, 1998) | fkbL (Acc No AAF86391) | |

Although the gene clusters of other closely related systems, including but not limited to those for the biosynthesis of FK523, meridamycin, FK525, antascomicin and tsukubamycin have not yet been sequenced, it can be anticipated that these will be shown to bear a close resemblance to those whose sequences have been determined, and, in particular, that these gene clusters will contain close homologues of several of the rapamycin modifying and precursor supply genes. Therefore, in a further aspect of the invention, genes from heterologous gene clusters from such closely related systems, including but not limited to FK506, FK520, FK523, antascomicin, meridamycin, FK525, 'hyg' and tsukubamycin can be included in gene cassettes in place of or in addition to their rapamycin homologues for complementation and/or partial complementation of a rapamycin producer strain containing a gene deletion or deletions including but not limited to the genes rapK, rapI, rapQ, rapM, rapN/O, rapL and rapJ.

It is well known to those skilled in the art that polyketide gene clusters may be expressed in heterologous hosts (Pfeifer and Khosla, 2001). Accordingly, the present invention includes the transfer of the rapamycin biosynthetic gene cluster with or without resistance and regulatory genes, either complete or containing deletions, for complementation in heterologous hosts. Methods and vectors for the transfer as defined above of such large pieces of DNA are well known in the art (Rawlings, 2001; Staunton and Weissman, 2001) or are provided herein in the methods disclosed. In is this context a preferred host cell strain is a prokaryote, more preferably an actinomycete or *Escherichia coli* still more preferably include, but are not limited to *S. hygroscopicus*, *S. hygroscopicus* sp., *S. hygroscopicus* var. *ascomyceticus*, *Streptomyces tsukubaensis*, *Streptomyces coelicolor*, *Streptomyces lividans*, *Saccharopolyspora erythraea*, *Streptomyces fradiae*, *Streptomyces avermitilis*, *Streptomyces cinnamonensis*, *Streptomyces limosus*, *Streptomyces albus*, *Streptomyces griseofuscus*, *Streptomyces longisporoflavus*, *Streptomyces venezuelae*, *Micromonospora griseorubida*, *Amycolatopsis mediterranei* or *Actinoplanes* sp. N902-109.

In another aspect, the rapamycin analogues of the invention may be obtained by a process comprising the steps of:
a) constructing a deletion strain, by the methods of the invention; the deletion including, but not limited to, the genes rapK, rapQ, rapN/O, rapM, rapL, rapJ and rapI, or a sub-set thereof;
b) culturing the strain under conditions suitable for polyketide production;
c) optionally, isolating the rapamycin analogue intermediate produced;
d) constructing a biotransformation strain containing a gene cassette comprising all or a sub-set of the genes deleted;
e) feeding the rapamycin analogue intermediate in culture supernatant or isolated as in step c) to a culture of the biotransformation strain under suitable biotransformation conditions
f) optionally isolating the rapamycin analogue produced.

Suitable host strains for the construction of the biotransformation strain include the native host strain in which the rapamycin biosynthetic gene cluster has been deleted, or substantially deleted or inactivated, so as to abolish polyketide synthesis, or a heterologous host strain. Methods for the expressing of gene cassettes comprising one or a plurality of modifying or precursor supply genes in heterologous hosts are described in WO 01/79520. In this context heterologous hosts suitable for biotransformation of the said FKBP-ligand analogue intermediates include, but are not limited to, *S. hygroscopicus*, *S. hygroscopicus* sp., *S. hygroscopicus* var. *ascomyceticus*, *Streptomyces tsukubaensis*, *Streptomyces coelicolor*, *Streptomyces lividans*, *Saccharopolyspora erythraea*, *Streptomyces fradiae*, *Streptomyces avermitilis*, *Streptomyces cinnamonensis*, *Streptomyces rimosus*, *Streptomyces albus*, *Streptomyces griseofuscus*, *Streptomyces longisporoflavus*, *Streptomyces venezuelae*, *Micromonospora griseorubida*, *Amycolatopsis mediterranei*, *Escherichia coli* and *Actinoplanes* sp. N902-109.

The close structural relationship between rapamycin and FK506, FK520, FK523, 'hyg', meridamycin, antascomicin, FK525 and tsukubamycin, among others, and the established homologies between genes involved in the biosynthesis of rapamycin and FK506 and FK520 (vide supra), renders obvious the application of the methods of the present invention to these closely related systems. In a further aspect, therefore, the invention includes the construction of deletion strains of the producer strains of closely related compounds, including but not limited to FK506, FK520, FK523, 'hyg', antascomicin, meridamycin, FK525 and tsukubamycin containing a gene deletion or deletions of modifying and/or precursor supply genes, and more particularly including but not limited to genes with similar functions as rapK, rapI, rapQ, rapM, rapN/O, rapL and rapJ, and their complementation or partial complementation with a gene or gene cassettes comprising all or a sub-set of the deleted homologous genes, or their functional homologues from heterologous gene clusters, including but not limited to rapK, rapI, rapQ, rapM, rapN/O, rapL and rapJ to produce recombinant strains capable of producing polyketide analogues varying from the parent polyketide in the incorporation of alternative precursors and/or the extent of post-PKS modification. Further, the invention provides a method of producing said polyketide analogues by culturing said recombinant host strains, and optionally isolating the polyketide analogues produced.

In a further aspect, the invention provides a method for the production of recombinant host strains capable of producing polyketide FKBP-ligand analogues (other than rapamycin) varying from the parent polyketide in the incorporation of alternative precursors and/or the extent of post-PKS modification, comprising the construction of a genomic deletion strain from which all or a portion of the auxiliary genes have been removed, and its partial complementation by a gene cassette comprising one or a plurality of the deleted genes and/or their homologues, and further a method of producing said polyketide analogues by culturing said recombinant host strain, and optionally isolating the polyketide analogues produced. It is well known in the art that in most cases that auxiliary genes are co-located with polyketide synthase genes in a gene cluster (Hopwood, 1997; Motamedi and Shafiee, 1998; Wu et al., 2000) thus facilitating creation of the deletion strain. The auxiliary genes to be deleted may or may not naturally form a contiguous sequence, however, once the deletion strain has been created the partial complementation by gene cassettes provides an expeditious approach to the production of recombinant strains in which one or a plurality of the said genes have been deleted. Therefore, in a further aspect, the invention provides a method for the combinatorial production of recombinant host strains capable of producing polyketide FKBP-ligand analogues (other than rapamycin) varying from the parent polyketide in the incorporation of alternative precursors and/or the extent of post-PKS modification, comprising the partial complementation of the said genomic deletion strain by a combinatorial library of gene cassettes comprising one or a plurality of the deleted genes, and further a method of producing said polyketide analogues by culturing said recombinant host strains under conditions suitable for polyketide production, and optionally isolating the polyketide analogues produced. In this context a preferred recombinant host cell strain is a prokaryote, more preferably an actinomycete, still more preferably a strain selected from *S. hygroscopicus*, *S. hygroscopicus* sp., *S. hygroscopicus* var. *ascomyceticus*, *Streptomyces tsukubaensis*, *Streptomyces coelicolor*, *Streptomyces lividans*, *Saccharopolyspora erythraea*, *Streptomyces fradiae*, *Streptomyces avermitilis*, *Streptomyces cinnamonensis*, *Streptomyces rimosus*, *Streptomyces albus*, *Streptomyces griseofuscus*, *Streptomyces longisporoflavus*, *Streptomyces venezuelae*, *Micromonospora griseorubida*, *Amycolatopsis mediterranei* or *Actinoplanes* sp. N902-109.

Those skilled in the art will appreciate that the methods of the present invention could be applied to recombinant host strains in which the polyketide synthase (PKS) has been altered by genetic engineering to express a modified rapamycin or other polyketide analogue. The prior art describes several methods for the production of novel polyketides by the deletion or inactivation of individual domains (WO93/13663, WO97/92358), construction of hybrid polyketide synthases (WO98/01546, WO00/00618, WO00/01827) or alteration of domain specificity by site-directed mutagenesis (WO02/14482).

It is well known in the art that non-ribosomal peptides are biosynthesised by Non-Ribosomal Peptide Synthases (NRPSs) via the stepwise condensation of successive amino acid building blocks, in a process analogous to that of polyketide biosynthesis (for review see Marahiel et al., 1997; Schwarzer and Marahiel, 2001). It is well known that several non-ribosomal peptides include unusual amino-acid residues (modified, proteinogenic amino acids and/or non-proteinogenic amino acids) and carboxy acids, the biosynthetic genes for which are co-located with the non-ribosomal peptide synthase genes in the non-ribosomal peptide gene cluster (Marahiel et al., 1997; Konz and Marahiel, 1999; Blanc et al., 1997). In several cases, the non-ribosomal peptide product initially released from the NRPS is further modified by a set of enzymes, including but not limited to glycosyl transferases, reductases, acylation or heterocyclic ring formation (Konz and Marahiel, 1999; Blanc et al., 1995). These include the antibiotics chloroeremomycin, pristinamycin, vancomycin and bleomycin (Konz and Marahiel, 1999; Du et al., 2000). The genes for these post-NRPS enzymes are also typically co-located in the biosynthetic gene cluster (Marahiel et al., 1997; Schwarzer and Marahiel, 2001). Therefore, in a further aspect, the invention includes a method for the production of non-ribosomal peptide analogues, varying from the parent non-ribosomal peptide in the incorporation of alternative precursor amino-acids and/or the extent of post-NRPS modification, comprising the construction of a genomic deletion strain from which all or a portion of the genes encoding the native amino-acid precursor synthesis and/or post-NRPS enzymes have been removed, and its partial complementation by a gene cassette comprising one or a plurality of the deleted genes and/or their homologues, and further a method of producing said non-ribosomal peptide analogues by culturing said recombinant host strain, and optionally isolating the non-ribosomal peptide analogues produced. The post-NRPS and precursor biosynthesis genes to be deleted may or may not naturally form a contiguous sequence, however, once the deletion strain has been created the partial complementation by gene cassettes provides an expeditious approach to the production of recombinant strains in which one or a plurality of the said genes have been deleted. Therefore, in a further aspect, the invention provides a method for the combinatorial production of recombinant host strains capable of producing non-ribosomal peptide analogues varying from the parent non-ribosomal peptide in the incorporation of alternative precursors and/or the extent of post-NRPS modification, comprising the partial complementation of the said genomic deletion strain by a combinatorial library of gene cassettes comprising one or a plurality of the deleted genes, and further a method of producing said non-ribosomal peptide analogues by culturing said recombinant host strains under conditions suitable for non-ribosomal peptide production, and optionally isolating the non-ribosomal peptide analogues produced. In this context a preferred recombinant host cell strain is a prokaryote, more preferably an actinomycete, still more preferably a strain selected from *S. hygroscopicus, S. hygroscopicus* sp., *S. hygroscopicus* var. *ascomyceticus, Streptomyces tsukubaensis, Streptomyces coelicolor, Streptomyces lividans, Saccharopolyspora erythraea, Streptomyces fradiae,* *Streptomyces avermitills, Streptomyces cinnamonensis, Streptomyces rimosus, Streptomyces albus, Sfreptomyces griseofuscus, Streptomyces longisporoflavus, Streptomyces venezuelae, Micromonospora griseorubida, Amycolatopsis mediterranei* or *Actinoplanes* sp. N902-109.

It is well known that many actinomycetes contain multiple biosynthetic gene clusters for different secondary metabolites, including polyketides and non-ribosomally synthesised peptides. Specifically, it has been demonstrated that strains of *S. hygroscopicus* produce a variety of polyketides and non-ribosomally synthesised peptides in addition to rapamycin, FK506, FK520, FK523, meridamycin, FK525, antascomicin and tsukubamycin. These include, but are not limited to, elaiophyllin, bialaphos, hygromycin, augustmycin, endomycin (A, B), glebomycin, hygroscopin, ossamycin and nigericin. These additional biosynthetic gene clusters represent a competing requirement for biosynthetic precursors and an additional metabolic demand on the host strain. In order to enhance production of the desired rapamycin, or other polyketide, analogues, it may therefore be advantageous to delete or inactivate any other biosynthetic gene clusters present in the host strain. Methods for the deletion or inactivation of biosynthetic gene clusters are well known in the art.

In a further aspect of this class, the invention provides a mutasynthesis methodology for the complementation of recombinant deletion strains In a further aspect, *S. hygroscopicus* strains of the present invention containing a deletion of rapL may be fed with analogues of the naturally incorporated amino acid, L-pipecolic acid, to produce new analogues of rapamycin in which the pipecolyl residue is replaced. Prior art describes that a rapL mutant can be complemented by the addition of L-pipecolic acid to the culture (Khaw et al., 1998). Similarly, it was demonstrated that rapamycin analogues were isolated after the feeding and incorporation of L-pipecolic acid analogues, L-proline, L-trans-4-hydroxyproline, L-cis-4-hydroxyproline, L-cis-3-hydroxyproline, trans-3aza-bicyclo[3,1,0]hexane-2-carboxylic acid (WO98/54308). Using *S. hygroscopicus* MG2-10 as strain background to express genes or gene cassettes encoding for post-PKS modifying steps not including rapL or rapL homologues, a library of *S. hygroscopicus* strains is generated, capable of producing a plurality of modified products on feeding with L-pipecolic acid analogues. Suitable L-pipecolic acid analogues include alkyl-, halo-, hydroxy-, and amino-substituted pipecolic acids and prolines, and more particularly L-proline, L-trans-4-hydroxyproline, L-cis-4-hydroxyproline, L-cis-3-hydroxyproline, trans-3-aza-bicyclo[3,1,0]hexane-2-carboxylic acid and L-pipecolic acid analogues demonstrated to catalyse PP-ATP exchange measured by a modification of Lipmann's method (Nielsen et al., 1991) including L-4-hydroxyproline, 1-hydroxyproline, 2-hydroxyproline, 3-hydroxyproline, trans-3-methyl-L-proline, cis-3-methylproline, cis-3-methyl-DL-proline, cis,trans-4-methylproline, cis-4-methyl-DL-proline, trans-4-methyl-DL-proline, trans-4-aminoproline, cis-4-chloro-L-proline, 5-iminoproline hydrochloride, cis-5-methyl-DL-proline, (+)-piperazic acid, 5-chloropipecolic acid, 5-hydroxypipecolic acid, cis-4-hydroxy-L-pipecolic acid, trans-4-hydroxy-D-pipecolic acid, 4-hydroxyallopipecolic acid, thiazolidine-4-carboxylic acid (Nielsen et al.,1991). This approach is exemplified in Example 7.

The production of a limited number of novel rapamycirn analogues after feeding-close structural analogues of the natural 4,5-dihydroxycyclohex-1-enecarboxylic acid starter unit to cultures of *S. hygroscopicus* has previously been described, thus demonstrating that the loading module of the rapamycin polyketide synthase has some flexibility with respect to the starter acid (P. A. S. Lowden, PhD dissertation, University of Cambridge, 1997). However, these methods led to the production of a mixture of products. In a further aspect, the present invention allows for the production of rapamycin and related FKBP-ligand analogues by feeding strains of the present invention with analogues of the naturally incorporated 4,5-dihydroxycyclohex-1-enecarboxylic acid starter unit to produce rapamycin analogues incorporating alternative starter units including, but not limited to, cyclohexane carboxylic acid, 3-cis,4-trans-4-dihydroxycyclohexane carboxylic acid, 1-cyclohexene carboxylic acid, 3-cyclohexene carboxylic acid, cycloheptane carboxylic acid, 2-norborane carboxylic acid, 3-hydroxycyclohexane carboxylic acid, 4-hydroxycyclohexane carboxylic acid, 3-methylcyclohexane carboxylic acid, 4-methylcyclohexane carboxylic acid, 3-(cis/trans)methoxycyclohexane carboxylic acid, 4-(cis/trans)methoxycyclohexane carboxylic acid, 4-oxo cyclohexane carboxylic acid, 3-fluoro-4-hydroxycarboxylic acid and 4-fluoro-3-hydroxycarboxylic acid, 3-cyclohexane oxide carboxylic acid, 3,4-cis-dihydroxycyclohexane carboxylic acid, 3-chloro-4-hydroxycarboxylic acid and 4-chloro-3-hydroxycarboxylic acid (and the pair of opposite diastereomers), cyclohexylpropionic acid, 4-tert-Butylcyclohexane carboxylic acid and simple esters and salts thereof. This approach is exemplified in Examples 8, 19 and 20.

Additionally, structural analogues of biosynthetic precursors of the 4,5-dihydroxycyclohex-1-enecarboxylic acid starter unit may be fed (Lowden et al., 2001), leading to production of novel rapamycin analogues incorporating alternative starter units.

However, these methods can lead to the production of mixed groups of products; therefore, the present invention additionally provides a method for removing the competition between the endogenously produced starter unit and the alternative starter acid analogues that are fed in order to improve the efficiency of production of novel rapamycin analogues.

In order to remove the competition between the endogenously produced natural starter unit and the alternative starter acid analogues fed, it is preferable to disrupt the biosynthesis of the natural 4,5-dihydroxycyclohex-1enecarboxylic acid starter unit. This may be achieved by deletion or inactivation of one or more of the genes involved in the biosynthesis of the natural 4,5-dihydroxycyclohex-1-enecarboxylic acid starter unit from shikimic acid (Lowden et al., 2001) or the biosynthesis of shikimic acid itself. In the latter case, it may be necessary to supplement cultures with aromatic amino acids (phenyl alanine, tyrosine, tryptophan). Alternatively, endogenous production of the natural 4,5-dihydroxycyclohex-1-ene carboxylic acid starter unit may be suppressed by the addition of a chemical inhibitor of shikimic acid biosynthesis. Such inhibitors are well known in the literature.

In a further aspect, the invention makes use of the surprising discovery that rapK is involved in the supply of the biosynthetic precursor(s), e.g. 4,5-dihydroxycyclohex-1-ene carboxylic acid starter unit of rapamycin and therefore that deletion or inactivation of rapK or a rapK homologue provides a strain lacking in competition between the natural starter unit and fed non-natural starter units. In another aspect, the invention provides a method for the efficient incorporation of fed acids including, but not limited to those described below.

Therefore in one aspect of the invention the method comprises feeding starter units of the formula

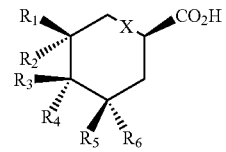

where X=bond or $CH_2$ and $R_1$, $R_2$, $R_3$, $R_4$, $R_5$ and $R_6$ may be the same or different and may independently be Cl, F, OH, SH, H, alkyl, CN, Br, $R_7$, $OR^7$, $C(O)R_7$ or $HNR_7$ where $R_7$ is a C1-C4 alkyl; $R_1$ and $R_3$, $R_2$ and $R_4$, $R_3$ and $R_5$, $R_4$ and $R_6$, $R_1$ and $R_5$, or $R_2$ and $R_6$ may be joined as either a substituted or unsubstituted methylene link, an ether link, a thia link or an amino link, $R_1$ and $R_2$, $R_3$ and $R_4$ or $R_5$ and $R_6$ may be taken together as a ketone; provided that no more than 4 of $R_1$, $R_2$, $R_3$, $R_4$, $R_5$ or $R_6$ may be Cl; no more than 2 of $R_1$, $R_2$, $R_3$, $R_4$, $R_5$ or $R_6$ may be $HNR_7$; no more than 2 of $R_1$, $R_2$, $R_3$, $R_4$, $R_5$ or $R_6$ may be SH and both R groups from one carbon on the ring are not OH.

In a preferred embodiment the starter unit is not selected from the group consisting of: cyclohexane carboxylic acid, 3-cis,4-trans-dihydroxycyclohexane carboxylic acid, cycloheptane carboxylic acid and 3-(cis/trans)-methylcyclohexane carboxylic acid In preferred embodiments: where $R_1$, $R_2$, $R_3$, $R_4$, $R_5$ or $R_6$ are a combination of F and OH substitution no more than 3 of $R_{1-6}$ are substituted and the remainder are H. Where $R_1$, $R_2$, $R_3$, $R_4$, $R_5$ or $R_6$ are a combination of Cl and OH substitution no more than 3 of $R_{1-6}$ are substituted and the remainder are H. Where any two of $R_1$, $R_2$, $R_3$, $R_4$, $R_5$ or $R_6$ are OH and any two remaining R groups are F on one carbon the remainder are H. Where two of $R_1$, $R_2$, $R_3$, $R_4$, $R_5$ or $R_6$ are Cl the remainder are H. Where two of $R_1$, $R_2$, $R_3$, $R_4$, $R_5$ or $R_6$ are Cl, not originating from the same carbon, and a further R is OH the remainder are H. Where one of $R_1$, $R_2$, $R_3$, $R_4$, $R_5$ or $R_6$ is alkyl and the remainder are H; the alkyl group shall have a linear length of no greater than 3 carbons. Where one of $R_1$, $R_2$, $R_3$, $R_4$, $R_5$ or $R_6$ is $NHR_7$ the remainder are H.

In more highly preferred embodiments: where two of $R_1$, $R_2$, $R_3$, $R_4$, $R_5$ or $R_6$ are OH and a third R group is F, the remainder are H. Where two of $R_1$, $R_2$, $R_3$, $R_4$, $R_5$ or $R_6$ are F the remainder are H. Where two of $R_1$, $R_2$, $R_3$, $R_4$, $R_5$ or $R_6$ are OH the remainder are H. Where two of $R_1$, $R_2$, $R_3$, $R_4$, $R_5$ or $R_6$ are OH and a third R group is Cl the remainder are H. Where two of $R_1$, $R_2$, $R_3$, $R_4$, $R_5$ or $R_6$ are F, and a third R group is OH the remainder are H. Where one of $R_1$, $R_2$, $R_3$, $R_4$, $R_5$ or $R_6$ is SH the remainder are H. Where one of $R_1$, $R_2$, $R_3$, $R_4$, $R_5$ or $R_6$ is SH and a second R group is OH (not originating from the same carbon) the remainder are H.

In still more highly preferred embodiments: where one of $R_1$, $R_2$, $R_3$, $R_4$, $R_5$ or $R_6$ is F the remainder are H. Where of $R_1$, $R_2$, $R_3$, $R_4$, $R_5$ or $R_6$ are Cl the remainder are H. Where one of $R_1$, $R_2$, $R_3$, $R_4$, $R_5$ or $R_6$, are F and a second R group is OH (not originating from the same carbon) the remainder are H. Where one of $R_1$, $R_2$, $R_3$, $R_4$, $R_5$ or $R_6$ is Cl and a second R group is OH (not originating from the same carbon) the remainder are H. Where one of $R_1$, $R_2$, $R_3$, $R_4$, $R_5$ or $R_6$ is alkyl and the remainder are H; the alkyl group shall contain no more than 4 carbons and have a linear length of no greater than 3 carbons. Where one of $R_1$, $R_2$, $R_3$, $R_4$, $R_5$ or $R_6$ is alkyl and a second R group is OH (not originating from the same carbon) and remainder are H; the alkyl group shall contain no more than 4 carbons and have a linear length of no greater than 3 carbons.

A further aspect of the invention comprises feeding starter units of the formula

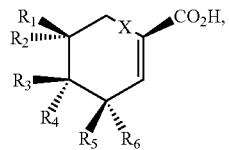

where X=bond or $CH_2$ and $R_1$, $R_2$, $R_3$, $R_4$, $R_5$ and $R_6$ may be the same or different and may independently be Cl, F, OH, SH, H, alkyl, CN, Br, $R_7$, $OR^7$, $C(O)R_7$ or $HNR_7$ where $R_7$ is a C1-C4 alkyl; $R_1$ and $R_3$, $R_2$ and $R_4$, $R_3$ and $R_5$, $R_4$ and $R_6$, $R_1$ and $R_5$, or $R_2$ and $R_6$ may be joined as either a substituted or unsubstituted methylene link, an ether link, a thia link or an amino link, $R_1$ and $R_2$, $R_3$ and $R_4$ or $R_5$ and $R_6$ may be taken together as a ketone; provided that no more than 4 of $R_1$, $R_2$, $R_3$, $R_4$, $R_5$ or $R_6$ may be Cl; no more than 2 of $R_1$, $R_2$, $R_3$, $R_4$, $R_5$ or $R_6$ may be no more than 2 of $R_1$, $R_2$, $R_3$, $R_4$, $R_5$ or $R_6$ may be SH and both R groups from one carbon on the ring are not OH.

In a preferred embodiment the starter unit is not selected from the group consisting of: 1-cyclohexene carboxylic acid and 1-cycloheptene carboxylic acid In preferred embodiments, where $R_1$, $R_2$, $R_3$, $R_4$, $R_5$ or $R_6$ are a combination of F and OH substitution no more than 3 of $R_{1-6}$ are substituted and the remainder are H. Where $R_1$, $R_2$, $R_3$, $R_4$, $R_5$ or $R_6$ are a combination of Cl and OH substitution no more than 3 of $R_{1-6}$ are substituted and the remainder are H. Where any two of $R_1$, $R_2$, $R_3$, $R_4$, $R_5$ or $R_6$ are OH and two of the remaining R groups are F on the same carbon the remainder are H. Where two of $R_1$, $R_2$, $R_3$, $R_4$, $R_5$ or $R_6$ are Cl the remainder are H. Where two of $R_1$, $R_2$, $R_3$, $R_4$, $R_5$ or $R_6$ are Cl, not originating from the same carbon, and a further R group is OH the remainder are H. Where one of $R_1$, $R_2$, $R_3$, $R_4$, $R_5$ or $R_6$ is alkyl and the remainder are H; the alkyl group shall have a linear length of no greater than 3 carbons. Where one of $R_1$, $R_2$, $R_3$, $R_4$, $R_5$ or $R_6$ is $NHR_7$ the remainder are H.

In more highly preferred embodiments: where two of $R_1$, $R_2$, $R_3$, $R_4$, $R_5$ or $R_6$ are OH and a third R group is F, the remainder are H. Where two of $R_1$, $R_2$, $R_3$, $R_4$, $R_5$ or $R_6$ are F the remainder are H. Where two of $R_1$, $R_2$, $R_3$, $R_4$, $R_5$ or $R_6$ are OH the remainder are H. Where two of $R_1$, $R_2$, $R_3$, $R_4$, $R_5$ or $R_6$ are OH and a third R group is Cl the remainder are H. Where two of $R_1$, $R_2$, $R_3$, $R_4$, $R_5$ or $R_6$ are F, and a third R group is OH the remainder are H. Where one of $R_1$, $R_2$, $R_3$, $R_4$, $R_5$ or $R_6$ is SH the remainder are H. Where one of $R_1$, $R_2$, $R_3$, $R_4$, $R_5$ or $R_6$ is SH and a second R group is OH (not originating from the same carbon) the remainder are H.

In still more highly preferred embodiments: where one of $R_1$, $R_2$, $R_3$, $R_4$, $R_5$ or $R_6$ is F the remainder are H. Where of $R_1$, $R_2$, $R_3$, $R_4$, $R_5$ or $R_6$ are Cl the remainder are H. Where one of $R_1$, $R_2$, $R_3$, $R_4$, $R_5$ or $R_6$, are F and a second R group is OH (not originating from the same carbon) the remainder are H. Where one of $R_1$, $R_2$, $R_3$, $R_4$, $R_5$ or $R_6$ is Cl, a second R group is OH (not originating from the same carbon) the remainder are H. Where one of $R_1$, $R_2$, $R_3$, $R_4$, $R_5$ or R is alkyl and the remainder are H; the alkyl group shall contain no more than 4 carbons and have a linear length of no greater than 3 carbons. Where one of $R_1$, $R_2$, $R_3$, $R_4$, $R_5$ or $R_6$ is alkyl and a second R group is OH (not originating from the same carbon) the remainder are H; and the alkyl group shall contain no more than 4 carbons and have a linear length of no greater than 3 carbons.

A further aspect of the invention comprises feeding starter units of the formula:

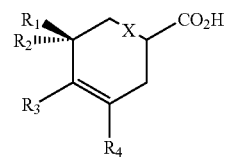

where X=bond or $CH_2$, $R_1$ and $R_2$, may be the same or different and may independently be F, Cl, OH, SH, H, CN, $OR_7$, $C(O)R_7$, or $NHR_7$ wherein $R_7$ is a C1-C4 alkyl, $R_1$ and $R_2$ may also be taken together to form a ketone, a spirocyclopropyl group or with $-OCH_2-$, $-CH_2O-$, $-SCH_2-$ or $-CH_2S-$; furthermore $R_3$, and $R_4$ may be the same or different and may independently be be F, Cl, Br, $OR_7$, H or CN; provided that both R groups from one carbon on the ring are not OH.

In a preferred embodiment the starter unit shall not be 5-cis-hydroxyl-3-cyclohexene carboxylic acid.

In preferred embodiments, Where two of $R_1$, $R_2$, $R_3$, or $R_4$ are F the remainder are H. Where one of $R_1$, $R_2$, $R_3$, or $R_4$ is Cl the remainder are H. Where one of $R_3$, or $R_4$ is F and one of R1 or R2 is OH the remainder are H. Where one of $R_3$ or $R_4$ is Cl and one of $R_1$ or $R_2$ is OH the remainder are H. Where one of $R_1$ or $R_2$ is SH the remainder are H. Where one of $R_1$, $R_2$, $R_3$, or $R_4$ is alkyl and the remainder are H; the alkyl group shall contain no more than 4 carbons and have a linear length of no greater than 3 carbons. Where one of $R_3$ or $R_4$ is alkyl and $R_1$ or $R_2$ is OH the remainder are H; and the alkyl group shall contain no more than 4 carbons and have a linear length of no greater than 3 carbons.

In more highly preferred embodiment where one of $R_1$, $R_2$, $R_3$, or $R_4$ is F the remainder are H. Where one of $R_1$, $R_2$, $R_3$, or $R_4$ is Cl the remainder are H A further aspect of the invention comprises feeding starter units of the formula

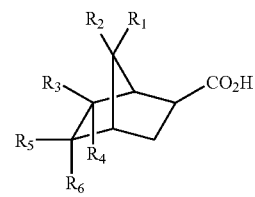

where $R_1$, $R_2$, $R_3$, $R_4$, $R_5$ or $R_6$ may be the same or different and may independently be be Cl, F, OH, SH, H, alkyl, CN, Br, $R_7$, $OR^7$, $C(O)R_7$ or $HNR_7$ where $R_7$ is a C1-C4 alkyl; $R_1$ and $R_3$, $R_2$ and $R_4$, $R_3$ and $R_5$, $R_4$ and $R_6$, $R_1$ and $R_5$, or $R_2$ and $R_6$ may be joined as either a substituted or unsubstituted methylene link, an ether link, a thia link or an amino link, $R_3$ and $R_4$ or $R_5$ and $R_6$ may be taken together as a ketone;provided that both R groups from one carbon on the ring are not OH.

In preferred embodiments: Where two of $R_1$, $R_2$, $R_3$, $R_4$, $R_5$ or $R_6$ are F the remainder are H. Where two of $R_1$, $R_2$, $R_3$, $R_4$, $R_5$ or $R_6$ are OH, the remainder are H. Where two of $R_1$, $R_2$, $R_3$, $R_4$, $R_5$ or $R_6$ are OH, and a third R group is F the remainder are H. Where two of $R_1$, $R_2$, $R_3$, $R_4$, $R_5$ or $R_6$ are OH, and a third R group is Cl the remainder are H. Where two of $R_1$, $R_2$, $R_3$, $R_4$, $R_5$ or $R_6$ are F and a third R group is OH the remainder are H. Where one of $R_1$, $R_2$, $R_3$, $R_4$, $R_5$ or $R_6$ is Br the remainder are H. Where one of $R_1$, $R_2$, $R_3$, $R_4$, $R_5$ or $R_6$ is Br and a second R group is OH the remainder are H In more preferred embodiments: Where one of $R_1$, $R_2$, $R_3$, $R_4$, $R_5$ or $R_6$ is F the remainder are H. Where one of $R_1$, $R_2$, $R_3$, $R_4$, $R_5$ or $R_6$ are Cl the remainder are H. Where one of $R_1$, $R_2$, $R_3$, $R_4$, $R_5$ or $R_6$ is F and a second R group is OH (not originating from the same carbon) the remainder are H. Where one of $R_1$, $R_2$, $R_3$, $R_4$, $R_5$ or $R_6$ is Cl and a second R group is OH (not originating from the same carbon) the remainder are H. Where one of $R_1$, $R_2$, $R_3$, $R_4$, $R_5$ or $R_6$ is SH the remainder are H. Where one $R_1$, $R_2$, $R_3$, $R_4$, $R_5$ or $R_6$ is SH and a second R group is OH (not originating from the same carbon) the remainder are H. Where one of $R_1$, $R_2$, $R_3$, $R_4$, $R_5$ or $R_6$ is alkyl and the remainder are H; the alkyl group shall contain no more than 4 carbons and have a linear length of no greater than 3 carbons. Where one of $R_1$, $R_2$, $R_3$, $R_4$, $R_5$ or $R_6$ alkyl and a second R group is OH (not originating from the same carbon) the remainder are H; and the alkyl group shall contain no more than 4 carbons and have a linear length of no greater than 3 carbons A further aspect of the invention comprises feeding starter units of the formula

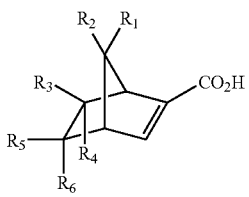

where $R_1$, $R_2$, $R_3$, $R_4$, $R_5$ or $R_6$ may be the same or different and may independently be be Cl, F, OH, SH, H, alkyl, CN, Br, $R_7$, $OR^7$, $C(O)R_7$ or $HNR_7$ where $R_7$ is a C1-C4 alkyl; $R_1$ and $R_3$, $R_2$ and $R_4$, $R_{3\ l\ and\ R5}$, $R_4$ and $R_6$, $R_1$ and $R_5$, or $R_2$ and $R_6$ may be joined as either a substituted or unsubstituted methylene link, an ether link, a thia link or an amino link, $R_3$ and $R_4$ or $R_5$ and $R_6$ may be taken together as a ketone; provided that both R groups from one carbon on the ring are not OH.

In preferred embodiments: where $R_1$, $R_2$, $R_3$, $R_4$, $R_5$ or $R_6$ are a combination of F and OH substitution no more than 3 of $R_{1-6}$ are substituted and the remainder are H. Where $R_1$, $R_2$, $R_3$, $R_4$, $R_5$ or $R_6$ are a combination of Cl and OH substitution no more than 3 of $R_{1-6}$ are substituted and the remainder are H. Where two of $R_1$, $R_2$, $R_3$, $R_4$, $R_5$ or $R_6$ are OH and two of the remaining R groups are F on one carbon the remainder are H. Where two of $R_1$, $R_2$, $R_3$, $R_4$, $R_5$ or $R_6$ are Cl the remainder are H. Where two of $R_1$, $R_2$, $R_3$, $R_4$, $R_5$ or $R_6$ are Cl (not originating from the same carbon) and a third R group is OH, the remainder are H. Where one of $R_1$, $R_2$, $R_3$, $R_4$, $R_5$ or $R_6$ is alkyl and the remainder are H; the alkyl group shall have a linear length of no greater than 3 carbons. Where two of $R_1$, $R_2$, $R_3$, $R_4$, $R_5$ or $R_6$ are SH the remainder are H. Where one of $R_1$, $R_2$, $R_3$, $R_4$, $R_5$ or $R_6$ is $HNR_7$ the remainder are H.

In more preferred embodiments: Where two of $R_1$, $R_2$, $R_3$, $R_4$, $R_5$ or $R_6$ are F the remainder are H. Where two of $R_1$, $R_2$, $R_3$, $R_4$, $R_5$ or $R_6$ are OH the remainder are H. Where two of $R_1$, $R_2$, $R_3$, $R_4$, $R_5$ or $R_6$ are OH and a third R group is F, the remainder are H. Where two of $R_1$, $R_2$, $R_3$, $R_4$, $R_5$ or $R_6$ are OH and a third R group is Cl the remainder are H. Where two of $R_1$, $R_2$, $R_3$, $R_4$, $R_5$ or $R_6$ are F, and a third R groups is OH the remainder are H. Where one of $R_1$, $R_2$, $R_3$, $R_4$, $R_5$ or $R_6$ is Br the remainder are H. Where one $R_1$, $R_2$, $R_3$, $R_4$, $R_5$ or $R_6$ is Br and a second R group is OH (not originating from the same carbon) the remainder are H. Where one of $R_1$, $R_2$, $R_3$, $R_4$, $R_5$ or $R_6$ is SH the remainder are H. Where one of $R_1$, $R_2$, $R_3$, $R_4$, $R_5$ or $R_6$ is SH and a second R groups is OH (not originating from the same carbon) the remainder are H.

In more preferred embodiments: Where one of $R_1$, $R_2$, $R_3$, $R_4$, $R_5$ or $R_6$ is F the remainder are H. Where one of $R_1$, $R_2$, $R_3$, $R_4$, $R_5$ or R is Cl the remainder are H. Where one of $R_1$, $R_2$, $R_3$, $R_4$, $R_5$ or $R_6$ is F and a second R group is OH (not originating from the same carbon) the remainder are H. Where one of $R_1$, $R_2$, $R_3$, $R_4$, $R_5$ or $R_6$ is Cl and a second R group is OH (not originating from the same carbon) the remainder are H. Where one of $R_1$, $R_2$, $R_3$, $R_4$, $R_5$ or $R_6$ is alkyl and the remainder are H; the alkyl group shall contain no more than 4 carbons and have a linear length of no greater than 3 carbons. Where one of $R_1$, $R_2$, $R_3$, $R_4$, $R_5$ or $R_6$ is alkyl and a second R group is OH (not originating from the same carbon) the remainder are H; and the alkyl group shall contain no more than 4 carbons and have a linear length of no greater than 3 carbons.

A further aspect of the invention comprises feeding starter units of the formula

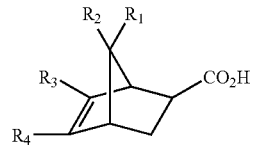

where $R_1$ and $R_2$, may be the same or different and may independently be F, Cl, OH, SH, H, CN, $OR_7$, $C(O)R_7$, or $NHR_7$ wherein $R_7$ is a C1-C4 alkyl, $R_1$ and $R_2$ may also be taken together to form a ketone, a spirocyclopropyl group or with $-OCH_2-$, $-CH_2O-$, $-SCH_2-$ or $-CH_2S-$; furthermore $R_3$, and $R_4$ may be the same or different and may independently be be F, Cl, Br, $OR_7$, H or CN; provided that both R groups from one carbon on the ring are not OH.

In preferred embodiments: Where one of $R_1$, $R_2$, $R_3$ and $R_4$ is F the remainder are H. Where one of $R_1$, $R_2$, $R_3$ and $R_4$ is Cl the remainder are H. Where one of $R_1$, $R_2$, $R_3$ and $R_4$ is F and a second R groups is OH (not originating from the same carbon) the remainder are H. Where one of $R_1$, $R_2$, $R_3$ and $R_4$ is Cl and a second R group is OH (not originating from the same carbon) the remainder are H. Where one of $R_1$, $R_2$, $R_3$ and $R_4$ is SH the remainder are H. Where one of $R_1$, $R_2$, $R_3$ and $R_4$ is alkyl the remainder are H; and the alkyl group shall contain no more than 4 carbons and have a linear length of no greater than 3 carbons. Where one of $R_1$, $R_2$, $R_3$ and $R_4$ is alkyl and a second R groups is OH (not originating from the same carbon) the remainder are H; and the alkyl group shall contain no more than 4 carbons and have a linear length of no greater than 3 carbons. Where two of $R_1$, $R_2$, $R_3$ and $R_4$ are F the remainder are H.

An additional aspect of the invention comprises feeding starter units of the formula

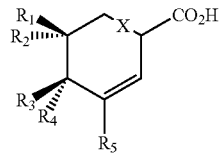

where X=bond or CH$_2$; and R$_1$, R$_2$, R$_3$, R$_4$ or R$_5$ may be the same or different and may independently be be Cl, F, OH, SH, H, alkyl, CN, Br, R$_7$, OR$^7$, C(O)R$_7$ or HNR$_7$ where R$_7$ is a C1-C4 alkyl, R$_1$ and R$_3$, R$_2$ and R$_4$, may be taken together as a ketone or linked as either a substituted or unsubstituted methylene link, an ether link, a thia link or an amino link where R$_1$ and R$_2$ or R$_3$ and R$_4$ are linked as a spiro-cyclopropyl group or with —OCH$_2$— or —CH$_2$O— or —SCH$_2$— or —CH$_2$S—, R$_5$ may be F, CL, OR$_7$, H or CN; provided that no more than two of R$_1$, R$_2$, R$_3$, R$_4$ or R$_5$ are SH and that both R groups attached to one carbon are not OH.

In preferred embodiments: where R$_1$, R$_2$, R$_3$, R$_4$ or R$_5$ are a combination of F and OH no more than 3 of R$_1$, R$_2$, R$_3$, R$_4$ or R$_5$ are substituted and the remainder are H. Where R$_1$, R$_2$, R$_3$, R$_4$ or R$_5$ are a combination of Cl and OH no more than 3 of R$_{1-5}$ are substituted and the remainder are H. Where R$_1$, R$_2$, R$_3$, R$_4$ or R$_5$ are a combination of two are OH (not on the same carbon) and two are F on one carbon the remainder are H. Where two of R$_1$, R$_2$, R$_3$, R$_4$ or R$_5$ are Cl the remainder are H. Where two of R$_1$, R$_2$, R$_3$, R$_4$ or R$_5$ are Cl (not originating from the same carbon) and a third R group is OH the remainder are H. Where one of R$_1$, R$_2$, R$_3$, R$_4$ or R$_5$ is alkyl the remainder are H; and the alkyl group shall have a linear length of no greater than 3 carbons. Where two of R$_1$, R$_2$, R$_3$, R$_4$ or R$_5$ are SH the remainder are H. Where one of R$_1$, R$_2$, R$_3$, R$_4$ or R$_5$ is NHR$_7$ the remainder are H. Where one of R$_1$, R$_2$, R$_3$, R$_4$ or R$_5$ is SH the remainder are H.

In more highly preferred embodiments: where one of R$_1$, R$_2$, R$_3$, R$_4$ or R$_5$ is OH the remainder are H. Where one of R$_1$, R$_2$, R$_3$, R$_4$ or R$_5$ is F the remainder are H. Where one of R$_1$, R$_2$, R$_3$, R$_4$ or R$_5$ is Cl the remainder are H. Where one of R$_1$, R$_2$, R$_3$, R$_4$ or R$_5$ is F and a second R group is OH (not originating from the same carbon) the remainder are H. Where one of R$_1$, R$_2$, R$_3$, R$_4$ or R$_5$ is Cl and a second R groups is OH (not originating from the same carbon) the remainder are H. Where one of R$_1$, R$_2$, R$_3$, R$_4$ or R$_5$ is SH and a second R group is OH (not originating from the same carbon) the remainder are H. Where one of R$_1$, R$_2$, R$_3$, R$_4$ or R$_5$ is alkyl the remainder are H; and the alkyl group shall contain no more than 4 carbons and have a linear length of no greater than 3 carbons. Where one of R$_1$, R$_2$, R$_3$, R$_4$ or R$_5$ is alkyl and a second R group is OH (not originating from the same carbon) the remainder are H; and the alkyl group shall contain no more than 4 carbons and have a linear length of no greater than 3 carbons. Where two of R$_1$, R$_2$, R$_3$, R$_4$ or R$_5$ are F the remainder are H. Where two of R$_1$, R$_2$, R$_3$, R$_4$ or R$_5$ are OH the remainder are H. Where two of R$_1$, R$_2$, R$_3$, R$_4$ or R$_5$ ate OH and a third R group is F the remainder are H. Where two of R$_1$, R$_2$, R$_3$, R$_4$ or R$_5$ are OH and a third R groups is Cl the remainder are H. Where two of R$_1$, R$_2$, R$_3$, R$_4$ or R$_5$ are F and a third R group is OH the remainder are H.

An additional aspect of the invention comprises feeding starter units of the formula

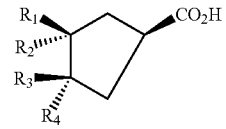

where R$_1$, R$_2$, R$_3$ and R$_4$ may be the same or different and may independently be Cl, F, OH, SH, H, alkyl, CN, Br, R$_7$, OR$^7$, C(O)R$_7$ or HNR$_7$ where R$_7$ is a C1-C4 alkyl, R$_1$ and R$_2$ or R$_3$ and R$_4$ may be taken together to form a ketone, provided that two R groups attached to the same carbon are not both OH.

In preferred embodiments: Where one of R$_1$, R$_2$, R$_3$ or R$_4$ is F the remainder are H. Where one of R$_1$, R$_2$, R$_3$ or R$_4$ is Cl the remainder are H. Where one of R$_1$, R$_2$, R$_3$ or R$_4$ is Br the remainder are H. Where one of R$_1$, R$_2$, R$_3$ or R$_4$ is OH the remainder are H. Where one of R$_1$, R$_2$, R$_3$ or R$_4$ is F and a second R group is OH (not originating from the same carbon) the remainder are H. Where one of R$_1$, R$_2$, R$_3$ or R$_4$ is Cl and a second R groups is OH (not originating from the same carbon) the remainder are H. Where one of R$_1$, R$_2$, R$_3$ or R$_4$ is SH the remainder are H. Where one of R$_1$, R$_2$, R$_3$ or R$_4$ is SH and a second R groups is OH (not originating from the same carbon) the remainder are H. Where one of R$_1$, R$_2$, R$_3$ or R$_4$ is alkyl the remainder are H; and the alkyl group shall contain no more than 4 carbons and have a linear length of no greater than 3 carbons. Where one of R$_1$, R$_2$, R$_3$ or R$_4$ is alkyl and a second R groups is OH (not originating from the same carbon) the remainder are H; and the alkyl group shall contain no more than 4 carbons and have a linear length of no greater than 3 carbons. Where two of R$_1$, R$_2$, R$_3$ or R$_4$ are F the remainder are H. Where two of R$_1$, R$_2$, R$_3$ or R$_4$ are OH the remainder are H. Where two of R$_1$, R$_2$, R$_3$ or R$_4$ are OH and a third R group is F the remainder are H. Where two of R$_1$, R$_2$, R$_3$ or R$_4$ are OH and a third R group is Cl the remainder are H. Where two of R$_1$, R$_2$, R$_3$ or R$_4$ are F and a third R group is OH the remainder are H.

In a preferred embodiment the present invention provides a method for the efficient incorporation of: 2-norbornane carboxylic acid; 2-(cis/trans)-hydroxycyclohexane carboxylic acid; 3-(cis/trans)-hydroxycyclohexane carboxylic acid; 4-(cis/trans)-hydroxycyclohexane carboxylic acid; 2-(cis/trans)-methylcyclohexane carboxylic acid; 4-(cis/trans)-methylcyclohexane carboxylic acid; 3-(cis/trans)-methoxycyclohexane carboxylic acid; 4(cis/trans)-methoxycyclohexane carboxylic acid; 4-oxocyclohexane carboxylic acid; ethyl 2-oxocyclohexane carboxylic acid; 4-trans-n-pentylcyclohexane carboxylic acid; 2-trans-aminocyclohexane carboxylic acid; 4-cis-aminocyclohexane carboxylic acid; 4-(cis/trans)-aminomethylcyclohexane carboxylic acid; cyclopentane carboxylic acid; cyclobutane carboxylic acid; 1-methylcyclohexane carboxylic acid; 3-trans-hydroxy-4-cis-fluorocyclohexane carboxylic acid and 4-trans-hydroxy-3-cis-fluorocyclohexane carboxylic acid; 3-cis-hydroxy-4-trans-fluorocyclohexane carboxylic acid and 4-cis-hydroxy-3-trans-fluorocyclohexane carboxylic acid; 3-cis-hydroxy-4-trans-chlorocyclohexane carboxylic acid and 4-cis-hydroxy-3-trans-chlorocyclohexane carboxylic acid; 3-trans-hydroxy-4-cis-chlorocyclohexane carboxylic acid and 4-trans-hydroxy-3-cis-chlorocyclohexane carboxylic acid; 3-trans-cyclohexeneoxide carboxylic acid; 3-cis-cyclohexeneoxide carboxylic acid; 3,4-cis-dihydroxycyclohexane carboxylic acid and 3,4-trans-dihydroxy-cyclohexane carboxylic acid; cyclohexaneacetic acid; cyclohexanepropionic acid or 4-cis/trans-tert-butylcyclohexane carboxylic acid or simple esters or salts thereof into FKBP-ligand analogues by a strain with rapK or a rapK homologue deleted or inactivated. In a more preferred embodiment the present invention provides a method for the efficient incorporation of: 3-(cis/trans)-hydroxycyclohexane carboxylic acid; 4-(cis/trans)-hydroxycyclohexane carboxylic acid; 3-(cis/trans)-methoxycyclohexane carboxylic acid; 4-(cis/trans)-methoxycyclohexane carboxylic acid; 4-oxo cyclohexane carboxylic acid; cyclobutane carboxylic acid; 3-trans-hydroxy-4-cis-fluorocyclohexane carboxylic acid and 4-trans-hydroxy-3-cis-fluorocyclohexane carboxylic acid; 3-cis-hydroxy-4trans-fluorocyclohexane carboxylic acid and 4-cis-hydroxy-3-trans-fluorocyclohexane carboxylic acid; 3-cis-hydroxy-4-trans-chlorocyclohexane carboxylic acid and 4-cis-hydroxy-3-trans-chlorocyclohexane carboxylic acid; 3-trans-hydroxy-4-cis-chlorocyclohexane carboxylic acid and 4-trans-hydroxy-3-cis-chlorocyclohexane carboxylic acid; 3-trans-cyclohexeneoxide carboxylic acid; 3-cis-cyclohexeneoxide carboxylic acid; 3,4-cis-dihydroxycyclohexane carboxylic acid and 3,4-trans-dihydroxycyclohexane carboxylic acid; cyclohexanepropionic acid; 4-cis/trans-tert-butylcyclohexane carboxylic acid or simple esters or salts thereof into FKBP-ligand analogues by a strain with rapK or a rapK homologue deleted or inactivated.

In a specific embodiment of the present invention the fed starter units are not: cyclohexane carboxylic acid, 3-cis,4-trans-dihydroxycyclohexane carboxylic acid, 1-cyclohexene carboxylic acid, 3-cyclohexene carboxylic acid, cycloheptane carboxylic acid, 3-(cis/trans)-methylcyclohexane carboxylic acid, 4-(cis/trans)-methylcyclohexane carboxylic acid, 1-cycloheptene carboxylic acid or 5-cis-hydroxyl-3-cyclohexene carboxylic acid.

The strains for use in the embodiments described above are selected from the group comprising: *Streptomyces hygroscopicus* subsp. *hygroscopicus* NRRL 5491, *Actinoplanes* sp. N902-109 FERM BP-3832, *Streptomyces* sp. AA6554, *Streptomyces hygroscopicus* var *ascomyceticus* MA 6475 ATCC 14891, *Streptomyces hygroscopicus* var. *ascomyceticus* MA 6678 ATCC 55087, *Streptomyces hygroscopicus* var *ascomyceticus* MA 6674, *Streptomyces hygroscopicus* var. *ascomyceticus* ATCC 55276, *Streptomyces hygroscopicus* subsp. *ascomyceticus* ATCC 14891, *Streptomyces tsukubaensis* No.9993 FERM BP-927, *Streptomyces hygroscopicus* subsp. *yakushimaensis, Streptomyces* sp. DSM 4137, *Streptomyces* sp. DSM 7348, *Micromonospora* n.sp. A92-306401 DSM 8429, *Steptomyces* sp. MA 6858 ATCC 55098, *Steptomyces* sp. MA 6848. In a preferred embodiment said strain is selected from the group consisting of *Streptomyces hygroscopicus* subsp. *hygroscopicus* NRRL 5491, *Actinoplanes* sp. N902-109 FERM BP-3832, *Streptomyces* sp. M6554, *Streptomyces hygroscopicus* var. *ascomyceticus* MA 6475 ATCC 14891, *Streptomyces hygroscopicus* var *ascomyceticus* MA 6678 ATCC 55087, *Streptomyces hygroscopicus* var. *ascomyceticus* MA 6674, *Streptomyces hygroscopicus* var *ascomyceticus* ATCC 55276, *Streptomyces hygroscopicus* subsp. *ascomyceticus* ATCC 14891, *Streptomyces tsukubaensis* No.9993 FERM BP-927, *Streptomyces hygroscopicus* subsp. *yakushimaensis, Streptomyces* sp. DSM 4137, *Streptomyces* sp. DSM 7348, *Micromonospora* n.sp. A92-306401 DSM 8429 or *Streptomyces* sp. MA 6858 ATCC 55098. In a more highly preferred embodiment the strain is the rapamycin producer *S. hygroscopicus* subsp. *hygroscopicus*.

In the methods for the efficient incorporation of fed carboxylic acids described above the compounds produced are analogues of the FKBP-ligands as described herein, for example but without limitation: rapamycin, FK506, FK520, FK523, FK525, antascomicin, meridamycin and tsukubamycin. In a preferred embodiment the compounds produced are analogues of rapamycin, FK506 or FK520. In a more highly preferred embodiment the compounds produced are analogues of rapamycin; these compounds correspond to Formula II or Formula III as described below.

Additionally, the methods described above may be used to generate novel FK506 and FK520 analogues which correspond to Formula I below:

Formula I:

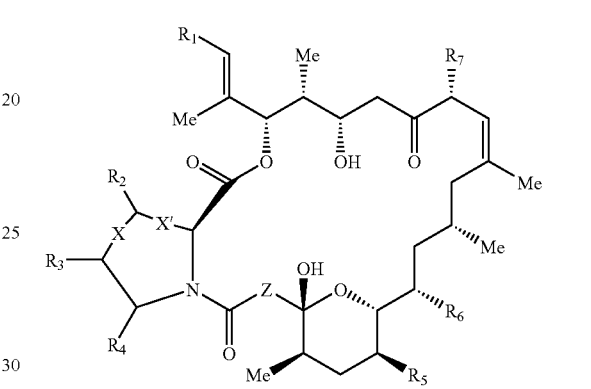

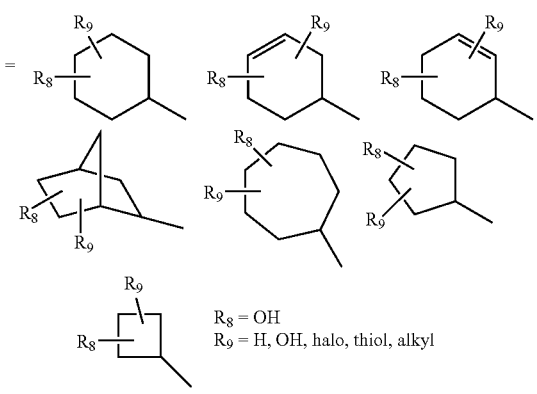

$R_8$ = OH
$R_9$ = H, OH, halo, thiol, alkyl $R_2$ = H, alkyl, halo, hydroxyl, thiol
$R_3$ = H, alkyl, halo, hydroxyl, thiol
$R_4$ = H, alkyl, halo, hydroxyl, thiol
$R_5$ = OMe, Me or H
$R_6$ = OMe, Me or H $R_7$=$CH_2CH_3$ or $CH_2CH$=$CH_2$
Z=keto or $CH_2$
X=X'=bond; X=bond and X'=$CH_2$, S, O or X=$CH_2$, S, O, fused cyclopropyl unit and X'=bond In a preferred embodiment,

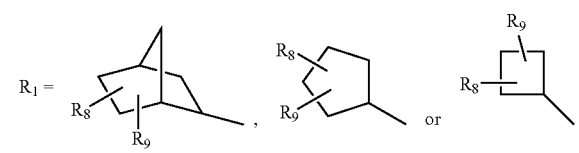

Where $R_8$=OH and $R_9$=H, OH, halo, alkyl or thiol.

In a further preferred embodiment

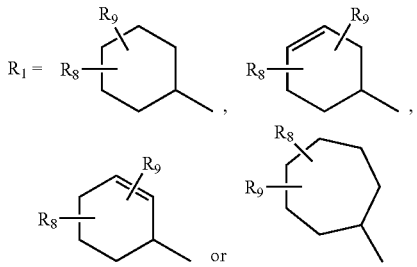

where $R_8$=OH and $R_9$=halo.

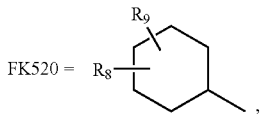

where $R_8$=4-trans-OH, $R_9$=3-cis-OCH$_3$, and $R_2$=$R_3$=$R_4$=H, X=CH$_2$, X'=bond, Z=keto, $R_5$=$R_6$=OCH$_3$ and $R_7$=CH$_2$CH$_3$

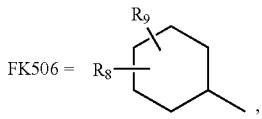

where $R_5$=4-trans-OH, $R_9$=3-cis-OCH$_3$, and $R_2$=$R_3$=$R_4$=H, X=CH$_2$, X'=bond, Z=keto, $R_5$=$R_6$=OCH$_3$ and $R_7$=CH$_2$CH=CH$_2$ Thus, for example, the recombinant strain *S. hygroscopicus* MG2-10 can be cultured in the presence of cyclohexane carboxylic acid to produce 9-deoxo-16-O-desmethyl-27-desmethoxy-39-desmethoxy-rapamycin (Example 12). It can be seen by one skilled in the art that homologues to rapK in other biosynthetic clusters that encode FKBP-ligands, including, but not limited to, FK506, FK520, FK523, FK525, meridamycin, tsukubamycin, antascomicin and 'hyg' can also be deleted or inactivated allowing efficient feeding of starter unit carboxylic acids leading to the production of novel analogues.

In another aspect, *S. hygroscopicus* strains of the invention (including rapL or rapL homologues or not including rapL or rapL homologues and/or including rapK or rapK homologues or not including rapK or rapK homologues) may be fed with analogues of L-pipecolic acid, as described above, in combination with analogues of the natural 4,5-dihydroxycyclohex-1-enecarboxylic acid starter unit, as described above, to produce rapamycin analogues in which both the starter unit and the pipecolyl residue have been replaced. This approach is exemplified in Examples 10, 11 and 12.

The present invention provides a process for producing FKBP-ligand analogues varying in the extent of post-PKS modification and/or in which the pipecolic acid residue has been replaced, and optionally the starter 4,5-dihydroxycyclohex-1-enecarboxylic acid residue has been replaced. This process comprises the step of deleting or inactivating one or more genes in the microorganism host cell involved in the production of the precursor compound, L-pipecolic acid and/or 4,5-dihydroxycyclohex-1-ene carboxylic acid, required for biosynthesis of the rapamycin polyketide/NRPS template and/or in its subsequent post-PKS modification, thereby to suppress the production of the natural product. The process further comprises transforming the microorganism host cells with nucleic acid encoding polyketide-modifying genes to restore polyketide production, culturing the transformed host cells under conditions suitable for polyketide production and optionally isolating the rapamycin analogues produced.

The present invention provides a process for the production of FKBP-ligand analogues including, but not limited to FK506, FK520, FK523, FK525, tsukubamycin, antascomicin, meridamycin and 'hyg', varying in the extent of post-PKS modification and/or in which the amino acid residue has been replaced, and optionally the starter unit has been replaced. This process comprises the step of deleting or inactivating one or more genes in the microorganism host cell involved in the production of the precursor amino acid residue and/or starter unit, required for the biosynthesis of the polyketide/NRPS template and/or in its subsequent post-PKS modification, thereby to suppress the production of the natural product. The process further comprises transforming the microorganism host cells with nucleic acid encoding polyketide-modifying genes to restore polyketide production, culturing the transformed host cells under conditions suitable for polyketide production and optionally isolating polyketide analogues produced.

The present invention provides novel FKBP-ligand analogues.

In a further aspect the present invention provides the following FK520 analogues: 31-desmethoxy-FK520, 31-desmethoxy-31-cis-hydroxy-32-trans-hydroxy-FK520, 31-desmethoxy-31-cis-hydroxy-32-cis-hydroxy-FK520, 31-desmethoxy-31-trans-hydroxy-32-trans-hydroxy-FK520, 31-O-desmethyl-32-dehydroxy-FK520, 31-O-desmethyl-FK520, 31-desmethoxy-31-methyl-FK520, 31-O-desmethyl-32-dehydroxy-32-methyl-FK520, 31-O-desmethyl-32dehydroxy-32-fluoro-FK520, 31-desmethoxy-31-fluoro-FK520, 31-O-desmethyl-32-dehydroxy-32-chloro-FK520, 31-desmethoxy-31-chloro-FK520, 31-O-desmethyl-32-dehydroxy-32-tert-butyl-FK520, 29-de(3-methoxy-4-hydroxy-cyclohexyl)-29-(hydroxy-cycloheptyl)-FK520, 29-de(3-methoxy-4-hydroxy-cyclohexyl)-29-(hydroxy-norbornyl)-FK520, 9-deoxo-31-desmethoxy-FK520, 9-deoxo-31-desmethoxy-31-cis-hydroxy-32-trans-hydroxy-FK520, 9-deoxo-31-desmethoxy-31-cis-hydroxy-32-cis-hydroxy-FK520, 9-deoxo-31-desmethoxy-31-trans-hydroxy-32-trans-hydroxy-FK520, 9-deoxo-31-O-desmethyl-32-dehydroxy-FK520, 9-deoxo-31-O-desmethyl-FK520, 9-deoxo-31-desmethoxy-31-methyl-FK520, 9-deoxo-31-O-desmethyl-32-dehydroxy-32-methyl-FK520, 9-deoxo-31-O-desmethyl-32-dehydroxy-32-fluoro-FK520, 9-deoxo-31-desmethoxy-31-fluoro-FK520, 9-deoxo-31-O-desmethyl-32-dehydroxy-32-chloro-FK520, 9-deoxo-31-desmethoxy-31-chloro-FK520, 9-deoxo-31-O-desmethyl-32-dehydroxy-32-tert-butyl-FK520, 9-deoxo-29-de(3-methoxy-4-hydroxy-cyclohexyl)-29-(hydroxy-cycloheptyl)-FK520, 9-deoxo-29-de(3-methoxy-4-hydroxy-cyclohexyl)-29-(hydroxy-norbornyl)-FK520, 30-desmethoxy-prolyl-FK520, 30-desmethoxy-30-cis-hydroxy-31-trans-hydroxy-prolyl-FK520, 30-desmethoxy-30-cis-hydroxy-31-cis-hydroxy-prolyl-FK520, 30-desmethoxy-30-trans-hydroxy-31-transhydroxy-prolyl-FK520, 30-O-desmethyl-31-dehydroxy-prolyl-FK520, 30-O-desmethyl-prolyl-FK520, 30-desmethoxy-30-methyl-prolyl-FK520, 30-O-desmethyl-31-dehydroxy-31-methyl-prolyl-FK520, 30-O-desmethyl-31-dehydroxy-31-fluoro-prolyl-FK520, 30-desmethoxy-30-fluoro-prolyl-FK520, 30-O-desmethyl-31-dehydroxy-31-chloro-prolyl-FK520, 30-desmethoxy-30-chloro-prolyl-FK520, 30-desmethyl-31-dehydroxy-31-tert-butyl-prolyl-FK520, 28-de(3-methoxy-4-hydroxy-cyclohexyl)-28-(hydroxy-cycloheptyl)-FK520, 28-de(3-methoxy-4-hydroxy-cyclohexyl)-28-(hydroxy-norbornyl)-FK520, 8-deoxo-30-desmethoxy-31-hydroxy-prolyl-FK520, 8-deoxo-30-desmethoxy-30-cis-hydroxy-31-trans-hydroxy-prolyl-FK520, 8-deoxo-30-desmethoxy-30-cis-hydroxy-31-cis-hydroxy-prolyl-FK520, 8-deoxo-30-desmethoxy-30-trans-hydroxy-31-trans-hydroxy-prolyl-FK520, 8-deoxo-30-O-desmethyl-31-dehydroxy-prolyl-FK520, 8-deoxo-30-O-desmethyl-prolyl-FK520, 8-deoxo-30-desmethoxy-30-methyl-prolyl-FK520, 8-deoxo-30-O-desmethyl-31-dehydroxy-31-methyl-prolyl-FK520, 8-deoxo-30-O-desmethyl-31-dehydroxy-31-fluoro-prolyl-FK520, 8-deoxo-30-desmethoxy-30-fluoro-prolyl-FK520, B-deoxo-30-O-desmethyl-31-dehydroxy-31-chloro-prolyl-FK520, 8-deoxo-30-desmethoxy-30-chloro-prolyl-FK520, 8-deoxo-30-O-desmethyl-31-dehydroxy-31-tert-butyl-prolyl-FK520, 8-deoxo-28-de(3-methoxy-4-hydroxy-cyclohexyl)-28-(hydroxy-cycloheptyl)-prolyl-FK520, 8-deoxo-28-de(3-methoxy-4-hydroxy-cyclohexyl)-28-(hydroxy-norbornyl)-prolyl-FK520, 30-desmethoxy-3-hydroxy-prolyl-FK520, 30desmethoxy-30-cis-hydroxy-31-trans-hydroxy-3-hydroxy-prolyl-FK520, 30-desmethoxy-30-cis-hydroxy-31-cis-hydroxy-3-hydroxy-prolyl-FK520, 30-desmethoxy-30-trans-hydroxy-31-trans-hydroxy-3-hydroxy-prolyl-FK520, 30-O-desmethyl-31-dehydroxy-3-hydroxy-prolyl-FK520, 30-desmethyl-3-hydroxy-prolyl-FK520, 30-desmethoxy-30-methyl-3-hydroxy-prolyl-FK520, 30-O-desmethyl-31-dehydroxy-31-methyl-3-hydroxy-prolyl-FK520, 30-O-desmethyl-31-dehydroxy-31-fluoro-3-hydroxy-prolyl-FK520, 30-desmethoxy-30-fluoro-3-hydroxy-prolyl-FK520, 30-O-desmethyl-31-dehydroxy-31-chloro-3-hydroxy-prolyl-FK520, 30-desmethoxy-30-chloro-3-hydroxy-prolyl-FK520, 30-O-desmethyl-31-dehydroxy-31-tert-butyl-3-hydroxy-prolyl-FK520, 28-de(3-methoxy-4-hydroxy-cyclohexyl)-28-(hydroxy-cycloheptyl)-3-hydroxy-prolyl-FK520, 28-de(3-methoxy-4-hydroxy-cyclohexyl)-28-(hydroxy-norbornyl)-3-hydroxy-prolyl-FK520, 8-deoxo-30-desmethoxy-31-hydroxy-3-hydroxy-prolyl-FK520, 8-deoxo-30-desmethoxy-30-cis-hydroxy-31-trans-hydroxy-3-hydroxy-prolyl-FK520, 8-deoxo-30-desmethoxy-30-cis-hydroxy-31-cis-hydroxy-3-hydroxy-prolyl-FK520, 8-deoxo-30-desmethoxy-30-trans-hydroxy-31-trans-hydroxy-3-hydroxy-prolyl-FK520, 8-deoxo-30-O-desmethyl-31-dehydroxy-3-hydroxy-prolyl-FK520, 8-deoxo-30-O-desmethyl-3-hydroxy-prolyl-FK520, 8-deoxo-30-desmethoxy-30-methyl-3-hydroxy-prolyl-FK520, 8-deoxo-30-O-desmethyl-31-dehydroxy-31-methyl-3-hydroxy-prolyl-FK520, 8-deoxo-30-O-desmethyl-31-dehydroxy-31-fluoro-3-hydroxy-prolyl-FK520, 8-deoxo-30-desmethoxy-30-fluoro-3-hydroxy-prolyl-FK520, 8-deoxo-30-O-desmethyl-31-dehydroxy-31-chloro-3-hydroxy-prolyl-FK520, 8-deoxo-30-desmethoxy-30-chloro-3-hydroxy-prolyl-FK520, 8-deoxo-30-O-desmethyl-31-dehydroxy-31-tert-butyl-3-hydroxy-prolyl-FK520, 8-deoxo-28-de(3-methoxy-4-hydroxy-cyclohexyl)-28-(hydroxy-cycloheptyl)-3-hydroxy-prolyl-FK520, 8-deoxo-28-de(3-methoxy-4-hydroxy-cyclohexyl)-28-(hydroxy-norbornyl)-3-hydroxy-prolyl-FK520, 30-desmethoxy-4-hydroxy-prolyl-FK520, 30-desmethoxy-30-cis-hydroxy-31-trans-hydroxy-4-hydroxy-prolyl-FK520, 30-desmethoxy-30-cis-hydroxy-31-cis-hydroxy-4-hydroxy-prolyl-FK520, 30-desmethoxy-30-trans-hydroxy-31-trans-hydroxy-4-hydroxy-prolyl-FK520, 30-O-desmethyl-31-dehydroxy-4-hydroxy-prolyl-FK520, 30-O-desmethyl-4-hydroxy-prolyl-FK520, 30-desmethoxy-30-methyl-4-hydroxy-prolyl-FK520, 30-O-desmethyl-31-dehydroxy-31-methyl-4-hydroxy-prolyl-FK520, 30-O-desmethyl-31-dehydroxy-31-fluoro-4-hydroxy-prolyl-FK520, 30-desmethoxy-30-fluoro-4-hydroxy-prolyl-FK520, 30-O-desmethyl-31-dehydroxy-31-chloro-4-hydroxy-prolyl-FK520, 30-desmethoxy-30-chloro-4-hydroxy-prolyl-FK520, 30-O-desmethyl-31-dehydroxy-31-tert-butyl-4-hydroxy-prolyl-FK520, 28de(3-methoxy-4-hydroxy-cyclohexyl)-28-(hydroxy-cycloheptyl)-4-hydroxy-prolyl-FK520, 28-de(3-methoxy-4-hydroxy-cyclohexyl)-28-(hydroxy-norbornyl)-4-hydroxy-prolyl-FK520, 8deoxo-30-desmethoxy-31-hydroxy-4-hydroxy-prolyl-FK520, 8-deoxo-30-desmethoxy-30-cis-hydroxy-31-trans-hydroxy-4-hydroxy-prolyl-FK520, 8-deoxo-30-desmethoxy-30-cis-hydroxy-31-cis-hydroxy-4-hydroxy-prolyl-FK520, 8-deoxo-30-desmethoxy-30-trans-hydroxy-31-trans-hydroxy-4-hydroxy-prolyl-FK520, 8-deoxo-30-O-desmethyl-31-dehydroxy-4-hydroxy-prolyl-FK520, 8-deoxo-30-O-desmethyl-4-hydroxy-prolyl-FK520, 8-deoxo-30-desmethoxy-30-methyl-4-hydroxy-prolyl-FK520, 8-deoxo-30-O-desmethyl-31-dehydroxy-31-methyl-4-hydroxy-prolyl-FK520, 8-deoxo-30-desmethyl-31-dehydroxy-31-fluoro-4-hydroxy-prolyl-FK520, 8-deoxo-30-desmethoxy-30-fluoro-4-hydroxy-prolyl-FK520, 8-deoxo-30-O-desmethyl-31-dehydroxy-31-chloro-4-hydroxy-prolyl-FK520, 8-deoxo-30-desmethoxy-30-chloro-3-hydroxy-4-hydroxy-prolyl-FK520, 8-deoxo-30-O-desmethyl-31-dehydroxy-31-tert-butyl-4-hydroxy-prolyl-FK520, 8-deoxo-28-de(3-methoxy-4-hydroxy-cyclohexyl)-28-(hydroxy-cycloheptyl)-4-hydroxy-prolyl-FK520, 8-deoxo-28-de(3-methoxy-4-hydroxy-cyclohexyl)-28-(hydroxy-norbornyl)-4-hydroxy-prolyl-FK520, 31-desmethoxy-trans-3-bicyclo[3.1.0.]FK520, 31-desmethoxy-31-cis-hydroxy-32-trans-hydroxy-trans-3-bicyclo[3.1.0.]FK520, 31-desmethoxy-31-cis-hydroxy-32-cis-hydroxy-trans-3-bicyclo[3.1.0.]FK520, 31-desmethoxy-31-trans-hydroxy-32-trans-hydroxy-trans-3-bicyclo[3.1.0.]FK520, 31-O-desmethyl-32-dehydroxy-trans-3-bicyclo[3.1.0.]FK520, 31-O-desmethyl-trans-3-bicyclo[3.1.0.]FK520, 31-desmethyl-31-methyl-trans-3-bicyclo[3.1.0.]FK520, 31-O-desmethyl-32-dehydroxy-32-methyl-trans-3-bicyclo[3.1.0.]FK520, 31-desmethyl-32-dehydroxy-32-fluoro-trans-3-bicyclo[3.1.0.]FK520, 31-desmethoxy-31-fluoro-trans-3-bicyclo[3.1.0.]FK520, 31-O-desmethyl-32-dehydroxy-32-chloro-trans-3-bicyclo[3.1.0.]FK520, 31-desmethoxy-31-chloro-trans-3-bicyclo[3.1.0.]FK520, 31-O-desmethyl-32-dehydroxy-32-tert-butyl-trans-3-bicyclo[3.1.0.]FK520, 29-de(3-methoxy-4-hydroxy-cyclohexyl)-29-(hydroxy-cycloheptyl)-trans-3-bicyclo[3.1.0.]FK520, 29-de(3-methoxy-4-hydroxy-cyclohexyl)-29-(hydroxy-norbornyl)-trans-3-bicyclo[3.1.0.]FK520, 9deoxo-31-desmethoxy-trans-3-bicyclo[3.1.0.]FK520, 9-deoxo-31-desmethoxy-31-cis-hydroxy-32-trans-hydroxy-trans-3-bicyclo[3.1.0.]FK520, 9-deoxo-31-desmethoxy-31-cis-hydroxy-32-cis-hydroxy-trans-3-bicyclo[3.1.0.]FK520, 9-deoxo-31-desmethoxy-31-trans-hydroxy-32-trans-hydroxy-trans-3-bicyclo[3.1.0.]FK520, 9-deoxo-31-O-desmethyl-32-dehydroxy-trans-3-bicyclo[3.1.0.]FK520, 9-deoxo-31-O-desmethyl-trans-3-bicyclo[3.1.0.]FK520, 9-deoxo-31-desmethoxy-31-methyl-trans-3-bicyclo[3.1.0.]FK520, 9-deoxo-31-O-desmethyl-32-dehydroxy-32-methyl-trans-3-bicyclo[3.1.0.]FK520, 9-deoxo-31-O-desmethyl-32-dehydroxy-32-fluoro-trans-3-bicyclo[3.1.0.]FK520, 9-deoxo-31-desmethoxy-31-fluoro-trans-3-bicyclo[3.1.0.]FK520, 9-deoxo-31O-desmethyl-32-dehydroxy-32-chloro-trans-3-bicyclo[3.1.0.]FK520, 9-deoxo-31-desmethoxy-31-chloro-trans-3-bicyclo[3.1.0]FK520, 9-deoxo-31-O-desmethyl-32-dehydroxy-32-tert-butyl-trans-3-bicyclo[3.1.0.]FK520, 9deoxo-29-de(3-methoxy-4-hydroxy-cyclohexyl)-29-(hydroxy-cycloheptyl)-trans-3-bicyclo[3.1.o.]FK520, 9-deoxo-29-de(3-methoxy-4-hydroxy-cyclohexyl)-29-(hydroxy-norbornyl)-trans-3-bicyclo[3.1.0.]FK520, In a preferred embodiment, the present invention provides the following FK520 analogues: 31-desmethoxy-31-cis-hydroxy-32-trans-hydroxy-FK520, 31-desmethoxy-31-cis-hydroxy-32-cis-hydroxy-FK520, 31-desmethoxy-31-trans-hydroxy-32-trans-hydroxy-FK520, 31-desmethoxy-31-methyl-FK520, 31-desmethoxy-31-fluoro-FK520, 31-desmethoxy-31-chloro-FK520, 31-desmethyl-32-dehydroxy-32-tert-butyl-FK520, 29-de(3-methoxy-4-hydroxy-cyclohexyl)-29-(hydroxy-cycloheptyl)-FK520, 29-de(3-methoxy-4-hydroxy-cyclohexyl)-29-(hydroxy-norbornyl)-FK520, 9-deoxo-31-desmethoxy-31-cis-hydroxy-32-trans-hydroxy-FK520, 9-deoxo-31-desmethoxy-31-cis-hydroxy-32-cis-hydroxy-FK520, 9-deoxo-31-desmethoxy-31-trans-hydroxy-32-trans-hydroxy-FK520, 9-deoxo-31-desmethoxy-31-methyl-FK520, 9-deoxo-31-desmethoxy-31-fluoro-FK520, 9-deoxo-31-desmethoxy-31-chloro-FK520, 9-deoxo-31-O-desmethyl-32-dehydroxy-32-tert-butyl-FK520, 9-deoxo-29-de(3-methoxy-4-hydroxy-cyclohexyl)-29-(hydroxy-cycloheptyl)-FK520, 9-deoxo-29-de(3-methoxy-4-hydroxy-cyclohexyl)-29-(hydroxy-norbornyl)-FK520, 30-desmethoxy-30-cis-hydroxy-31-trans-hydroxy-prolyl-FK520, 30-desmethoxy-30-cis-hydroxy-31-cis-hydroxy-prolyl-FK520, 30-desmethoxy-30-trans-hydroxy-31-trans-hydroxy-prolyl-FK520, 30-desmethoxy-30-methyl-prolyl-FK520, 30-desmethoxy-30-fluoro-prolyl-FK520,-30-desmethoxy-30-chloro-prolyl-FK520, 30-desmethyl-31-dehydroxy-31-tert-butyl-prolyl-FK520, 28-de(3-methoxy-4-hydroxy-cyclohexyl)-28-(hydroxy-cycloheptyl)-FK520, 28-de(3-methoxy-4-hydroxy-cyclohexyl)-28-(hydroxy-norbornyl)-FK520, 8-deoxo-30-desmethoxy-31-hydroxy-prolyl-FK520, 8-deoxo-30-desmethoxy-30-cis-hydroxy-31-trans-hydroxy-prolyl-FK520, 8-deoxo-30-desmethoxy-30-cis-hydroxy-31-cis-hydroxy-prolyl-FK520, 8-deoxo-30-desmethoxy-30-trans-hydroxy-31-trans-hydroxy-prolyl-FK520, 8-deoxo-30-O-desmethyl-31-dehydroxy-prolyl-FK520, 8-deoxo-30-O-desmethyl-prolyl-FK520, 8-deoxo-30-desmethoxy-30-methyl-prolyl-FK520, 8-deoxo-30-O-desmethyl-31-dehydroxy-31-methyl-prolyl-FK520, 8-deoxo-30-O-desmethyl-31-dehydroxy-31-fluoro-prolyl-FK520, 8-deoxo-30-desmethoxy-30-fluoro-prolyl-FK520, 8-deoxo-30-O-desmethyl-31-dehydroxy-31-chloro-prolyl-FK520, 8-deoxo-30-desmethoxy-30-chloro-prolyl-FK520, 8-deoxo-30-O-desmethyl-31-dehydroxy-31-tert-butyl-prolyl-FK520, 8-deoxo-28-de(3-methoxy-4-hydroxy-cyclohexyl)-28-(hydroxy-cycloheptyl)-prolyl-FK520, 8-deoxo-28-de(3-methoxy-4-hydroxy-cyclohexyl)-28-(hydroxy-norbornyl)-prolyl-FK520, 30-desmethoxy-3-hydroxy-prolyl-FK520, 30-desmethoxy-30-cis-hydroxy-31-trans-hydroxy-3-hydroxy-prolyl-FK520, 30-desmethoxy-30-cis-hydroxy-31-cis-hydroxy-3-hydroxy-prolyl-FK520, 30-desmethoxy-30-trans-hydroxy-31-trans-hydroxy-3-hydroxy-prolyl-FK520, 30-O-desmethyl-31-dehydroxy-3-hydroxy-prolyl-FK520, 30-O-desmethyl-3-hydroxy-prolyl-FK520, 30-desmethoxy-30-methyl-3-hydroxy-prolyl-FK520, 30-O-desmethyl-31-dehydroxy-31-methyl-3-hydroxy-prolyl-FK520, 30-O-desmethyl-31-dehydroxy-31-fluoro-3-hydroxy-prolyl-FK520, 30-desmethoxy-30-fluoro-3-hydroxy-prolyl-FK520, 30-O-desmethyl-31-dehydroxy-31-chloro-3-hydroxy-prolyl-FK520, 30-desmethoxy-30-chloro-3-hydroxy-prolyl-FK520, 30-O-desmethyl-31-dehydroxy-31-tert-butyl-3-hydroxy-prolyl-FK520, 28-de(3-methoxy-4-hydroxy-cyclohexyl)-28-(hydroxy-cycloheptyl)-3-hydroxy-prolyl-FK520, 28-de(3-methoxy-4-hydroxy-cyclohexyl)-28-(hydroxy-norbornyl)-3-hydroxy-prolyl-FK520, 8-deoxo-30-desmethoxy-31-hydroxy-3-hydroxy-prolyl-FK520, 8-deoxo-30-desmethoxy-30-cis-hydroxy-31-trans-hydroxy-3-hydroxy-prolyl-FK520, 8-deoxo-30-desmethoxy-30-cis-hydroxy-31-cis-hydroxy-3-hydroxy-prolyl-FK520, 8-deoxo-30-desmethoxy-30-trans-hydroxy-31-trans-hydroxy-3-hydroxy-prolyl-FK520, 8-deoxo-30-O-desmethyl-31-dehydroxy-3-hydroxy-prolyl-FK520, 8-deoxo-30-O-desmethyl-3-hydroxy-prolyl-FK520, 8-deoxo-30-desmethoxy-30-methyl-3-hydroxy-prolyl-FK520, 8-deoxo-30-O-desmethyl-31-dehydroxy-31-methyl-3-hydroxy-prolyl-FK520, 8-deoxo-30-O-desmethyl-31-dehydroxy-31-fluoro-3-hydroxy-prolyl-FK520, 8-deoxo-30-desmethoxy-30-fluoro-3-hydroxy-prolyl-FK520, 8-deoxo-30-O-desmethyl-31-dehydroxy-31-chloro-3-hydroxy-prolyl-FK520, 8-deoxo-30-desmethoxy-30-chloro-3-hydroxy-prolyl-FK520, 8-deoxo-30-O-desmethyl-31-dehydroxy-31-tert-butyl-3-hydroxy-prolyl-FK520, 8-deoxo-28-de(3-methoxy-4-hydroxy-cyclohexyl)-28-(hydroxy-cycloheptyl)-3-hydroxy-prolyl-FK520, 8-deoxo-28-de(3-methoxy-4-hydroxy-cyclohexyl)-28-(hydroxy-norbornyl)-3-hydroxy-prolyl-FK520, 30-desmethoxy-4-hydroxy-prolyl-FK520, 30-desmethoxy-30-cis-hydroxy-31-trans-hydroxy-4-hydroxy-prolyl-FK520, 30-desmethoxy-30-cis-hydroxy-31-cis-hydroxy-4-hydroxy-prolyl-FK520, 30-desmethoxy-30-trans-hydroxy-31-trans-hydroxy-4-hydroxy-prolyl-FK520, 30-O-desmethyl-31-dehydroxy-4-hydroxy-prolyl-FK520, 30-O-desmethyl-4-hydroxy-prolyl-FK520, 30-desmethoxy-30-methyl-4-hydroxy-prolyl-FK520, 30-O-desmethyl-31-dehydroxy-31-methyl-4-hydroxy-prolyl-FK520, 30-O-desmethyl-31-dehydroxy-31-fluoro-4-hydroxy-prolyl-FK520, 30-desmethoxy-30-fluoro-4-hydroxy-prolyl-FK520, 30-O-desmethyl-31-dehydroxy-31-chloro-4-hydroxy-prolyl-FK520, 30-desmethoxy-30-chloro-4-hydroxy-prolyl-FK520, 30O-desmethyl-31-dehydroxy-31-tert-butyl-4-hydroxy-prolyl-FK520, 28-de(3-methoxy-4-hydroxy-cyclohexyl)-28-(hydroxy-cycloheptyl)-4-hydroxy-prolyl-FK520, 28-de(3-methoxy-4-hydroxy-cyclohexyl)-28-(hydroxy-norbornyl)-4-hydroxy-prolyl-FK520, 8-deoxo-30-desmethoxy-31-hydroxy-4-hydroxy-prolyl-FK520, 8-deoxo-30-desmethoxy-30-cis-hydroxy-31-trans-hydroxy-4-hydroxy-prolyl-FK520, 8-deoxo-30-desmethoxy-30-cis-hydroxy-31-cis-hydroxy-4-hydroxy-prolyl-FK520, 8-deoxo-30-desmethoxy-30-trans-hydroxy-31-trans-hydroxy-4-hydroxy-prolyl-FK520, 8-deoxo-30-O-desmethyl-31-dehydroxy-4-hydroxy-prolyl-FK520, 8-deoxo-30-O-desmethyl-4-hydroxy-prolyl-FK520, 8-deoxo-30-desmethoxy-30-methyl-4-hydroxy-prolyl-FK520, 8-deoxo-30-O-desmethyl-31-dehydroxy-31-methyl-4-hydroxy-prolyl-FK520, 8-deoxo-30-O-desmethyl-31-dehydroxy-31-fluoro-4-hydroxy-prolyl-FK520, 8-deoxo-30-desmethoxy-30-fluoro-4-hydroxy-prolyl-FK520, 8-deoxo-30-O-desmethyl-31-dehydroxy-31-chloro-4-hydroxy-prolyl-FK520, 8-deoxo-30-desmethoxy-30-chloro-3-hydroxy-4-hydroxy-prolyl-FK520, 8-deoxo-30-O-desmethyl-31-dehydroxy-31-tert-butyl-4-hydroxy-prolyl-FK520, 8-deoxo-28-de(3-methoxy-4-hydroxy-cyclohexyl)-28-(hydroxy-cycloheptyl)-4-hydroxy-prolyl-FK520, 8-deoxo-28-de(3-methoxy-4-hydroxy-cyclohexyl)-28-(hydroxy-norbornyl)-4-hydroxy-prolyl-FK520, 31-desmethoxy-trans-3-bicyclo[3.1.0.]FK520, 31-desmethoxy-31-cis-hydroxy-32-trans-hydroxy-trans-3-bicyclo[3.1.0.]FK520, 31-desmethoxy-31-cis-hydroxy-32-cis-hydroxy-trans-3-bicyclo[3.1.0.]FK520, 31-desmethoxy-31-trans-hydroxy-32-trans-hydroxy-trans-3-bicyclo[3.1.0.]FK520, 31-O-desmethyl-32-dehydroxy-trans-3-bicyclo[3.1 0.]FK520, 31-O-desmethyl-trans-3-bicyclo[3.1.0.]FK520, 31-desmethoxy-31-methyl-trans-3-bicyclo[3.1.0.]FK520, 31-O-desmethyl-32-dehydroxy-32-methyl-trans-3-bicyclo[3.1.0.]FK520, 31-O-desmethyl-32-dehydroxy-32-fluoro-trans-3-bicyclo[3.1.0.]FK520, 31-desmethoxy-31-fluoro-trans-3-bicyclo[3.1.0.]FK520, 31-O-desmethyl-32-dehydroxy-32-chloro-trans-3-bicyclo[3.1.0.]FK520, 31-desmethoxy-31-chloro-trans-3-bicyclo[3.1.0.]FK520, 31-O-desmethyl-32-dehydroxy-32-tert-butyl-trans-3-bicyclo[3.1.0.]FK520, 29-de(3-methoxy-4-hydroxy-cyclohexyl)-29-(hydroxy-cycloheptyl)-trans-3-bicyclo[3.1.0.]FK520, 29-de(3-methoxy-4-hydroxy-cyclohexyl)-29-(hydroxy-norbornyl)-trans-3-bicyclo[3.1.0.]FK520, 9-deoxo-31-desmethoxy-trans-3-bicyclo[3.1.0.]FK520, 9-deoxo-31-desmethoxy-31-cis-hydroxy-32-trans-hydroxy-trans-3-bicyclo[3.1.0.]FK520, 9-deoxo-31-desmethoxy-31-cis-hydroxy-32-cis-hydroxy-trans-3-bicyclo[3.1.0.]FK520, 9-deoxo-31-desmethoxy-31-trans-hydroxy-32-trans-hydroxy-trans-3-bicyclo[3.1.0.]FK520, 9-deoxo-31-O-desmethyl-32-dehydroxy-trans-3-bicyclo[3.1.0.]FK520, 9-deoxo-31-O-desmethyl-trans-3-bicyclo[3.1.0.]FK520, 9-deoxo-31-desmethoxy-31-methyl-trans-3-bicyclo[3.1.0.]FK520, 9-deoxo-31-O-desmethyl-32-dehydroxy-32-methyl-trans-3-bicyclo[3.1.0.]FK520, 9-deoxo-31-O-desmethyl-32-dehydroxy-32-fluoro-trans-3-bicyclo[3.1.0.]FK520, 9-deoxo-31-desmethoxy-31-fluoro-trans-3-bicyclo[3.1.0.]FK520, 9-deoxo-31-O-desmethyl-32-dehydroxy-32-chloro-trans-3-bicyclo[3.1.0.]FK520, 9-deoxo-31-desmethoxy-31-chloro-trans-3-bicyclo[3.1.0.]FK520, 9-deoxo-31-O-desmethyl-32-dehydroxy-32-tert-butyl-trans-3-bicyclo[3.1.0.]FK520, 9-deoxo-29-de(3-methoxy-4-hydroxy-cyclohexyl)-29-(hydroxy-cycloheptyl)-trans-3-bicyclo[3.1.0.]FK520, 9-deoxo-29-de(3-methoxy-4-hydroxy-cyclohexyl)-29-(hydroxy-norbornyl)-trans-3-bicyclo[3.1.0.]FK520, In a more highly preferred embodiment, the present invention provides the following novel FK520 analogues: 31-desmethoxy-31-methyl-FK520, 31-desmethoxy-31-fluoro-FK520, 31-desmethoxy-31-chloro-FK520, 31-O-desmethyl-32-dehydroxy-32-tert-butyl-FK520, 29-de(3-methoxy-4-hydroxy-cyclohexyl)-29-(hydroxy-cycloheptyl)-FK520, 29-de(3-methoxy-4-hydroxy-cyclohexyl)-29-(hydroxy-norbornyl)-FK520, 9-deoxo-31-desmethoxy-31-methyl-FK520, 9-deoxo-31-desmethoxy-31-fluoro-FK520, 9-deoxo-31-desmethoxy-31-chloro-FK520, 9-deoxo-31-O-desmethyl-32-dehydroxy-32-tert-butyl-FK520, 9-deoxo-29-de(3-methoxy-4-hydroxy-cyclohexyl)-29-(hydroxy-cycloheptyl)-FK520, 9-deoxo-29-de(3-methoxy-4-hydroxy-cyclohexyl)-29-(hydroxy-norbornyl)-FK520, 30-desmethoxy-30-methyl-prolyl-FK520, 30-desmethoxy-30-fluoro-prolyl-FK520, 30-desmethoxy-30-chloro-prolyl-FK520, 30-desmethyl-31-dehydroxy-31-tert-butyl-prolyl-FK520, 28-de(3-methoxy-4-hydroxy-cyclohexyl)-28-(hydroxy-cycloheptyl)-FK520, 28-de(3-methoxy-4-hydroxy-cyclohexyl)-28-(hydroxy-norbornyl)-FK520, 8-deoxo-30-desmethoxy-31-hydroxy-prolyl-FK520, 8-deoxo-30-desmethoxy-30-cis-hydroxy-31-trans-hydroxy-prolyl-FK520, 8-deoxo-30-desmethoxy-30-cis-hydroxy-31-cis-hydroxy-prolyl-FK520, 8-deoxo-30-desmethoxy-30-trans-hydroxy-31-trans-hydroxy-prolyl-FK520, 8-deoxo-30-O-desmethyl-prolyl-FK520, 8-deoxo-30-desmethoxy-30-methyl-prolyl-FK520, 8-deoxo-30-O-desmethyl-31-dehydroxy-31-methyl-prolyl-FK520, 8-deoxo-30-O-desmethyl-31-dehydroxy-31-fluoro-prolyl-FK520, 8-deoxo-30-desmethoxy-30-fluoro-prolyl-FK520, 8-deoxo-30-O-desmethyl-31-dehydroxy-31-chloro-prolyl-FK520, 8-deoxo-30-desmethoxy-30-chloro-prolyl-FK520, 8-deoxo-30-O-desmethyl-31-dehydroxy-31-tert-butyl-prolyl-FK520, 8-deoxo-28-de(3-methoxy-4-hydroxy-cyclohexyl)-28-(hydroxy-cycloheptyl)-prolyl-FK520, 8-deoxo-28-de(3-methoxy-4-hydroxy-cyclohexyl)-28-(hydroxy-norbornyl)-prolyl-FK520, 30-desmethoxy-3-hydroxy-prolyl-FK520, 30-desmethoxy-30-cis-hydroxy-31-trans-hydroxy-3-hydroxy-prolyl-FK520, 30-desmethoxy-30-cis-hydroxy-31-cis-hydroxy-3-hydroxy-prolyl-FK520, 30-desmethoxy-30-trans-hydroxy-31-trans-hydroxy-3-hydroxy-prolyl-FK520, 30-O-desmethyl-31-dehydroxy-3-hydroxy-prolyl-FK520, 30-O-desmethyl-3-hydroxy-prolyl-FK520, 30-desmethoxy-30-methyl-3-hydroxy-prolyl-FK520, 30-desmethoxy-31-dehydroxy-31-methyl-3-hydroxy-prolyl-FK520, 30-O-desmethyl-31-dehydroxy-31-fluoro-3-hydroxy-prolyl-FK520, 30-desmethoxy-30-fluoro-3-hydroxy-prolyl-FK520, 30-O-desmethyl-31-dehydroxy-31-chloro-3-hydroxy-prolyl-FK520, 30-desmethoxy-30-chloro-3-hydroxy-prolyl-FK520, 30-O-desmethyl-31-dehydroxy-31-tert-butyl-3-hydroxy-prolyl-FK520, 28-de(3-methoxy-4-hydroxy-cyclohexyl)-28-(hydroxy-cycloheptyl)-3-hydroxy-prolyl-FK520, 28-de(3-methoxy-4-hydroxy-cyclohexyl)-28-(hydroxy-norbornyl)-3-hydroxy-prolyl-FK520, 8-deoxo-30-desmethoxy-31-hydroxy-3-hydroxy-prolyl-FK520, 8-deoxo-30-desmethoxy-30-cis-hydroxy-31-trans-hydroxy-3-hydroxy-prolyl-FK520, 8-deoxo-30-desmethoxy-30-cis-hydroxy-31-cis-hydroxy-3-hydroxy-prolyl-FK520, 8-deoxo-30-desmethoxy-30-trans-hydroxy-31-trans-hydroxy-3-hydroxy-prolyl-FK520, 8-deoxo-30-O-desmethyl-31-dehydroxy-3-hydroxy-prolyl-FK520, 8-deoxo-30-O-desmethyl-3-hydroxy-prolyl-FK520, 8-deoxo-30-desmethoxy-30-methyl-3-hydroxy-prolyl-FK520, 8-deoxo-30-O-desmethyl-31-dehydroxy-31-methyl-3-hydroxy-prolyl-FK520, 8-deoxo-30-O-desmethyl-31-dehydroxy-31-fluoro-3-hydroxy-prolyl-FK520, 8-deoxo-30-desmethoxy-30-fluoro-3-hydroxy-prolyl-FK520, 8-deoxo-30-O-desmethyl-31-dehydroxy-31-chloro-3-hydroxy-prolyl-FK520, 8-deoxo-30-desmethoxy-30-chloro-3-hydroxy-prolyl-FK520, 8-deoxo-30-O-desmethyl-31-dehydroxy-31-tert-butyl-3-hydroxy-prolyl-FK520, 8-deoxo-28-de(3-methoxy-4-hydroxy-cyclohexyl)-28-(hydroxy-cycloheptyl)-3-hydroxy-prolyl-FK520, 8-deoxo-28-de(3-methoxy-4-hydroxy-cyclohexyl)-28-(hydroxy-norbornyl)-3-hydroxy-prolyl-FK520, 30-desmethoxy-4-hydroxy-prolyl-FK520, 30-desmethoxy-30-cis-hydroxy-31-trans-hydroxy-4-hydroxy-prolyl-FK520, 30-desmethoxy-30-cis-hydroxy-31-cis-hydroxy-4-hydroxy-prolyl-FK520, 30-desmethoxy-30-trans-hydroxy-31-trans-hydroxy-4-hydroxy-prolyl-FK520, 30-O-desmethyl-31-dehydroxy-4-hydroxy-prolyl-FK520, 30-O-desmethyl-4-hydroxy-prolyl-FK520, 30-desmethoxy-30-methyl-4-hydroxy-prolyl-FK520, 30-O-desmethyl-31-dehydroxy-31-methyl-4-hydroxy-prolyl-FK520, 30-O-desmethyl-31-dehydroxy-31-fluoro-4-hydroxy-prolyl-FK520, 30-desmethoxy-30-fluoro-4-hydroxy-prolyl-FK520, 30-O-desmethyl-31-dehydroxy-31-chloro-4-hydroxy-prolyl-FK520, 30-desmethoxy-30-chloro-4-hydroxy-prolyl-FK520, 30-O-desmethyl-31-dehydroxy-31-tert-butyl-4-hydroxy-prolyl-FK520, 28-de(3-methoxy-4-hydroxy-cyclohexyl)-28-(hydroxy-cycloheptyl)-4-hydroxy-prolyl-FK520, 28-de(3-methoxy-4- hydroxy-cyclohexyl)-28-(hydroxy-norbornyl)-4-hydroxy-prolyl-FK520, 8-deoxo-30-desmethoxy-31-hydroxy-4-hydroxy-prolyl-FK520, 8-deoxo-30-desmethoxy-30-cis-hydroxy-31-trans-hydroxy-4-hydroxy-prolyl-FK520, 8-deoxo-30-desmethoxy-30-cis-hydroxy-31-cis-hydroxy-4-hydroxy-prolyl-FK520, 8-deoxo-30-desmethoxy-30-trans-hydroxy-31-trans-hydroxy-4-hydroxy-prolyl-FK520, 8-deoxo-30-desmethyl-31-dehydroxy-4-hydroxy-prolyl-FK520, 8-deoxo-30-O-desmethylhydroxy-prolyl-FK520, 8-deoxo-30-desmethoxy-30-methyl-4-hydroxy-prolyl-FK520, 8-deoxo-30-O-desmethyl-31-dehydroxy-31-methyl-4-hydroxy-prolyl-FK520, 8-deoxo-30-desmethyl-31-dehydroxy-31-fluoro-4-hydroxy-prolyl-FK520, 8-deoxo-30-desmethoxy-30-fluoro-4-hydroxy-prolyl-FK520, 8-deoxo-30-O-desmethyl-31-dehydroxy-31-chloro-hydroxy-prolyl-FK520, 8-deoxo-30-desmethoxy-30-chloro-3-hydroxy-4-hydroxy-prolyl-FK520, 8-deoxo-30-O-desmethyl-31-dehydroxy-31-tert-butyl-4-hydroxy-prolyl-FK520, 8-deoxo-28-de(3-methoxy-4-hydroxy-cyclohexyl)-28-(hydroxy-cycloheptyl)-4-hydroxy-prolyl-FK520, 8-deoxo-28-de(3-methoxy-4-hydroxy-cyclohexyl)-28-(hydroxy-norbornyl)-4-hydroxy-prolyl-FK520, 31-desmethoxy-trans-3-bicyclo[3.1.0.]FK520, 31-desmethoxy-31-cis-hydroxy-32-trans-hydroxy-trans-3-bicyclo[3.1.0.]FK520, 31-desmethoxy-31-cis-hydroxy-32-cis-hydroxy-trans-3-bicyclo[3.1.0.]FK520, 31-desmethoxy-31-trans-hydroxy-32-trans-hydroxy-trans-3-bicyclo[3.1.0.]FK520, 31-O-desmethyl-32-dehydroxy-trans-3-bicyclo[3.1.0.]FK520, 31-O-desmethyl-trans-3-bicyclo[3.1.0.]FK520, 31-desmethoxy-31-methyl-trans-3-bicyclo[3.1.0.]FK520, 31-O-desmethyl-32-dehydroxy-32-methyl-trans-3-bicyclo[3.1.0.]FK520, 31-O-desmethyl-32-dehydroxy-32-fluoro-trans-3-bicyclo[3.1.0.]FK520, 31-desmethoxy-31-fluoro-trans-3-bicyclo[3.1.0.]FK520, 31-O-desmethyl-32-dehydroxy-32-chloro-trans-3-bicyclo[3.1.0.]FK520, 31-desmethoxy-31-chloro-trans-3-bicyclo[3.1.0.]FK520, 31-O-desmethyl-32-dehydroxy-32-tert-butyl-trans-3-bicyclo[3.1.0.]FK520, 29-de(3-methoxy-4-hydroxy-cyclohexyl)-29-(hydroxy-cycloheptyl)-trans-3-bicyclo[3.1.0.]FK520, 29-de(3-methoxy-4-hydroxy-cyclohexyl)-29-(hydroxy-norbornyl)-trans-3-bicyclo[3.1.0.]FK520, 9-deoxo-31-desmethoxy-trans-3-bicyclo[3.1.0.]FK520, 9-deoxo-31-desmethoxy-31-cis-hydroxy-32-trans-hydroxy-trans-3-bicyclo[3.1.0.]FK520, 9-deoxo-31-desmethoxy-31-cis-hydroxy-32-cis-hydroxy-trans-3-bicyclo[3.1.0.]FK520, 9-deoxo-31-desmethoxy-31-trans-hydroxy-32-trans-hydroxy-trans-3-bicyclo[3.1.0.]FK520, 9-deoxo-31-O-desmethyl-32-dehydroxy-trans-3-bicyclo[3.1.0.]FK520, 9-deoxo-31-O-desmethyl-trans-3-bicyclo[3.1.0.]FK520, 9-deoxo-31-desmethoxy-31-methyl-trans-3-bicyclo[3.1.0.]FK520, 9-deoxo-31-O-desmethyl-32-dehydroxy-32-methyl-trans-3-bicyclo[3.1.0.]FK520, 9-deoxo-31-O-desmethyl-32-dehydroxy-32-fluoro-trans-3-bicyclo[3.1.0.]FK520, 9-deoxo-31-desmethoxy-31-fluoro-trans-3-bicyclo[3.1.0.]FK520, 9-deoxo-31-O-desmethyl-32-dehydroxy-32-chloro-trans-3-bicyclo[3.1.0.]FK520, 9-deoxo-31-desmethoxy-31-chloro-trans-3-bicyclo[3.1.0.]FK520, 9-deoxo-31-O-desmethyl-32-dehydroxy-32-tert-buty-trans-3-bicyclo[3.1.0.]FK520, 9-deoxo-29-de(3-methoxy-4-hydroxy-cyclohexyl)-29-(hydroxy-cycloheptyl)-trans-3-bicyclo[3.1.0.]FK520, 9-deoxo-29-de(3-methoxy-4-hydroxy-cyclohexyl)-29-(hydroxy-norbornyl)-trans-3-bicyclo[3.1.0.]FK520.

In a further aspect the present invention provides the following FK506 analogues: 31-desmethoxy-FK506, 31-desmethoxy-31-cis-hydroxy-32-trans-hydroxy-FK506, 31-desmethoxy-31-cis-hydroxy-32-cis-hydroxy-FK506, 31-desmethoxy-31-trans-hydroxy-32-trans-hydroxy-FK506, 31-O-desmethyl-32-dehydroxy-FK506, 31-O-desmethyl-FK506, 31-desmethoxy-31-methyl-FK506, 31-O-desmethyl-32-dehydroxy-32-methyl-FK506, 31-O-desmethyl-32-dehydroxy-32-fluoro-FK506, 31-desmethoxy-31-fluoro-FK506, 31-O-desmethyl-32-dehydroxy-32-chloro-FK506, 31-desmethoxy-31-chloro-FK506, 31-O-desmethyl-32-dehydroxy-32-tert-butyl-FK506, 29-de(3-methoxy-4-hydroxy-cyclohexyl)-29-(hydroxy-cycloheptyl)-FK506, 29-de(3-methoxy-4-hydroxy-cyclohexyl)-29-(hydroxy-norbornyl)-FK506, 9-deoxo-31-desmethoxy-FK506, 9-deoxo-31-desmethoxy-31-cis-hydroxy-32-trans-hydroxy-FK506, 9-deoxo-31-desmethoxy-31-cis-hydroxy-32-cis-hydroxy-FK506, 9-deoxo-31-desmethoxy-31-trans-hydroxy-32-trans-hydroxy-FK506, 9-deoxo-31-O-desmethyl-32-dehydroxy-FK506, 9-deoxo-31-O-desmethyl-FK506, 9-deoxo-31-desmethoxy-31-methyl-FK506, 9-deoxo-31-O-desmethyl-32-dehydroxy-32-methyl-FK506, 9-deoxo-31-O-desmethyl-32-dehydroxy-32-fluoro-FK506, 9-deoxo-31-desmethoxy-31-fluoro-FK506, 9-deoxo-31-O-desmethyl-32-dehydroxy-32-chloro-FK506, 9-deoxo-31-desmethoxy-31-chloro-FK506, 9-deoxo-31-O-desmethyl-32-dehydroxy-32-tert-butyl-FK506, 9-deoxo-29-de(3-methoxy-4-hydroxy-cyclohexyl)-29-(hydroxy-cycloheptyl)-FK506, 9-deoxo-29-de(3-methoxy-4-hydroxy-cyclohexyl)-29-(hydroxy-norbornyl)-FK506, 30-desmethoxy-prolyl-FK506, 30-desmethoxy-30-cis-hydroxy-31-trans-hydroxy-prolyl-FK506, 30-desmethoxy-30-cis-hydroxy-31-cis-hydroxy-prolyl-FK506, 30-desmethoxy-30-trans-hydroxy-31-trans-hydroxy-prolyl-FK506, 30-O-desmethyl-31-dehydroxy-prolyl-FK506, 30-O-desmethyl-prolyl-FK506, 30-desmethoxy-30-methyl-prolyl-FK506, 30-O-desmethyl-31-dehydroxy-31-methyl-prolyl-FK506, 30-O-desmethyl-31-dehydroxy-31-fluoro-prolyl-FK506, 30-desmethoxy-30-fluoro-prolyl-FK506, 30-O-desmethyl-31-dehydroxy-31-chloro-prolyl-FK506, 30-desmethoxy-30-chloro-prolyl-FK506, 30-O-desmethyl-31-dehydroxy-31-tert-butyl-prolyl-FK506, 28-de(3-methoxy-4-hydroxy-cyclohexyl)-28-(hydroxy-cycloheptyl)-FK506, 28-de(3-methoxy-4-hydroxy-cyclohexyl)-28-(hydroxy-norbornyl)-FK506, 8-deoxo-30-desmethoxy-31-hydroxy-prolyl-FK506, 8-deoxo-30-desmethoxy-30-cis-hydroxy-31-trans-hydroxy-proyl-FK506, 8-deoxo-30-desmethoxy-30-cis-hydroxy-31-cis-hydroxy-prolyl-FK506, 8-deoxo-30-desmethoxy-30-trans-hydroxy-31-trans-hydroxy-prolyl-FK506, 8-deoxo-30-O-desmethyl-31-dehydroxy-prolyl-FK506, 8-deoxo-30-O-desmethyl-prolyl-FK506, 8-deoxo-30-desmethoxy-30-methyl-prolyl-FK506, 8-deoxo-30-O-desmethyl-31-dehydroxy-31-methyl-prolyl-FK506, 8-deoxo-30-desmethyl-31-dehydroxy-31-fluoro-prolyl-FK506, 8-deoxo-30-desmethoxy-30fluoro-prolyl-FK506, 8-deoxo-30-O-desmethyl-31-dehydroxy-31-chloro-prolyl-FK506, 8-deoxo-30-desmethoxy-30-chloro-prolyl-FK506, 8-deoxo-30-O-desmethyl-31-dehydroxy-31-tert-butyl-prolyl-FK506, 8-deoxo-28-de(3-methoxy-4-hydroxy-cyclohexyl)-28-(hydroxy-cycloheptyl)-prolyl-FK506, 8-deoxo-28-de(3-methoxy-4-hydroxy-cyclohexyl)-28-(hydroxy-norbornyl)-prolyl-FK506, 30-desmethoxy-3-hydroxy-prolyl-FK506, 30-desmethoxy-30-cis-hydroxy-31-trans-hydroxy-3-hydroxy-prolyl-FK506, 30-desmethoxy-30-cis-hydroxy-31-cis-hydroxy-3-hydroxy-prolyl-FK506, 30-desmethoxy-30-trans-hydroxy-31-trans-hydroxy-3-hydroxy-prolyl-FK506, 30-O-desmethyl-31-dehydroxy-3-hydroxy-prolyl-FK506, 30-O-desmethyl-3-hydroxy-prolyl-FK506, 30-desmethoxy-30-methyl-3-hydroxy-prolyl-FK506, 30-O-desmethyl-31-dehydroxy-31-methyl-3-hydroxy-prolyl-FK506, 30-O-desmethyl-31-dehydroxy-31-fluoro-3-hydroxy-prolyl-FK506, 30-desmethoxy-30-fluoro-3-hydroxy-prolyl-FK506, 30-O-desmethyl-31-dehydroxy-31-chloro-3-hydroxy-prolyl-FK506, 30-desmethoxy-30-chloro-3-hydroxy-prolyl-FK506, 30-O-desmethyl-31-dehydroxy-31-tert-butyl-3-hydroxy-prolyl-FK506, 28-de(3-methoxy-4-hydroxy-cyclohexyl)-28-(hydroxy-cycloheptyl)-3-hydroxy-prolyl-FK506, 28-de(3-methoxy-4-hydroxy-cyclohexyl)-28-(hydroxy-norbornyl)-3-hydroxy-prolyl-FK506, 8-deoxo-30-desmethoxy-31-hydroxy-3-hydroxy-prolyl-FK506, 8-deoxo-30-desmethoxy-30-cis-hydroxy-31-trans-hydroxy-3-hydroxy-prolyl-FK506, 8-deoxo-30-desmethoxy-30-cis-hydroxy-31-cis-hydroxy-3-hydroxy-prolyl-FK506, 8-deoxo-30-desmethoxy-30-trans-hydroxy-31-trans-hydroxy-3-hydroxy-prolyl-FK506, 8-deoxo-30-O-desmethyl-31-dehydroxy-3-hydroxy-prolyl-FK506, 8-deoxo-30-O-desmethyl-3-hydroxy-prolyl-FK506, 8-deoxo-30-desmethoxy-30-methyl-3-hydroxy-prolyl-FK506, 8-deoxo-30-O-desmethyl-31-dehydroxy-31-methyl-3-hydroxy-prolyl-FK506, 8-eoxo-30-O-desmethyl-31-dehydroxy-31-fluoro-3-hydroxy-prolyl-FK506, 8-deoxo-30-desmethoxy-30-fluoro-3-hydroxy-prolyl-FK506, 8-deoxo-30-O-desmethyl-31-dehydroxy-31-chloro-3-hydroxy-prolyl-FK506, 8-deoxo-30-desmethoxy-30-chloro-3-hydroxy-3-hydroxy-prolyl-FK506, 8-deoxo-30-O-desmethyl-31-dehydroxy-31-tert-butyl-3-hydroxy-prolyl-FK506, 8-deoxo-28-de(3-methoxy-4-hydroxy-cyclohexyl)-28-(hydroxy-cycloheptyl)-3-hydroxy-prolyl-FK506, 8-deoxo-28-de(3-methoxy-4-hydroxy-cyclohexyl)-28-(hydroxy-norbornyl)-3-hydroxy-prolyl-FK506, 30-desmethoxy-4-hydroxy-prolyl-FK506, 30-desmethoxy-30-cis-hydroxy-31-trans-hydroxy-4-hydroxy-prolyl-FK506, 30-desmethoxy-30-cis-hydroxy-31-cis-hydroxy-4-hydroxy-prolyl-FK506, 30-desmethoxy-30-trans-hydroxy-31-trans-hydroxy-4-hydroxy-prolyl-FK506, 30-O-desmethyl-31-dehydroxy-4-hydroxy-prolyl-FK506, 30-O-desmethyl-4-hydroxy-prolyl-FK506, 30-desmethoxy-30-methyl-4-hydroxy-prolyl-FK506, 30-O-desmethyl-31-dehydroxy-31-methyl-4-hydroxy-prolyl-FK506, 30-O-desmethyl-31-dehydroxy-31-fluoro-4-hydroxy-prolyl-FK506, 30-desmethoxy-30-fluoro-4-hydroxy-prolyl-FK506, 30-O-desmethyl-31-hydroxy-31-chloro-hydroxy-prolyl-FK506, 30-desmethoxy-30-chloro-4-hydroxy-prolyl-FK506, 30-O-desmethyl-31-dehydroxy-31-tert-butyl-4-hydroxy-prolyl-FK506, 28-de(3-methoxy-4-hydroxy-cyclohexyl)-28-(hydroxy-cycloheptyl)-4-hydroxy-prolyl-FK506, 28-de(3-methoxy-4-hydroxy-cyclohexyl)-28-(hydroxy-norbornyl)-4-hydroxy-prolyl-FK506, 8-deoxo-30-desmethoxy-31-hydroxy-4-hydroxy-prolyl-FK506, 8-deoxo-30-desmethoxy-30-cis-hydroxy-31-trans-hydroxy-4-hydroxy-prolyl-FK506, 8-deoxo-30-desmethoxy-30-cis-hydroxy-31-cis-hydroxy-4-hydroxy-prolyl-FK506, 8-deoxo-30-desmethoxy-30-trans-hydroxy-31-trans-hydroxy-4-hydroxy-prolyl-FK506, 8-deoxo-30-O-desmethyl-31-dehydroxy-4-hydroxy-prolyl-FK506, 8-deoxo-30-O-desmethyl-4-hydroxy-prolyl-FK506, 8-deoxo-30-desmethoxy-30-methyl-4-hydroxy-prolyl-FK506, 8-deoxo-30-O-desmethyl-31-dehydroxy-31-methyl-4-hydroxy-prolyl-FK506, 8-deoxo-30-O-desmethyl-31-dehydroxy-31-fluoro-4-hydroxy-prolyl-FK506, 8-deoxo-30-desmethoxy-30-fluoro-4-hydroxy-prolyl-FK506, 8-deoxo-30-O-desmethyl-31-dehydroxy-31-chloro-4-hydroxy-prolyl-FK506, 8-deoxo-30-desmethoxy-30-chloro-3-hydroxy-4-hydroxy-prolyl-FK506, 8-deoxo-30-O-desmethyl-31-dehydroxy-31-tert-butyl-4-hydroxy-prolyl-FK506, 8-deoxo-28-de(3-methoxy-4-hydroxy-cyclohexyl)-28-(hydroxy-cycloheptyl)-4-hydroxy-prolyl-FK506, 8-deoxo-28-de(3-methoxy-4-hydroxy-cyclohexyl)-28-(hydroxy-norbornyl)-4-hydroxy-prolyl-FK506, 31-desmethoxy-trans-3-bicyclo[3.1.0.]FK506, 31-desmethoxy-31-cis-hydroxy-32-trans-hydroxy-trans-3-bicyclo[3.1.0.]FK506, 31-desmethoxy-31-cis-hydroxy-32-cis-hydroxy-trans-3-bicyclo[3.1.0.]FK506, 31-desmethoxy-31-trans-hydroxy-32-trans-hydroxy-trans-3-bicyclo[3.1.0.]FK506, 31-O-desmethyl-32-dehydroxy-trans-3-bicyclo[3.1.0.]FK506, 31-O-desmethyl-trans-3-bicyclo[3.1.0.]FK506, 31-desmethoxy-31-methyl-trans-3-bicyclo[3.1.0.]FK506, 31-O-desmethyl-32-dehydroxy-32-methyl-trans-3-bicyclo[3.1.0.]FK506, 31-O-desmethyl-32-dehydroxy-32-fluoro-trans-3-bicyclo[3.1.0.]FK506, 31-desmethoxy-31-fluoro-trans-3-bicyclo[3.1.0.]FK506, 31-O-desmethyl-32-dehydroxy-32-chloro-trans-3-bicyclo[3.1.0.]FK506, 31-desmethoxy-31-chloro-trans-3-bicyclo[3.1.0.]FK506, 31-O-desmethyl-32-dehydroxy-32-tert-butyl-trans-3-bicyclo[3.1.0.]FK506, 29-de(3-methoxy-4-hydroxy-cyclohexyl)-29-(hydroxy-cycloheptyl)-trans-3-bicyclo[3.1.0.]FK506, 29-de(3-methoxy-4-hydroxy-cyclohexyl)-29-(hydroxy-4-norbornyl)-trans-3-bicyclo[3.1.0.]FK506, 9-deoxo-31-desmethoxy-trans-3-bicyclo[3.1.0.]FK506, 9-deoxo-31-desmethoxy-31-cis-hydroxy-32-trans-hydroxy-trans-3-bicyclo[3.1.0.]FK506, 9-deoxo-31-desmethoxy-31-cis-hydroxy-32-cis-hydroxy-trans-3-bicyclo[3.1.0.]FK506, 9-deoxo-31-desmethoxy-31-trans-hydroxy-32-trans-hydroxy-trans-3-bicyclo[3.1.0.]FK506, 9-deoxo-31-O-desmethyl-32-dehydroxy-trans-3-bicyclo[3.1.0.]FK506, 9-deoxo-31-O-desmethyl-trans-3-bicyclo[3.1.0.]FK506, 9-deoxo-31-desmethoxy-31-methyl-trans-3-bicyclo[3.1.0.]FK506, 9-deoxo-31-O-desmethyl-32-dehydroxy-32-methyl-trans-3-bicyclo[3.1.0.]FK506, 9-deoxo-31-O-desmethyl-32-dehydroxy-32-fluoro-trans-3-bicyclo[3.1.0.]FK506, 9-deoxo-31-desmethoxy-31-fluoro-trans-3-bicyclo[3.1.0.]FK506, 9-deoxo-31-O-desmethyl-32-dehydroxy-32-chloro-trans-3-bicyclo[3.1.0.]FK506, 9-deoxo-31-desmethoxy-31-chloro-trans-3-bicyclo[3.1.0.]FK506, 9-deoxo-31-O-desmethyl-32-dehydroxy-32-tert-butyl-trans-3-bicyclo[3.1.0.]FK506, 9-deoxo-29-de(3-methoxy-4-hydroxy-cyclohexyl)-29-(hydroxy-cycloheptyl)-trans-3-bicyclo[3.1.0.]FK506, 9-deoxo-29-de(3-methoxy-4-hydroxy-cyclohexyl)-29-(hydroxy-norbornyl)-trans-3-bicyclo[3.1.0.]FK506, In a preferred embodiment, the present invention provides the following FK506 analogues: 31-desmethoxy-31-cis-hydroxy-32-trans-hydroxy-FK506, 31-desmethoxy-31-cis-hydroxy-32-cis-hydroxy-FK506, 31-desmethoxy-31-trans-hydroxy-32-trans-hydroxy-FK506, 31-desmethoxy-31-methyl-FK506, 31-O-desmethyl-32-dehydroxy-32-tert-butyl-FK506, 29-de(3-methoxy-4-hydroxy-cyclohexyl)-29-(hydroxy-cycloheptyl)-FK506, 29-de(3-methoxy-4-hydroxy-cyclohexyl)-29-(hydroxy-norbornyl)-FK506, 9-deoxo-31-desmethoxy-31-cis-hydroxy-32-trans-hydroxy-FK506, 9-deoxo-31-desmethoxy-31-cis-hydroxy-32-cis-hydroxy-FK506, 9-deoxo-31-desmethoxy-31-trans-hydroxy-32-trans-hydroxy-FK506, 9-deoxo-31-desmethoxy-31-methyl-FK506, 9-deoxo-31-O-desmethyl-32-dehydroxy-32-tert-butyl-FK506, 9-deoxo-29-de(3-methoxy-4-hydroxy-cyclohexyl)-29-(hydroxy-cycloheptyl)-FK506, 9deoxo-29de(3-methoxy-4-hydroxy-cyclohexyl)-29-(hydroxy-norbornyl)-FK506, 30-desmethoxy-30-cis-hydroxy-31-trans-hydroxy-prolyl-FK506, 30-desmethoxy-30-cis-hydroxy-31-cis-hydroxy-prolyl-FK506, 30-desmethoxy-30-trans-hydroxy-31-trans-hydroxy-prolyl-FK506, 30-desmethoxy-30-methyl-prolyl-FK506, 30-O-desmethyl-31-dehydroxy-31-tert-butyl-prolyl-FK506, 28-de(3-methoxy-4-hydroxy-cyclohexyl)-28-(hydroxy-cycloheptyl)-FK506, 28-de(3-methoxy-4-hydroxy-cyclohexyl)-28-(hydroxy-norbornyl)-FK506, 8-deoxo-30-desmethoxy-30-cis-hydroxy-31-trans-hydroxy-prolyl-FK506, 8-deoxo-30- desmethoxy-30-cis-hydroxy-31-cis-hydroxy-prolyl-FK506, 8-deoxo-30-desmethoxy-30-trans-hydroxy-31-trans-hydroxy-prolyl-FK506, 8-deoxo-30-desmethoxy-30-methyl-prolyl-FK506, 8-deoxo-30-O-desmethyl-31-dehydroxy-31-tert-butyl-prolyl-FK506, 8-deoxo-28-de(3-methoxy-4-hydroxy-cyclohexyl)-28-(hydroxy-cycloheptyl)-prolyl-FK506, 8-deoxo-28-de(3-methoxy-4-hydroxy-cyclohexyl)-28-(hydroxy-norbornyl)-prolyl-FK506, 30-desmethoxy-3-hydroxy-prolyl-FK506, 30-desmethoxy-30-cis-hydroxy-31-trans-hydroxy-3-hydroxy-prolyl-FK506, 30-desmethoxy-30-cis-hydroxy-31-cis-hydroxy-3-hydroxy-prolyl-FK506, 30-desmethoxy-30-trans-hydroxy-31-trans-hydroxy-3-hydroxy-prolyl-FK506, 30-O-desmethyl-31-dehydroxy-3-hydroxy-prolyl-FK506, 30-O-desmethyl-3-hydroxy-prolyl-FK506, 30-desmethoxy-30-methyl-3-hydroxy-prolyl-FK506, 30-O-desmethyl-31-dehydroxy-31-methyl-3-hydroxy-prolyl-FK506, 30-O-desmethyl-31-dehydroxy-31-fluoro-3-hydroxy-prolyl-FK506, 30-desmethoxy-30-fluoro-3-hydroxy-prolyl-FK506, 30-O-desmethyl-31-dehydroxy-31-chloro-3-hydroxy-prolyl-FK506, 30-desmethoxy-30-chloro-3-hydroxy-prolyl-FK506, 30-O-desmethyl-31-dehydroxy-31-tert-butyl-3-hydroxy-prolyl-FK506, 28-de(3-methoxy-4-hydroxy-cyclohexyl)-28-(hydroxy-cycloheptyl)-3-hydroxy-prolyl-FK506, 28-de(3-methoxy-4-hydroxy-cyclohexyl)-28-(hydroxy-norbornyl)-3-hydroxy-prolyl-FK506, 8-deoxo-30-desmethoxy-31-hydroxy-3-hydroxy-prolyl-FK506, 8-deoxo-30-desmethoxy-30-cis-hydroxy-31-trans-hydroxy-3-hydroxy-prolyl-FK506, 8-deoxo-30-desmethoxy-30-cis-hydroxy-31-cis-hydroxy-3-hydroxy-prolyl-FK506, 8-deoxo-30-desmethoxy-30-trans-hydroxy-31-trans-hydroxy-3-hydroxy-prolyl-FK506, 8-deoxo-30-O-desmethyl-31-dehydroxy-3-hydroxy-prolyl-FK506, 8-deoxo-30-O-desmethyl-3-hydroxy-prolyl-FK506, 8-deoxo-30-desmethoxy-30-methyl-3-hydroxy-prolyl-FK506, 8-deoxo-30-O-desmethyl-31-dehydroxy-31-methyl-3-hydroxy-prolyl-FK506, 8-deoxo-30-O-desmethyl-31-dehydroxy-31-fluoro-3-hydroxy-prolyl-FK506, 8-deoxo-30-desmethoxy-30-fluoro-3-hydroxy-prolyl-FK506, 8-deoxo-30-O-desmethyl-31-dehydroxy-31-chloro-3-hydroxy-prolyl-FK506, 8-deoxo-30-desmethoxy-30-chloro-3-hydroxy-3-hydroxy-prolyl-FK506, 8-deoxo-30-O-desmethyl-31-dehydroxy-31-tert-butyl-3-hydroxy-prolyl-FK506, 8-deoxo-28-de(3-methoxy-4-hydroxy-cyclohexyl)-28-(hydroxy-cycloheptyl)-3-hydroxy-prolyl-FK506, 8-deoxo-28-de(3-methoxy-4-hydroxy-cyclohexyl)-28-(hydroxy-norbornyl)-3-hydroxy-prolyl-FK506, 30-desmethoxy-4-hydroxy-prolyl-FK506, 30-desmethoxy-30-cis-hydroxy-31-trans-hydroxy-4-hydroxy-prolyl-FK506, 30-desmethoxy-30-cis-hydroxy-31-cis-hydroxy-4-hydroxy-prolyl-FK506, 30-desmethoxy-30-trans-hydroxy-31-trans-hydroxy-4-hydroxy-prolyl-FK506, 30-O-desmethyl-31-dehydroxy-4-hydroxy-prolyl-FK506, 30-O-desmethyl-hydroxy-prolyl-FK506, 30-desmethoxy-30-methyl-4-hydroxy-prolyl-FK506, 30-O-desmethyl-31-dehydroxy-31-methyl-4-hydroxy-prolyl-FK506, 30-O-desmethyl-31-dehydroxy-31-fluoro-4-hydroxy-prolyl-FK506, 30-desmethoxy-30-fluoro-4-hydroxy-prolyl-FK506, 30-O-desmethyl-31-dehydroxy-31-chloro-4-hydroxy-prolyl-FK506, 30-desmethoxy-30-chloro-4-hydroxy-prolyl-FK506, 30-O-desmethyl-31-dehydroxy-31-tert-butyl-4-hydroxy-prolyl-FK506, 28-de(3-methoxy-4-hydroxy-cyclohexyl)-28-(hydroxy-cycloheptyl)-4-hydroxy-prolyl-FK506, 28-de(3-methoxy-4-hydroxy-cyclohexyl)-28-(hydroxy-norbornyl)-4-hydroxy-prolyl-FK506, 8-deoxo-30-desmethoxy-31-hydroxy-4-hydroxy-prolyl-FK506, 8-deoxo-30-desmethoxy-30-cis-hydroxy-31-trans-hydroxy-4-hydroxy-prolyl-FK506, 8-deoxo-30-desmethoxy-30-cis-hydroxy-31-cis-hydroxy-4-hydroxy-prolyl-FK506, 8-deoxo-30-desmethoxy-30-trans-hydroxy-31-trans-hydroxy-4-hydroxy-prolyl-FK506, 8-deoxo-30-O-desmethyl-31-dehydroxy-4-hydroxy-prolyl-FK506, 8-deoxo-30-O-desmethyl-4-hydroxy-prolyl-FK506, 8-deoxo-30-desmethoxy-30-methyl-4-hydroxy-prolyl-FK506, 8-deoxo-30-O-desmethyl-31-dehydroxy-31-methyl-4-hydroxy-prolyl-FK506, 8-deoxo-30-O-desmethyl-31-dehydroxy-31-fluoro-4-hydroxy-prolyl-FK506, 8-deoxo-30-desmethoxy-30-fluoro-4-hydroxy-prolyl-FK506, 8-deoxo-30-O-desmethyl-31-dehydroxy-31-chloro-4-hydroxy-prolyl-FK506, 8-deoxo-30-desmethoxy-30-chloro-3-hydroxy-4-hydroxy-prolyl-FK506, 8-deoxo-30-O-desmethyl-31-dehydroxy-31-tert-butyl-4-hydroxy-prolyl-FK506, 8-deoxo-28-de(3-methoxy-4-hydroxy-cyclohexyl)-28-(hydroxy-cycloheptyl)-4-hydroxy-prolyl-FK506, 8-deoxo-28-de(3-methoxy-4-hydroxy-cyclohexyl)-28-(hydroxy-norbornyl)-4-hydroxy-prolyl-FK506, 31-desmethoxy-trans-3-bicyclo[3.1.0.]FK506, 31-desmethoxy-31-cis-hydroxy-32-trans-hydroxy-trans-3-bicyclo[3.1.0.]FK506, 31-desmethoxy-31-cis-hydroxy-32-cis-hydroxy-trans-3-bicyclo[3.1.0.]FK506, 31-desmethoxy-31-trans-hydroxy-32-trans-hydroxy-trans-3-bicyclo[3.1.0.]FK506, 31-O-desmethyl-32-dehydroxy-trans-3-bicyclo[3.1.0.]FK506, 31-O-desmethyl-trans-3-bicyclo[3.1.0.]FK506, 31-desmethoxy-31-methyl-trans-3-bicyclo[3.1.0.]FK506, 31-O-desmethyl-32-dehydroxy-32-methyl-trans-3-bicyclo[3.1.0.]FK506, 31-O-desmethyl-32-dehydroxy-32-fluoro-trans-3-bicyclo[3.1.0.]FK506, 31-desmethoxy-31-fluoro-trans-3-bicyclo[3.1.0.]FK506, 31-O-desmethyl-32-dehydroxy-32-chloro-trans-3-bicyclo[3.1.0.]FK506, 31-desmethoxy-31-chloro-trans-3-bicyclo[3.1.0.]FK506, 31-O-desmethyl-32-dehydroxy-32-tert-butyl-trans-3-bicyclo[3.1.0.]FK506, 29-de(3-methoxy-4-hydroxy-cyclohexyl)-29-(hydroxy-cycloheptyl)-trans-3-bicyclo[3.1.0.]FK506, 29-de(3-methoxy-4-hydroxy-cyclohexyl)-29-(hydroxy-norbornyl)-trans-3-bicyclo[3.1.0.]FK506, 9-deoxo-31-desmethoxy-trans-3-bicyclo[3.1.0.]FK506, 9-deoxo-31-desmethoxy-31-cis-hydroxy-32-trans-hydroxy-trans-3-bicyclo[3.1.0.]FK506, 9-deoxo-31-desmethoxy-31-cis-hydroxy-32-cis-hydroxy-trans-3-bicyclo[3.1.0.]FK506, 9-deoxo-31-desmethoxy-31-trans-hydroxy-32-trans-hydroxy-trans-3-bicyclo[3.1.0.]FK506, 9-deoxo-31-O-desmethyl-32-dehydroxy-trans-3-bicyclo[3.1.0.]FK506, 9deoxo-31-O-desmethyl-trans-3-bicyclo[3.1.0.]FK506, 9-deoxo-31-desmethoxy-31-methyl-trans-3-bicyclo[3.1.0.1]FK506, 9-deoxo-31-O-desmethyl-32-dehydroxy-32-methyl-trans-3-bicyclo[3.1.0.]FK506, 9-deoxo-31-O-desmethyl-32-dehydroxy-32-fluoro-trans-3-bicyclo[3.1.0.]FK506, 9-deoxo-31-desmethoxy-31-fluoro-trans-3-bicyclo[3.1.0.]FK506, 9-deoxo-31-O-desmethyl-32-dehydroxy-32-chloro-trans-3-bicyclo[3.1.0.]FK506, 9-deoxo-31-desmethoxy-31-chloro-trans-3-bicyclo[3.1.0.]FK506, 9-deoxo-31-O-desmethyl-32-dehydroxy-32-tert-butyl-trans-3-bicyclo[3.1.0.]FK506, 9-deoxo-29-de(3-methoxy-4-hydroxy-cyclohexyl)-29-(hydroxy-cycloheptyl)-trans-3-bicyclo[3.1.0.]FK506, 9-deoxo-29-de(3-methoxy-4-hydroxy-cyclohexyl)-29-(hydroxy-norbornyl)-trans-3-bicyclo[3.1.0.]FK506.

In a more highly preferred embodiment, the present invention provides the following FK506 analogues: 31-desmethoxy-31-methyl-FK506, 31-O-desmethyl-32-dehydroxy-32-tert-butyl-FK506, 29-de(3-methoxy-4-hydroxy-cyclohexyl)-29-(hydroxy-cycloheptyl)-FK506, 29-de(3-methoxy-4-hydroxy-cyclohexyl)-29-(hydroxy-norbornyl)-FK506, 9-deoxo-31-desmethoxy-31-methyl-FK506, 9-deoxo-31-O-desmethyl-32-dehydroxy-32-tert-butyl-FK506, 9-deoxo-29-de(3-methoxy-4-hydroxy-cyclohexyl)-

29-(hydroxy-cycloheptyl)-FK506, 9-deoxo-29-de(3-methoxy-4-hydroxy-cyclohexyl)-29-(hydroxy-norbornyl)-FK506, 30-desmethoxy-30-methyl-prolyl-FK506, 30-O-desmethyl-31-dehydroxy-31-tert-butyl-prolyl-FK506, 28-de(3-methoxy-4-hydroxy-cyclohexyl)-28-(hydroxy-cycloheptyl)-FK506, 28-de(3-methoxy-4-hydroxy-cyclohexyl)-28-(hydroxy-norbornyl)-FK506, 8-deoxo-30-desmethoxy-30-methyl-prolyl-FK506, 8-deoxo-30-O-desmethyl-31-dehydroxy-31-tert-butyl-prolyl-FK506, 8-deoxo-28-de(3-methoxy-4-hydroxy-cyclohexyl)-28-(hydroxy-cycloheptyl)-prolyl-FK506, 8-deoxo-28-de(3-methoxy-4-hydroxy-cyclohexyl)-28-(hydroxy-norbornyl)-prolyl-FK506, 30-desmethoxy-3-hydroxy-prolyl-FK506, 30-desmethoxy-30-cis-hydroxy-31-trans-hydroxy-3-hydroxy-prolyl-FK506, 30-desmethoxy-30-cis-hydroxy-31-cis-hydroxy-3-hydroxy-prolyl-FK506, 30-desmethoxy-30-trans-hydroxy-31-trans-hydroxy-3-hydroxy-prolyl-FK506, 30-O-desmethyl-31-dehydroxy-3-hydroxy-prolyl-FK506, 30-O-desmethyl-3-hydroxy-prolyl-FK506, 30-desmethoxy-30-methyl-3-hydroxy-prolyl-FK506, 30-O-desmethyl-31-dehydroxy-31-methyl-3-hydroxy-prolyl-FK506, 30-O-desmethyl-31-dehydroxy-31-fluoro-3-hydroxy-prolyl-FK506, 30-desmethoxy-30-fluoro-3-hydroxy-prolyl-FK506, 30-O-desmethyl-31-dehydroxy-31-chloro-3-hydroxy-prolyl-FK506, 30-desmethoxy-30-chloro-3-hydroxy-prolyl-FK506, 30-O-desmethyl-31-dehydroxy-31-tert-butyl-3-hydroxy-prolyl-FK506, 28-de(3-methoxy-4-hydroxy-cyclohexyl)-28-(hydroxy-cycloheptyl)-3-hydroxy-prolyl-FK506, 28-de(3-methoxy-4-hydroxy-cyclohexyl)-28-(hydroxy-norbornyl)-3-hydroxy-prolyl-FK506, 8-deoxo-30-desmethoxy-31-hydroxy-3-hydroxy-prolyl-FK506, 8-deoxo-30-desmethoxy-30-cis-hydroxy-31-trans-hydroxy-3-hydroxy-prolyl-FK506, 8-deoxo-30-desmethoxy-30-cis-hydroxy-31-cis-hydroxy-3-hydroxy-prolyl-FK506, 8-deoxo-30-desmethoxy-30-trans-hydroxy-31-trans-hydroxy-3-hydroxy-prolyl-FK506, 8-deoxo-30-O-desmethyl-31-dehydroxy-3-hydroxy-prolyl-FK506, 8-deoxo-30-O-desmethyl-3-hydroxy-prolyl-FK506, 8-deoxo-30-desmethoxy-30-methyl-3-hydroxy-prolyl-FK506, 8-deoxo-30-O-desmethyl-31-dehydroxy-31-methyl-3-hydroxy-prolyl-FK506, 8-deoxo-30-O-desmethyl-31-dehydroxy-31-fluoro-3-hydroxy-prolyl-FK506, 8-deoxo-30-desmethoxy-30-fluoro-3-hydroxy-prolyl-FK506, 8-deoxo-30-O-desmethyl-31-dehydroxy-31-chloro-3-hydroxy-prolyl-FK506, 8-deoxo-30-desmethoxy-30-chloro-3-hydroxy-3-hydroxy-prolyl-FK506, 8-deoxo-30-O-desmethyl-31-dehydroxy-31-tert-butyl-3-hydroxy-prolyl-FK506, 8-deoxo-28-de(3-methoxy-4-hydroxy-cyclohexyl)-28-(hydroxy-cycloheptyl)-3-hydroxy-prolyl-FK506, 8-deoxo-28-de(3-methoxy-4-hydroxy-cyclohexyl)-28-(hydroxy-norbornyl)-3-hydroxy-prolyl-FK506, 30-desmethoxy-4-hydroxy-prolyl-FK506, 30-desmethoxy-30-cis-hydroxy-31-trans-hydroxy-4-hydroxy-prolyl-FK506, 30-desmethoxy-30-cis-hydroxy-31-cis-hydroxy-4-hydroxy-prolyl-FK506, 30-desmethoxy-30-trans-hydroxy-31-trans-hydroxy-4-hydroxy-prolyl-FK506, 30-O-desmethyl-31-dehydroxy-4-hydroxy-prolyl-FK506, 30-O-desmethyl-4-hydroxy-prolyl-FK506, 30-desmethoxy-30-methyl-4-hydroxy-prolyl-FK506, 30-O-desmethyl-31-dehydroxy-31-methyl-4-hydroxy-prolyl-FK506, 30-O-desmethyl-31-dehydroxy-31-fluoro-4-hydroxy-prolyl-FK506, 30-desmethoxy-30-fluoro-4-hydroxy-prolyl-FK506, 30-O-desmethyl-31-dehydroxy-31-chloro-4-hydroxy-prolyl-FK506, 30-desmethoxy-30-chloro-4-hydroxy-prolyl-FK506, 30-O-desmethyl-31-dehydroxy-31-tert-butyl-4-hydroxy-prolyl-FK506, 28-de(3-methoxy-4-hydroxy-cyclohexyl)-28-(hydroxy-cycloheptyl)-4-hydroxy-prolyl-FK506, 28-de(3-methoxy-4-hydroxy-cyclohexyl)-28-(hydroxy-norbornyl)-4-hydroxy-prolyl-FK506, 8-deoxo-30-desmethoxy-31-hydroxy-4-hydroxy-prolyl-FK506, 8-deoxo-30-desmethoxy-30-cis-hydroxy-31-trans-hydroxy-4-hydroxy-prolyl-FK506, 8-deoxo-30-desmethoxy-30-cis-hydroxy-31-cis-hydroxy-4-hydroxy-prolyl-FK506, 8-deoxo-30-desmethoxy-30-trans-hydroxy-31-trans-hydroxy-4-hydroxy-prolyl-FK506, 8-deoxo-30-desmethyl-31-dehydroxy-4-hydroxy-prolyl-FK506, 8-deoxo-30-O-desmethyl-4-hydroxy-prolyl-FK506, 8-deoxo-30-desmethoxy-30-methyl-4-hydroxy-prolyl-FK506, 8-deoxo-30-O-desmethyl-31-dehydroxy-31-methyl-4-hydroxy-prolyl-FK506, 8-deoxo-30-O-desmethyl-31-dehydroxy-31-fluoro-4-hydroxy-prolyl-FK506, 8-deoxo-30-desmethoxy-30-fluoro-4-hydroxy-prolyl-FK506, 8-deoxo-30-O-desmethyl-31-dehydroxy-31-chloro-4-hydroxy-prolyl-FK506, 8-deoxo-30-desmethoxy-30-chloro-3-hydroxy-4-hydroxy-prolyl-FK506, 8-deoxo-30-O-desmethyl-3-dehydroxy-31-tert-butyl-4-hydroxy-prolyl-FK506, 8-deoxo-28-de(3-methoxy-4-hydroxy-cyclohexyl)-28-(hydroxy-cycloheptyl)-4-hydroxy-prolyl-FK506, 8-deoxo-28-de(3-methoxy-4-hydroxy-cyclohexyl)-28-(hydroxy-norbornyl)-4-hydroxy-prolyl-FK506, 31-desmethoxy-trans-3-bicyclo[3.1.0.]FK506, 31-desmethoxy-31-cis-hydroxy-32-trans-hydroxy-trans-3-bicyclo[3.1.0.]FK.506, 31-desmethoxy-31-cis-hydroxy-32-cis-hydroxy-trans-3-bicyclo[3.1.0.]FK506, 31-desmethoxy-31-trans-hydroxy-32-trans-hydroxy-trans-3-bicyclo[3.1.0.]FK506, 31-O-desmethyl-32-dehydroxy-trans-3-bicyclo[3.1.0.]FK506, 31-O-desmethyl-trans-3-bicyclo[3.1.0.]FK506, 31-desmethoxy-31-methyl-trans-3-bicyclo[3.1.0.]FK506, 31-O-desmethyl-32-dehydroxy-32-methyl-trans-3-bicyclo[3.1.0.]FK506, 31-O-desmethyl-32-dehydroxy-32-fluoro-trans-3-bicyclo[3.1.0.]FK506, 31-desmethoxy-31-fluoro-trans-3-bicyclo[3.1.0.]FK506, 31-O-desmethyl-32-dehydroxy-32-chloro-trans-3-bicyclo[3.1.0.]FK506, 31-desmethoxy-31-chloro-trans-3-bicyclo[3.1.0.]FK506, 31-O-desmethyl-32-dehydroxy-32-tert-butyl-trans-3-bicyclo[3.1.0.]FK506, 29-de(3-methoxy-4-hydroxy-cyclohexyl)-29-(hydroxy-cycloheptyl)-trans-3-bicyclo[3.1.0.]FK506, 29-de(3-methoxy-4-hydroxy-cyclohexyl)-29-(hydroxy-norbornyl)-trans-3-bicyclo[3.1.0.]FK506, 9-deoxo-31-desmethoxy-trans-3-bicyclo[3.1.0.]FK506, 9-deoxo-31-desmethoxy-31-cis-hydroxy-32-trans-hydroxy-trans-3-bicyclo[3.1.0.]FK506, 9-deoxo-31-desmethoxy-31-cis-hydroxy-32-cis-hydroxy-trans-3-bicyclo[3.1.0.]FK506, 9-deoxo-31-desmethoxy-31-trans-hydroxy-32-trans-hydroxy-trans-3-bicyclo[3.1.0.]FK506, 9-deoxo-31-O-desmethyl-32-dehydroxy-trans-3-bicyclo[3.1.0.]FK506, 9-deoxo-31-O-desmethyl-trans-3-bicyclo[3.1.0.]FK506, 9-deoxo-31-desmethoxy-31-methyl-trans3-bicyclo[3.1.0.]FK506, 9-deoxo-31-O-desmethyl-32-dehydroxy-32-methyl-trans-3-bicyclo[3.1.0.]FK506, 9-deoxo-31-O-desmethyl-32-dehydroxy-32-fluoro-trans-3-bicyclo[3.1.0.]FK506, 9-deoxo-31-desmethoxy-31-fluoro-trans-3-bicyclo[3.1.0.]FK506, 9-deoxo-31-O-desmethyl-32-dehydroxy-32-chloro-trans-3-bicyclo[3.1.0.]FK506, 9-deoxo-31-desmethoxy-31-chloro-trans-3-bicyclo[3.1.0.]FK506, 9-deoxo-31-O-desmethyl-32-dehydroxy-32-tert-butyl-trans-3-bicyclo[3.1.0.]FK506, 9-deoxo-29-de(3-methoxy-4-hydroxy-cyclohexyl)-29-(hydroxy-cycloheptyl)-trans-3-bicyclo[3.1.0.]FK506, 9-deoxo-29-de(3-methoxy-4-hydroxy-cyclohexyl)-29-hydroxy-norbornyl)-trans-3-bicyclo[3.1.0.]FK506.

In further aspects the invention provides:

A: Compounds of the formula:

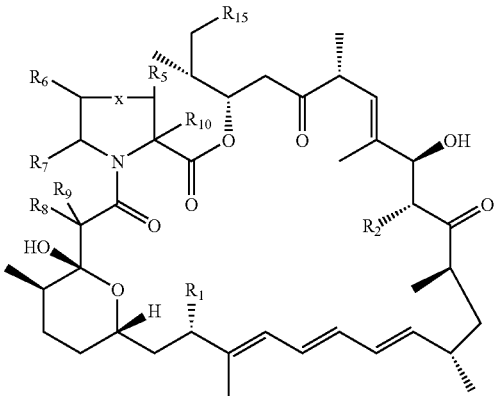

where:
x=bond or $CHR_{11}$, or —$CHR_6$-x-$CHR_5$— is

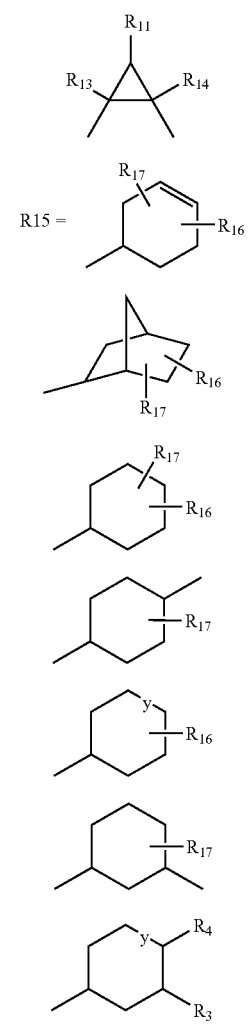

$R_1$=OH, $OCH_3$
$R_2$=H, OH, $OCH_3$
$R_3$=H, OH, $CH_3$, F, Cl, $OCH_3$
$R_4$=H, OH, $CH_3$, F, Cl
$R_5$=H, OH
$R_6$=H, OH
$R_7$=H
$R_8$=H, keto
$R_9$=H, keto
$R_{10}$=H
$R_{11}$=H
$R_{13}$=H
$R_{14}$=H
$R_{16}$=OH, $OCH_3$
$R_{17}$=H, OH, Cl, F and
y=bond, $CH_2$ with the proviso that the compounds do not include the following:

i) where $R_1$=$OCH_3$ in combination with $R_2$=H, $R_{15}$=C, $R_{16}$=cis-3-OH, $R_{17}$=trans-4-OH, $R_5$=H, $R_6$=H, $R_7$=H, $R_8$=H, $R_9$=H, $R_{10}$=H, $R_{11}$=H, x=$CHR_{11}$;

ii) where $R_1$=OH in combination with $R_2$=$OCH_3$, $R_{15}$=C, $R_{16}$=cis-3-OH, $R_{17}$=trans-4-OH, $R_5$=H, $R_6$=H, $R_7$=H, $R_8$,$R_9$=keto, $R_{10}$=H $R_{11}$=H, x=$CHR_{11}$;

iii) where $R_1$=OH in combination with $R_2$=OH, $R_{15}$=C, R16=cis-3-$OCH_3$, $R_{17}$=trans-4-OH, $R_5$=H, $R_6$=H, $R_7$=H, $R_8$,$R_9$=keto, $R_{10}$=H, $R_{11}$=H, x=$CHR_{11}$;

iv) where $R_1$=OH in combination with $R_2$=H, $R_{15}$=C, $R_{16}$=cis-3-$OCH_3$, $R_{17}$=trans-4-OH, $R_5$=H, $R_6$=H, $R_7$=H, $R_8$,$R_9$=keto, $R_{10}$=H, $R_{11}$=H, x=$CHR_{11}$;

v) where $R_1$=$OCH_3$ in combination with $R_2$=H, $R_{15}$=C, $R_{16}$=cis-3-OH, $R_{17}$=trans-4-OH, $R_5$=H, $R_6$=H, $R_7$=H, $R_8$,$R_9$=keto, $R_{10}$=H, $R_{11}$=H, x=$CHR_{11}$;

vi) where $R_1$=$OCH_3$ in combination with $R_2$=H, $R_{15}$=C, $R_{16}$=cis-3-$OCH_3$, $R_{17}$=trans-4-OH, $R_5$=H, $R_6$=H, $R_7$=H, $R_8$=H, $R_9$=H, $R_{10}$=H, $R_{11}$=H, x=$CHR_{11}$;

vii) except where $R_1$=$OCH_3$ in combination with $R_2$=OH, $R_{15}$=C, $R_{16}$=cis-3-$OCH_3$, $R_{17}$=trans-4-OH, $R_5$=H, $R_6$=H, $R_7$=H, $R_8$=H, $R_9$=H, $R_{10}$=H, $R_{11}$=H, x=$CHR_{11}$;

viii) where $R_1$=$OCH_3$ in combination with $R_2$=$OCH_3$, $R_{15}$=C, $R_{16}$=cis-3-$OCH_3$, $R_{17}$=trans-4-OH, $R_5$=H, $R_6$=H, $R_7$=H, $R_8$=H, $R_9$=H, $R_{10}$=H, $R_{11}$=H, x=$CHR_{11}$;

ix) where $R_1$=OH in combination with $R_2$=$OCH_3$, $R_{15}$=C, $R_{16}$=cis-3-$OCH_3$, $R_{17}$=trans-4-OH, $R_5$=H, $R_6$=H, $R_7$=H, $R_8$,$R_9$=keto, $R_{10}$=H, $R_{11}$=H, x=$CHR_{11}$;

x) where $R_1$=$OCH_3$ in combination with $R_2$=OH, $R_{15}$=C, $R_{16}$=cis-3-$OCH_3$, $R_{17}$=trans-4-OH, $R_5$=H, $R_6$=H, $R_7$=H, $R_8$,$R_9$=keto, $R_{10}$=H, $R_{11}$=H, x=$CHR_{11}$;

xi) where $R_1$=$OCH_3$ in combination with $R_2$=H, $R_{15}$=C, $R_{16}$=cis-3-$OCH_3$, $R_{17}$=trans-4-OH, $R_5$=H, $R_6$=H, $R_7$=H, $R_8$,$R_9$=keto, $R_{10}$=H, $R_{11}$=H, x=$CHR_{11}$;

xii) where $R_1$=$OCH_3$ in combination with $R_2$=$OCH_3$, $R_{15}$=C, $R_{16}$=cis-3-OH, $R_{17}$=trans-4-OH, $R_5$=H, $R_6$=H, $R_7$=H, $R_8$,$R_9$=keto, $R_{10}$=H, $R_{11}$=H, x=$CHR_{11}$;

xiii) where $R_1$=$OCH_3$ in combination with $R_2$=H, $R_{15}$=C, $R_{16}$=cis-3-$OCH_3$, $R_{17}$=trans-4-OH, $R_5$=H, $R_6$=H, $R_7$=H, $R_8$=H, $R_9$=H, $R_{10}$=H, x=bond;

xiv) where $R_1$=OCH$_3$ in combination with $R_2$=OCH$_3$, $R_{15}$=C, $R_{16}$=cis-3-OCH$_3$, $R_{17}$=trans-4-OH, $R_5$=H, $R_6$=H, $R_7$=H, $R_8$=H, $R_9$=H, $R_{10}$=H, x=bond;

xv) where $R_1$=OCH$_3$ in combination with $R_2$=OH, $R_{15}$=C, $R_{16}$=cis-3-OCH$_3$, $R_{17}$=trans-4-OH, $R_5$=H, $R_6$=H, $R_7$=H, $R_8,R_9$=keto, $R_{10}$=H, x=bond;

xvi) where $R_1$=OCH$_3$ in combination with $R_2$=H, $R_{15}$=C, $R_{16}$=cis-3-OCH$_3$, $R_{17}$=trans-4-OH, $R_5$=H, $R_6$=H, $R_7$=H, $R_8,R_9$=keto, $R_{10}$=H, x=bond;

xvii) where $R_1$=OCH$_3$ in combination with $R_2$=OCH$_3$, $R_{15}$=C, $R_{16}$=H, $R_{17}$=OH, $R_5$=H, $R_6$=H, $R_7$=H, $R_8,R_9$=keto, $R_{10}$=H, $R_{11}$=H, x=CHR$_{11}$;

xviii) where —CHR$_6$-x-CHR$_5$— is

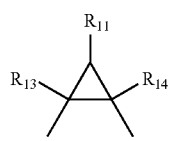

and $R_{11}$=H, $R_{13}$=H, $R_{14}$=H, in combination with $R_1$=OCH$_3$, $R_2$=OCH$_3$, $R_{15}$=C, $R_{16}$=cis-3OCH$_3$, $R_{17}$=trans-4-OH, $R_7$=H, $R_8$, $R_9$=keto, $R_{10}$=H;

xix) where $R_{15}$=G, $R_{16}$=cis-3-OCH$_3$, $R_{17}$=trans-4-OH, y=bond, in combination with $R_1$=OCH$_3$, $R_2$=H, $R_5$=H, $R_6$=OH, $R_7$=H, $R_{11}$=H, x=bond, $R_8,R_9$=keto, $R_{10}$=H xx) where $R_{15}$=G, $R_3$=H, $R_4$=trans-OH, y=bond, in combination with $R_1$=OCH$_3$, $R_2$=OCH$_3$, $R_5$=H, $R_6$=H, $R_7$=H, $R_{11}$=H, x=CHR$_{11}$, $R_8$, $R_9$=keto, $R_{10}$=H xxi) where $R_{15}$=G, $R_3$=H, $R_4$=OH, y=CH$_2$ in combination with $R_1$=OCH$_3$, $R_2$=OCH$_3$, $R_5$=H, $R_6$=H, $R_7$=H, $R_{11}$=H, x=CHR$_{11}$, $R_8,R_9$=keto, $R_{10}$=H xxii) where $R_{15}$=G, $R_3$=cis-OH, $R_4$=H, y=bond, in combination with $R_1$=OCH$_3$, $R_2$=OCH$_3$, $R_5$=H, $R_6$=H, $R_7$=H, $R_{11}$=H, x=CHR$_{11}$, $R_8,R_9$=keto, $R_{10}$=H xxiii) where $R_{15}$=G, $R_3$=CH$_3$, $R_4$=OH, y=bond, in combination with $R_1$=OCH$_3$, $R_2$=OCH$_3$, $R_5$=H, $R_6$=H, $R_7$=H, $R_{11}$=H, x=CHR$_{11}$, $R_8,R_9$=keto, $R_{10}$=H xxiv) where $R_{15}$=G, $R_3$=H, $R_4$=OH, y=CH$_2$, in combination with $R_1$=OH, $R_2$=OH, $R_5$=H, $R_6$=H, $R_7$=H, $R_{11}$=H, x=CHR$_{11}$, $R_8$=$R_9$=H, $R_{10}$=H xxv) where $R_{15}$=G, $R_3$=H, $R_4$=OH, y=CH$_2$, in combination with $R_1$=OCH$_3$, $R_2$=OCH$_3$, $R_5$=H, $R_6$=H, $R_7$=H, $R_{11}$=H, x=CHR$_{11}$, $R_8$=$R_9$=H, $R_{10}$=H xxvi) where $R_{15}$=G, $R_3$=H, $R_4$=OH, y=CH$_2$, in combination with $R_1$=OH, $R_2$=OCH$_3$, $R_5$=H, $R_6$=H, $R_7$=H, $R_{11}$=H, x=CHR$_{11}$, $R_8$=$R_9$=H, $R_{10}$=H xxvii) where $R_{15}$=G, $R_3$=H, $R_4$=OH, y=CH$_2$, in combination with $R_1$=OH, $R_2$=H, $R_5$=H, $R_6$=H, $R_7$=H, $R_{11}$=H, x=CHR$_{11}$, $R_8$=$R_9$=H, $R_{10}$=H;

xxviii) where $R_{15}$=G, $R_3$=H, $R_4$=OH, y=CH$_2$, in combination with $R_1$=OH, $R_2$=OCH$_3$, $R_5$=H, $R_6$=H, $R_7$=H, $R_{11}$=H, x=CHR$_{11}$, $R_8,R_9$=keto, $R_{10}$=H xxix) where $R_{15}$=G, $R_3$=H, $R_4$=OH, y=CH$_2$, in combination with $R_1$=OCH$_3$, $R_2$=H, $R_5$=H, $R_6$=H, $R_7$=H, $R_{11}$=H, x=CHR$_{11}$, $R_8,R_9$=keto, $R_{19}$=H B. Compounds according to the formula below

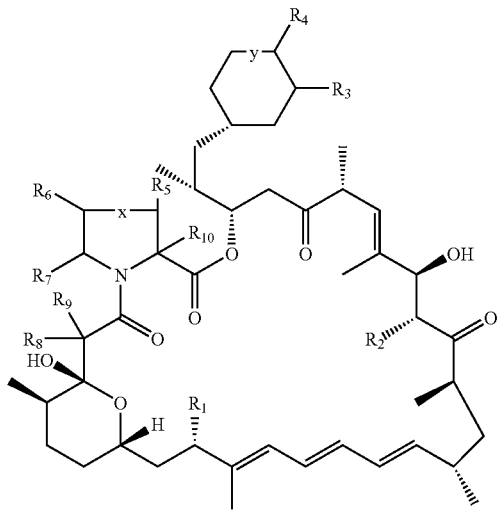

where
$R_1$=OH, OCH$_3$
$R_2$=H, OH, OCH$_3$
$R_3$=H, OH, CH$_3$, OCH$_3$
$R_4$=H, OH
$R_5$=H
$R_6$=H, OH
$R_7$=H
$R_8$=H, keto
$R_9$=H, keto
$R_{10}$=H
x=bond, CH$_2$ or —CHR$_5$-x-CHR$_5$— is

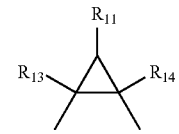

$R_{11}$=H
$R_{13}$=H
$R_{14}$=H
y=bond, CH$_2$ with the proviso that the compounds do not include the following:
 i) where $R_3$=H, $R_4$=trans-OH, y=bond, in combination with $R_1$=OCH$_3$, $R_2$=OCH$_3$, $R_5$=H, $R_6$=H, $R_7$=H, x=CH$_2$, $R_8,R_9$=keto, $R_{10}$=H
 ii) where $R_3$=H, $R_4$=OH, y=CH$_2$ in combination with $R_1$=OCH$_3$, $R_2$=OCH$_3$, $R_5$=H, $R_6$=H, $R_7$=H, x=CH$_2$, $R_8,R_9$=keto, $R_{10}$=H
 iii) where $R_3$=cis-OH, $R_4$=H, y=bond, in combination with $R_1$=OCH$_3$, $R_2$=OCH$_3$, $R_5$=H, $R_6$=H, $R_7$=H, x=CH$_2$, $R_8,R_9$=keto, $R_{10}$=H
 iv) where $R_3$=CH$_3$, $R_4$=OH, y=bond, in combination with $R_1$=OCH$_3$, $R_2$=OCH$_3$, $R_5$=H, $R_6$=H, $R_7\alpha$H, x=CH$_2$, $R_8,R_9$=keto, $R_{10}$=H
 v) where $R_3$=H, $R_4$=OH, y=CH$_2$, in combination with $R_1$=OH, $R_2$=OH, $R_5$=H, $R_6$=H, $R_7$=H, x=CH$_2$, $R_8$=$R_9$=H, $R_{10}$=H vi) where $R_3$=H, $R_4$=OH, y=$CH_2$, in combination with $R_1$=$OCH_3$, $R_2$=$OCH_3$, $R_5$=H, $R_6$=H, $R_7$=H, x=$CH_2$, $R_8$=$R_9$=H, $R_{10}$=H vii) where $R_3$=H, $R_4$=OH, y=$CH_2$, in combination with $R_1$=OH, $R_2$=$OCH_3$, $R_5$=H, $R_6$=H, $R_7$=H, x=$CH_2$, $R_8$=$R_9$=H, $R_{10}$=H viii) where $R_3$=H, $R_4$=OH, y=$CH_2$, in combination with $R_1$=OH, $R_2$=H, $R_5$=H, $R_6$=H, $R_7$=H, x=$CH_2$, $R_8$=$R_9$=H, $R_{10}$=H;

ix) where $R_3$=H, $R_4$=OH, y=$CH_2$, in combination with $R_1$=OH, $R_2$=$OCH_3$, $R_5$=H, $R_6$=H, $R_7$=H, x=$CH_2$, $R_8$,$R_9$=keto, $R_{10}$=H x) where $R_3$=H, $R_4$=OH, y=$CH_2$, in combination with $R_1$=$OCH_3$, $R_2$=H, $R_5$=H, $R_6$=H, $R_7$=H, x=$CH_2$, $R_8$,$R_9$=keto, $R_{10}$=H xi) where $R_3$=$OCH_3$, $R_4$=OH, y=bond, in combination with $R_1$=$OCH_3$, $R_2$=H, $R_5$=H, $R_6$=OH, $R_7$=H, x=bond, $R_8$, $R_9$=keto, $R_{10}$=H xii) where —$CHR_6$-x-$CHR_5$— is

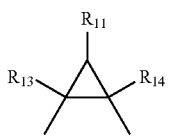

and $R_{11}$=H, $R_{13}$=H, $R_{14}$=H, in combination with $R_1$=$OCH_3$, $R_2$=$OCH_3$, $R_3$=$OCH_3$, $R_4$=OH, $R_7$=H, $R_8$,$R_9$=keto, $R_{10}$=H xiii) where $R_1$=$OCH_3$ in combination with $R_2$=H, $R_3$=$OCH_3$, $R_4$=OH, $R_5$=H, $R_6$=H, $R_7$=H, $R_8$=H, $R_9$=H, $R_{10}$=H, x=bond, y=bond xiv) where $R_1$=$OCH_3$ in combination with $R_2$=$OCH_3$, $R_3$=$OCH_3$, $R_4$=OH, $R_5$=H, $R_6$=H, $R_7$=H, $R_8$=H, $R_9$=H, $R_{10}$=H, x=bond, y=bond xv) where $R_1$=$OCH_3$ in combination with $R_2$=OH, $R_3$=$OCH_3$, $R_4$=OH, $R_5$=H, $R_6$=H, $R_7$=H, $R_8$,$R_9$=keto, $R_{10}$=H, x=bond, y=bond xvi) where $R_1$=$OCH_3$ in combination with $R_2$=H, $R_3$=$OCH_3$, $R_4$=OH, $R_5$=H, $R_6$=H, $R_7$=H, $R_8$,$R_9$=keto, $R_{10}$=H, x=bond, y=bond xvii) where $R_1$=$OCH_3$, $R_2$=H, $R_3$=OH, $R_4$=OH, $R_8$=H, $R_9$=H xviii) where $R_1$=$OCH_3$, $R_2$=H, $R_3$=$OCH_3$, $R_4$=OH, $R_8$=H, $R_9$=H xix) where $R_1$=$OCH_3$, $R_2$=H, $R_3$=OH, $R_4$=OH, $R_8$,$R_9$=keto xx) where $R_1$=OH, $R_2$=OH, $R_3$=$OCH_3$, $R_4$=OH, $R_8$,$R_9$=keto xxi) where $R_1$=$OCH_3$, $R_2$=$OCH_3$, $R_3$=OH, $R_4$=OH, $R_8$,$R_9$=keto xxii) where $R_1$=$OCH_3$, $R_2$=OH, $R_3$=$OCH_3$, $R_4$=OH, $R_8$,$R_9$=keto xxiii) where $R_1$=$OCH_3$, $R_2$=$OCH_3$, $R_3$=$OCH_3$, $R_4$=OH, $R_8$=H, $R_9$=H C. A compound selected from the group consisting of: 9-deoxo-16-O-desmethyl-27-desmethoxy-39-O-desmethyl-rapamycin (prerapamycin), 9-deoxo-16-O-desmethyl-27-O-desmethyl-39-O-desmethyl-rapamycin, 16-O-desmethyl-27-desmethoxy-39-O-desmethyl-rapamycin, 9-deoxo-16-O-desmethyl-39-O-desmethyl-rapamycin, 9-deoxo-16-O-desmethyl-27-desmethoxy-rapamycin, 16-O-desmethyl-27-O-desmethyl-39-O-desmethyl-rapamycin, 9-deoxo-27-O-desmethyl-39-O-desmethyl-rapamycin, 9-deoxo-16-O-desmethyl-27-O-desmethyl-rapamycin, 27-desmethyl-39-O-desmethyl-rapamycin , 9-deoxo-16-O-desmethyl-rapamycin, 9-deoxo-39-O-desmethyl-rapamycin, 8-deoxo-15-O-desmethyl-26-desmethoxy-38-O-desmethyl-prolylrapamycin (pre-prolylrapamycin), 8-deoxo-15-O-desmethyl-26-O-desmethyl-38-O-desmethyl-prolylrapamycin, 15-O-desmethyl-26-desmethoxy-38-O-desmethyl-prolylrapamycin, 8-deoxo-26-desmethoxy-38-O-desmethyl-prolylrapamycin, 8-deoxo-15-O-desmethyl-38-O-desmethyl-prolylrapamycin, 8-deoxo-15-O-desmethyl-26-desmethoxy-prolylrapamycin, 15-O-desmethyl-26-O-desmethyl-38-O-desmethyl-prolylrapamycin, 8-deoxo-26-O-desmethyl-38-O-desmethyl-prolylrapamycin, 8-deoxo-15-O-desmethyl-26-O-desmethyl-prolylrapamycin, 15-O-desmethyl-38-O-desmethyl-prolylrapamycin, 15-O-desmethyl-26-O-desmethyl-prolylrapamycin, 15-O-desmethyl-26-desmethoxy-prolylrapamycin, 26-desmethoxy-38-O-desmethyl-prolylrapamycin, 26-O-desmethyl-38-O-desmethyl-prolylrapamycin, 8-deoxo-15-O-desmethyl-prolylrapamycin, 8-deoxo-26-O-desmethyl-prolylrapamycin, 8-deoxo-38-O-desmethyl-prolylrapamycin, 15-O-desmethyl-prolylrapamycin, 38-O-desmethyl-prolylrapamycin, 9-deoxo-16-O-desmethyl-27-desmethoxy-39-desmethoxy-rapamycin, 9-deoxo-16-O-desmethyl-27-O-desmethyl-39-desmethoxy-rapamycin, 16-O-desmethyl-27-desmethoxy-39-desmethoxy-rapamycin, 9-deoxo-27-desmethoxy-39-desmethoxy-rapamycin, 9-deoxo-16-O-desmethyl39-desmethoxy-rapamycin, 16-O-desmethyl-27-O-desmethyl-39-desmethoxy-rapamycin, 9-deoxo-27-O-desmethyl-39-desmethoxy-rapamycin, 16-O-desmethyl-39-desmethoxy-rapamycin, 27-desmethoxy-39-desmethoxy-rapamycin, 27-O-desmethyl-39-desmethoxy-rapamycin, 9-deoxo-39-desmethoxy-rapamycin, 8-deoxo-15-O-desmethyl-26-desmethoxy-38-desmethoxy-prolylrapamycin, 8-deoxo-15-O-desmethyl-26-O-desmethyl-38-desmethoxy-prolylrapamycin, 15-O-desmethyl-26-desmethoxy-38-desmethoxy-prolylrapamycin, 8-deoxo-26-desmethoxy-38-desmethoxy-prolylrapamycin, 8-deoxo-15-O-desmethyl-38-desmethoxy-prolylrapamycin, 15-O-desmethyl-26-O-desmethyl-38-desmethoxy-prolylrapamycin, 8-deoxo-26-O-desmethyl-38-desmethoxy-prolylrapamycin, 15-O-desmethyl-38-desmethoxy-prolylrapamycin, 26-desmethoxy-38-desmethoxy-prolylrapamycin, 26-O-desmethyl-38-desmethoxy-prolylrapamycin, 8-deoxo-38-desmethoxy-prolylrapamycin, 38-desmethoxy-prolylrapamycin, 9-deoxo-16-O-desmethyl-27-desmethoxy-36-de(3-cis-methoxy-4-trans-hydroxycyclohexyl)-36-(hydroxycyclohexenyl)rapamycin, 9-deoxo-16-O-desmethyl-27-desmethoxy-36-de(3-cis-methoxytrans-hydroxycyclohexyl)-36-(dihydroxy cyclohexyl)rapamycin, 9-deoxo-16-O-desmethyl-27-desmethoxy-36-de(3-cis-methoxy-4-trans-hydroxycyclohexyl)-36-(hydroxynorbornyl)rapamycin, 9-deoxo-16-O-desmethyl-27-desmethoxy-36-de(3-cis-methoxy-4-trans-hydroxycyclohexyl)-36-(3-methyl-4-hydroxycyclohexyl)rapamycin, 9-deoxo-16-O-desmethyl-27-desmethoxy-36-de(3-cis-methoxy-4-trans-hydroxycyclohexyl)-36-(4-methyl hydroxycyclohexyl) rapamycin, 9-deoxo-16-O-desmethyl-27-desmethoxy-36-de(3-cis-methoxy-4-trans-hydroxycyclohexyl)-36-(3-fluoro-4-hydroxycyclohexyl)rapamycin, 9-deoxo-16-O-desmethyl-27-desmethoxy-36-de(3-cis-methoxy-4-trans-hydroxycyclohexyl)-36-(3-hydroxy-4-fluorocyclohexyl) rapamycin, 9-deoxo-16-O-desmethyl-27-desmethoxy-36-de(3-cis-methoxy-4-trans-hydroxycyclohexyl)-36-(3-chloro-4-hydroxycyclohexyl)rapamycin, 9-deoxo-16-O-desmethyl-27-desmethoxy-36-de(3-cis-methoxy-4-trans-hydroxycyclohexyl)-36-(3-hydroxy-4-chlorocyclohexyl)

rapamycin, 9-deoxo-16-O-desmethyl-27-desmethoxy-36-de(3-cis-methoxy-4-trans-hydroxycyclohexyl)-36-(3-cis-4-cis-dihydroxycyclohexyl)rapamycin, 9-deoxo-16-O-desmethyl-27-desmethoxy-36-de(3-cis-methoxy-4-trans-hydroxycyclohexyl)-36-(3-trans-4-trans-dihydroxycyclohexyl)rapamycin, 9-deoxo-16-O-desmethyl-27-O-desmethyl-39-O-desmethyl rapamycin, 9-deoxo-16-O-desmethyl-27O-desmethyl-36-de(3-cis-methoxy-4-trans-hydroxycyclohexyl)-36-(hydroxycyclohexenyl)rapamycin, 9-deoxo-16-O-desmethyl-27-O-desmethyl-36-de(3-cis-methoxy-4-trans-hydroxycyclohexyl)-36-(hydroxynor-bornyl)rapamycin, 9-deoxo-16-O-desmethyl-27-O-desmethyl-36-de(3-cis-methoxy-4-trans-hydroxycyclohexyl)-36-(4-methyl hydroxycyclohexyl)rapamycin.

In a specific embodiment the present invention describes methods to produce and optionally-isolate the following compounds (FIG. 10, FIG. 11, FIG. 12, FIG. 13, and FIGS. 14, 15, 16 and FIG. 17):

TABLE II

| Compound no: | Name: |
|---|---|
| 1. | 9-deoxo-16-O-desmethyl-27-desmethoxy-39-O-desmethyl-rapamycin (prerapamycin) |
| 2. | 9-deoxo-16-O-desmethyl-27-O-desmethyl-39-O-desmethyl-rapamycin |
| 3. | 16-O-desmethyl-27-desmethoxy-39-O-desmethyl-rapamycin |
| 4. | 9-deoxo-27-desmethoxy-39-O-desmethyl-rapamycin |
| 5. | 9-deoxo-16-O-desmethyl-39-O-desmethyl-rapamycin |
| 6. | 9-deoxo-16-O-desmethyl-27-desmethoxy-rapamycin |
| 7. | 16-O-desmethyl-27-O-desmethyl-39-O-desmethyl-rapamycin |
| 8. | 9-deoxo-27-O-desmethyl-39-O-desmethyl-rapamycin |
| 9. | 9-deoxo-16-O-desmethyl-27-O-desmethyl-rapamycin |
| 10. | 16-O-desmethyl-39-O-desmethyl-rapamycin |
| 11. | 16-O-desmethyl-27-O-desmethyl-rapamycin |
| 12. | 16-O-desmethyl-27-desmethoxy-rapamycin |
| 13. | 27-desmethoxy-39-O-desmethyl-rapamycin |
| 14. | 27-O-desmethyl-39-O-desmethyl-rapamycin |
| 15. | 9-deoxo-16-O-desmethyl-rapamycin |
| 16. | 9-deoxo-27-desmethoxy-rapamycin |
| 17. | 9-deoxo-27-O-desmethyl-rapamycin |
| 18. | 9-deoxo-39-O-desmethyl-rapamycin |
| 19. | 9-deoxo-rapamycin |
| 20. | 16-O-desmethyl-rapamycin |
| 21. | 27-O-desmethyl-rapamycin |
| 22. | 27-desmethoxy-rapamycin |
| 23. | 39-O-desmethyl-rapamycin |
| 24. | 8-deoxo-15-O-desmethyl-26-desmethoxy-38-O-desmethyl-prolylrapamycin (pre-prolylrapamycin) |
| 25. | 8-deoxo-15-O-desmethyl-26-O-desmethyl-38-O-desmethyl-prolylrapamycin |
| 26. | 15-O-desmethyl-26-desmethoxy-38-O-desmethyl-prolylrapamycin |
| 27. | 8-deoxo-26-desmethoxy-38-O-desmethyl-prolylrapamycin |
| 28. | 8-deoxo-15-O-desmethyl-38-O-desmethyl-prolylrapamycin |
| 29. | 8-deoxo-15-O-desmethyl-26-desmethoxy-prolylrapamycin |
| 30. | 15-O-desmethyl-26-O-desmethyl-38-O-desmethyl-prolylrapamycin |
| 31. | 8-deoxo-26-O-desmethyl-38-O-desmethyl-prolylrapamycin |
| 32. | 8-deoxo-15-O-desmethyl-26-O-desmethyl-prolylrapamycin |
| 33. | 15-O-desmethyl-38-O-desmethyl-prolylrapamycin |
| 34. | 15-O-desmethyl-26-O-desmethyl-prolylrapamycin |
| 35. | 15-O-desmethyl-26-desmethoxy-prolylrapamycin |
| 36. | 26-desmethoxy-38-O-desmethyl-prolylrapamycin |
| 37. | 26-O-desmethyl-38-O-desmethyl-prolylrapamycin |
| 38. | 8-deoxo-15-O-desmethyl-prolylrapamycin |
| 39. | 8-deoxo-26-desmethoxy-prolylrapamycin |
| 40. | 8-deoxo-26-O-desmethyl-prolylrapamycin |
| 41. | 8-deoxo-38-O-desmethyl-prolylrapamycin |
| 42. | 8-deoxo-prolylrapamycin |
| 43. | 15-O-desmethyl-prolylrapamycin |
| 44. | 26-O-desmethyl-prolylrapamycin |
| 45. | 26-desmethoxy-prolylrapamycin |
| 46. | 38-O-desmethyl-prolylrapamycin |
| 47. | 9-deoxo-16-O-desmethyl-27-desmethoxy-39-desmethoxy-rapamycin |
| 48. | 9-deoxo-16-O-desmethyl-27-O-desmethyl-39-desmethoxy-rapamycin |
| 49. | 16-O-desmethyl-27-desmethoxy-39-desmethoxy-rapamycin |
| 50. | 9-deoxo-27-desmethoxy-39-desmethoxy-rapamycin |
| 51. | 9-deoxo-16-O-desmethyl-39-desmethoxy-rapamycin |
| 52. | 16-O-desmethyl--27-O-desmethyl-39-desmethoxy-rapamycin |
| 53. | 9-deoxo-27-O-desmethyl-39-desmethoxy-rapamycin |
| 54. | 16-O-desmethyl-39-desmethoxy-rapamycin |
| 55. | 27-desmethoxy-39-desmethoxy-rapamycin |
| 56. | 27-O-desmethyl-39-desmethoxy-rapamycin |
| 57. | 9-deoxo-39-desmethoxy-rapamycin |
| 58. | 39-O-desmethoxy-rapamycin |
| 59. | 8-deoxo-15-O-desmethyl-26-desmethoxy-38-desmethoxy-prolylrapamycin |
| 60. | 8-deoxo-15-O-desmethyl-26-O-desmethyl-38-desmethoxy-prolylrapamycin |
| 61. | 15-O-desmethyl-26-desmethoxy-38-desmethoxy-prolylrapamycin |
| 62. | 8-deoxo-26-desmethoxy-38-desmethoxy-prolylrapamycin |
| 63. | 8-deoxo-15-O-desmethyl-38-desmethoxy-prolylrapamycin |

TABLE II-continued

| Compound no: | Name: |
|---|---|
| 64. | 15-O-desmethyl-26-O-desmethyl-38-desmethoxy-prolylrapamycin |
| 65. | 8-deoxo-26-O-desmethyl-38-desmethoxy-prolylrapamycin |
| 66. | 15-O-desmethyl-38-desmethoxy-prolylrapamycin |
| 67. | 26-desmethoxy-38-desmethoxy-prolylrapamycin |
| 68. | 26-O-desmethyl-38-desmethoxy-prolylrapamycin |
| 69. | 8-deoxo-38-desmethoxy-prolylrapamycin |
| 70. | 38-desmethoxy-prolylrapamycin |
| 71 | 9-deoxo-16-O-desmethyl-27-desmethoxy-36-de(3-cis-methoxy-4-trans-hydroxycyclohexyl)-36-(hydroxycyclohexenyl) rapamycin |
| 72 | 9-deoxo-16-O-desmethyl-27-desmethoxy-36-de(3-cis-methoxy-4-trans-hydroxycyclohexyl)-36-(dihydroxy cyclohexyl) rapamycin |
| 73 | 9-deoxo-16-O-desmethyl-27-desmethoxy-36-de(3-cis-methoxy-4-trans-hydroxycyclohexyl)-36-(hydroxynorbornyl) rapamycin |
| 74 | 9-deoxo-16-O-desmethyl-27-desmethoxy-36-de(3-cis-methoxy-4-trans-hydroxycyclohexyl)-36-(3-methyl-4-hydroxycyclohexyl) rapamycin |
| 75 | 9-deoxo-16-O-desmethyl-27-desmethoxy-36-de(3-cis-methoxy-4-trans-hydroxycyclohexyl)-36-(4-methyl hydroxycyclohexyl) rapamycin |
| 76 | 9-deoxo-16-O-desmethyl-27-desmethoxy-36-de(3-cis-methoxy-4-trans-hydroxycyclohexyl)-36-(3-fluoro-4-hydroxycyclohexyl) rapamycin |
| 77 | 9-deoxo-16-O-desmethyl-27-desmethoxy-36-de(3-cis-methoxy-4-trans-hydroxycyclohexyl)-36-(3-hydroxy-4-fluorocyclohexyl) rapamycin |
| 78 | 9-deoxo-16-O-desmethyl-27-desmethoxy-36-de(3-cis-methoxy-4-trans-hydroxycyclohexyl)-36-(3-chloro-4-hydroxycyclohexyl) rapamycin |
| 79 | 9-deoxo-16-O-desmethyl-27-desmethoxy-36-de(3-cis-methoxy-4-trans-hydroxycyclohexyl)-36-(3-hydroxy-4-chlorocyclohexyl) rapamycin |
| 80 | 9-deoxo-16-O-desmethyl-27-desmethoxy-36-de(3-cis-methoxy-4-trans-hydroxycyclohexyl)-36-(3-cis-4-cis-dihydroxycyclohexyl) rapamycin |
| 81 | 9-deoxo-16-O-desmethyl-27-desmethoxy-36-de(3-cis-methoxy-4-trans-hydroxycyclohexyl)-36-(3-trans-4-trans-dihydroxycyclohexyl) rapamycin |
| 82 | 9-deoxo-16-O-desmethyl-27-O-desmethyl-39-O-desmethyl rapamycin |
| 83 | 9-deoxo-16-O-desmethyl-27O-desmethyl-36-de(3-cis-methoxy-4-trans-hydroxycyclohexyl)-36-(hydroxycyclohexenyl) rapamycin |
| 84 | 9-deoxo-16-O-desmethyl-27-O-desmethyl-36-de(3-cis-methoxy-4-trans-hydroxycyclohexyl)-36-(hydroxynorbornyl) rapamycin |
| 85 | 9-deoxo-16-O-desmethyl-27-O-desmethyl-36-de(3-cis-methoxy-4-trans-hydroxycyclohexyl)-36-(4-methyl hydroxycyclohexyl) rapamycin |
| 86 | 9-deoxo-16-O-desmethyl-27-desmethoxy-36-de(3-cis-methoxy-4-trans-hydroxycyclohexyl)-36-(hydroxycycloheptyl) rapamycin |
| 87 | 9-deoxo-16-O-desmethyl-27-O-desmethyl-36-de(3-cis-methoxy-4-trans-hydroxycyclohexyl)-36-(hydroxycycloheptyl) rapamycin |

In a further aspect, the invention provides the following novel rapamycin analogues:

TABLE III

| Compound no: | Name: |
|---|---|
| 1. | 9-deoxo-16-O-desmethyl-27-desmethoxy-39-O-desmethyl-rapamycin (pre-rapamycin) |
| 2. | 9-deoxo-16-O-desmethyl-27-O-desmethyl-39-O-desmethyl-rapamycin |
| 3. | 16-O-desmethyl-27-desmethoxy-39-O-desmethyl-rapamycin |
| 5. | 9-deoxo-16-O-desmethyl-39-O-desmethyl-rapamycin |
| 6. | 9-deoxo-16-O-desmethyl-27-desmethoxy-rapamycin |
| 7. | 16-O-desmethyl-27-O-desmethyl-39-O-desmethyl-rapamycin |
| 8. | 9-deoxo-27-O-desmethyl-39-O-desmethyl-rapamycin |
| 9. | 9-deoxo-16-O-desmethyl-27-O-desmethyl-rapamycin |
| 14. | 27-O-desmethyl-39-O-desmethyl-rapamycin |
| 15. | 9-deoxo-16-O-desmethyl-rapamycin |
| 18. | 9-deoxo-39-O-desmethyl-rapamycin |
| 24. | 8-deoxo-15-O-desmethyl-26-desmethoxy-38-O-desmethyl-prolylrapamycin (pre-prolylrapamycin) |
| 25. | 8-deoxo-15-O-desmethyl-26-O-desmethyl-38-O-desmethyl-prolylrapamycin |
| 26. | 15-O-desmethyl-26-desmethoxy-38-O-desmethyl-prolylrapamycin |
| 27. | 8-deoxo-26-desmethoxy-38-O-desmethyl-prolylrapamycin |
| 28. | 8-deoxo-15-O-desmethyl-38-O-desmethyl-prolylrapamycin |
| 29. | 8-deoxo-15-O-desmethyl-26-desmethoxy-prolylrapamycin |
| 30. | 15-O-desmethyl-26-O-desmethyl-38-O-desmethyl-prolylrapamycin |
| 31. | 8-deoxo-26-O-desmethyl-38-O-desmethyl-prolylrapamycin |
| 32. | 8-deoxo-15-O-desmethyl-26-O-desmethyl-prolylrapamycin |
| 33. | 15-O-desmethyl-38-O-desmethyl-prolylrapamycin |
| 34. | 15-O-desmethyl-26-O-desmethyl-prolylrapamycin |

TABLE III-continued

| Compound no: | Name: |
|---|---|
| 35. | 15-O-desmethyl-26-desmethoxy-prolylrapamycin |
| 36. | 26-desmethoxy-38-O-desmethyl-prolylrapamycin |
| 37. | 26-O-desmethyl-38-O-desmethyl-prolylrapamycin |
| 38. | 8-deoxo-15-O-desmethyl-prolylrapamycin |
| 40. | 8-deoxo-26-O-desmethyl-prolylrapamycin |
| 41. | 8-deoxo-38-O-desmethyl-prolylrapamycin |
| 43. | 15-O-desmethyl-prolylrapamycin |
| 46. | 38-O-desmethyl-prolylrapamycin |
| 47. | 9-deoxo-16-O-desmethyl-27-desmethoxy-39-desmethoxy-rapamycin |
| 48. | 9-deoxo-16-O-desmethyl-27-O-desmethyl-39-desmethoxy-rapamycin |
| 49. | 16-O-desmethyl-27-desmethoxy-39-desmethoxy-rapamycin |
| 50. | 9-deoxo-27-desmethoxy-39-desmethoxy-rapamycin |
| 51. | 9-deoxo-16-O-desmethyl-39-desmethoxy-rapamycin |
| 52. | 16-O-desmethyl-27-O-desmethyl-39-desmethoxy-rapamycin |
| 53. | 9-deoxo-27-O-desmethyl-39-desmethoxy-rapamycin |
| 54 | 16-O-desmethyl-39-desmethoxy-rapamycin |
| 55. | 27-desmethoxy-39-desmethoxy-rapamycin |
| 56. | 27-O-desmethyl-39-desmethoxy-rapamycin |
| 57. | 9-deoxo-39-desmethoxy-rapamycin |
| 59. | 8-deoxo-15-O-desmethyl-26-desmethoxy-38-desmethoxy-prolylrapamycin |
| 60. | 8-deoxo-15-O-desmethyl-26-O-desmethyl-38-desmethoxy-prolylrapamycin |
| 61. | 15-O-desmethyt-26-desmethoxy-38-desmethoxy-prolylrapamycin |
| 62. | 8-deoxo-26-desmethoxy-38-desmethoxy-prolylrapamycin |
| 63. | 8-deoxo-15-O-desmethyl-38-desmethoxy-prolylrapamycin |
| 64. | 15-O-desmethyl-26-O-desmethyl-38-desmethoxy-prolylrapamycin |
| 65. | B-deoxo-26-O-clesmethyl-38-desmethoxy-protylrapamycin |
| 66. | 15-O-desmethyl-38-desmethoxy-prolylrapamycin |
| 67. | 26-desmethoxy-38-desmethoxy-prolylrapamycin |
| 68. | 26-O-desmethyl-38-desmethoxy-prolylrapamycin |
| 69. | 8-deoxo-38-desmethoxy-prolylrapamycin |
| 70. | 38-desmethoxy-prolylrapamycin |
| 71 | 9-deoxo-16-O-desmethyl-27-desmethoxy-36-de(3-cis-methoxy-4-trans-hydroxycyclohexyl)-36-(hydroxycyclohexenyl) rapamycin |
| 72 | 9-deoxo-16-O-desmethyl-27-desmethoxy-36-de(3-cis-methoxy-4-trans-hydroxycyclohexyl)-36-(dihydroxy cyclohexyl) rapamycin |
| 73 | 9-deoxo-16-O-desmethyi-27-desmethoxy-36-de(3-cis-methoxy-4-trans-hydroxycyclohexyl)-36-(hydroxynorbomyl) rapamycin |
| 74 | 9-deoxo-16-O-desmethyl-27-desmethoxy-36-de(3-cis-methoxy-4-trans-hydroxycyclohexyl)-36-(3-methyl-4-hydroxycyclohexyl) rapamycin |
| 75 | 9-deoxo-16-O-desmethyl-27-desmethoxy-36-de(3-cis-methoxy-4-trans-hydroxycyclohexyl)-36-(4-methyi hydroxycyclohexyl) rapamycin |
| 76 | 9-deoxo-16-O-desmethyl-27-desmethoxy-36-de(3-cts-methoxy-4-trans-hydroxycyclohexyl)-36-(3-fluoro-4-hydroxycyclohexyl) rapamycin |
| 77 | 9-deoxo-16-O-desmethyl-27-desmethoxy-36-de(3-cis-methoxy-4-trans-hydroxycyclohexyl)-36-(3-hydroxy-4-fluorocyclohexyl) rapamycin |
| 78 | 9-deoxo-16-O-desmethyl-27-desmethoxy-36-de(3-cis-methoxy-4-trans-hydroxycyclohexyl)-36-(3-chloro-4-hydroxycyclohexyl) rapamycin |
| 79 | 9-deoxo-16-O-desmethyl-27-desmethoxy-36-de(3-cis-methoxy-4-trans-hydroxycyclohexyl)-36-(3-hydroxy-4-chlorocyclohexyl) rapamycin |
| 80 | 9-deoxo-16-O-desmethyl-27-desmethoxy-36-de(3-cis-methoxy-4-trans-hydroxycyclohexyl)-36-(3-cis-4-cis-dihydroxycyclohexyl) rapamycin |
| 81 | 9-deoxo-16-O-desmethyf-27-desmethoxy-36-de(3-cis-methoxy-4-trans-hydroxycyclohexyl)-36-(3-trans.-4-trans-dihydroxycyclohexyl) rapamycin |
| 82 | 9-deoxo-16-O-desmethyl-27-O-desmethyl-39-O-desmethyl rapamycin |
| 83 | 9-deoxo-16-O-desmethyl-270-desmethyl-36-de(3-cis-methoxy-4-trans-hydroxycyclohexyl)-36-(hydroxycyclohexenyl) rapamycin |
| 84 | 9-deoxo-16-O-desmethyl-27-O-desmethyt-36-de(3-cis-methoxy-4-trans-hydroxycyclohexyl)-36-(hydroxynorbomyl) rapamycin |
| 85 | 9-deoxo-16-O-desmethyl-27-O-desmethyl-36-de(3-cis-methoxy-4-trans-hydroxycyclohexyl)-36-(4-methyl hydroxycyclohexyl) rapamycin |

In a further aspect, the invention provides novel rapamycin analogues of

Formula II:

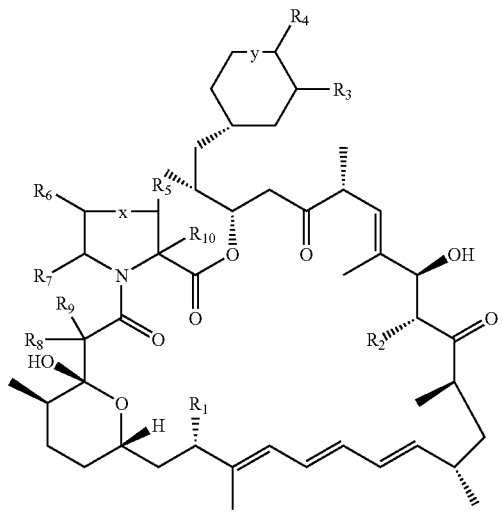

where
x=bond or $CHR_{11}$, or —$CHR_6$-x-$CHR_5$— is

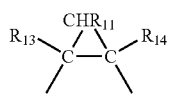

y=bond or $CHR_{12}$
$R_1$=OH, $OCH_3$
$R_2$=H, OH, $OCH_3$
$R_3$=H, OH, $OCH_3$, alkyl-, halo-, amino-, thiol-residue
$R_4$=H, OH, $OCH_3$, alkyl-, halo-, amino-, thiol-residue
$R_5$=H, alkyl-, halo-, hydroxy-residue
$R_6$=H, alkyl-, halo-, hydroxy-residue
$R_7$=H, alkyl-, halo-, hydroxy-residue
$R_8$, $R_9$=O or H,H
$R_{10}$=H, alkyl-, halo-, hydroxy-residue
$R_{11}$=H, alkyl-, halo-, hydroxy-residue
$R_{12}$=H, alkyl-, halo-, hydroxy-residue
$R_{13}$=H, alkyl-, halo-, hydroxy-residue
$R_{14}$=H, alkyl-, halo-, hydroxy-residue Additionally, the present invention also provides novel rapamycin analogues of Formula III:

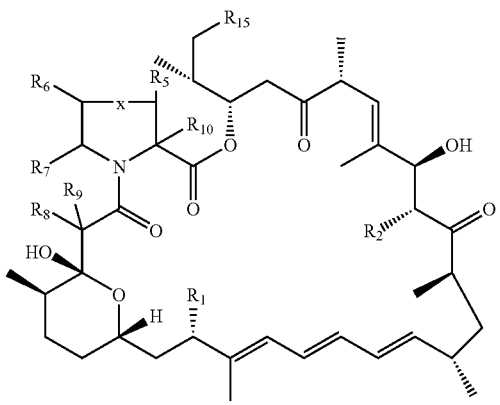

where:
x=bond or $CHR_{11}$, or —$CHR_6$-x-$CHR_5$— is

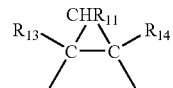

$R_1$=OH, $OCH_3$
$R_2$=H, OH, $OCH_3$
$R_5$=H, alkyl-, halo-, hydroxy-residue
$R_6$=H, alkyl-, halo-, hydroxy-residue
$R_7$=H, alkyl-, halo-, hydroxy-residue
$R_8$, $R_9$=O or H,H
$R_{10}$=H, alkyl-, halo-, hydroxy-residue
$R_{11}$=H, alkyl-, halo-, hydroxy-residue
$R_{12}$=H, alkyl-, halo-, hydroxy-residue
$R_{13}$=H, alkyl-, halo-, hydroxy-residue
$R_{14}$=H, alkyl-, halo-, hydroxy-residue $R_{15}$ = 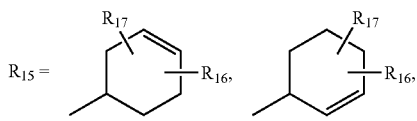

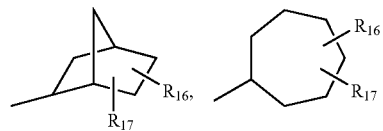

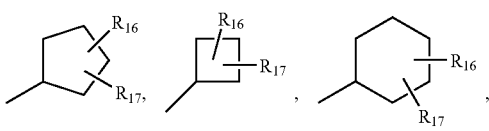

$R_{16}$=OH
H, OH, halo-, thiol-, alkyl-

The novel rapamycin analogues are useful directly, and as templates for further semi-synthesis or bioconversion to produce compounds useful, as immunosuppressants, antifungal agents, anticancer agents, neuroregenerative agents or agents for the treatment of psoriasis, rheumatoid arthritis, fibrosis and other hyperproliferative diseases.

Therefore in a further aspect, the present invention provides use of the FKBP-ligand analogues generated in the manufacture of a medicament for the treatment of cancer, the treatment of fungal infections, the treatment of autoimmune, inflammatory, proliferative and hyperproliferative diseases or the maintenance of immunosuppression.

One skilled in the art would be able by routine experimentation to determine the ability of these compounds to inhibit fungal growth (e.g. Baker, H., et al., 1978; NCCLS Reference method for broth dilution antifungal susceptibility testing for yeasts: Approved standard M27-A, 17(9). 1997), and for example but without limitation using the methods described in Example 19. Additionally, one skilled in the art would be able by routine experimentation to determine the ability of these compounds to inhibit tumour cell growth, for example but without limitation using the methods described in Example 19, (also see Dudkin, L., et al., 2001; Yu et al. 2001). In a further aspect the compounds of this invention are useful for inducing immunosuppression and therefore relate to methods of therapeutically or prophylactically inducing a suppression of a human's or an animal's immune system for the treatment or prevention of rejection of transplanted organs or tissue, the treatment of autoimmune, inflammatory, proliferative and hyperproliferative diseases (examples include but are not inclusively limited to autoimmune diseases, diabetes type 1, acute or chronic rejection of an organ or tissue transplant, asthma, tumours or hyperprolific disorders, psoriasis, eczema, rheumatoid arthritis, fibrosis, allergies and food related allergies). Such assays are well known to those of skill in the art, for example but without limitation: Immunosuppressant activity—Warner, L. M.,et al., 1992, Kahan et al. (1991) & Kahan & Camardo, 2001); Allografts—Fishbein, T. M., et al., 2002, Kirchner et al. 2000; Autoimmune/Inflammatory/Asthma—Carlson, R. P. et al., 1993, Powell, N. et al., 2001; Diabetes I—Rabinovitch, A. et al., 2002; Psoriasis—Reitamo, S. et al., 2001; Rheumatoid arthritis—Foey, A., et al., 2002; Fibrosis—Zhu, J. et al., 1999, Jain, S., et al., 2001, Gregory et al. 1993

The ability of the compounds of this invention to induce immunosuppression may be demonstrated in standard tests used for this purpose, for example but without limitation using the methods described in example 19. In a further aspect the compounds of this invention are useful in relation to antifibrotic, neuroregenerative and anti-angiogenic mechanisms, one skilled in the art would be able by routine experimentation to determine the ability of these compounds to prevent angiogenesis (e.g. Guba, M.,et al., 2002, ). One of skill in the art would be able by routine experimentation to determine the utility of these compounds in stents (e.g. Morice, M. C., et al., 2002). Additionally, one of skill in the art would be able by routine experimentation to determine the neuroregenerative ability of these compounds (e.g. Myckatyn, T. M., et al., 2002, Steiner et al. 1997)

BRIEF DESCRIPTION OF THE FIGURES

FIG. 11 Structures of compounds 3, 7, 10, 11, 12, 13, 14, 20, 21, 22 and 23

FIG. 12 Structures of compounds 24, 25, 27, 28, 29, 31, 32, 38, 39, 40, 41 and 42

FIG. 20 Pre-rapamycin correlation spectroscopy (COSY) indicated by solid arrows, Pre-rapamycin total correlation spectroscopy (TOCSY) indicated by dotted arrows.

FIG. 21 Corrections in the DNA sequence of rapN, the corrected sequence is shown on top (SEQ ID NO: 1) and the published sequence (acc no: X86780, nt 91764-92978) is shown underneath (SEQ ID NO: 2).

FIG. 22 Corrections in the amino acid sequence of RapN, the corrected sequence is shown on top (SEQ ID NO: 3) and the published sequence (acc no: X86780) is shown underneath (SEQ ID NO: 4).

FIG. 23 Corrections in the DNA sequence of rapM, the corrected sequence is shown on top (SEQ ID NO: 5) and the published sequence (acc no: X86780, nt 92992-93945 complement) is shown underneath (SEQ ID NO: 6).

FIG. 24 Corrections in the amino acid sequence of RapM, the corrected sequence is shown on top (SEQ ID NO: 7) and the published sequence (acc no: X86780) is shown underneath (SEQ ID NO: 8).

FIG. 25 Corrections in the DNA sequence of rapL, the corrected sequence is shown on top (SEQ ID NO: 9), the published sequence (ace no: X86780, nt 94047-95078 complement) is shown at the bottom (SEQ ID NO: 10).

FIG. 26 Corrections in the amino acid sequence of RapL, the corrected sequence is shown at the top (SEQ ID NO: 11) and the published sequence (acc no: X86780) is shown underneath (SEQ ID NO: 12)

FIG. 27 Corrections in the DNA sequence of rapK, the corrected sequence is shown at the top (SEQ ID NO: 13) and the published sequence (ace no: X86780, nt 95430-96434) is shown at the bottom (SEQ ID NO: 14).

FIG. 28 Corrections in the amino acid sequence of RapK, the corrected sequence is shown at the top (SEQ ID NO: 15) and the published sequence (acc no: X86780) is shown underneath (SEQ ID NO: 16).

FIG. 29 Corrections in the DNA sequence of rapJ, the corrected sequence is shown at the top (SEQ ID NO: 17) and the published sequence (acc no: X86780, nt 96465-97625) is shown at the bottom (SEQ ID NO: 18).

FIG. 30 Corrections in the amino acid sequence of RapJ, the corrected sequence is shown at the top (SEQ ID NO: 19) and the published sequence (ace no: X86780) is shown underneath (SEQ ID NO: 20).

FIG. 31 Corrections in the DNA sequence of rapI, the corrected sequence is shown at the top (SEQ ID NO: 21) and the published sequence (acc no: X86780, nt 97622-98404) is shown at the bottom (SEQ ID NO: 22).

FIG. 32 Corrections in the amino acid sequence of RapI, the corrected sequence is shown at the top (SEQ ID NO: 23) and the published sequence (acc no: X86780) is shown underneath (SEQ ID NO: 24).

FIG. 33 Corrections in the DNA sequence of rapQ, the corrected sequence is shown at the top (SEQ ID NO: 25) and the published sequence (acc no: X86780, nt 90798-91433) is shown at the bottom (SEQ ID NO: 26).

FIG. 34 Corrections in the amino acid sequence of RapQ, the corrected sequence is shown at the top (SEQ ID NO: 27) and the published sequence (acc no: X86780) is shown underneath (SEQ ID NO: 28).

MATERIALS AND METHODS

Materials

Figure 1:
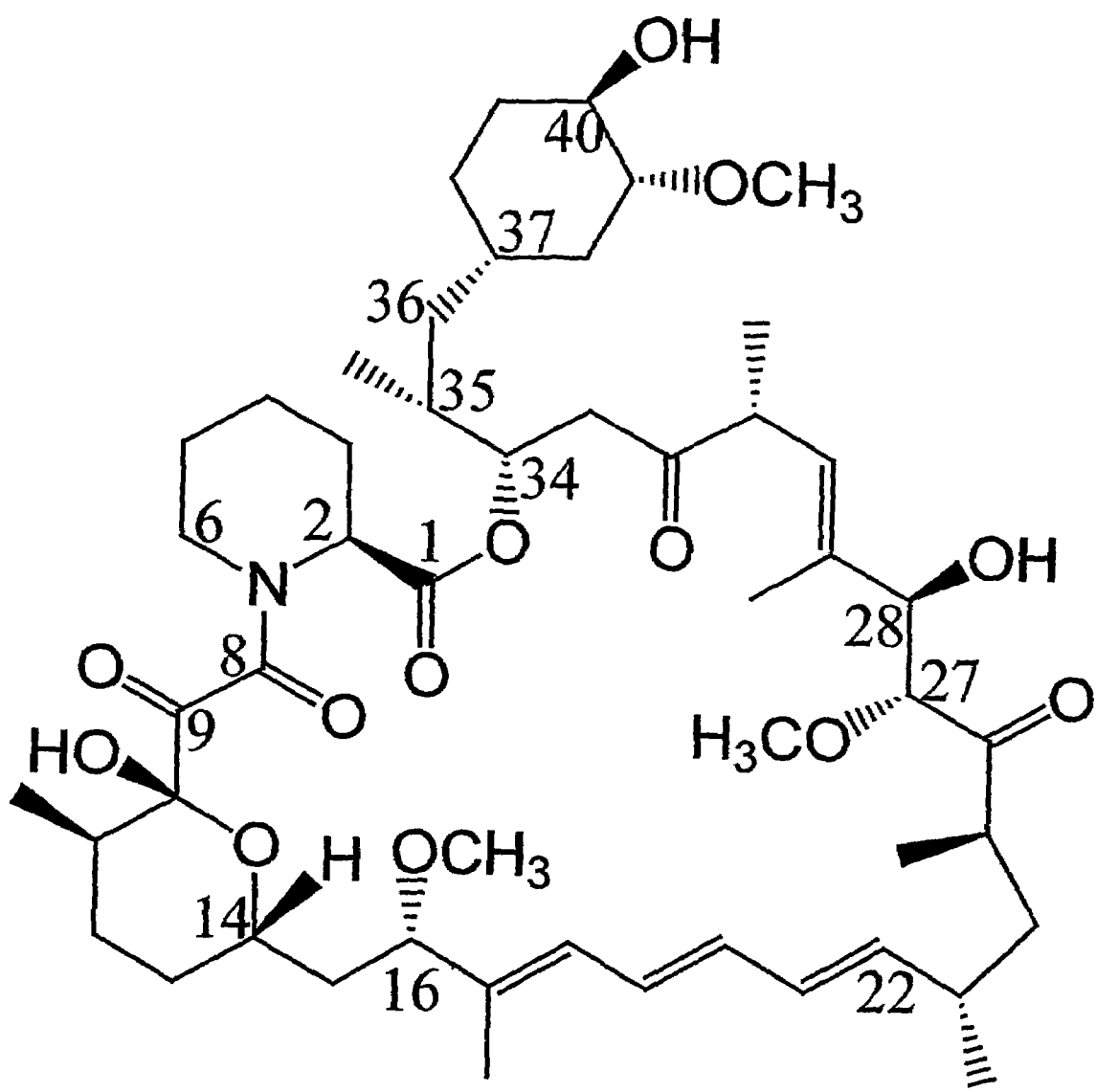
FIG. 1 Structure of rapamycin, the sections to the left of the line represent the binding domain and those to the right indicate the effector domain.
Figure 2:
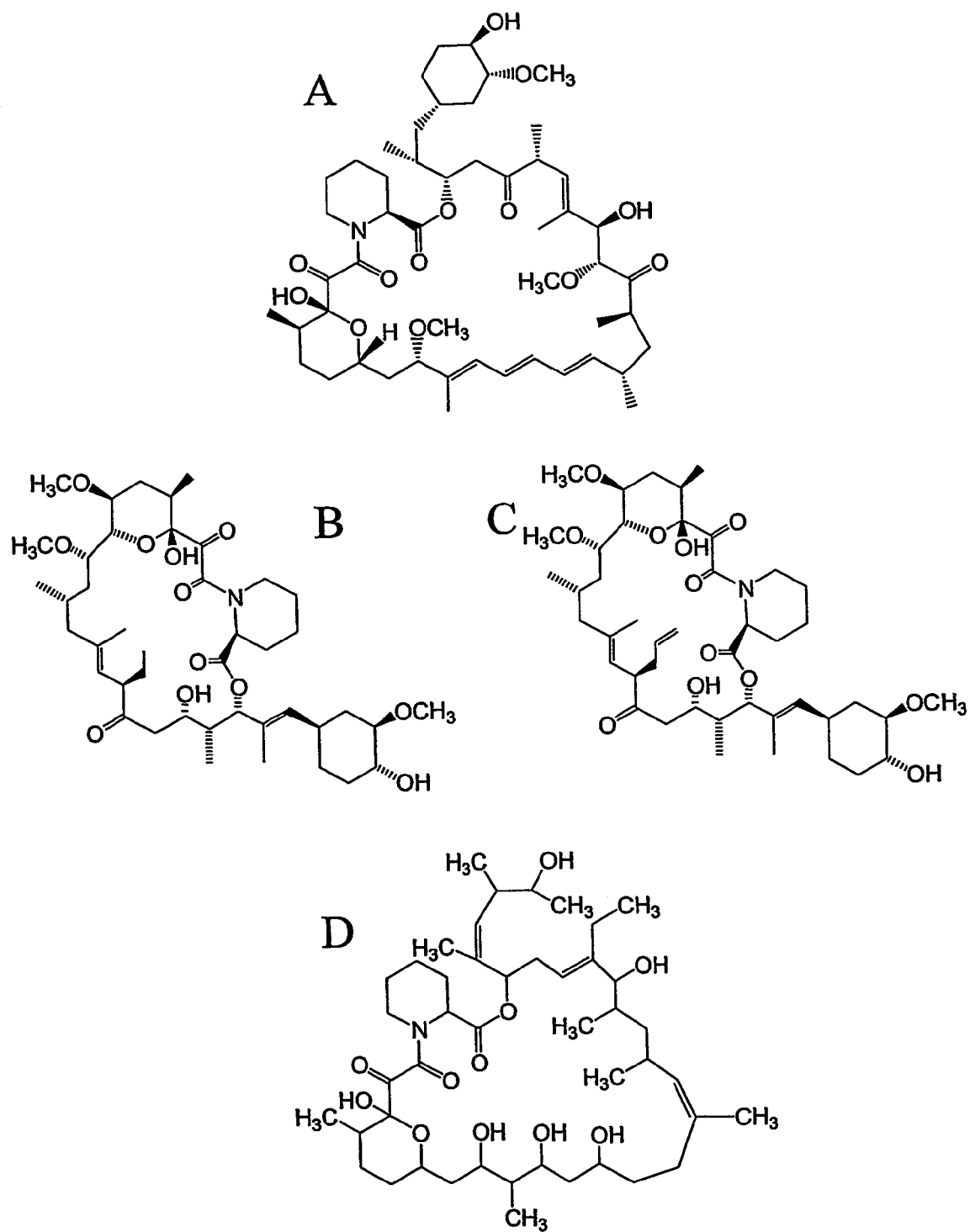
FIG. 2 Structure of rapamycin (A), FK-506 (B), FK-520 (C) and meridamycin (D)

All molecular biology enzymes and reagents were from commercial sources. D/L pipecolic acid was obtained from Sigma.

Starter Materials

Table IV summarises the sources of the acids used in the feeding experiments described in the Examples section. For those compounds that were purchased details of the source are given. A brief synthetic method is given for those starter acids that were synthesised in house. A person of skill in the art will appreciate that variations on the methods described are routine and are within the scope of the present invention.

TABLE IV

| Acid | Company | Stock number | synthesis |
|---|---|---|---|
| cyclohexane carboxylic acid | Aldrich | 10,183-4 | |
| 3-cis,4-trans-dihydroxycyclohexane carboxylic acid | | | in house by method of Lowden PhD thesis |
| 1-cyclohexene carboxylic acid | Aldrich | 32,836-7 | |
| 3-cyclohexene carboxylic acid | Aldrich | 45,375-7 | |
| cycloheptane carboxylic acid | Aldrich | C9,850-0 | |
| methyl-2-norbornane cerboxylate | Aldrich | S40,932-4 | |
| 2-(cis/trans)-hydroxycyclohexane carboxylic acid | U. Nottingham | | Syn by Dr R Goss |
| 3-(cis/trans)-hydroxycyclohexane carboxylic acid | U. Nottingham | | Syn by Dr R Goss |
| 4-(cis/trans)-hydroxycyclohexane carboxylic acid | U. Nottingham | | Syn by Dr R Goss |
| 2-(cis/trans)-methylcyclohexane carboxylic acid | Aldrich | 33,060-4 | |
| 3-(cis/trans)-methylcyclohexane carboxylic acid | Aldrich | 33,061-2 | |
| 4-(cis/trans)-methylcyclohexane carboxylic acid | Aldrich | 33,062-0 | |
| 3-(cis/trans)-methoxycyclohexane carboxylic acid | Aldrich | 33,283-6 | |
| 4-(cis/trans)-methoxycyclohexane carboxylic acid | Aldrich | 33,284-4 | |
| ethyl 4-cyclohexanone carboxylate | Aldrich | 32,062-5 | |
| ethyl 2-cyclohexanone carboxylate | Aldrich | 16,699-5 | |
| 4-trans-n-pentylcyclohexane carboxylic acid | Aldrich | 26,160-2 | |
| 2-trans-aminocyclohexane carboxylic acid | Aldrich | A7331 | |
| 4-cis-aminocyclohexane carboxylic acid | Aldrich | 40,485-3 | |
| 4-(cis/trans)-(aminomethyl)-cyclohexane carboxylic acid | Aldrich | S42,955-4 | |
| Cyclopentane carboxylic acid | Aldrich | C11,200-3 | |
| Cyclobutane carboxylic acid | Aldrich | C9,560-9 | |
| 1-methylcyclohexane carboxylic acid | Aldrich | 14,282-4 | |
| Mixture of 3-trans-hydroxy-4-cis-fluorocyclohexane carboxylic acid and 4-trans-hydroxy-3-cis-fluorocyclohexane carboxylic acid OR mixture of 3-cis-hydroxy-4-trans-fluorocyclohexane carboxylic acid and 4-cis-hydroxy-3-trans-fluorocyclohexane carboxylic acid | | | in house, Method B |
| mixture of 3-cis-hydroxy-4-trans-chlorocyclohexane carboxylic acid and 4-cis-hydroxy-3-trans-chlorocyclohexane carboxylic acid | | | in house, Method C |
| Mixture of 3-trans-hydroxy-4-cis-chlorocyclohexane carboxylic acid and 4-trans-hydroxy-3-cis-chlorocyclohexane carboxylic acid | | | in house, Method C |

TABLE IV-continued

| Acid | Company | Stock number | synthesis |
|---|---|---|---|
| 3-trans-cyclohexeneoxide carboxylic acid | | | in house, Method A |
| 3-cis-cyclohexeneoxide carboxylic acid | | | in house, Method A |
| Mixture of 3,4-cis-dihydroxycyclohexane carboxylic acid and 3,4-trans-dihydroxycyclohexane carboxylic acid | | | in house, Method D |
| Cyclohexaneacetic acid | Aldrich | C10,450-7 | |
| Cyclohexanepropionic acid | Aldrich | 16,147 | |
| 4-cis/trans-tert-butylcyclohexane carboxylic acid | Aldrich | 37,493-8 | |

Synthesis of 3-cis,4-trans-dihydroxycyclohexane carboxylic acid

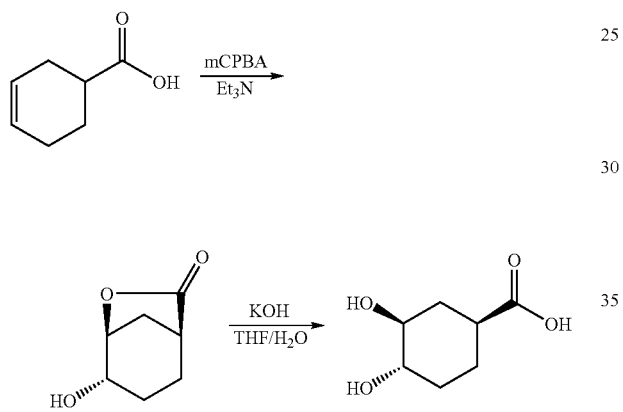

Racemic 3-cis,4trans-dihydroxycyclohexane carboxylic acid was readily attainable from commercially available racemic 3-cyclohexene carboxylic acid. This acid was epoxidised through treatment with meta-chloroperbenzoic acid and converted to the lactone in situ by the addition of base (triethylamine), thus setting up the relative stereochemistries. This lactone was then hydrolysed by the action of aqueous potassium hydroxide, and the final product purified over ion exchange resin, (see PAS Lowden Thesis 1997, Corey, E. J. and Huang, H., 1989).

Method A:

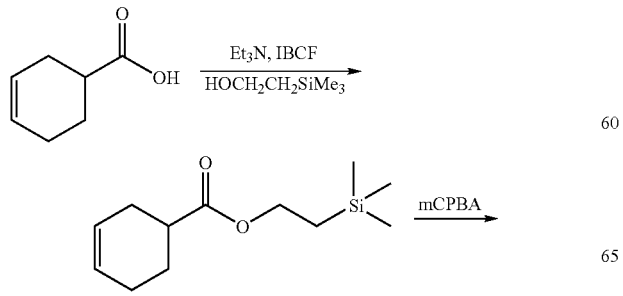

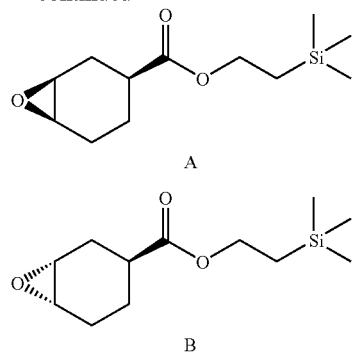

Epoxides A and B were synthesised by standard steps. Cyclohex-3-ene carboxylic acid was protected with 2-trimethylsilylethanol following activation with isobutylchloroformate and triethylamine. The resultant ester was treated with meta-chloroperbenzoic acid and the resultant racemic mix of diastereomers separated on normal phase silica. The epoxides were either reacted on (see below) or deprotected directly by the treatment of trifluoroacetic acid, to liberate the respective free acids.

Method B:

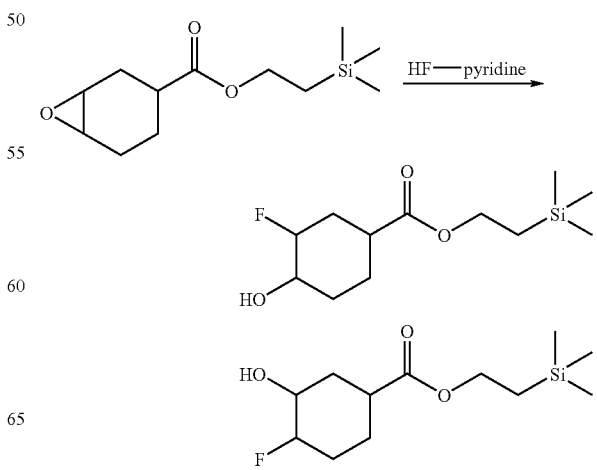

A protected epoxide was treated with anhydrous HF-pyridine to effect the ring opening to produce a pair of racemic regiomers, containing F and OH in a trans arrangement (as previously demonstrated for cyclohexene oxide). The esters were then deprotected with trifluoroacetic acid to liberate the free acids, (see Welch, J. T. and Seper, K., W., 1988)

Method C

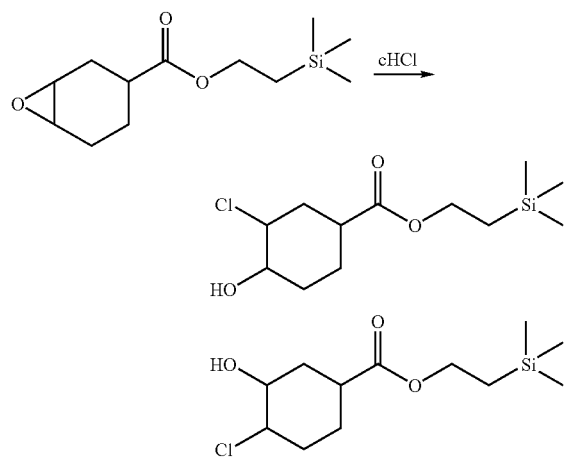

A protected epoxide was treated with concentrated hydrochloric acid suspended organic solvent to affect the ring opening to produce a pair of racemic regiomers, containing Cl and OH in a trans arrangement (as previously demonstrated for cyclohexene oxide). The esters were then deprotected with trifluoroacetic acid to liberate the free acids, (see Chini, M., Crotti, P., et al., 1992)

Method D

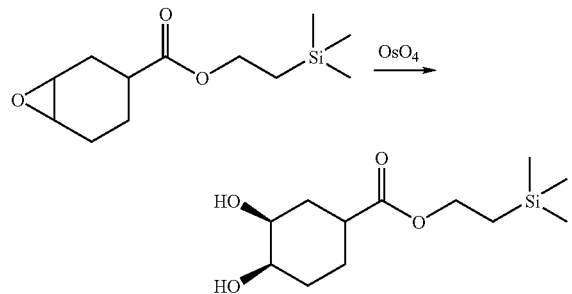

cis-dihydroxylcyclocarboxylic acids were generated by treating protected epoxides with a catalytic amount of osmium tetraoxide together with a co-oxidant. The esters were then deprotected with trifluoroacetic acid to liberate the free acids.

Bacterial Strains and Growth Conditions

Escherichia coli DH10B (GibcoBRL) was grown in 2xTY medium as described by Sambrook et al. (1989) and E. coil ET12567(pUB307) as described in MacNeil et al. (1992) and E. coli ET12567(pUZ8002) as described in Paget et al. (1999) in 2xTY medium with kanamycin (25 µg/ml). The vectors pUC18 and Litmus28 were obtained from New England Biolabs. Vector pSET152 is described in Bierman et al., (1992a). E. coli transform ants were selected for with 100 µg/ml ampicillin or 50 µg/ml apramycin.

The rapamycin producer S. hygroscopicus ATCC29253 and its derivatives were maintained on medium 1 agar plates (see below) at 26° C., and cultivated in TSBGM (Tryptic Soy Broth with 1.0% glucose and 100 mM MES, pH 6.0) as described in (Khaw et al., 1998), supplemented with 100 µg/ml apramycin when required.

Liquid cultures were grown at 25° C. in side-baffled Erlenmeyer flasks with shaking at 300 rpm.

The streptomycin resistant mutant S. hygroscopicus MG1C was selected using standard procedures and maintained on medium 1 with streptomycin (50 µg/ml).

Feeding Methods:

Spore stocks of all strains were prepared after growth on medium 1, preserved in 20% w/v glycerol:10% w/v lactose in distilled water and stored at −80° C. Vegetative cultures were prepared by inoculating 100 µl of frozen stock into 50 ml medium 6 in 250 ml flask. The culture was incubated for 36 to 48 hours at 28° C., 250 rpm.

Feeding procedure: Vegetative cultures were inoculated at 0.5 ml into 7 ml medium 7 in 50 ml tubes. Cultivation was carried out for 7 days, 26° C., 250 rpm. The feeding/addition of the selected carboxylic acids ("non-natural starters" or "natural starters") were carried out at 24 and 48 hours after inoculation and were fed at 1 mM or 3 mM.

| Medium 1: Modified A-medium | | | |
|---|---|---|---|
| component | Source | Catalogue # | g/l |
| Corn steep powder | Sigma | C-8160 | 2.5 g |
| Yeast extract | Difco | 0127-17 | 3 g |
| Calcium carbonate | Sigma | C5929 | 3 g |
| Iron sulphate | Sigma | F8633 | 0.3 g |
| BACTO agar | | | 20 g |
| Wheat starch | Sigma | S2760 | 10 g |
| Water to | | | 1 L |

The media was then sterilised by autoclaving 121° C., 15 min.

| Medium 2 (Box et al., 1995) | |
|---|---|
| component | g/L |
| Soy peptone-SL (Marcor) | 10 |
| Glucose (Sigma G-7021) | 20 |
| Baker's Yeast | 5 |
| NaCl (Sigma) | 2 |
| Trace Elements | |
| $ZnSO_4 \cdot 7H_2O$ | 0.05 |
| $MgSO_4 \cdot 7H_2O$ | 0.125 |
| $MnSO_4 \cdot 4H_2O$ | 0.01 |
| $FeSO_4 \cdot 7H_2O$ | 0.02 |

Adjust pH to 7.0

| Medium 3 (Wilkinson et al., 2000) | |
|---|---|
| component | g/L |
| Dextrose (Sigma) | 15 |
| Glycerol (BDH-Merck) | 15 |
| Soypeptone (Marcor-SL) | 15 |

-continued

Medium 3 (Wilkinson et al., 2000)

| component | g/L |
|---|---|
| NaCl (Fisher) | 3 |
| CaCO$_3$ (Sigma) | 1 |

Medium 4 (U.S. Pat. No. 3,993,749)

| Component | g/L |
|---|---|
| Soybean flour (Arkasoy 50) | 30 |
| Glucose (Sigma G-7021) | 20 |
| Ammonium sulphate | 15 |
| KH$_2$PO$_4$ (Sigma) | 5 |
| Trace Elements | |
| ZnSO$_4$•7H$_2$O | 0.05 |
| MgSO$_4$•7H$_2$O | 0.125 |
| MnSO$_4$•4H$_2$O | 0.01 |
| FeSO$_4$•7H$_2$O | 0.02 |

Adjust pH to 6.0

Medium 5 (Box et al., 1995)

| Component | g/L |
|---|---|
| Soybean flour (Arkasoy 50) | 20 |
| Glucose (Sigma G-7021) | 20 |
| Baker's Yeast | 6 |
| K$_2$HPO$_4$ (Sigma) | 2.5 |
| KH$_2$PO$_4$ (Sigma) | 2.5 |
| NaCl (Sigma) | 5 |
| Glycerol (BDH) | 30 |
| Soybean oil | 10 |
| Trace Elements | |
| ZnSO$_4$•7H$_2$O | 0.05 |
| MgSO$_4$•7H$_2$O | 0.125 |
| MnSO$_4$•4H$_2$O | 0.01 |
| FeSO$_4$•7H$_2$O | 0.02 |

Adjust pH to 6.4

Medium 6: RapV7 Seed medium

| Component | Per L |
|---|---|
| Soy bean flour (Nutrisoy) | 5 g |
| Dextrin (White, Prolab) | 35 g |
| Corn Steep Solids (Sigma) | 4 g |
| Glucose | 10 g |
| (NH$_4$)$_2$SO$_4$ | 2 g |
| Lactic acid (80%) | 1.6 ml |
| CaCO$_3$(Sigma) | 7 g |

Adjust pH to 7.5 with 1M NaOH.

Medium 7: MD6 medium (Fermentation medium)

| Component | Per L |
|---|---|
| Soy bean flour (Nutrisoy) | 30 g |
| Corn starch (Sigma) | 30 g |
| Dextrin (White, Prolab) | 19 g |
| Fructose | 20 g |
| Yeast (Allinson) | 3 g |
| Corn Steep Solids (Sigma) | 1 g |
| L-Lysine | 2.5 g |
| KH$_2$PO$_4$ | 2.5 g |
| K$_2$HPO$_4$ | 2.5 g |
| (NH$_4$)$_2$SO$_4$ | 10 g |
| NaCl | 5 g |
| CaCO$_3$ (Caltec) | 10 g |
| MnCL$_2$x4H$_2$O | 10 mg |
| MgSO$_4$x7H$_2$O | 2.5 mg |
| FeSO$_4$x7H$_2$O | 120 mg |
| ZnSO$_4$x7H$_2$O | 50 mg |
| MES (2-morpholinoethane sulphuric acid monohydrate) | 21.2 g | pH is corrected to 6.0 with 1M NaOH
Before sterilization 0.4 ml of Sigma α-amylase (BAN 250) is added to 1 L of medium.
Medium is sterilised for 20 min at 121° C.

Medium 8: MD3 medium (fermentation medium)

| Component | Per L |
|---|---|
| Soy flour (Nutrisoy) | 31.25 g |
| White Dextrin (Prolab) | 18.75 g |
| KH$_2$PO$_4$ | 5 g |
| (NH$_4$)$_2$SO$_4$ | 1.25 g |
| MnCl$_2$•4H$_2$O | 10 mg |
| MgSO$_4$•7H$_2$O | 2.5 mg |
| FeSO$_4$•7H$_2$O | 120 mg |
| ZnSO$_4$•7H$_2$O | 50 mg |
| SAG 417 | 1.2 mL |
| pH to 6.4 with NaOH | |
| L-lysine | 0.625 g |
| Glucose (40% w/v) | 50 mL |

Description of Strains

All strains shared the wild type morphology, with cream vegetative mycelia, white aerial hyphae, developing grey spores turning black and characteristically hygroscopic. Preferably spores for use in the generation of the recombinant strains as described herein were dark grey in colour, as defined in Fan 4, 202 C to B, more preferably they are as defined in Fan 4, 202 B (Royal Horticultural Society Colour Chart 2001, available from The Royal Horticultural Society, 80 Vincent Square, London, SW1P 2PE).

DNA Manipulation and Sequencing

DNA manipulations, PCR and electroporation procedures were carried out as described in Sambrook et al. (1989). Southern hybridisations were carried out with probes labelled with digoxigenin using the DIG DNA labelling kit as described by the manufacturer (Boehringer Mannheim). DNA sequencing was performed as described previously (Gaisser et al., 2000).

Fermentation of *Streptomyces hygroscopicus* Strains

*Streptomyces hygroscopicus* strains were cultured from a frozen spore stock in cryopreservative (20% glycerol 10% lactose w/v in distilled water) on Medium 1 (see Materials and Methods) and spores were harvested after 10-20 days growth at 29° C. Alternatively, spores from frozen working stocks were inoculated directly into pre-culture medium. A primary pre-culture was inoculated with the harvested spores and cultured in 250 ml Erlenmeyer flasks containing 50 ml Medium 6 (see Materials and Methods), shaken at 250 rpm with a two-inch throw, at 30° C., for two days. The primary pre-culture was used to inoculate secondary pre-cultures of Medium 6 (see Materials and Methods), at 10% v/v, which was shaken at 300 rpm with a one-inch throw, at 28° C., for a further 24 h. Secondary pre-cultures were used to inoculate, at 10% v/v, production Medium 8 (see Materials and Methods) containing 0.01% v/v SAG 417 antifoam and allowed to ferment in a stirred bioreactor for five to seven days at 26° C. Airflow was set to 0.75 vvm, over pressure at 0.5 bar and the impeller tip speed was controlled between 0.98 msg$^{-1}$ and 2.67 ms$^{-1}$. Additional SAG 417 was added on demand. pH was controlled at 6-7 with ammonium (10% v/v) or sulphuric acid (1 M) and glucose solution (40% wNv) was drip fed on initiation of ammonium demand.

Extraction and High Performance Liquid Chromatography (HPLC) Analysis Method (A)

Centrifugation was carried out on 50 ml of the fermentation broth and the supernatant and the mycelium were extracted separately as follows. The mycelia were washed with H$_2$O and extracted with 50 ml of methanol for 16 hours at 4° C. The cell debris was removed by centrifugation, the methanol evaporated to dryness then dissolved in 200 μl methanol. The supernatant of the fermentation broth was extracted twice with an equal volume of ethyl acetate. The organic layer was dried over Na$_2$SO$_4$, evaporated to dryness and then dissolved in 200 μl methanol. HPLC analysis was performed on a Hewlett Packard HP1100 liquid chromatograph with variable wavelength detector or a Finnigan MAT LCQ (Finnigan, Calif.) instrument. High-resolution spectra were obtained on a Bruker BioApex II 4.7 T Fourier Transform-Ion Cyclotron Resonance (FT-ICR) mass spectrometer (Bruker, Bremen, FRG).

For NMR analysis, the bacterial broth was centrifuged, the supernatant extracted with three equal volumes of ethylacetate and the mycelia extracted with methanol as described above. The extracts were combined, dried (Na$_2$SO$_4$) and evaporated under reduced pressure to yield a white solid.

Proton detected NMR spectra ($^1$H, DQF-COSY, TOCSY, HMQC, HMBC, NOESY) were recorded on a Bruker Advance DRX500 spectrometer which operated at 500 MHz at 27° C., with the exception of example 6, where the Bruker Advance DRX500 spectrometer was operated at 500 MHz at 10° C. Chemical shifts are described in parts per million (ppm) on the δ scale and are referenced to CHCl$_3$ at $\delta_H$ 7.26 ($^1$H) and CHCl$_3$ at $\delta_C$ 77.0 ($^{13}$C). J values are given in Hertz (Hz).

Extraction, Isolation and Analysis Protocols (B).

Extraction and Purification Protocol:

The fermentation broth was clarified by centrifugation to provide supernatant and cells. The supernatant was applied to a column (16×15 cm) of Diaion® HP20 resin (Supelco), washed with water followed by 75% MeOH/H$_2$O and then eluted with MeOH. The cells were mixed to homogeneity with an equal volume of acetone. After at least 30 minutes the acetone slurry was clarified by centrifugation and the supernatant decanted. The pelleted cells were similarly extracted twice more with acetone. The acetone extract was combined with the MeOH from the HP20 column and the solvent was removed in vacuo to give an aqueous concentrate. The aqueous (typically 1-2 L) was extracted with EtOAc (3×1-2 L) and the solvent removed in vacuo to give an oily crude extract (typically 20 g). The oily residue was dissolved in a minimal volume of EtOAc and dried onto silica. The coated silica was applied to a silica column (400 g, 36×6 cm) that was eluted sequentially with acetone/hexane mixtures ranging from 25% acetone initially to 100% acetone. The fractions containing rapamycin analogues were identified by HPLC (280 nm) using conditions described within:

The rapamycin analogue-containing fractions were combined and the solvent was removed in vacuo. The residue was further chromatographed over Sephadex LH20, eluting with 10:10:1 chloroform/heptane/ethanol. The semipurified rapamycin analogues were purified by reverse phase (C18) high performance liquid chromatography using a Gilson HPLC, eluting a Phenomenex 21.2×250 mm Luna 5 μm C18 BDS column at 21 mL/min, isocratic elution with 50% to 70% CH$_3$CN/H$_2$O mixtures depending on the polarity of the rapamycin analogue.

Analysis of Culture Broths

An aliquot of whole broth (1 mL) was shaken with CH$_3$CN (1 mL) for 30 minutes. The mixture was clarified by centrifugation and the supernatant analysed by HPLC with diode array detection. The HPLC system comprised an Agilent HP1100 equipped with a BDS HYPERSIL C18 3 μm 4.6×150 mm column (ThermoHypersil-Keystone) heated to 40° C. The gradient elution was from 55% mobile phase B to 95% mobile phase B over 10 minutes followed by an isocratic hold at 95% mobile phase B for 2 minutes with a flow rate of 1 mL/min. Mobile phase A was 10% acetonitrile:90% water, containing 10 mM ammonium acetate and 0.1% trifluoroacetic acid, mobile phase B was 90% acetonitrile:10% water, containing 10 mM ammonium acetate and 0.1% trifluoroacetic acid. Rapamycin analogues were identified by the presence of the characteristic rapamycin triene, centred on 278 nm. FK506 and FK520 analogues are identified by LC-MS analysis.

Analysis by LCMS

The HPLC system described above was coupled to a Bruker Daltonics Esquire3000 electrospray mass spectrometer. The same column and gradient elution scheme were used as described above. Mobile phase A was water, mobile phase B was acetonitrile. Positive negative switching was used over a scan range of 500 to 1000 Dalton.

EXAMPLE 1

Conjugation of S. hygroscopicus

The plasmid to be conjugated into S. hygroscopicus was transformed by electroporation into the dam$^-$ dcm$^-$ ET12567 E. coli strain containing either pUB307 as described in MacNeil et al. (1992) or pUZ8002 as described in Paget et al. (1999). A preculture was used (over night culture, 30° C.) to inoculate fresh 2xTY (with 50 μg/ml apramycin and 25 μg/ml kanamycin) at a dilution of 1/25 and grown with shaking at 37° C. to an optical density at 595 nm of 0.25-0.6. The cells from this broth were washed twice with 2xTY, then resuspended with 0.5 ml of 2xTY per 25 ml original culture. The quality of the spore stock used is critical for the success of this method. In this context the age of the spores when harvested and the use of medium 1 are crucial for the isolation of high-quality spore suspension. To isolate high-quality spore suspensions of S. hygroscopicus, pre-dried plates of medium 1 agar (see Materials and Methods section) were spread with S. hygroscopicus spores or mycelia using standard microbiological techniques followed by incubation at 26°-28° C. for 14-21 days. Spores were harvested by addition of 1-2 ml of sterile 20% w/v glycerol or water by standard techniques. An aliquot of 200 µl of the S. hygroscopicus spore suspension was washed in 500 µl of 2xTY, resuspended in 500 µl of 2xTY, subjected to heat shock at 50° C. for 10 minutes then cooled on ice. An aliquot of 0.5 ml of the E. coli suspension was mixed with the heat-shocked spores and this mixture plated on medium 1 agar plates. These plates were incubated at 26°-28° C. for 16 hours before overlaying with 1 mg of nalidixic acid and 1 mg of apramycin per plate. Exconjugant colonies usually appeared after 3-7 days.

Use in S.hygroscopicus MG2-10 of an Alternative Integrating Vector, pRT801

Conjugation was also carried out using the ΦBT1-based integrating vector pRT801 into S.hygroscopicus MG2-10 as described above. Exconjugants were patched on to medium 1 containing 50 µg/ml apramycin and 50 µg/ml nalidixic acid, and shown to be apramycin resistant.

EXAMPLE 2

Figure 4:
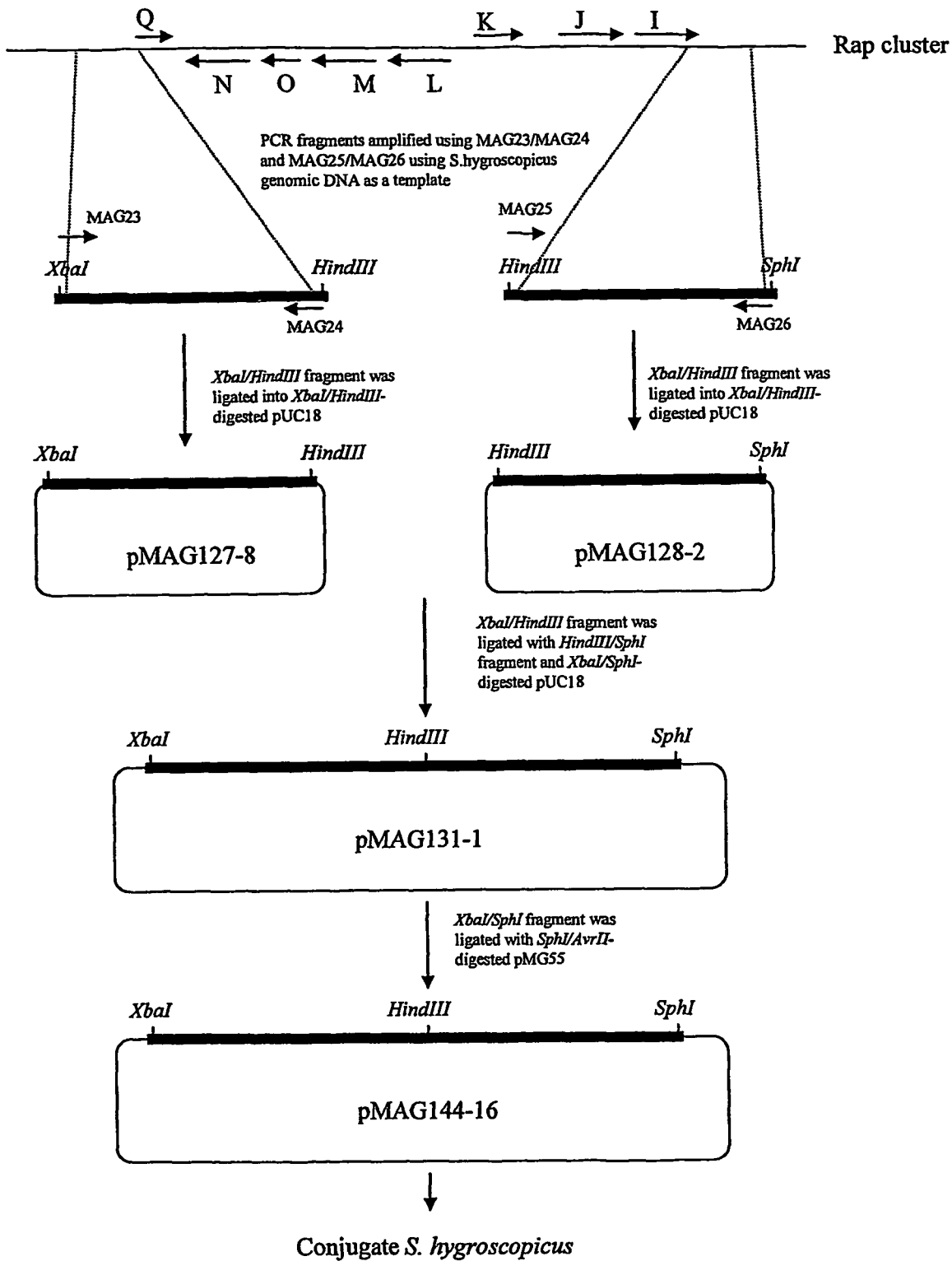
FIG. 4 A flow chart demonstrating the cloning strategy for the isolation of pMAG144-16 to create MG2-10.

Isolation of the S. hygroscopicus Mutant MG2-10 Carrying the Chromosomal Deletion of rapQONMLKJI (FIG. 4)

An S. hygroscopicus mutant (MG2-10) in which the rapamycin modifying genes rapQ, rapO/N, rapM, rapL, rapK, rapJ and rapI were deleted was constructed as described below.

Isolation of the Streptomycin Resistant Mutant MG1C:

S.hygroscopicus NRRL5491 mycelia were spread onto plates of medium 1 containing 50 mg/ml streptomycin. Three colonies were isolated and labelled MG1A, MG1B and MG1C. These were conjugated as in example 1 with the plasmid pMG49, a derivative of pSET152 containing the rpsL gene from S.lividans TK24. Exconjugants from each of these conjugations were patched onto a plate if medium 1 containing 50 mg/ml apramycin and 50 mg/ml nalidixic acid, to confirm the presence of the plasmid pMG49. They were then streaked, along with the original strains MG1A, MG1B and MG1C, onto a both a plate of medium 1 containing no antibiotic and a plate of medium1 containing 50 mg/ml streptomycin. Growth was seen in all cases except the streaks of MG1A [pMG49], MG1B [pMG49] and MG1C [pMG49] on streptomycin, indicating that the w.t. rpsL gene from S.lividans TK24 conferred dominant streptomycin sensitivity on these strains. The production of pre-rapamycin was measured in MG1A, MG1B and MG1C and the best producer, MG1C, was kept for further work.

Conjugation of S. hygroscopicus MG1C

Conjugations were carried out as described in example 1 using the streptomycin resistant S. hygroscopicus MG1C and vector pMG55 derived constructs.

Figure 3:
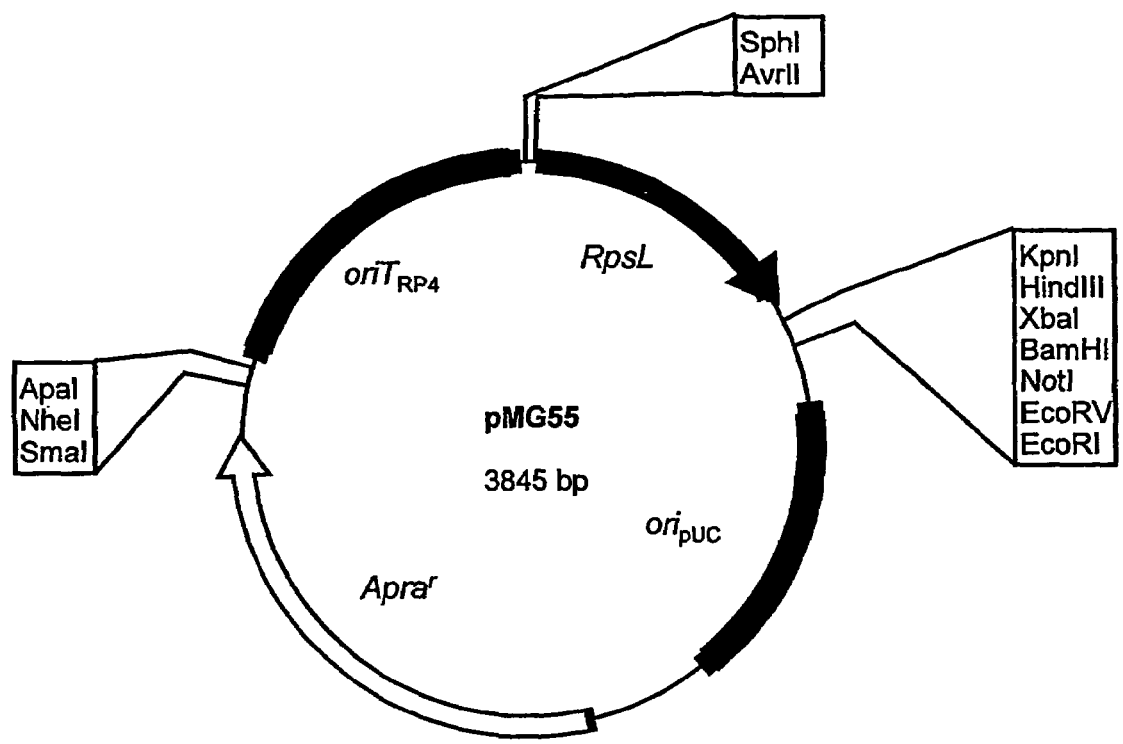
FIG. 3 Plasmid map of pMG55, a double recombination vector with RpsL positive selection and oriT for conjugation.

Construction of Conjugative Double Recombination Vector pMG55 (FIG. 3)

The primers MAG47 5'-GCAAGCTTGGTACCGA-CACGCTCGCCGAACAGG-3' (SEQ ID NO: 29) and MAG48 5'-GCGCATGCCCTAGGGTGTACATTACT-TCTCC-3' (SEQ ID NO: 30) were used to amplify the S.lividans rpsL gene using the plasmid pRPSL21 (Shima et al., 1996) as a template. The PCR fragment was digested with SphI and HindIII, isolated and ligated with the 3.2 kb fragment of pSET152 (Bierman et al., 1992b), which had been digested with SphI and HindIII. After transformation into E. coli DH10B, plasmid pMG55 was isolated. This plasmid was confirmed by sequencing. Plasmid pMG55 contains the rpsL gene to allow selection for double recombinants (Hosted and Balkt, 1997).

Isolation of the S. hygroscopicus Mutant MG2-10 Carrying the Chromosomal Deletion of rapQONMLKJI (FIG. 4)

The primers MAG23 5'-TATCTAGACTTCGCACGT-GCCTGGGACA-3' (SEQ ID NO: 31) and MAG24 5'-AG-MGCTTACCCMATCCAACATCACCT-3' (SEQ ID NO: 32) were used to amplify the left region of homology (from nt 89298 to nt 90798 in the rapamycin cluster as described in Schwecke et al.(Schwecke et al., 1995) using genomic DNA prepared from S. hygroscopicus NRRL5491 as a template. The 1.5 kb PCR product was digested with XbaI and HindIII and ligated into pUC18 cut with XbaI and HindIII. After transformation into E. coli. DH10B, the plasmid pMAG127-8 was isolated. The primers MAG25 5'-GGAAGCTTTGACCACACGCCGCCCGTTC-3' (SEQ ID NO: 33) and MAG26 5'-ATGCATGCCCGCCGCAAC-CCGCTGGCCT-3' (SEQ ID NO: 34) were used to amplify the right region of homology (from nt 98404 to nt 99904 in the rapamycin cluster as described in Schwecke et al. (1995)) using genomic DNA prepared from S. hygroscopicus NRRL5491 as a template. The 1.5 kb product of PCR was digested with HindIII and SphI and ligated into pUC18 cut with HindIII and SphI. After transformation into E. coli DH10B, the plasmid pMAG128-2 was isolated (FIG. 4). Both plasmids were checked by sequence analysis. The plasmid pMAG127-8 was digested with SphI and HindIII, the plasmid pMAG128-2 was digested with XbaI and HindIII and the 1.5 kb fragments were isolated from both plasmids. These fragments were ligated into pUC18 cut with SphI and XbaI and used to transform E. coli DH10B. The plasmid pMAG131-1 was isolated. This plasmid was digested with SphI and XbaI, the 3 kb fragment was isolated and ligated into pMG55 cut with SphI and AvrII and the DNA was used to transform E. coli DH10B. The plasmid pMAG144-16 was isolated and used to conjugate S. hygroscopicus MG1C. An apramycin resistant S. hygroscopicus colony was isolated, grown for 24 hours in TSBGM with shaking at 26° C., and spread onto medium 1 agar plates containing 50 µg/l streptomycin. Streptomycin resistant colonies were isolated and shown to be apramycin sensitive. The 7606 nt chromosomal deletion of the rapQONMLKJI region of the rapamycin cluster was verified in the mutant MG2-10 by using the 1.5 kb PCR product of MAG23 and MAG24 to probe EcoRI- and BamHI-digested chromosomal DNA. Analysis of the wild type S. hygroscopicus showed the expected 5.8 kb EcoRI and 5.9 kb BamHI band after hybridisation. When chromosomal DNA of MG2-10 was treated similarly, 9.6 kb EcoRI and 7.6 kb BamHI bands were detected, indicating that rapQONMLKJI had been removed.

EXAMPLE 3

Expression of rapK in the S. hygroscopicus Mutant MG2-10 Carrying the Chromosomal Deletion of rapQONMLKJI (FIG. 4)

Construction of Expression Vector pSGset1

The pSET152 (Bierman et al., 1992a) derived vector pCJR336 (kindly provided by Christine Martin and Corinne Squire) was created by cloning the primer dimer of CR347 5'-TAAACTAGTCCATCT-GAGAGTTTCATATGGCCCTATTCTGC- CCAGCCGCTCTAGAAAT-3' (SEQ ID NO: 35) and CR348 5'-ATTTCTAGAGCGGCTGGGCAGAAT-AGGGCCATATGAAACTCTCAGATGGACTAGTTTA-3' (SEQ ID NO: 36) into PvuII digested pSET152 using standard molecular biological techniques, thus introducing sites for the restriction enzymes SpeI, NdeI, and XbaI into pSET152. The orientation of the insert was confirmed by sequencing. Plasmid pCJR336 was digested using the restriction enzymes NdeI/SpeI and vector pSG142 (Gaisser et al., 2000) was digested identically. The resulting DNA bands of about 5.4 kb for pCJR336 and 1.2 kb for pSG142 were isolated followed by a ligation which was used to transform *E. coli* DH10B. The vector construct containing the actII-ORF4 regulator region was isolated and digested using the restriction enzyme XbaI followed by an alkaline phosphatase treatment according to standard protocols. The isolated DNA was ligated with a fragment of about 200 bp from plasmid pEXoleG2cas (pSG142 derivative containing the ca. 1.2 kb NdeI/BglII fragment of pSGcasOleG2 (WO01/79520) digested with the restriction enzymes XbaI and NheI. Vector pSGset1 was isolated and the correct orientation of the insert was verified using restriction digests and sequence analysis. Plasmid pSGset1 contains the actII-ORF4 regulator, the $P_{actII}$ promoter and the 6× His-tag coding sequence as well as the lambda $t_0$ transcriptional termination region (originating from plasmid pQE-16) and it can integrate site-specifically at the ΦC31 attachment site.

Cloning of rapK

The gene rapK was amplified by PCR using the primers BIOSG8 5'-GGGCATATGAGGCAATTGACTCCGCCG-GTCACGGCACCGTACTGCC-3' (SEQ ID NO: 37) and BIOSG9 5'-GGGGTCTAGAGGTCACGCCACCACAC-CCTCGATCTCGACC-3' (SEQ ID NO: 38), which introduce a NdeI site at the 5' end and a XbaI site at the 3' end of rapK. Plasmid pR19 (Schwecke et al., 1995) was used as a template. After treatment with T4 polynucleotide kinase using standard techniques the PCR product was ligated with SmaI-cut pUC18 and used to transform *E. coli* DH10B. The DNA sequence of rapK in the isolated plasmid pUCrapK was verified by sequence analysis. The differences in the DNA sequence compared to the published sequence (acc. no. X86780) are shown in FIG. 27. The resulting changes in RapK are shown in FIG. 28.

Isolation of pSGsetrapK

Plasmid pUCrapK was digested with NdeI and XbaI and the insert fragments were isolated and ligated into identically digested pSGset1. The ligation was used to transform *E. coli* DH10B using standard procedures and the transformants were analysed. Plasmid pSGsetrapK, was isolated and the construct was verified using restriction digests and sequence analysis.

EXAMPLE 4

Figure 6:
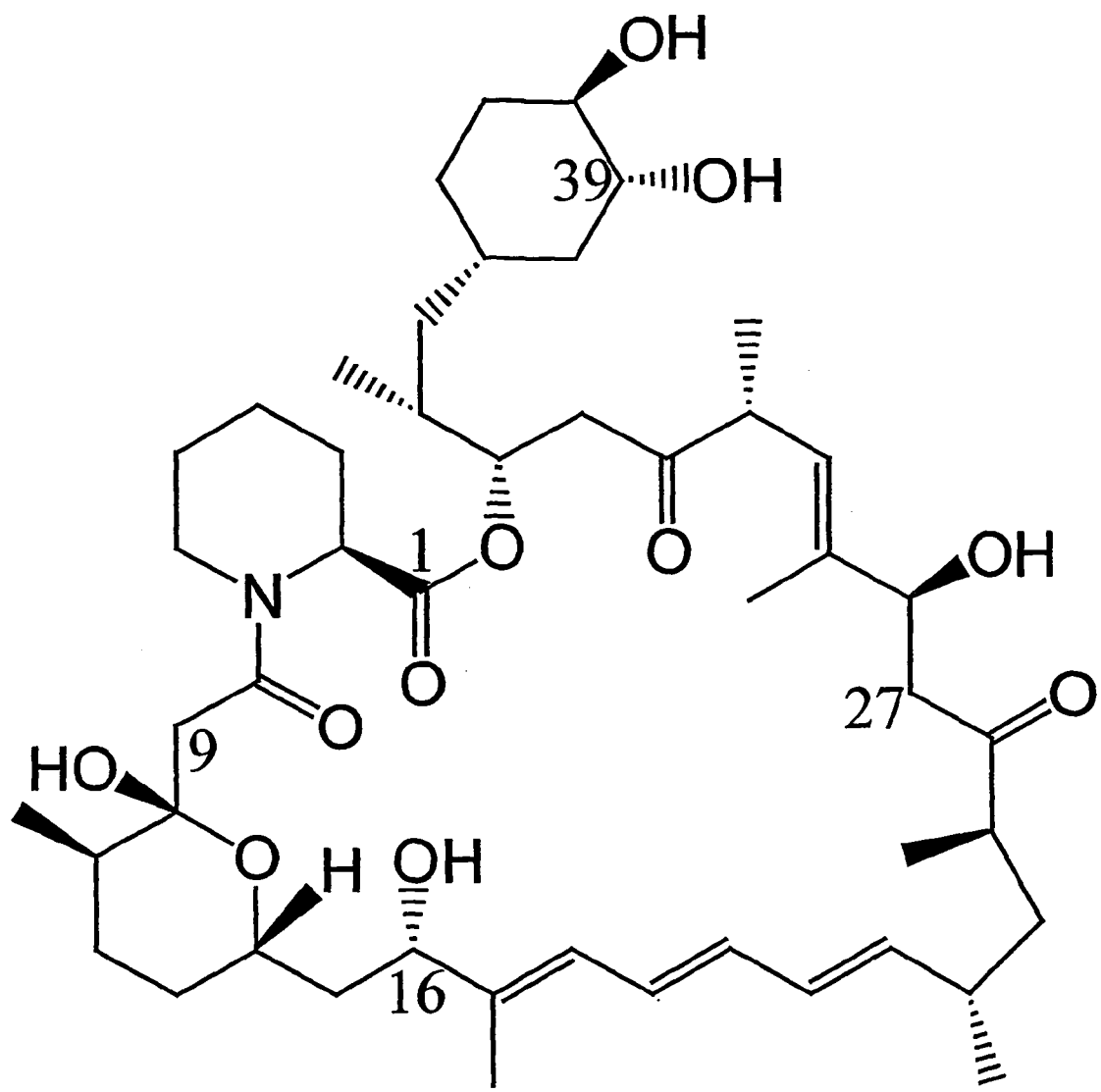
FIG. 6 Structure of 9-deoxo-16-O-desmethyl-27-desmethoxy-39-O-desmethyl rapamycin FIG. 7 Structure of 9-deoxo-16-O-desmethyl-27-desmethoxy-39-O-desmethyl prolylrapamycin FIG. 8 Structure of 9-deoxo-16-O-desmethyl-27-desmethoxy-39-desmethoxy rapamycin FIG. 9 Structure of 16-O-desmethyl-27-desmethoxy rapamycin FIG. 10 Structures of compounds 1, 2, 4, 5, 6, 8, 9, 15, 16, 17, 18 and 19

Identification of 9-deoxo-16-O-desmethyl-27-desmethoxy-39-O-desmethyl-rapamycin (pre-rapamycin, FIG. 6)

9-deoxo-16-O-desmethyl-27-desmethoxy-39-O-desmethyl-rapamycin (pre-rapamycin) was obtained by conjugating the *S. hygroscopicus* strain MG2-10 as described in Example 1 with pSGsetrapK and isolating the products produced on fermentation. This demonstrates that it is possible to complement the deletion of rapK in the MG2-10 strain and that, if the strain is fed with pipecolic acid, pre-rapamycin is produced, an analogue which is lacking the post-PKS modifications.

The plasmid pSGsetrapK was conjugated into *S. hygroscopicus* MG2-10 and the strain grown in TSBGM fed with 2 mg/l pipecolic acid at 25° C. with shaking. The mycelia were extracted with methanol and the culture broth was extracted with ethyl acetate as described previously.

Analysis of the culture broth of the pipecolic acid-fed *S. hygroscopicus* mutant MG2-10[pSGsetrapK] by HPLC with UV detection at 280 nm revealed the presence of two major new peaks with retention times of 4.0 and 5.1 minutes. Electrospray mass spectroscopy of these peaks revealed that both contained ions corresponding to a compound with a MW of 841.5. Neither of these peaks was seen in the culture extractions of the *S. hygroscopicus* NRRL 5491 strain or the mutant strain MG2-10 without the rapK expression plasmid pSGsetrapK MS/MS analysis of the ion with m/z of 864 (corresponding to the sodium adduct of pre-rapamycin) revealed that it fragmented into an ion with m/z of 735 corresponding to the loss of m/z 129 (pipecolic acid), or an ion with m/z of 556 corresponding to the loss of m/z 308 (C28-C42 of pre-rapamycin). This ion itself fragmented further to an ion with m/z 306, corresponding to the loss of m/z 250 (C14 to C27 of pre-rapamycin). This fragmentation pattern was identical to the pattern seen for rapamycin but with the second loss of m/z (−308) reduced by 14, corresponding to the absence of the C39 O-methyl group, the third loss of m/z (−250) reduced by 44, corresponding to the absence of the C27 methoxy and C16 O-methyl groups and the final ion (306) having a mass reduced by 14 corresponding to the absence of the C9 ketone group. This was evidence that the compound with MW 841.5 represents C-deoxo-16-O-desmethyl-27-desmethoxy-39-O-desmethyl-rapamycin (pre-rapamycin).

EXAMPLE 5

Preparation of Gene Cassettes for Expression in *S. hygroscopicus* MG2-10

Gene cassettes able to direct the expression of a variety of rapamycin modifying genes and combinations of modifying genes were constructed as described below.

Cloning of rapN/O

The contiguous genes rapN and rapO, hereafter designated rapN/O were amplified by PCR using the primers BIOSG2 5'-GGGATATGTCGACGACCGATCAGGGT-GAGACCGGAAAGGCCTG-3' (SEQ ID NO: 39) and BIOSG3 5'-GGGGTCTAGAGGTCAGTCCTGGGGTTC-GAGAAGCTCGCCGGTCTCCTT-3' (SEQ ID NO: 40), which introduce a NdeI site at the 5' end and a XbaI site at the 3' end of rapN/O. Plasmid pR19 (Schwecke et al., 1995) was used as a template. After treatment with T4 polynucleotide kinase using standard techniques the PCR product was ligated into SmaI-cut pUC18 and used to transform *E. coli* DH10B. The DNA sequence of rapN/O in the isolated plasmid pUCrapN/O was verified by sequence analysis. The differences in the DNA sequence compared to the published sequence (acc. no. X86780) are shown in FIG. 21. The resulting changes in RapN are shown in FIG. 22.

Cloning of rapM

The gene rapM was amplified by PCR using the primers BIOSG4 5'-GGGCATATGATCCAACCCGACGTCGT-GACCGCCTTCACAGCGG-3' (SEQ ID NO: 41) and BIOSG5 5'-GGGGTCTAGAGGTCACACGCGGACGGC-GATCTGGTGCCGATAGG-3' (SEQ ID NO: 42), which introduce a NdeI site at the 5' end and a XbaI site at the 3' end of rapM. Plasmid pR19 (Schwecke et al., 1995) was used as a template. After treatment with T4 polynucleotide kinase using standard techniques the PCR product was ligated into SmaI-cut pUC18 and used to transform *E. coli* DH10B. The DNA sequence of rapM in the isolated plasmid pUCrapM was verified by sequence analysis. The differences in the DNA sequence compared to the published sequence (acc. no. X86780) are shown in FIG. 23. The resulting changes in RapM are shown in FIG. 24.

Cloning of rapL

The gene rapL was amplified by PCR using the primers BIOSG6 5'-GGGCATATGCAGACCAAGGTTCTGTGC-CAGCGTGACATCAAG-3' (SEQ ID NO: 43) and BIOSG7 5'-GGGGTCTAGAGGTCACTACAGCGAG-TACGGATCGAGGACGTCCTCGGGCG-3' (SEQ ID NO: 44), which introduce a NdeI site at the 5' end and a XbaI site at the 3' end of rapL. Plasmid pR19 (Schwecke et al., 1995) was used as a template. After treatment with T4 polynucleotide kinase using standard techniques the PCR product was ligated into SmaI-cut pUC18 and used to transform *E. coli* DH10B. The DNA sequence of rapL in the isolated plasmid pUCrapL was verified by sequence analysis. The differences in the DNA sequence compared to the published sequence (acc. no. X86780) are shown in FIG. 25. The resulting changes in RapL are shown in FIG. 26.

Cloning of rapL$_{his}$

The gene rapL was amplified by PCR using the primers BIOSG6 5'-GGGCATATGCAGACCAAGGTTCTGTGC-CAGCGTGACATCAAG-3' (SEQ ID NO: 43) and BIOSG45 5'-GGAGATCTCAGCGAGTACGGATCGAG-GACGTCCTCGGGCG-3' (SEQ ID NO: 45), which introduce a NdeI site at the 5' end and a BglII site at the 3' end of rapL. Plasmid pR19 (Schwecke et al., 1995) was used as a template. After treatment with T4 polynucleotide kinase using standard techniques the PCR product was ligated into SmaI-cut pUC19 and used to transform *E. coli* DH10B. The DNA sequence of rapL in the isolated plasmid pUC19rapL$_{his}$ was verified by sequence analysis.

Cloning of rapK

The gene rapK was amplified by PCR using the primers BIOSG8 5'-GGGCATATGAGGCAATTGACTCCGCCG-GTCACGGCACCGTACTGCC-3' (SEQ ID NO: 37) and BIOSG9 5'-GGGGTCTAGAGGTCACGCCACCACAC-CCTCGATCTCGACC-3' (SEQ ID NO: 38), which introduce a NdeI site at the 5' end and a XbaI site at the 3' end of rapK. Plasmid-pR19 (Schwecke et al., 1995) was used as a template. After treatment with T4 polynucleotide kinase using standard techniques the PCR product was ligated with SmaI-cut pUC18 and used to transform *E. coli* DH10B. The DNA sequence of rapK in the isolated plasmid pUCrapK was verified by sequence analysis. The differences in the DNA sequence compared to the published sequence (acc. no. X86780) are shown in FIG. 27. The resulting changes in RapK are shown FIG. 28.

Isolation of pSGsetrpaN/O, pSGsetrapJ, pSGsetrapM, pSGsetrapQ, pSGsetrapI, pSGsetrapK, and pSGsetrapL Plasmids pUCrapN/O, pUCrapJ, pUCrapM, pUCrapI, pUCrapL, pUCrapK and pAHL42 were digested with NdeI and XbaI and the insert fragments, ranging in size from about 1.3 kb to 0.7 kb, were isolated and ligated into identically digested pSGset1. The ligations were used to transform *E. coli* DH10B using standard procedures and the transformants were analysed. Plasmids pSGsetrapN/O, pSGsetrapJ, pSGsetrapM, pSGsetrapQ, pSGsetrapI, pSGsetrapK, and pSGsetrapL were isolated and the constructs were verified using restriction digests and sequence analysis.

Cloning of rapJ

The gene rapJ was amplified by PCR using the primers BIOSG10 5'-GGGCATATGAGCACCGAAGCTCAG-CAAGAGAGCACGCCCACCGCACGCT-3' (SEQ ID NO: 46) and BIOSG11 5'-GGGGTCTAGAGGTCACTC-CGCTCCCCAGGTGACCGGAGCTCGGC-3' (SEQ ID NO: 47), which introduce a NdeI site at the 5' end and a XbaI site at the 3' end of rapJ. Plasmid pR19 (Schwecke et al., 1995) was used as a template. After treatment with T4 polynucleotide kinase using standard techniques the PCR product was ligated with SmaI-cut pUC18 and used to transform *E. coli* DH10B. The DNA sequence of rapJ in the isolated plasmid pUCrapJ was verified by sequence analysis. The differences in the DNA sequence compared to the published sequence (acc. no. X86780) are shown in FIG. 29. The resulting changes in RapJ are shown in FIG. 30.

Cloning of rapI

The gene rapI was amplified by PCR using the primers BIOSG12 5'-GGGCATATGAGCGCGTCCGTGCAGAC-CATCAAGCTGCC-3' (SEQ ID NO: 48) and BIOSG13 5'-GGGGTCTAGAGGTCAGGCGTCCCCGCG-GCGGGCGACGACCT-3' (SEQ ID NO: 49), which introduce a NdeI site at the 5' end and a XbaI site at the 3' end of rapI. Plasmid pAHL2 (kindly provided by Huai-Lo Lee) is derived from. pUC18 containing the rapI gene and was used as a template. After treatment with T4 polynucleotide kinase using standard techniques the PCR product was ligated with SmaI-cut pUC18 and used to transform *E. coli* DH10B. The DNA sequence of rapI in the isolated plasmid pUCrapI was verified by sequence analysis. The differences in the DNA sequence compared to the published sequence (acc. no. X86780) are shown in FIG. 31. The resulting changes in RapI are shown in FIG. 32.

Cloning of rapQ

The gene rapQ was amplified by PCR using the primers AHL21 5'-CATATGTTGGAATTGGGTACCCGCCTG-3' (SEQ ID NO: 50) and AHL22 5'-TCTAGACGCTCACGC-CTCCAGGGTG-3' (SEQ ID NO: 51), which introduce a NdeI site at the 5' end and a XbaI site at the 3' end of rapQ. Plasmid pR19 (Schwecke et al., 1995) was used as a template. After treatment with T4 polynucleotide kinase using standard techniques the PCR product was ligated with SmaI-cut pUC18 and used to transform *E. coli* DH10B. The DNA sequence of rapQ in the isolated plasmid pAHL42 was verified by sequence analysis. The differences in the DNA sequence compared to the published sequence (acc. no. X86780) are shown in FIG. 33. The resulting changes in RapQ are shown in FIG. 34.

Isolation of pUC18eryBVcas

The gene eryBV was amplified by PCR using the primers casOleG21 (WO01/79520) and 7966 5'-GGGGAATTC AGATCTGG TCTAGAGGTCAGCCGGCGTGGCGGCGCGTG AGT-TCCTCCAGTCGCGGGACGATCT-3' (SEQ ID NO: 52) and pSG142 (Gaisser et al., 2000) as template. The PCR fragment was cloned using standard procedures and plasmid pUC18eryBVcas was isolated with an NdeI site overlapping the start codon of eryBV and an XbaI and BglII site following the stop codon. The construct was verified by sequence analysis.

Isolation of Vector pSGLit1

The gene eryBV was amplified by PCR using the primers BIOSG1 5'-GGGTCTAGATCCGGACGAACGCATCGAT-TAATTAAGGAGGACACATA-3' (SEQ ID NO: 53) and 7966 5'-GGGGAATTCAGATCTGGTCTAGAGGT- CAGCCGGCGTGGCGGCGCGTGAGTTC CTC-CAGTCGCGGGACGATCT-3' (SEQ ID NO: 52), which introduce a XbaI site sensitive to Dam methylation at the 5' end and a XbaI site and a BglII site at 3' end of eryBV. Plasmid pUC18eryBVcas was used as a template. After treatment with T4 polynucleotide kinase using standard techniques the PCR product was ligated with SmaI-cut pUC18 and used to transform *E. coli* DH10B. The construct was then digested using BamHI/BglII and an about 1.3 kb DNA band was isolated from an agarose gel followed by the ligation with BamHI/BglII digested Litmus 28 vector DNA using standard procedures. The vector pSGLit1 was isolated and the DNA sequence of the insert was verified by sequence analysis.

Isolation of pSGsetrpaN/O, pSGsetrapJ, pSGsetrapM, pSGsetrapQ, pSGsetrapI, pSGsetrapK, and pSGsetrapL Plasmids pUCrapN/O, pUCrapJ, pUCrapM, pUCrapI, pUCrapL, pUCrapK and pAHL42 were digested with NdeI and XbaI and the insert fragments ranging in size from about 1.3 kb to 0.7 kb were isolated and ligated into identically digested pSGset1. The ligations were used to transform *E. coli* DH10B using standard procedures and the transformants were analysed. Plasmids pSGsetrapN/O, pSGsetrapJ, pSGsetrapM, pSGsetrapQ, pSGsetrapI, pSGsetrapK, and pSGsetrapL were isolated and the constructs were verified using restriction digests and sequence analysis.

Isolation of pSGLitrapN/O, pSGLitrapJ, pSGLitrapM, pSGLitrapQ, pSGLitrapI, pSGLitrapK, pSGLitrapL and pSGLitrapL$_{his}$ Plasmids pSGsetrpaN/O, pSGsetrapJ, pSGsetrapM, pSGsetrapQ, pSGsetrapI, pSGsetrapK, pSGsetrapL, and pUC19rapL$_{his}$ were digested using NdeI/BglII restriction enzymes and the bands ranging from about 0.7 to 1.3 kb were isolated followed by ligations with pSGLit1 digested with NdeI/BglII. The ligations were used to transform *E. coli* ET12567 and the transformants were analysed. Plasmids pSGLitrapN/O, pSGLitrapJ, pSGLitrapM, pSGLitrapQ, pSGLitrapI, pSGLitrapK, pSGLitrapL and pSGLitrapL$_{his}$ were isolated:

Isolation of Plasmids pSGsetrapKI, pSGsetrapKM, pSGsetrapKN/O, pSGsetrapKL, pSGsetrapKQ and pSGrapKJ The plasmids pSGLitrapN/O, pSGLitrapJ, pSGLitrapM, pSGLitrapQ, pSGLitrapI, and pSGLitrapL were digested using XbaI and the fragments ranging from about 0.8 to 1.3 kb were isolated followed by ligations with pSGsetrapK. digested with XbaI and treated with alkaline phosphatase using standard molecular biological techniques. The ligations were used to transform *E. coli* DH10B and the transformants were analysed. Plasmids pSGsetrapKI, pSGsetrapKM, pSGsetrapKN/O, pSGsetrapKL, pSGsetrapKQ and pSGrapKJ were isolated and the orientation of the insert was verified by restriction digest analysis. For the addition of rapL$_{his}$ these constructs were either digested with BglII/XbaI followed by partial digest with BglII as appropriate and the isolated vector fragments were ligated with the ~1 kb XbaI/BglII fragment of pSGLitrapL$_{his}$.

Isolation of Plasmids pSGsetrapKIJ, pSGsetrapKIM and pSGsetrapKIQ

The plasmids pSGLitrapJ, pSGLitrapM, and pSGLitrapQ were digested using XbaI and the fragments ranging from about 0.8 to 1.3 were isolated followed by ligations with pSGsetrapKI digested with XbaI and treated with alkaline phosphatase using standard molecular biological techniques. The ligabons were used to transform *E. coli* DH10B and the transformants were analysed. Plasmids pSGsetrapKIJ, pSG-setrapKIM, and pSGrapKIQ were isolated and the orientation of the insert was verified by restriction digest analysis. For the addition of rapL$_{his}$ these constructs were either digested with BglII/XbaI followed by partial digest with BglII as appropriate and the isolated vector fragments were ligated with the ~1 kb XbaI/BglII fragment of pSGLitrapL$_{his}$.

Isolation of Plasmids pSGsetrapKN/OI, pSGsetrapKN/OQ, pSGsetrapKN/OM and pSGsetrapKN/OJ.

The plasmids pSGLitrapI, pSGLitrapM, pSGLitrapJ, and pSGLitrapQ were digested using XbaI and the fragments ranging from about 0.8 to 1.3 were isolated followed by ligatons with pSGsetrapKN/O digested with XbaI and treated with alkaline phosphatase using standard molecular biological techniques. The ligations were used to transform *E. coli* DH10B and the transformants were analysed. Plasmids pSGsetrapKN/OI, pSGsetrapKN/OQ, pSGsetrapKN/OM and pSGrapKN/OJ were isolated and the orientation of the insert was verified by restriction digest analysis. For the addition of rapL$_{his}$ these constructs were either digested with BglII/XbaI followed by partial digest with BglII as appropriate and the isolated vector fragments were ligated with the ~1 kb XbaI/BglII fragment of pSGLitrapL$_{his}$.

Isolation of Plasmids pSGsetrapKJM and pSGsetrapKJQ

The plasmids pSGLitrapM and pSGLitrapQ were digested using XbaI and the fragments ranging from about 0.8 to 1.1 were isolated followed by a ligation with pSGsetrapKJ digested with XbaI and treated with alkaline phosphatase using standard molecular biological techniques. The ligations were used to transform *E. coli* DH10B and the transformants were analysed. Plasmids pSGsetrapKJM and pSGrapKJQ were isolated and the orientation of the insert was verified by restriction digest analysis. For the addition of rapL$_{his}$ these constructs were either digested with BglII/XbaI followed by partial digest with BglII as appropriate and the isolated vector fragments were ligated with the ~1 kb XbaI/BglII fragment of pSGLitrapL$_{his}$.

Using the same strategy outlined above, the following gene cassettes were isolated:

| | | |
|---|---|---|
| pSGsetrapKIJM | pSGsetrapKN/OJI | pSGsetrapKIQN/OM |
| pSGsetrapKIJQ | pSGsetrapKJMN/O | pSGsetrapKJMN/OQ |
| pSGsetrapKIJN/O | pSGsetrapKJQN/O | pSGsetrapKIJN/OMQ |
| pSGsetrapKIMN/O | pSGsetrapKIJN/OM | pSGsetrapN/OQ |
| pSGsetrapKIQN/O | pSGsetrapKIJN/OQ | pSGsetrapKIJMN/OQ |
| pSGsetrapKN/OMQ | pSGsetrapKIMN/OQ | |

Figure 5:
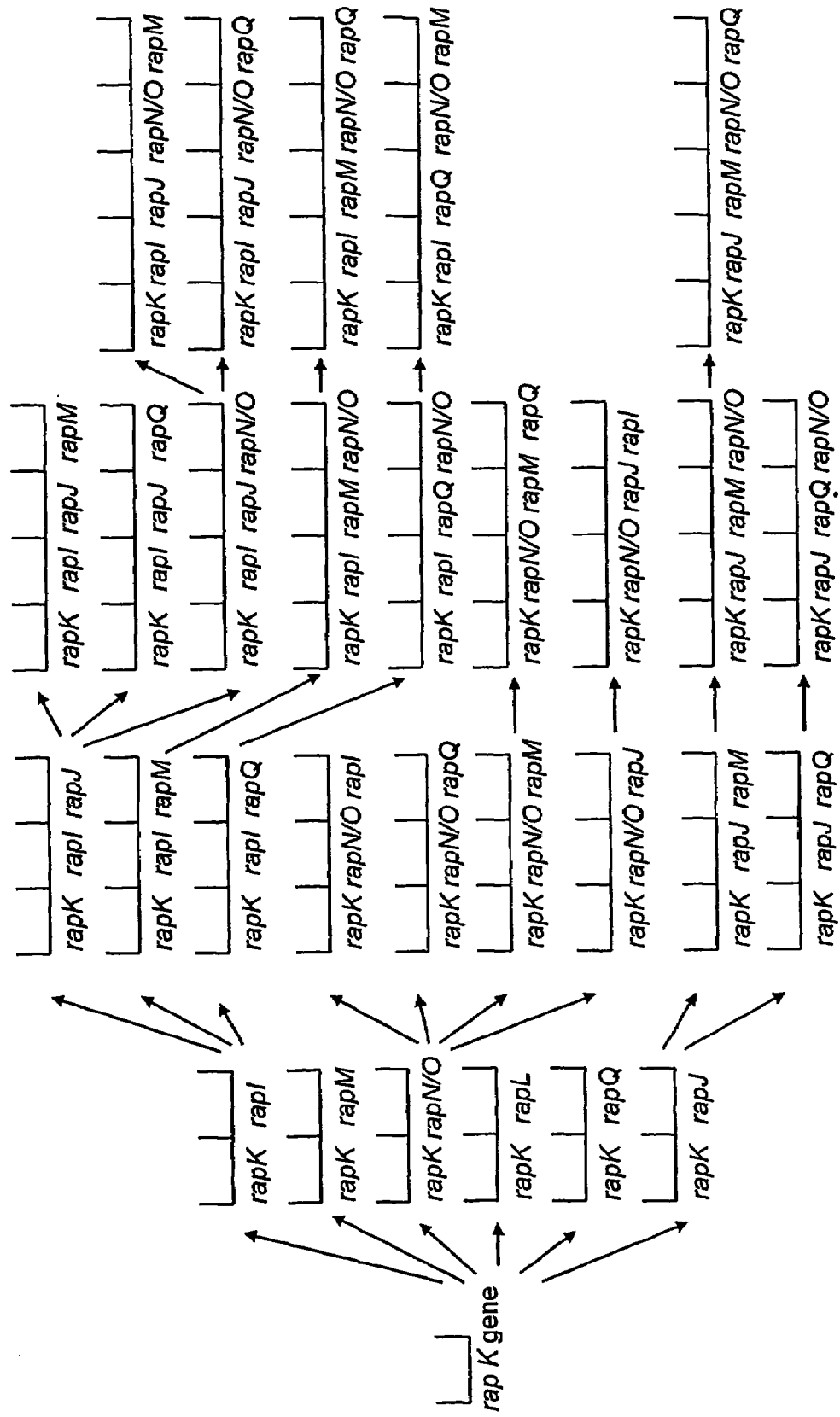
FIG. 5 Overview over the gene cassettes

An overview is given in FIG. 5.

For the addition of rapL$_{his}$ these cassette constructs were either digested with BglII/XbaI or with XbaI followed by partial digest with BglII as appropriate and the isolated vector fragments were ligated with the about 1 kb XbaI/BglII fragment of pSGLitrapL$_{his}$.

EXAMPLE 6

Isolation of 9-deoxo-16-O-desmethyl-27-desmethoxy-39-O-desmethyl-rapamycin (pre-rapamycin, FIG. 6)

9-Deoxo-16-O-desmethyl-27-desmethoxy-39-O-desmethyl-rapamycin (pre-rapamycin) was obtained by conjugating the *S. hygroscopicus* strain MG2-10 with pSGsetrapKL and isolating the products generated as described below.

This demonstrates that it is possible to complement the deletion of rapK and rapL in the MG2-10 strain and that pre-rapamycin is produced, an analogue which is lacking post-PKS modification. The feeding of pipecolic acid is not required when rapL is complemented confirming that rapL plays a role in the provision of pipecolic acid in the production of rapamycin.

S. hygroscopicus MG2-10[pSGsetrapKL] was cultured from a frozen working spore stock in cryopreservative (20% glycerol, 10% lactose w/v in distilled water) on Medium 1 (see Materials and Methods) and spores were harvested after 14 days growth at 29° C. A primary pre-culture was inoculated with the harvested spores and cultured in two 250 ml Erlenmeyer flasks containing 50 ml Medium 3 (see Materials and Methods), shaken at 250 rpm with a two-inch throw, at 30° C., for two days. The primary pre-culture was used to inoculate two secondary pre-cultures of Medium 2 (see Materials and Methods) and Medium 3, at 10% v/v, which was shaken at 300 rpm with a one-inch throw, at 25° C., for a further 24 h. Four litres of Medium 4 (see Materials and Methods) and Medium 5 (see Materials and Methods) were prepared containing 0.01% v/v Pluronic L101 antifoam (BASF). Production Medium 4 was inoculated with the secondary pre-culture in Medium 2 and Production Medium 5 was inoculated with the secondary pre-culture in Medium 3 at 10% v/v and allowed to ferment in a 7 L stirred bioreactor for five to seven days at 25° C. Airflow was set to 0.75 vvm and the impeller tip speed was controlled between 0.98 ms$^{-1}$ and 2.67 ms$^{-1}$. Additional Pluronic L101 was added on demand.

Figure 18:
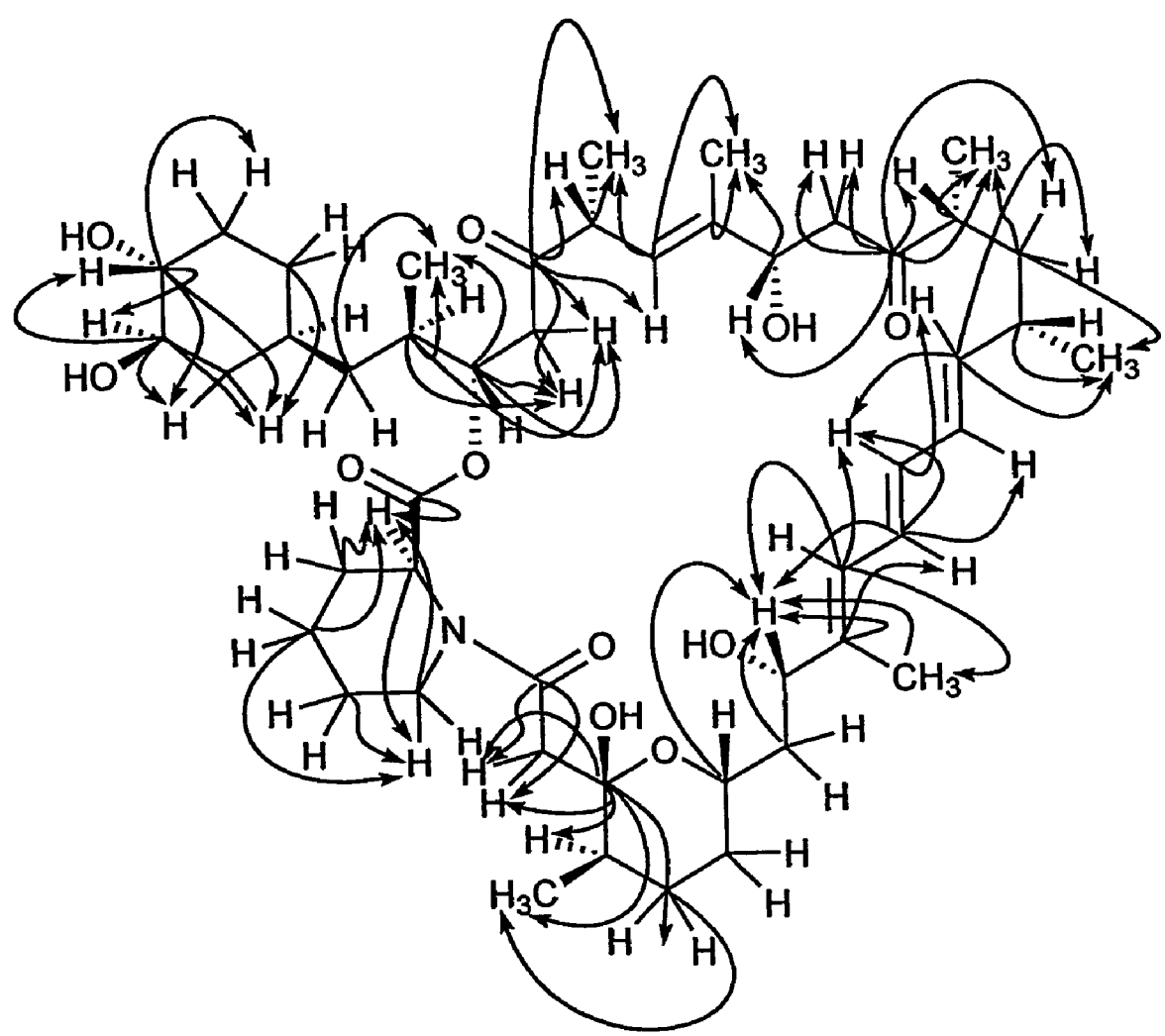
FIG. 18 Pre-rapamycin heteronuclear multiple bond coherence HMBC
Figure 19:
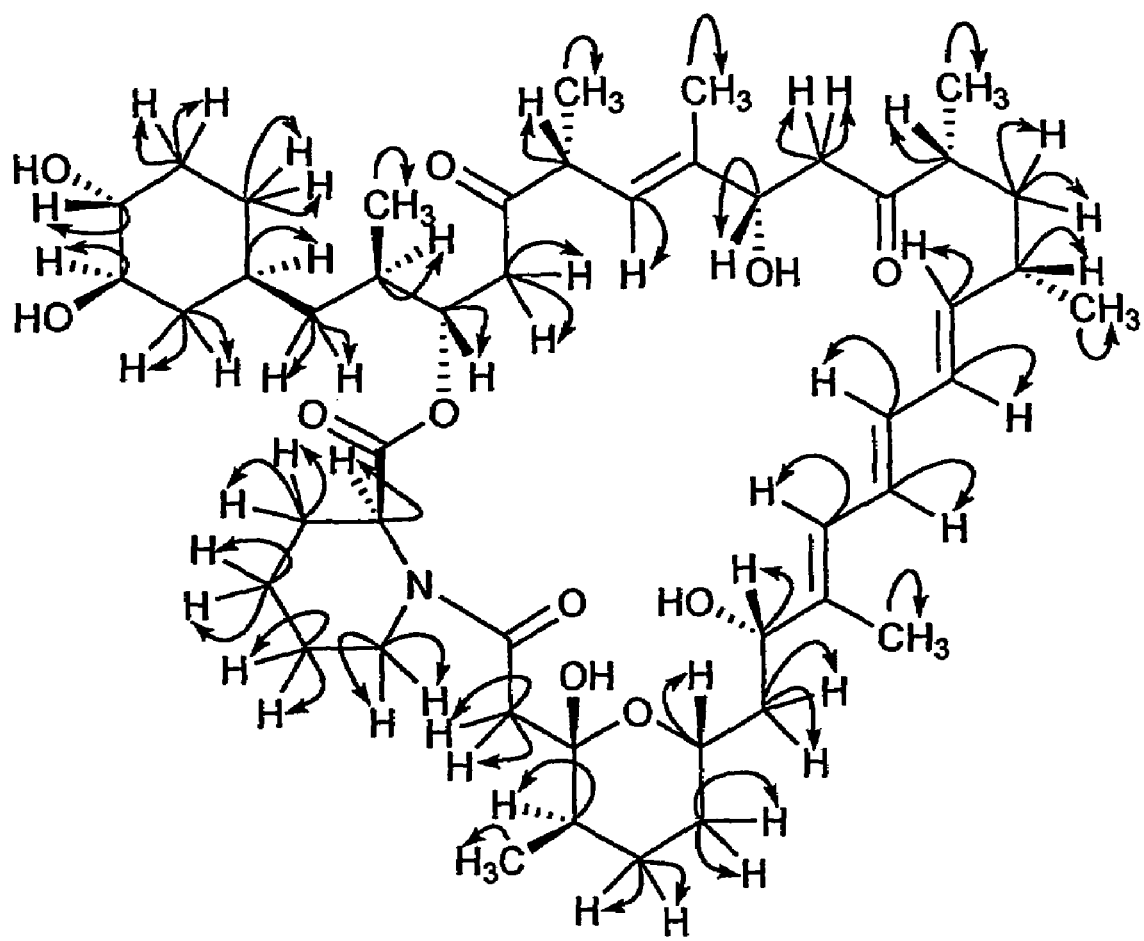
FIG. 19 Pre-rapamycin heteronuclear multiple quantum coherence HMQC

To confirm the structure of 9-deoxo-16-O-desmethyl-27-desmethoxy-39-O-desmethyl-rapamycin (pre-rapamycin), broths from Medium 4 and Medium 5 were extracted with ethyl acetate and reduced to a crude extract by evaporation. The extracts were defatted on partition with hexane:methanol:water and flashed through a 70 g silica cartridge starting with hexane and finishing with acetone. Pre-rapamycin fractions from each fermentation were pooled and flashed through a C18 cartridge starting with water and finishing with methanol. Pre-rapamycin (8.5 mg) was isolated after chromatography on Sephadex LH$_{20}$ using heptane:chloroform:ethanol as the mobile phase. This compound was analysed and the structure fully confirmed by NMR (FIGS. 18-20). The $^1$H and $^{13}$C NMR data are given in Table V below.

TABLE V $^1$H and $^{13}$C NMR data for pre-rapamycin

| Position | $\delta_H$ | multiplicity | coupling | $\delta_C$ |
|---|---|---|---|---|
| 1 | | | | 171.8 |
| 2 | 5.49 | | | 52.7 |
| 3a | 1.76 | | | 25.9 |
| 3b | 2.21 | | | |
| 4a | 1.21 | | | 20.9 |
| 4b | 1.75 | | | |
| 5a | 1.47 | | | 25.0 |
| 5b | 1.74 | | | |
| 6a | 3.27 | | | 45.1 |
| 6b | 3.87 | br. d | 12.8 | |
| 8 | | | | 171.6 |
| 9a | 2.46 | d | 12.8 | 41.4 |
| 9b | 3.23 | d | 12.8 | |
| 10 | | | | 98.9 |
| 11 | 1.60 | | | 38.1 |
| 12a | 1.52 | | | 27.6 |
| 12b | 1.65† | | | |
| 13a | 1.38 | | | 31.6 |
| 13b | 1.53 | | | |
| 14 | 4.00 | | | 71.5 |
| 15a | 1.48 | | | 40.6 |
| 15b | 1.70 | | | |
| 16 | 3.95 | br. d | 8.1 | 75.5 |
| 17 | | | | 139.2 |
| 18 | 6.39 | | | 122.6 |
| 19 | 6.33 | | | 128.1 |
| 20 | 6.17 | dd | 14.3, 10.7 | 131.4 |
| 21 | 6.04 | | | 130.9 |
| 22 | 5.26 | | | 138.1 |
| 23 | 2.21 | | | 37.2 |
| 24a | 1.26 | | | 39.8 |
| 24b | 1.64 | | | |
| 25 | 2.30 | | | 45.8 |
| 26 | | | | 215.3 |
| 27a | 2.42 | dd | 15.1, 4.7 | 44.8 |
| 27b | 2.89 | dd | 15.1, 5.8 | |
| 28 | 4.32 | dd | 5.5, 4.9 | 71.4 |
| 29 | | | | 138.6 |
| 30 | 5.26 | | | 123.7 |
| 31 | 3.20 | | | 45.5 |
| 32 | | | | 208.2 |
| 33a | 2.58 | dd | 18.1, 4.3 | 41.5 |
| 33b | 2.78 | dd | 18.1, 9.6 | |
| 34 | 5.18 | | | 76.0 |
| 35 | 1.72 | | | 31.9 |
| 36a | 1.00 | | | 37.3 |
| 36b | 1.07 | | | |
| 37 | 1.30 | | | 33.1 |
| 38a Ax. | 0.62 | ddd | 11.9, 11.9, 11.9 | 38.2 |
| 38b eq. | 1.83 | | | |
| 39 | 3.24 | | | 74.9 |
| 40 | 3.25 | | | 75.9 |
| 41a | 1.28 | | | 31.5 |
| 41b | 1.94 | | | |
| 42a | 0.98 | | | 32.2 |
| 42b | 1.61 | | | |
| 43 | 0.98 | d | 6.6 | 16.5 |
| 44 | 1.61 | s | | 14.1 |
| 45 | 1.04 | d | 6.8 | 21.3 |
| 46 | 0.95 | d | 6.8 | 15.2 |
| 47 | 1.66 | d | 0.9 | 14.1 |
| 48 | 0.99 | d | 6.8 | 15.7 |
| 49 | 0.89 | d | 6.6 | 17.4 |

†Assignment tentative

EXAMPLE 7

Figure 7:
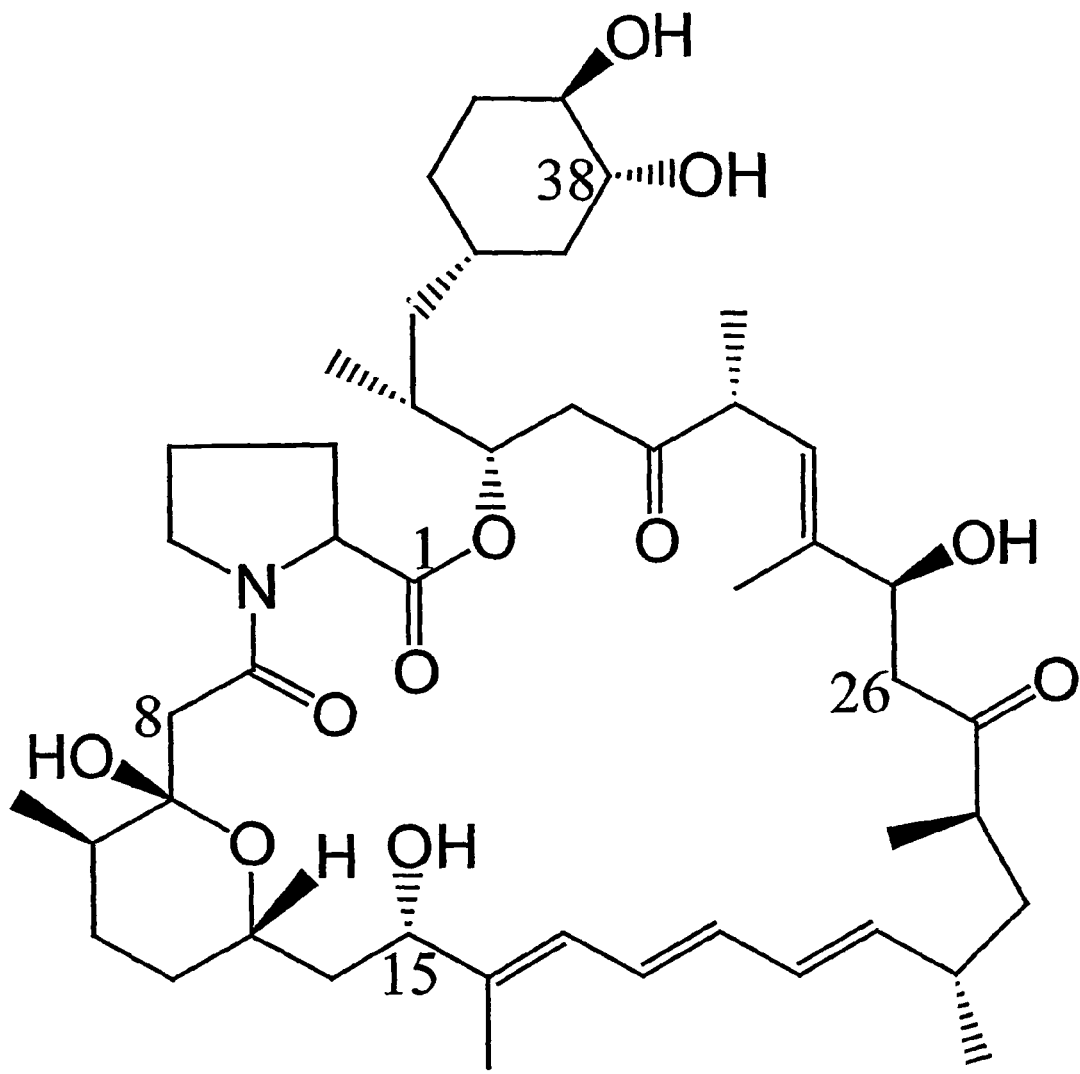

Isolation of 8-deoxo-15-O-desmethyl-26-desmethoxy-38-O-desmethyl-prolylrapamycin (pre-prolylrapamycin, FIG. 7)

Feeding of S. hygroscopicus MG2-10[pSEGrapK] with proline acid resulted in the production pre-prolylrapamycin as described below. This demonstrated that in the absence of rapL alternative pipecolic acid analogues are incorporated.

S. hygroscopicus MG2-10[pSGsetrapK] was grown in TSBGM fed with 1 mg/l proline at 25° C. with shaking. The mycelia were extracted with methanol and the culture broth was extracted with ethyl acetate as described previously.

Analysis of the culture broth of the proline-fed S. hygroscopicus mutant MG2-10[pSGietrapK] by HPLC with UV detection at 280 nm revealed the presence of two major new peaks with retention times of 4.5 and 4.6 minutes. Electrospray mass spectroscopy of these peaks revealed that both contained ions corresponding to a compound with a MW of 827.5. Neither of these peaks were seen in the cultures of S.

hygroscopicus NRRL 5491, S. hygroscopicus MG1C or S. hygroscopicus MG2-10 without the rapK expression plasmid pSGsetrapK. MS/MS analysis of the ion with m/z of 850 (corresponding to the sodium adduct of pre-prolylrapamycin) revealed that it fragmented into an ion with m/z of 735 corresponding to the loss of m/z 115 (proline), or an ion with m/z of 542 corresponding to the loss of m/z 308 (C27-C41 of pre-prolylrapamycin). This ion itself fragmented further to an ion with m/z 292, corresponding to the loss of m/z 250 (C13 to C26 of pre-prolylrapamycin). This fragmentation pattern was identical to the pattern seen for rapamycin but with the first loss of m/z (−115) reduced by 14 corresponding to the change from pipecolic acid to proline for the amino acid, the second loss of m/z (−308) reduced by 14, corresponding to the absence of the C38 O-methyl group, the third loss of m/z (−250) reduced by 44, corresponding to the absence of the C26 methoxy and C15 O-methyl groups and the final ion (306) having a mass reduced by 14 corresponding to the absence of the C8 ketone group and the change from pipecolic acid to proline. This was evidence that the compound with MW of 827.5 represents 8-deoxo-15-O-desmethyl-26-desmethoxy-38-O-desmethyl-prolylrapamycin (pre-prolylrapamycin).

EXAMPLE 8

Figure 8:
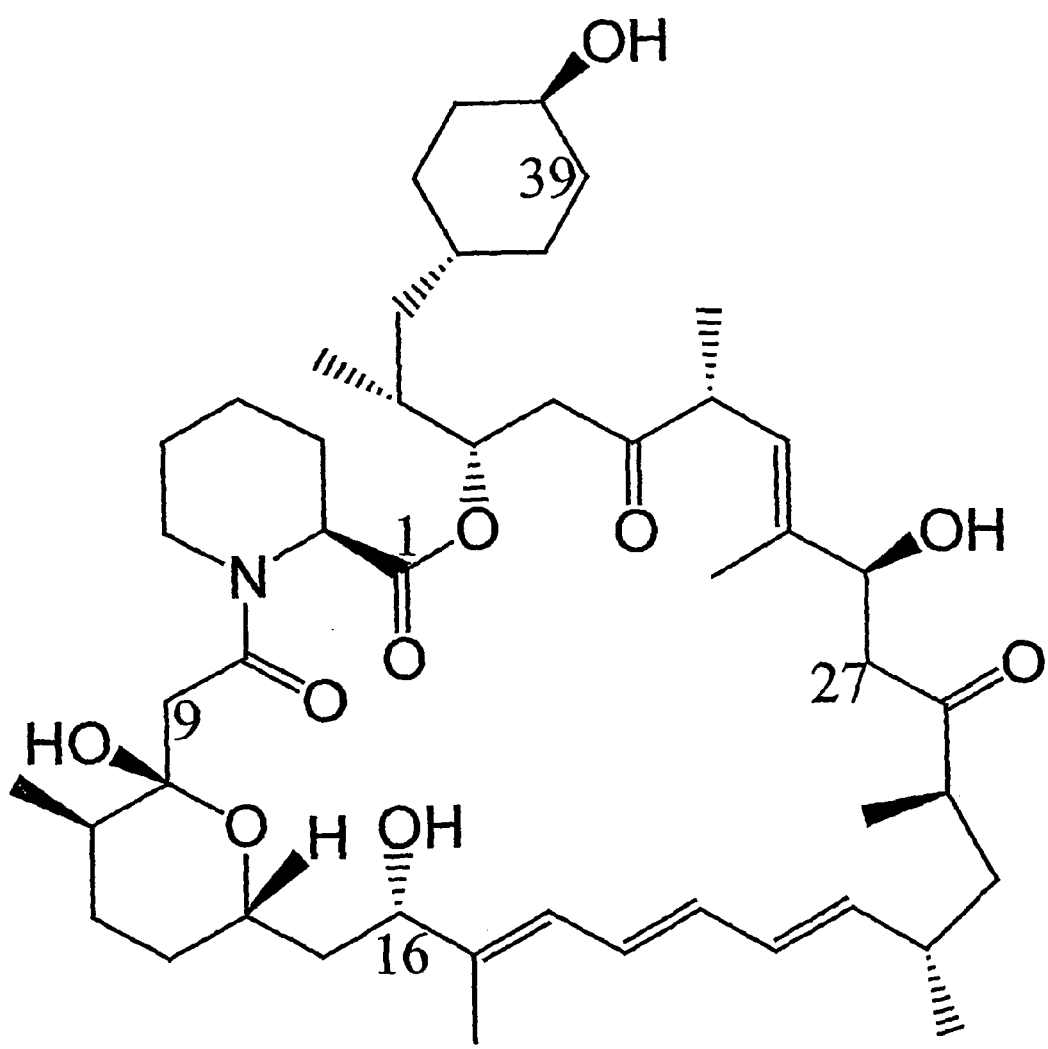

Isolation of 9-deoxo-16-O-desmethyl-27-desmethoxy-39-desmethoxy-rapamycin (39-dehydroxy pre-rapamycin, FIG. 8)

Feeding of S. hygroscopicus MG2-10[pSGsetrapK] with pipecolic acid and cyclohexane carboxylic acid resulted in the production of two major compounds, pre-rapamycin which corresponds to the incorporation of the natural starter unit and 39-dehydroxy pre-rapamycin, which corresponds to the incorporation of the fed starter unit.

S. hygroscopicus MG2-10[pSGsetrapK] was grown in TSBGM fed with 2 mg/l pipecolic acid and 1 mM cyclohexane carboxylic acid at 25° C. with shaking. The culture broth was extracted with ethyl acetate as described previously.

Analysis of the culture broth of the cyclohexane carboxylic acid-fed S. hygroscopicus mutant MG2-10[pSGsetrapK] by HPLC with UV detection at 280 nm revealed the presence of one major new peak with a retention time of 5.8 minutes. Electrospray mass spectroscopy of this peak revealed that it contained ions corresponding to a compound with a MW of 825.5. This peak was not seen in the cultures of S. hygroscopicus NRRL5491, S. hygroscopicus MG1C or S. hygroscopicus MG2-10 without the rapK expression plasmid pSGsetrapK. MS/MS analysis of the ion with m/z of 848 (corresponding to the sodium adduct of 39-dehydroxy pre-rapamycin) revealed that it fragmented into an ion with m/z of 719 corresponding to the loss of m/z 129 (pipecolic acid), or an ion with m/z of 556 corresponding to the loss of m/z 292 (C28-C42 of 39-dehydroxy pre-rapamycin). This ion itself fragmented further to an ion with m/z 306, corresponding to the loss of m/z 250 (C14 to C27 of 39-dehydroxy pre-rapamycin). This fragmentation pattern was identical to the pattern seen for pre-rapamycin but with the second loss of m/z (−292) reduced by 16, corresponding to the absence of the C39 hydroxy group. This was evidence that the compound with MW 825.5 represents 9-deoxo-16-O-desmethyl-27-desmethoxy-39-desmethoxy-rapamycin (39-dehydroxy-prerapamycin).

EXAMPLE 9

Figure 9:
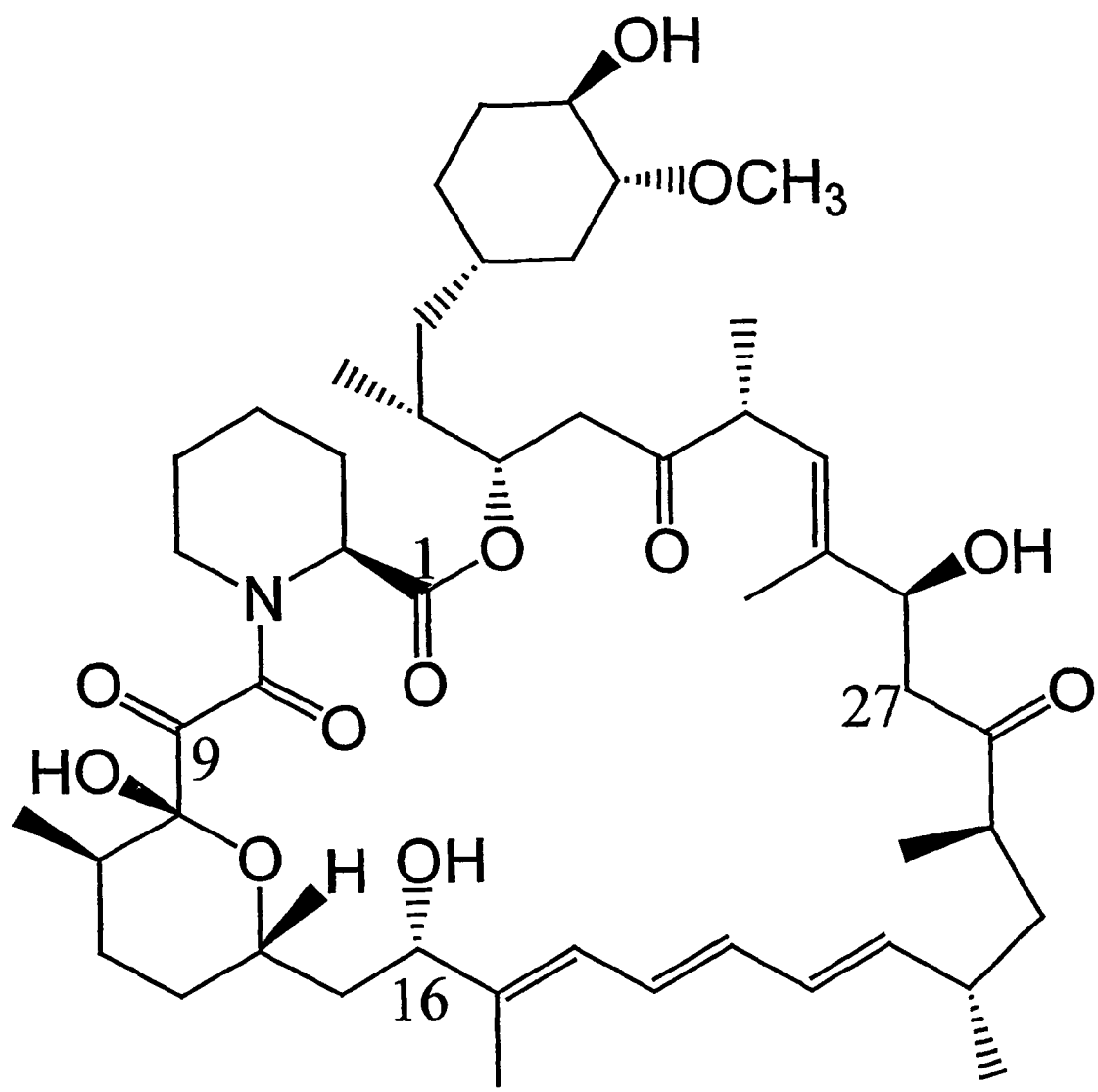
Figure 13:
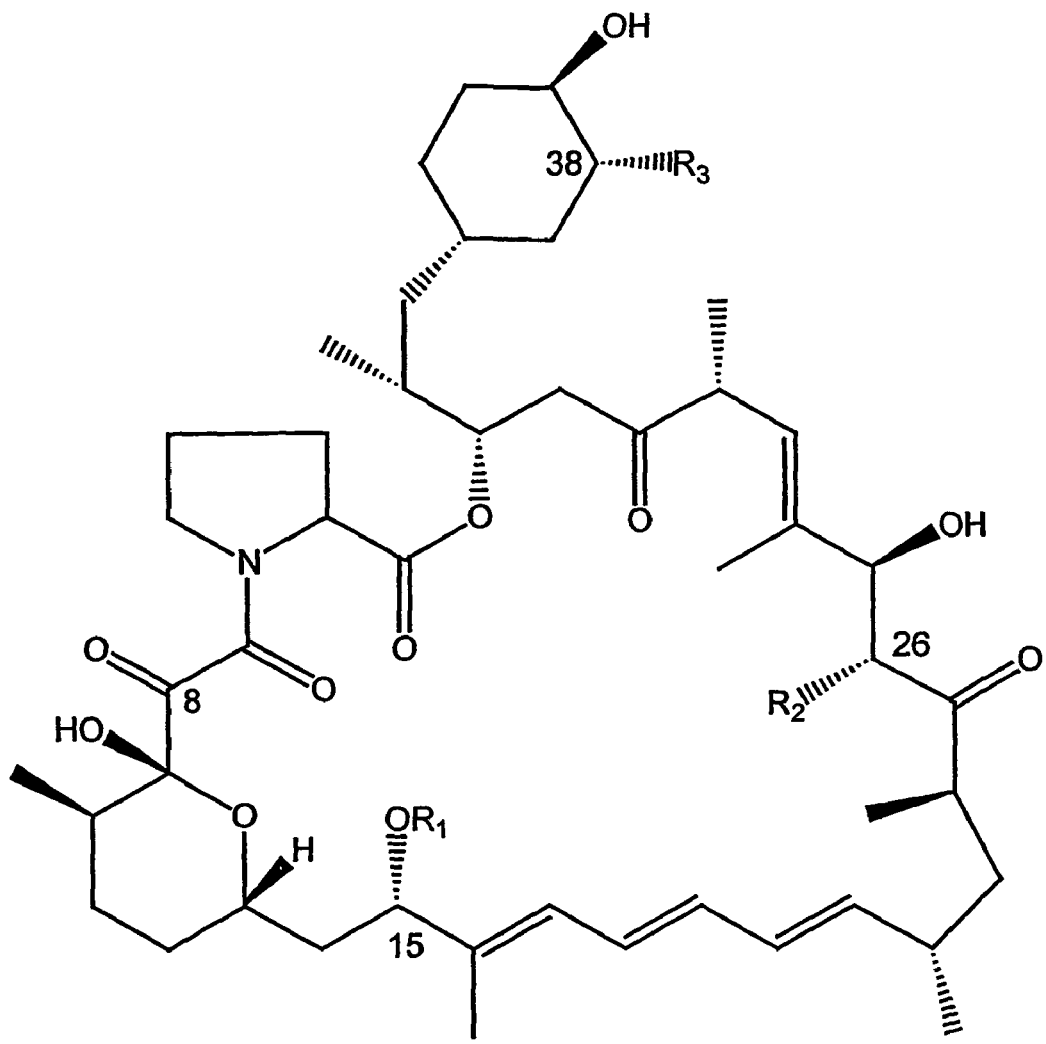
FIG. 13 Structures of compounds 26, 30, 33, 34, 35, 36, 37, 43, 44, 45, and 46
Figure 14:
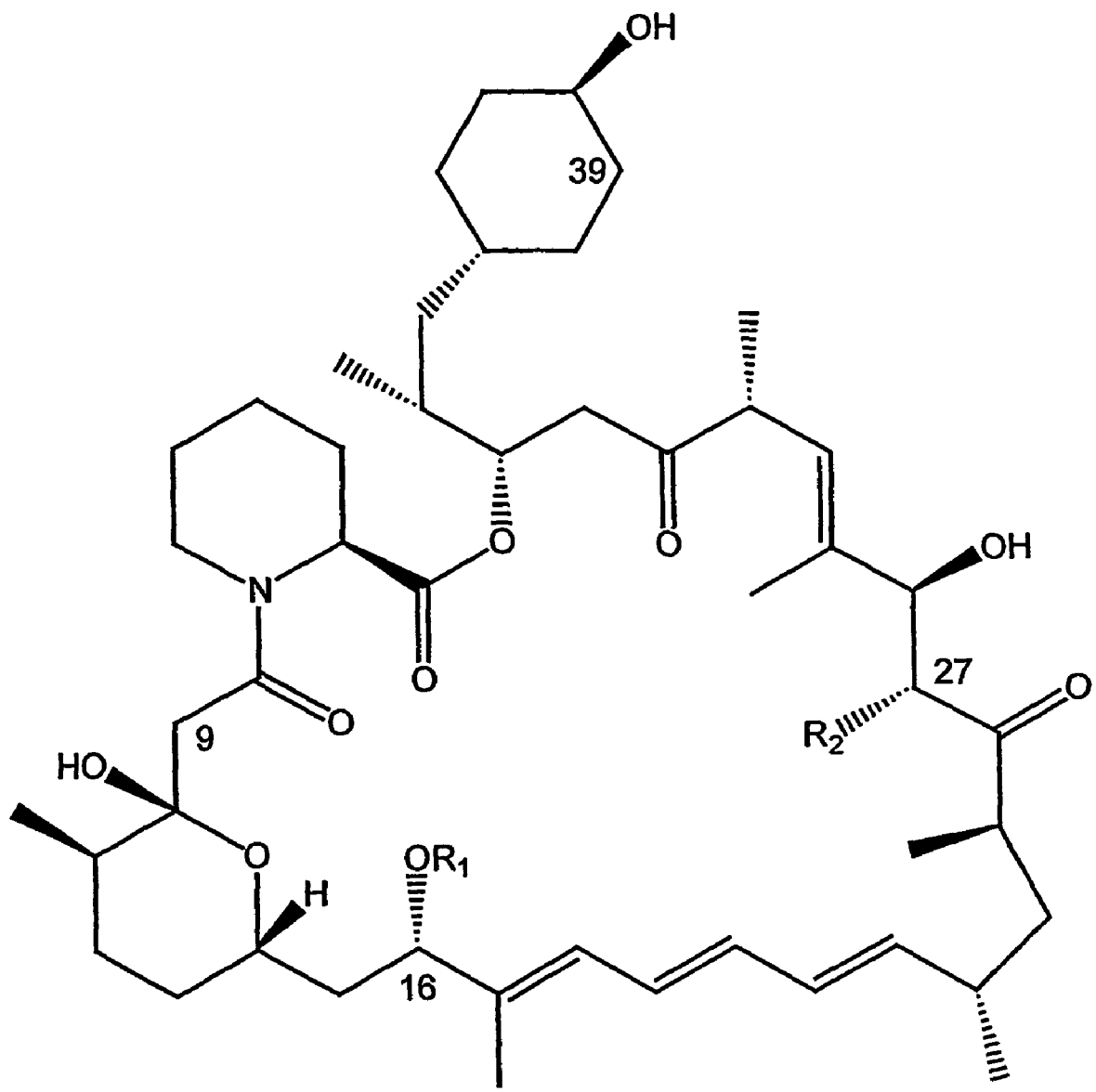
FIG. 14 Structures of compounds 47, 48, 50, 51, 53 and 57
Figure 15:
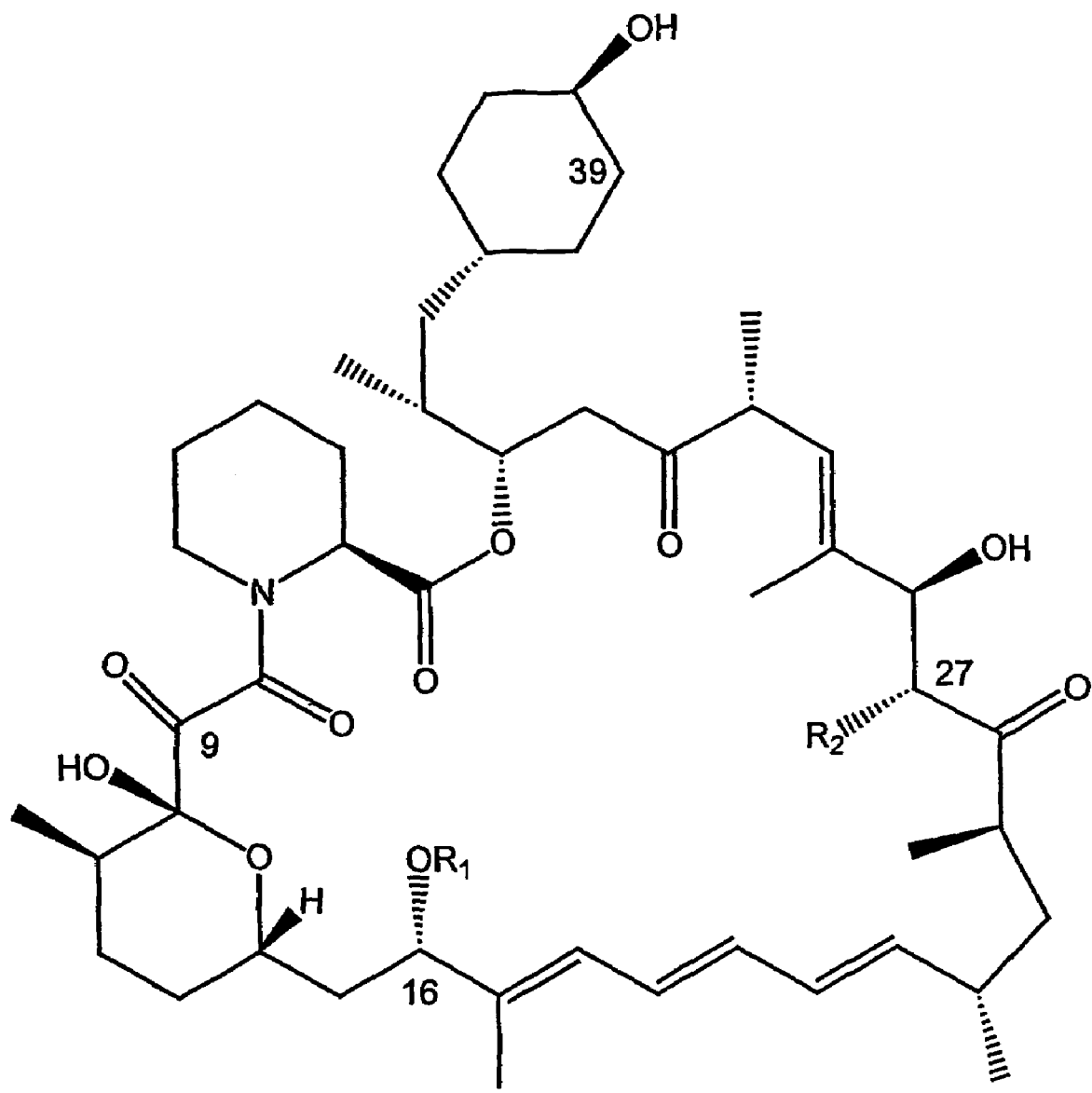
FIG. 15 Structures of compounds 49, 52, 54, 55, 56, and 58
Figure 16:
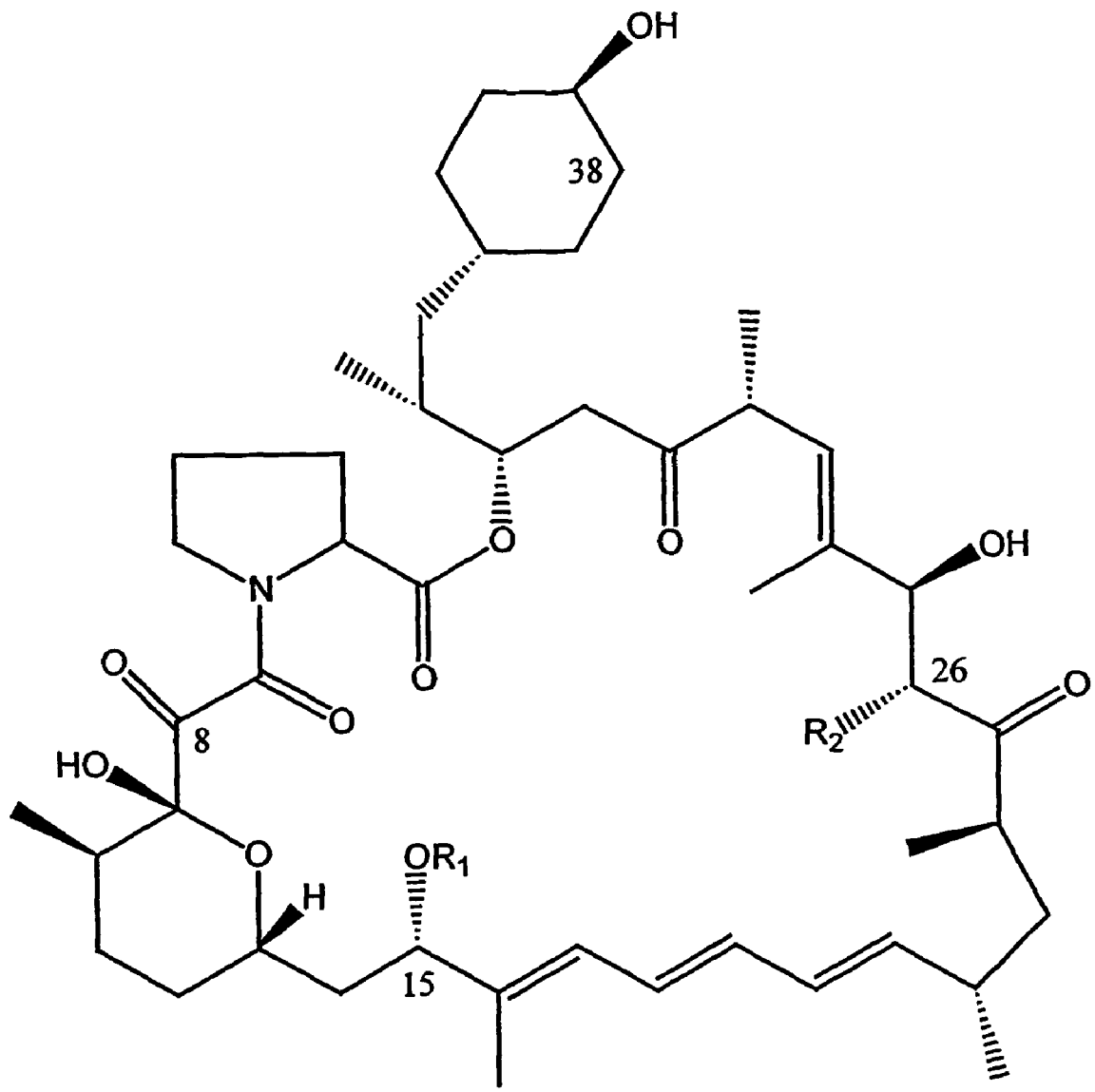
FIG. 16 Structure of compounds 61, 64, 66, 67, 68, and 70
Figure 17:
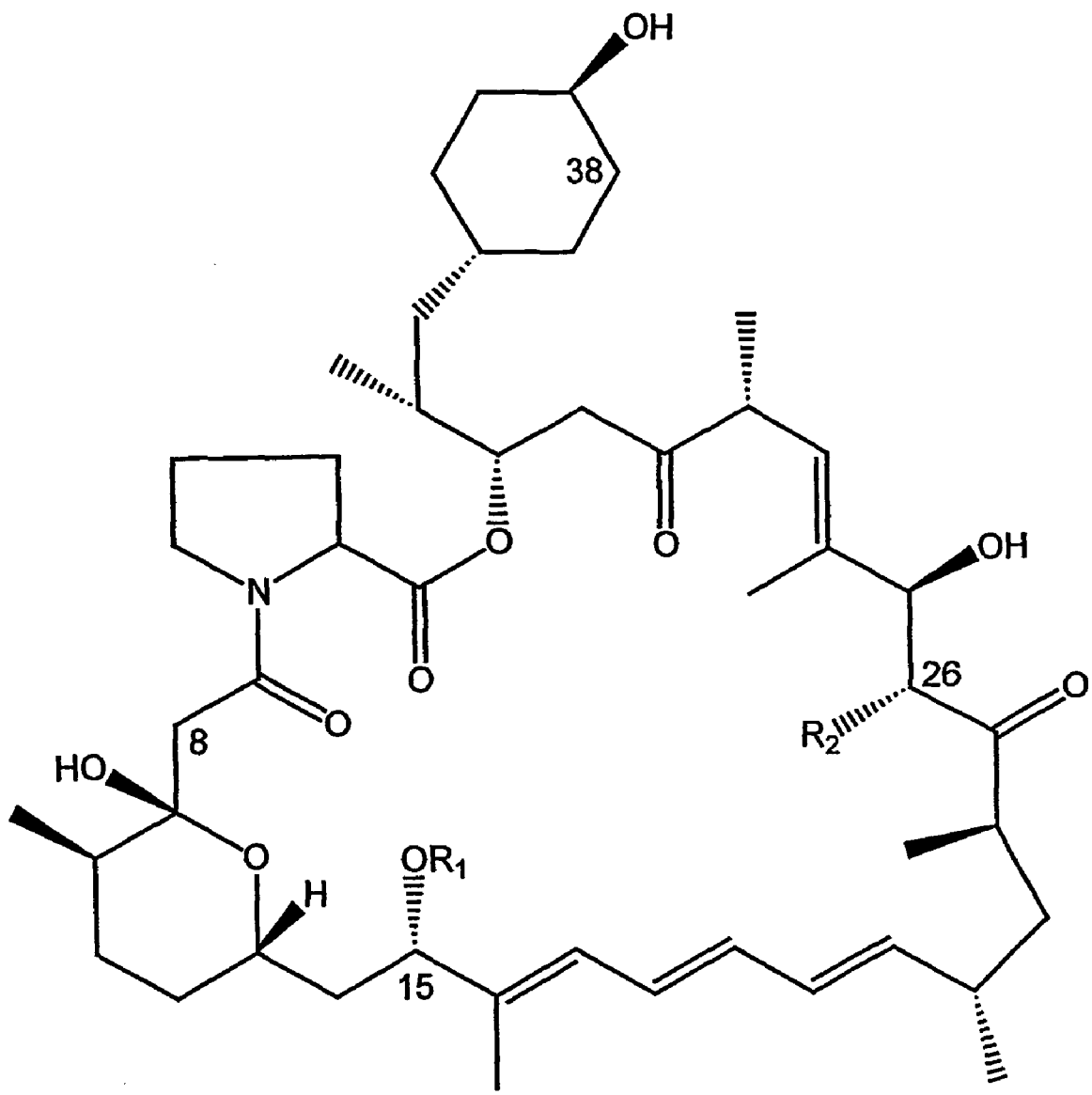
FIG. 17 Structure of compounds 59, 60, 62, 63, 65, and 69

Isolation of 16-O-desmethyl-27-desmethoxy-rapamycin (FIG. 9)

The S hygroscopicus strain MG2-10 was conjugated with pSGsetrapKIJ as described in Example 1. Feeding of this strain with pipecolic acid and isolation of the products produced on fermentation resulted in the production of 16-O-desmethyl-27-desmethoxy-rapamycin.

The plasmid pSGsetrapKIJ (FIG. 5) was conjugated into S. hygroscopicus MG2-10 and the strain grown in TSB GM fed with 2 mg/l pipecolic acid at 25° C. with shaking. The mycelia were extracted with methanol and the culture broth extracted with ethyl acetate as described previously.

Analysis of the extracts of the S. hygroscopicus mutant MG2-10[pSGsetrapKIJ] by electrospray mass spectroscopy revealed one major new peak of retention time 4.3 minutes which contained ions corresponding to a compound with a MW of 869. This peak was not seen in the cultures of S. hygroscopicus NRRL 5491, S. hygroscopicus MG1C S. hygroscopicus MG2-10 with or without the rapK expression plasmid pSGsetrapK. MS/MS analysis of the ion with m/z of 892 (corresponding to the sodium adduct of 16-O-desmethyl-27-desmethoxy-rapamycin) revealed that it fragmented into an ion with m/z of 763 corresponding to the loss of m/z 129 (pipecolic acid), or an ion with m/z of 570 corresponding to the loss of m/z 322 (C28-C42 of 16-O-desmethyl-27-desmethoxy-rapamycin). This ion itself fragmented further to an ion with m/z 320, corresponding to the loss of m/z 250 (C14 to C27 of 16-O-desmethyl-27-desmethoxy-rapamycin). This fragmentation pattern was identical to the pattern seen for rapamycin but with the third loss of m/z (−250) reduced by 44, corresponding to the absence of the C16 methyl and C27 methoxy groups. This was evidence that the compound with MW 869 was 16-O-desmethyl-27-desmethoxy-rapamycin.

EXAMPLE 10

Array Feeding

S. hygroscopicus MG2-10[pSGsetrapKI] was used to carry out an array feeding. Primary vegetafive cultures were prepared by innocculating medium with spore stock as described in the Materials and Methods. TSB GM medium was inoculated at 10% v/v using methods described in the materials and methods section. The following compounds were added as indicated in Table VI below

TABLE VI

|  | cyclohexane carboxylic acid (1 mM) | cyclohex-1-ene carboxylic acid (1 mM) | cycloheptane carboxylic acid (1 mM) |
|---|---|---|---|
| L-lysine (25.3 mM) | X | X | X |
| L-proline (44.7 mM) | X | X | X |
| DL-pipecolinic acid (39.8 mM) | X | X | X |
| trans-4-hydroxy proline (13 mM) | X | X | X |
| cis-4-hydroxy proline (0.2 mM) | X | X | X |

The cultures were incubated, extracted and measured using techniques described in the Material and Method section. Table VII shows the results of the analysis showing the ion (m/z) observed for each combination of starter carboxylic acid and amino acid:

TABLE VII

|  | cyclohexane carboxylic acid | cyclohex-1-one carboxylic acid | cycloheptane carboxylic acid |
|---|---|---|---|
| L-lysine | 848.5 | 848.5 | 862.4 |
| L-proline | 834.5 | 834.5 | 848.5 |
| DL-pipecolinic acid | 848.5 | 848.5 | 862.4 |
| trans-4-hydroxy proline | 850.5 | 850.5 | 864.5 |
| cis-4-hydroxy proline | 850.5 | n.a. | 864.5 |

These data demonstrate incorporation of the fed compounds.

EXAMPLE 11

Complementation of S.hygroscopicus MG2-10 with fkbO

To assess whether rapK homologous genes such as fkbO in S.hygroscopicus var. ascomyceticus and S. tsukubaensis, and orf5 in the partially sequenced 'hyg' cluster (Ruan et al., 1997) fulfil similar functions, complementation assays were carried out using fkbO as described below.

Isolation of pMG169-1

The gene fkbO from Strepomyces hygroscopicus var. ascomyceticus (ATCC 14891), an FK520 producer, was amplified by PCR using the primers fkbof 5'-GGGCATAT-GACCGATGCCGGACGCCA 3' (SEQ ID NO: 54) and fkbor 5' GGGGTCTAGATCACGCCACCATGCCTTCGA 3' (SEQ ID NO: 55), introducing a NdeI site at the 5'end and a XbaI site at the 3'end of fkbO. Genomic DNA isolated from S.hygroscopicus var. ascomyceticus (ATCC 14891) was used as a template. The amplified PCR product was subjected to digestion with NdeI and XbaI and ligated with NdeI-XbaI cut pSGsetI. The ligation was used to transform E.coli DH10B and the transformants were analysed using methods described in the Materials and Methods section. Plasmid pMG169-1 was isolated and verified by restriction digestion and S.hygroscopicus MG2-10 was transformed using methods described in the Materials and Methods section.

Heterologous Complementation of rapK by fkbO

S.hygroscopicus MG2-10[pMG.169-1] was grown in TSBGM fed with 2mg/l pipecolic acid at 25° C. with shaking. The culture broth and mycelia were extracted using methods described in the Materials and Methods section (Method A). Analysis of the extract with UV detection at 280 nm revealed the presence of two major new peaks with retention times of 4.5 and 4.6 minutes. Electrospray mass spectroscopy of these peaks revealed that both contained ions with a MW of 827.5 corresponding to two isomers of pre-rapamycin (Example 7).

EXAMPLE 12

Efficient Production of 9-deoxo-10-desmethyl-27-desmethoxy-39-desmethoxy-rapamycin (39-dehy-roxy pre-rapamycin, FIG. 8) in the Absence of Competition by Endogenous Starter Unit by Feeding to a rapK Knockout Mutant The ability of S. hygroscopicus strains MG2-10 and MG2-10[pSGsetrapK] to incorporate a different starter unit, cyclohexane carboxylic acid, was compared as described below. When fed cyclohexane carboxylic acid and pipecolic acid MG2-10 produced only one compound (39-dehydroxy pre-rapamycin) corresponding to incorporation of the fed starter unit only, whereas MG2-10[pSGsetrapK] produced two compounds in a 1:1 ratio, 39-dehydroxy pre-rapamycin and pre-rapamycin. This demonstrated that rapK is required for the incorporation of the natural endogenous starter unit and a rapK knock-out strain had no competition of the endogenous starter unit with the fed starter unit.

S. hygroscopicus MG2-10 was grown on TSBGM fed with 2 mg/L pipecolic acid and 1 mM cyclohexane carboxylic acid at 25° C. with shaking. The culture broth was extracted with ethyl acetate as described previously. Analysis of the extracts by HPLC with UV detection at 280 nm revealed the presence of one new major peak with a retention time of 5.8 min. However, S. hygroscopicus MG2-10 [pSGsetrapK] (Example 4), produced pre-rapamycin (FIG. 6) in addition to 39-dehydroxy pre-rapamycin in a ratio of ~1:1 when fed with cyclohexane carboxylic acid (Example 8, FIG. 8). Surprisingly, feeding of cyclohexane carboxylic acid to S. hygroscopicus MG2-10 resulted in a single product, 39-dehydroxy pre-rapamycin. The endogenous starter, 4,5-dihydroxycyclohex-1-ene carboxylic acid, was not incorporated in the absence of rapK. There was therefore no competition between the incorporation of the fed carboxylic acid and the endogenous starter.

EXAMPLE 13

Elucidation of the Function of RapM

Cultures of Streptomyces lividans TK24, S. lividans TK24[pSGsetrapM] and S. lividans TK24[pSGsetrapQ] were grown in TSBGM with shaking at 30° C. and fed with 20 μg/ml of pre-rapamycin. Controls remained unfed. After a further 5 days incubation, the cultures were extracted with ethylacetate and brought to dryness. Reconstitution and analysis by LC-MS identified no productioff of rapamycin analogues in the unfed controls. Two major new peaks were identified in the extract of S. lividans TK24[pSGsetrapM] fed pre-rapamycin, one at 2.5 min and one at 7.9 min. Electrospray mass spectroscopy of these peaks revealed that both contained ions corresponding to a compound with a MW of 855.6, consistent with 9-deoxo-16-O-methyl-27des-methoxy-39-O-desmethyl-rapamycin (16-O-methyl-pre-rapamycin). Two isomers were commonly observed when extracts were analysed by LC-MS in the absence of TFA. No new peaks were identified in the extracts of *S. lividans* TK24 or *S. lividans* TK24[pSGsetrapQ]. Unmodified pre-rapamycin was clearly evident. RapM was clearly responsible for methylation at the C16 hydroxyl, RapQ was not specific for this site.

EXAMPLE 14

Elucidation of the Function of RapJ

Cultures of *S. lividans* TK24, *S. lividans* TK24[pSGsetrapK], *S. lividans* TK24[pSGsetrapJ] and *S. lividans* TK24 [pSGsetrapKJ] were grown in TSBGM with shaking at 30° C. and fed with 40 µg/ml of prerapamycin. Controls remained unfed. After a further 5 days incubation, the cultures were extracted with ethylacetate and brought to dryness. Reconstitution and analysis by LC-MS identified no production of rapamycin analogues in the unfed controls. One major new peak at 4.9 min was identified in the extracts of *S. lividans* TK24[pSGsetrapKJ] and *S. lividans* TK24 [pSGsetrapJ] fed pre-rapamycin. Electrospray mass spectroscopy of this peak revealed that it contained ions corresponding to a compound with a MW of 855.5, consistent with 16-O-desmethyl-27-desmethoxy-39-O-desmethyl-rapamycin (C9 oxo-pre-rapamycin). In extracts of *S. lividans* TK24 and *S. lividans* TK24[pSGsetrapK] fed with pre-rapamycin, no new peaks were identified. Unmodified pre-rapamycin was clearly evident.

Due to the homology of RapJ with FkbD of the FK506 and FK520 cluster, RapJ has been postulated to oxidise pre-rapamycin at C9 to 9-hydroxy-16-O-desmethyl-27-desmethoxy-39-O-desmethyl-rapamycin (C9 OH-pre-rapamycin). RapK has been postulated to be responsible for the further conversion to the ketone. Surprisingly, in the presence of RapJ, but in the absence of RapK, 16-O-desmethyl-27-desmethoxy-39-O-desmethyl-rapamycin (C9 keto-pre-rapamycin) was formed. RapJ clearly has an oxidative function at C9, complete conversion to the ketone was observed. RapK does not have an oxidative function at C9.

EXAMPLE 15

Plasmids containing the following combinations of rapamycin modifying genes were constructed as described below: pMG260 (rapI, rapJ, rapN, rapO, and rapL), pMG261 (rapI, rapJ, rapN, rapO, rapM and rapL), pMG262 (rapI, rapJ, rapN, rapO, rapM, rapQ and rapL) pMG236 (rapN, rapO, rapQ and rapL) and pMG238 (rapJ and rapL).

Isolation of Plasmids pMG236 and pMG238

The plasmids pSGsetrapNOQ and pSGsetrapJ were digested using BglII/XbaI and the isolated vector fragments were ligated with the 1 kb XbaI/BglII fragment of pSGLitrapL$_{his}$. Plasmids pMG236 (expressing rapN, rapO, rapQ and rapL) and pMG238 (expressing rapJ and rapL) respectively, were isolated.

Isolation of Plasmids pMG260, pMG261 and pMG262

The plasmids pSGSetrapKIJNOL, pSGSetrapKIJMNOL, and pSGSetrapKIJMNOQL were digested using BglII and the isolated insert fragments (containing the rapamycin cluster genes from the BglII site in rapI to the BglII site after rapL) were ligated with the vector-containing fragment from pSGSetrapI digested with BglII. Plasmids pMG260 (expressing rapI, rapJ, rapN, rapO, and rapL), pMG261 (expressing rapI, rapJ, rapN, rapO, rapM and rapL), and pMG262 (expressing rapI, rapJ, rapN, rapO, rapM, rapQ and rapL) were isolated.

EXAMPLE 16

An *S.hygroscopicus* mutant (MG3) carrying the chromosomal deletion of rapK was constructed as described below. Heterologous complementation of rapK with fkbO can then be performed as described and will result in the restoration of rapamycin production demonstrating that fkbO is able to complement the function of rapK in *S. hygroscopicus*.

Isolation of the *S.hygroscopicus* Mutant MG3 Carrying the Chromosomal Deletion of rapK The primers RAPKF1 5'-CAAAGCTTCCTGGCGCG-GTTCGGCCGGCA-3' (SEQ ID NO: 56) and RAPKF2 5'-TGGCATGCCCTTCCCCGCCGTTCCCTGGC-3' (SEQ ID NO: 57) were used to amplify the left region of homology outside the gene rapK (from nt94403 to nt95429 in the rapamycin cluster as described in Schwecke et al., 1995) using genomic DNA prepared from *S.hygroscopicus* NRRL5491 as a template. The 1 kb PCR product was phosphorylated using T4 polynucleotide kinase and ligated into dephosphorylated SmaI cut pUC18. After transformation into *E.coli* DH10B, the plasmid pMG233-7 was isolated. The primers RAPKR1 5'-TGGCATGCCCCCGC-CGAGCTGACCTGGAA-3' (SEQ ID NO: 58) and RAPKR2 5'-GTTCTAGAGCTTACGCGTGATGTC-GAACG-3' (SEQ ID NO: 59) were used to amplify the right region of homology outside the gene rapK (from nt96435 to nt97428 in the rapamycin cluster as described in Schwecke et al., 1995) using genomic DNA prepared from *S.hygrmscopicus* NRRL5491 as a template. The, 1 kb PCR product was phosphorylated using T4 polynucleotide kinase and ligated into dephosphorylated SmaI cut pUC18. After transformation into *Ecoli* DH10B, the plasmid pMG257-7 was isolated. Both plasmids were checked by sequence analysis. The plasmid pMG233-7 was digested with SphI/XbaI and the 3.7 kb fragment was isolated, pMG257-7 was digested with SphI/XbaI and the 1 kb fragment isolated. These fragments were ligated and used to transform *E.coli* DH10B. The plasmid pMG268-12 was isolated. This plasmid was digested with HindIII/XbaI and the 2 kb fragment isolated and ligated into pMG55 cut with HindIII/XbaI and the DNA was used to transform *E.coli* DH10B. The plasmid pMG2781 was isolated and used to conjugate *S.hygroscopicus* MG1C.

Figure 35:
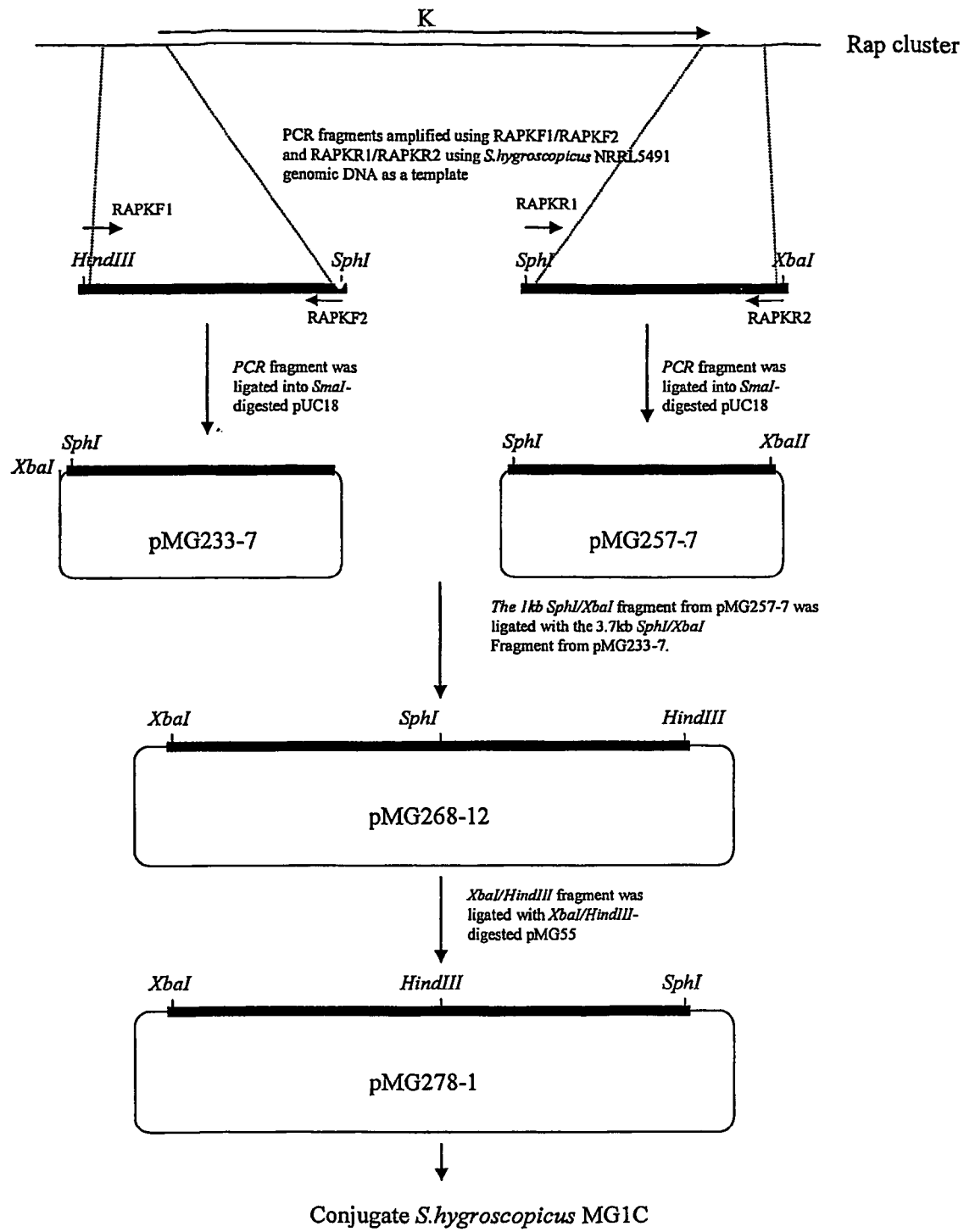
FIG. 35 A flow chart demonstrating the cloning strategy for the isolation of pMG2781 to create MG3.

An apramycin resistant colony is isolated, and is grown for 24 hours in TSBGM with shaking at 30° C. and spread onto medium 1 agar plates containing 50 ug/l streptomycin. Streptomycin resistant colonies are isolated and shown to be apramycin sensitive. The 1004 nt chromosomal deletion of rapK can be verified in the mutant MG3 by Southern blotting. An overview is given in FIG. 35.

*S.hygroscopicus* MG3 is grown in TSBGM at 26° C. with shaking. The culture broth and mycelia are extracted using methods as described in the Materials and Methods section. Analysis of the extract with UV detection reveals the presence of no peaks with the characteristic rapamycin triene.

Expression of fkbO in the *S.hygroscopicus* Mutant MG3 Carrying the Chromosomal Deletion of rapK Plasmid pMG169-1 (described in example 11) is transformed into *S.hygroscopicus* mutant MG3 using methods as described in the Materials and Methods section.

Heterologous Complementation of rapK by fkbO

S.hygroscopicus MG3pMG169-1 is grown in TSBGM at 26° C. with shaking. The culture broth and mycelia arere extracted using methods as described in the Materials and Methods section. Analysis of the extract with UV detection at 280 nm reveals the presence of two major new peaks. Electrospray mass spectroscopy of these peaks reveals that these contain ions with a MW of 913 corresponding to rapamycin.

EXAMPLE 17

Isolation and Heterologous Complementation of the S.hygroscopicus var ascomyceticus Mutant MG4 Carrying the Chromosomal Deletion of fkbO Isolation of the S.hygroscopicus var ascomyceticus Mutant MG4 Carrying the Chromosomal Deletion of fkbO The primers FKOF1 5'-GCTCTAGAGCCCGCG-GCTCGCCGGACACG-3' (SEQ ID NO: 60) and FKOF2 5'-CCCCTGCAGGCGTCCGGCATCGGTCATCAG-3' (SEQ ID NO: 61) were used to amplify the left region of homology (from nt45750 to nt46751 in the ascomycin cluster as described in Wu et al., 2000) using genomic DNA prepared from S.hygroscopicus var ascomyceticus ATCC14891 as a template. The 1 kb PCR product was phosphorylated using T4 polynucleotide kinase and ligated into dephosphorylated SmaI cut pUC18. After transformation into E.coli. DH10B, the plasmid pMG258-4 was isolated. The primers FKOR1 5'-CGCCTGCAGGGATACG-GTCCGCCGGGTCTGC-3' (SEQ ID NO: 62) and FKOR2 5'-CCAAGCTTGTACGGTTCGCCACGGGCGTGC-3' (SEQ ID NO: 63) were used to amplify the right region of homology (from nt47785 to nt48781 in the rapamycin cluster as described in Wu et al., 2000) using genomic DNA prepared from S.hygroscopicus var ascomyceticus ATCC14891 as a template. The 1 kb PCR product was phosphorylated using T4 polynucleotide kinase and ligated into dephosphorylated SmaI cut pUC18. After transformation into E.coli DH10B, the plasmid pMG259-5 was isolated. Both plasmids were checked by sequence analysis. The plasmid pMG258-4 was digested with SbfI/HindIII and the 3.7 kb fragment was isolated, pMG259-5 was digested with SbfI/HindIII and the 1 kb fragment isolated. These fragments were ligated and used to transform E.coli DH10B. The plasmid pMG265-1 was isolated. This plasmid was digested with HindIII/EcoRI and the 2 kb fragment isolated and ligated into pMG55 cut with HindIII/EcoRI and the DNA was used to transform E.coli DH10B. The plasmid pMG267-1 was isolated and used to conjugate S.hygroscopicus var ascomyceticus ATCC14891.

Figure 36:
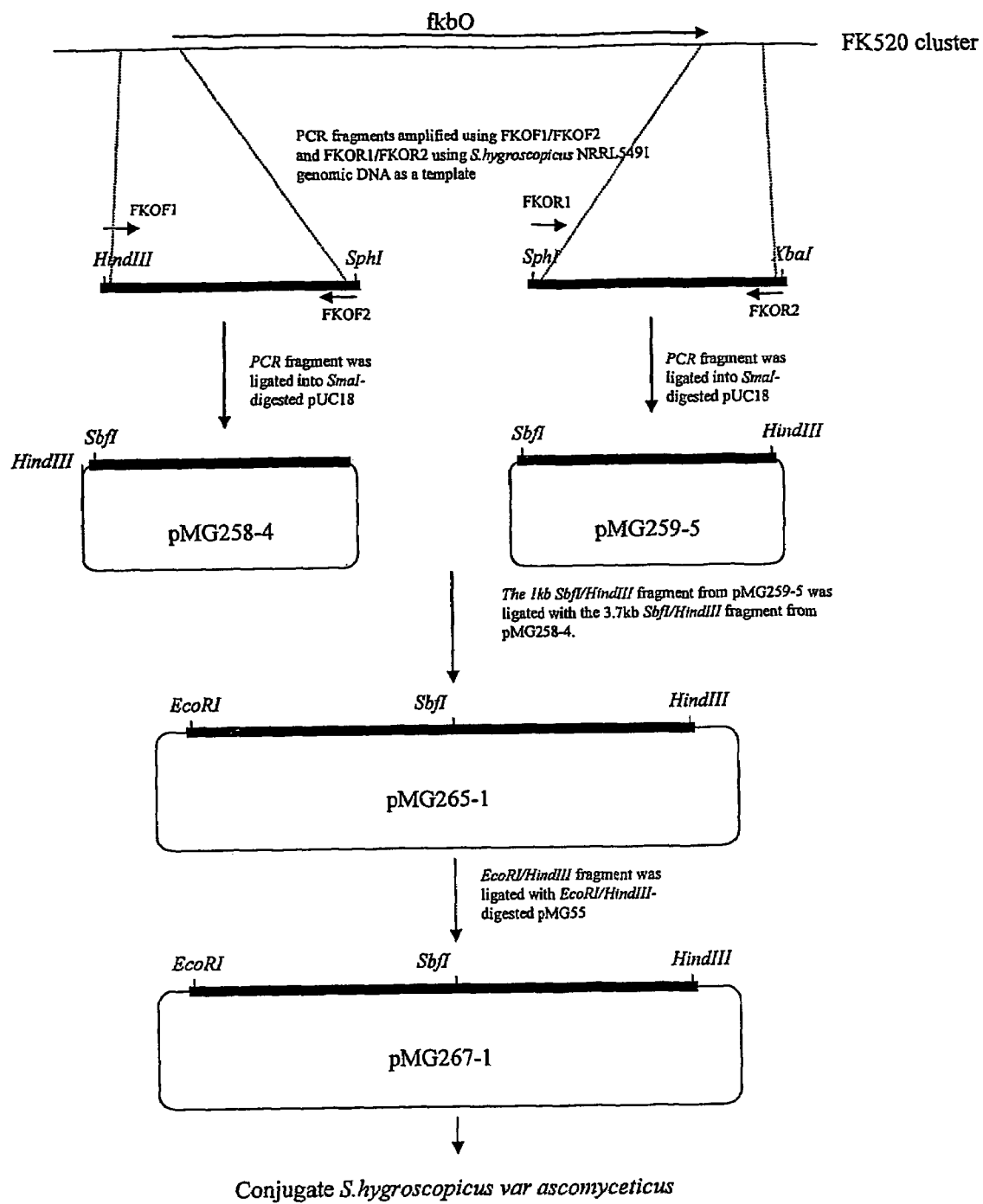
FIG. 36 A flow chart demonstrating the cloning strategy for the isolation of pMG267-1 to create MG4.

An apramycin resistant colony is isolated and is grown for 24 hours in TSBGM with shaking at 30° C. and spread onto medium 1 agar plates containing 50 ug/l streptomycin. Streptomycin resistant colonies are isolated and shown to be apramycin sensitive. The 1034nt chromosomal deletion of fkbO can be verified in the mutant MG4 by Southern blotting. An overview is given in FIG. 36.

Expression of RapK in the S.hygroscopicus var ascomyceticus Mutant MG4 Carrying the Chromosomal Deletion of fkbO Plasmid pSGsetRapK is transformed into S.hygroscopicus mutant MG4 as described in the Materials and Methods section.

Heterologous Complementation of fkbO by rapK

S.hygroscopicus var ascomyceticus MG4 pSGSetRapK is grown in TSBGM at 26° C. with shaking. The culture broth and mycelia are extracted using methods as described in the Materials and Methods section. The extract is analysed by LC-MS to reveal the presence of a major new peak and to reveal that this contains ions that correspond to FK520 (ascomycin).

EXAMPLE 18

It is obvious to those skilled in the art that other biosynthetic clusters that encode FKBP-ligands for example, FK506, can be modified such that the rapK homologue is deleted or inactivated using the methods as described herein. In FK506, for example; this could be done by amplifying PCR products against the regions either side of the fkbO gene (sequence accession number AF082099, AF082100), ligating these together in a vector such as pMG55, transforming the FK506-producing strain, selecting for the double crossover and confirming the removal of the fkbO gene by southern blotting.

EXAMPLE 19

Incorporation of Non-Natural Starter Units by the rapK Deletion Strain, S. hygroscopicus MG2-10, into Rapamycin Analogues in the Absence of Competition by Endogenous Natural Starter Unit As demonstrated in examples 10 and 12, the rapamycin PKS has a high degree of flexibility for non-natural starter units and in the absence of rapK, the system is free of competition from the natural starter. In this example, the degree of flexibility is further demonstrated.

S. hygroscopicus MG2-10 was grown, fed and extracted according to the feeding, extraction and analysis methods outlined in Materials and Methods (Method B). The range of carboxylic acids fed along with the compounds generated are listed below. Surprisingly, all of the carboxylic acids listed were incorporated as determined by observing the characteristic UV chromophore at 278 nm and electrospray mass spectrometry and resulted in the production of rapamycin analogues.

The rapamycin analogues generated corresponded to the formula below as described in Table VIII:

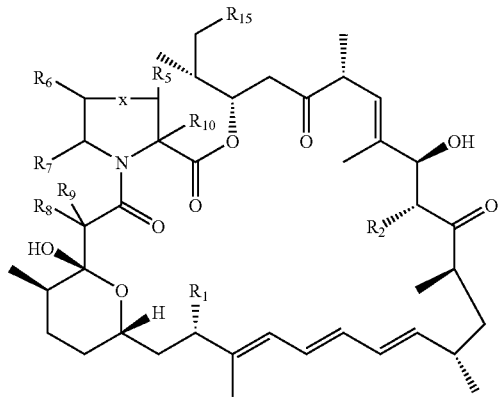

R_16 = OH
R_17 = OH, halo, thiol, alkyl
y = bond, CH_2

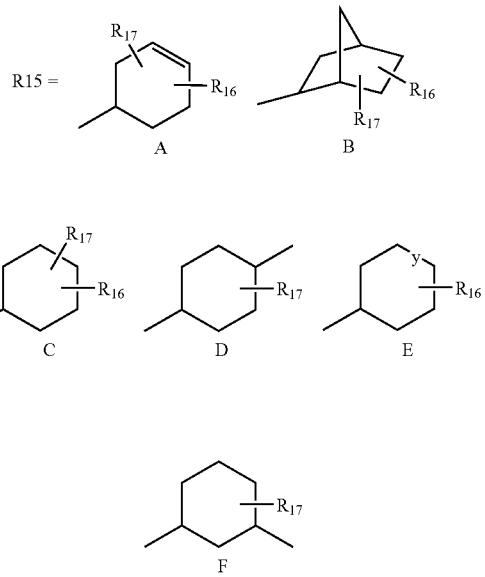

TABLE VIII

| Carboxylic acid starter unit fed. | M − H | [M + K] | Compound generated |
|---|---|---|---|
| cyclohexane carboxylic acid | 824.7 | 864.6 | $R_{15}$ = E, $R_{16}$ = 4-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 3-cis,4-trans-dihydroxycyclohexane carboxylic acid | 840.5 | 880.4 | $R_{15}$ = C, $R_{16}$ = 3-cis-OH, $R_{17}$ = 4-trans-OH, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 1-cyclohexene carboxylic acid | 824.4 | 864.3 | $R_{15}$ = E, $R_{16}$ = 3-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 3-cyclohexene carboxylic acid | 840.5 | 880.4 | $R_{15}$ = C, $R_{16}$ = OH, $R_{17}$ = OH, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
|  | 822.4 | 862.3 | $R_{15}$ = A, $R_{16}$ = OH, $R_{17}$ = H, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| cycloheptane carboxylic acid | 838.4 | 878.3 | $R_{15}$ = E, $R_{16}$ = OH, y = CH$_2$, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| Methyl 2-norbornane carboxylate | 836.2 | 876.2 | R15 = B, R16 = OH, R17 = H, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 3-hydroxycyclohexane carboxylic acid | 824.7 | 864.6 | $R_{15}$ = E, $R_{16}$ = 3-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 4-hydroxycyclohexane carboxylic acid | 824.6 | 864.6 | $R_{15}$ = E, $R_{16}$ = 4-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 3-methylcyclohexane carboxylic acid | 838.4 | 878.3 | $R_{15}$ = F, $R_{17}$ = OH, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 4-methylcyclohexane carboxylic acid | 838.4 | 878.3 | $R_{15}$ = D, $R_{17}$ = OH, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 3-(cis/trans)methoxycyclohexane carboxylic acid | 824.3 | 864.2 | $R_{15}$ = E, $R_{16}$ = 3-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| 4-(cis/trans)methoxycyclohexane carboxylic acid | 824.2 | 864.2 | $R_{15}$ = E, $R_{16}$ = 4-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |
| ethyl 4-cyclohexanone carboxylate | 824.3 | 864.2 | $R_{15}$ = E, $R_{16}$ = 4-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = CH$_2$ |

TABLE VIII-continued

| Carboxylic acid starter unit fed. | M − H | [M + K] | Compound generated |
|---|---|---|---|
| 3-fluoro-4-hydroxy cyclohexane carboxylic acid and 4-fluoro-3-hydrox cyclohexane ycarboxylic acid | 843.0 | 882.0 | $R_{15}$ = C, $R_{16}$ = OH, $R_{17}$ = F, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
| 3-cyclohexane oxide carboxylic acid | 841.0 | 880.8 | $R_{15}$ = C, $R_{16}$ = 3-cis-OH, $R_{17}$ = 4-trans-OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
| 3,4-cis-dihydroxycyclohexane carboxylic acid | 841.2 | 881.1 | $R_{15}$ = C, $R_{16}$ = 3-cis-OH, $R_{17}$ = 4-cis-OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 841.2 | 881.1 | $R_{15}$ = C, $R_{16}$ = 3-trans-OH, $R_{17}$ = 4-trans-OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
| 3-chloro-4-hydroxy cyclohexane carboxylic acid and 4-chloro-3-hydroxy cyclohexane carboxylic acid (and the pair of opposite diastereomers) | 858.8 | 898.8 | $R_{15}$ = C, $R_{16}$ = OH, $R_{17}$ = Cl, in combination with $R_1$ = OH, = H, $R_5$ = H, $R_6$ = H, $R_7$ = H, $R_8$ = H, $R_9$ = H, $R_{10}$ = H, x = $CH_2$ |
| cyclohexylpropionic acid | 825.0 | 864.9 | $R_{15}$ = C, $R_{16}$ = 3-cis-OH, $R_{17}$ = 4-trans-OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ TBC |

EXAMPLE 20

Incorporation of Non-Natural Starter Units by the rapK Deletion Strain, *S. hygroscopicus* MG2-10 [pSGsetrapN/OQL$_{his}$], into Rapamycin Analogues in the Absence of Competition by Endogenous Natural Starter Unit As demonstrated in examples 10, 12 and 19, the rapamycin PKS has a high degree of flexibility for non-natural starter units and in the absence of rapK, the system is free of competition from the natural starter. In this example, the degree of flexibility is further demonstrated.

*S. hygroscopicus* MG2-10[pSGsetrapN/OQL$_{his}$] was grown, fed and extracted according to the feeding, extraction and analysis methods outlined in Materials and Methods (Method B). The range of carboxylic acids fed along with the compounds generated are listed below. Surprisingly, all of the carboxylic acids listed were incorporated as determined by observing the characteristic UV chromophore at 278 nm and electrospray mass spectrometry and resulted in the production of rapamycin analogues.

The rapamycin analogues generated corresponded to the formula below as described in Table IX:

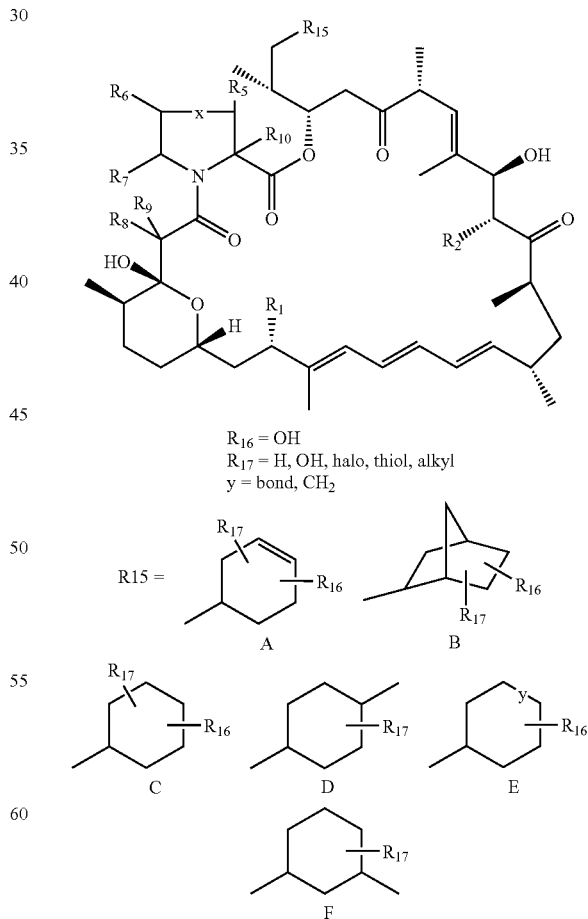

$R_{16}$ = OH
$R_{17}$ = H, OH, halo, thiol, alkyl
y = bond, $CH_2$

TABLE IX

| Carboxylic acid starter unit fed. | M − H | [M + K] | Compound generated |
|---|---|---|---|
| cyclohexane carboxylic acid | 840.4 | 880.4 | $R_{15}$ = E, $R_{16}$ = 4-OH, y = bond, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| 3-cis,4-trans-dihydroxycyclohexane carboxylic acid | 840.4 | 880.4 | $R_{15}$ = C, $R_{16}$ = 3-cis-OH, $R_{17}$ = 4-trans-OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 856.4 | 896.4 | $R_{15}$ = C, $R_{16}$ = 3-cis-OH, $R_{17}$ = 4-trans-OH, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| 1-cyclohexene carboxylic acid | 824.4 | 864.4 | $R_{15}$ = E, $R_{16}$ = 3-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 840.4 | 880.4 | $R_{15}$ = E, $R_{16}$ = 3-OH, y = bond, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| 3-cyclohexene carboxylic acid | 840.4 | 880.4 | $R_{15}$ = C, $R_{16}$ = OH, $R_{17}$ = OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 822.4 | 862.4 | $R_{15}$ = A, $R_{16}$ = OH, $R_{17}$ = H, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 840.4 | 880.4 | $R_{15}$ = A, $R_{16}$ = OH, $R_{17}$ = H, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| cycloheptane carboxylic acid | 854.4 | 894.4 | $R_{15}$ = E, $R_{16}$ = OH, y = $CH_2$, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| methyl-2-norbornane carboxylic acid | 852.4 | 892.4 | $R_{15}$ = B, $R_{16}$ = OH, $R_{17}$ = H, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| 3-hydroxycyclohexane carboxylic acid | 824.4 | 864.4 | $R_{15}$ = E, $R_{16}$ = 3-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
| 4-hydroxycyclohexane carboxylic acid | 840.4 | 880.4 | $R_{15}$ = E, $R_{16}$ = 4-OH, y = bond, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 824.4 | 864.4 | $R_{15}$ = E, $R_{16}$ = 4-OH, y = bond, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |
| 4-methylcyclohexane carboxylic acid | 838.4 | 878.4 | $R_{15}$ = D, $R_{17}$ = OH, in combination with $R_1$ = OH, $R_2$ = H, $R_5$ = H, $R_6$ = H, $R_7$ = H, $R_8$ = H, $R_9$ = H, $R_{10}$ = H, x = $CH_2$ |
|  | 854.4 | 894.4 | $R_{15}$ = D, $R_{17}$ = OH, in combination with $R_1$ = OH, $R_2$ = OH, $R_5$ = H, $R_6$ = H, $R_7$ = H, $R_8$ = H, $R_9$ = H, $R_{10}$ = H, x = $CH_2$ |

EXAMPLE 20

Incorporation of Non-Natural Starter Units by the rapK Deletion Strain, *S. hygroscopicus* MG3, into Rapamycin Analogues in the Absence of Competition by Endogenous Natural Starter Unit As demonstrated in examples 10, 12 and 19, the rapamycin PKS has a high degree of flexibility for non-natural starter units and in the absence of rapK, the system is free of competition from the natural starter. In this example, the degree of flexibility is further demonstrated.

*S. hygroscopicus* MG3 is grown, fed and extracted according to the feeding, extraction and analysis methods outlined in Materials and Methods (Method B). The range of carboxylic acids fed that can be fed is listed below. Incorporation of the carboxylic acids listed and production of rapamycin analogues is determined by observing the characteristic UV chromophore at 278 nm and electrospray mass spectrometry.

Carboxylic acid starter units that can be fed include. cyclohexane carboxylic acid, 3-cis,4trans-dihydroxycyclohexane carboxylic acid, 1-cyclohexene carboxylic acid, 3-cyclohexene carboxylic-acid, cycloheptane carboxylic acid, methyl 2-norbornane carboxylate, 3-hydroxycyclohexane carboxylic acid, 4-hydroxycyclohexane carboxylic acid, 3-methylcyclohexane carboxylic acid, 4-methylcyclohexane carboxylic acid, 3-(cis/trans)methoxycyclohexane carboxylic acid, 4-(cis/trans)methoxycyclohexane carboxylic acid, ethyl 4-cyclohexanone carboxylate, 3-fluoro-4-hydroxycarboxylic acid and 4-fluoro-3-hydroxycarboxylic acid, 3-cyclohexane oxide carboxylic acid, 3,4-cis-dihydroxycyclohexane carboxylic acid, 3-chloro-4-hydroxycarboxylic acid and 4-chloro-3-hydroxycarboxylic acid (and the pair of opposite diastereomers), cyclohexylpropionic acid and 4-tert-Butylcyclohexane carboxylic acid

EXAMPLE 21

Incorporation of Non-Natural Starter Units by the fkbO Deletion Strain, S. hygroscopicus var. ascomyceticus MG4, into FK520 Analogues in the Absence of Competition by Endogenous Natural Starter Unit As demonstrated in examples 10, 12, 19 and 20, the rapamycin PKS has a high degree of flexibility for non-natural starter units. In the absence of fkbO, the FK520 system is free of competition from the natural starter. In this example, the degree of flexibility of the FK520 PKS is investigated, free of competition from the natural starter.

S. hygroscopicus var. ascomyceticus MG4 is grown, fed and extracted according to the feeding, extraction and analysis methods outlined in Materials and Methods (Method B). Examples of the range of carboxylic acids that can be fed are given in Table IV. Incorporation of the carboxylic acids listed and production of FK520 analogues is determined by electrospray mass spectrometry.

EXAMPLE 22

Incorporation of Non-Natural Starter Acids into FK506 Analogues by an fkbO Deletion Mutant of S. tsukubaensis in Absence of Competition from the Natural Starter An fkbO deletion mutant of S. tsukubaensis is grown and fed according to the feeding methods outlined in Materials and Methods. A subset of the carboxylic acids listed in Table IV in Materials and Methods is fed. Analysis is performed as described in Method (B) of Materials and Methods.

EXAMPLE 23

Isolation of Product from Fermentation of S. hygroscopicus MG2-10[pSGsetrapKIL$_h$]

9-deoxo-16-desmethyl-27-desmethoxy-rapamycin was obtained by conjugating the S. hygroscopicus strain MG2-10 with pSGsetrapKIL$_h$ and isolating the fermentation products generated as described below. This demonstrates that it is possible to complement the deletion of rapK, rapI and rapL in the MG2-10 strain and that 9-deoxo-16-O-desmethyl-27-desmethoxy-rapamycin is produced, an analogue which is lacking the post-PKS modifications. The feeding of pipecolic acid is not required when rapL is complemented confirming that rapL plays a role in the provision of pipecolic acid in the production of rapamycin.

S. hygroscopicus MG2-10 [pSGsetKIL$_{his}$] was fermented (see Materials and Methods), extracted and isolated using the method (B) as outlined in Materials and Methods. The isocratic solvent system used for preparative HPLC was 60% $CH_3CN/H_2O$.

9-Deoxo-16-O-desmethyl-27-desmethoxy rapamycin (Compound 6) has the following characteristics:

Isolated yield: 22 mg

Molecular weight: 856

Molecular formula: $C_{49}H_{77}NO_{11}$

UV (by diode array detection during HPLC analysis): 268 nm, 278 nm, 288 nm

Electrospray MS: m/z for MNa$^+$=878, m/z for M–H=854

Table X below summarises the $^1$H and $^{13}$C NMR data for 9-deoxo-16-O-desmethyl-27-desmethoxy rapamycin in $CDCl_3$.

TABLE X

| Proton | $\delta_H$ | | multiplicity | coupling | | $\delta_c$ | |
|---|---|---|---|---|---|---|---|
| 1 | | | | | | 169.0 | 171.5 |
| 2 | 4.37 | 5.40 | | | | 55.6 | 52.5 |
| 3a | 1.51 | 1.75$^a$ | | | | 26.5 | 26.3 |
| 3b | 2.40 | 2.19 | | | | | |
| 4a | | | | | | | 20.9 |
| 4b | | | | | | | |
| 5a | 1.30 | 1.48 | | | | | 25.1 |
| 5b | 1.68 | 1.72 | | | | | |
| 6a | 4.45 | 3.26 | | | | 39.0 | 44.4 |
| 6b | 2.16 | 3.83 | | | | | |
| 8 | | | | | | 171.7 | 172.4 |
| 9a | 2.41 | 2.54 | | | | 38.7 | 40.2 |
| 9b | 2.67 | 2.89 | | | | | |
| 10 | | | | | | 98.4 | 99.7 |
| 10-OH | 6.62 | 5.34 | br. s | | | | |
| 11 | 1.37 | 1.51 | | | | 38.7 | 38.7 |
| 12a | 1.67 | 1.62 | | | | 27.3 | 27.6 |
| 12b | 1.48 | 1.48 | | | | | |
| 13a | 1.29 | 1.32 | | | | | |
| 13b | | | | | | | |
| 14 | 4.21 | 3.87 | | | | 71.3 | 69.6 |
| 15a | 1.47$^b$ | 1.50 | | | | | |
| 15b | 1.66 | 1.65 | | | | | |
| 16 | 4.21 | 4.06 | dd | 6.1, 6.1 | | 76.0 | 75.6 |
| 17 | | | | | | 141.6 | 138.4 |
| 18 | 6.08 | 6.22 | d | d | 11.2 | 11.2 | 122.5 | 125.0 |
| 19 | 6.38 | 6.31 | dd | dd | 14.0, 11.2 | 14.7, 11.2 | 128.6 | 127.7 |
| 20 | 6.01 | 6.17 | dd | | 14.5, 10.5 | 131.1 | 132.2 |
| 21 | 6.04 | 6.04 | | | | 130.3 | 130.3 |
| 22 | 5.18 | 5.30 | dd | dd | 14.1, 9.1 | 14.9, 9.3 | 139.4 | 139.1 |
| 23 | 2.11 | 2.15 | | | | 39.5 | 37.3 |
| 24a | 1.34 | 1.35 | | | | 40.3 | 40.3 |
| 24b | 1.68 | 1.67 | | | | | |
| 25 | 2.43 | 2.44 | | | | 45.5 | 46.3 |

TABLE X-continued

| Proton | | $\delta_H$ | | multiplicity | | coupling | | $\delta_c$ | |
|---|---|---|---|---|---|---|---|---|---|
| 26 | | | | | | | | 215.2 | 216.1 |
| 27a | | 2.53 | 2.60 | | | | | 46.7 | 47.9 |
| 27b | | 2.65 | 2.43 | | | | | | |
| 28 | | 4.33 | 4.39 | dd | | 7.9, 3.2 | | 71.7 | 71.9 |
| 29 | | | | | | | | 139.6 | 139.6 |
| 30 | | 5.36 | 5.45 | d | | | 9.9 | 123.7 | 125.4 |
| 31 | | 3.24 | 3.37 | | | | | 46.4 | 45.6 |
| 32 | | | | | | | | 209.0 | 209.1 |
| 33a | | 2.63 | 2.63 | | | | | 39.4 | 39.4 |
| 33b | | 2.95 | 2.95 | | | | | | |
| 34 | | 5.13 | 5.38 | | | | | 76.0 | 74.2 |
| 35 | | 1.93 | 1.98[b] | | | | | 32.7 | 32.7 |
| 36a | | 1.04 | 1.03 | | | | | 37.8 | 39.8 |
| 36b | | 1.17 | 1.16 | | | | | | |
| 37 | | 1.34 | 1.38 | | | | | 33.2 | 33.2 |
| 38a | ax. | 0.61 | 0.73 | ddd | ddd | 11.9, 11.9, 11.9 | 11.9, 11.9, 11.9 | 33.9 | 34.5 |
| 38b | eq. | 2.04 | 2.09 | | | | | | |
| 39 | | 2.90 | 2.91 | | | | | 84.5 | 84.4 |
| 40 | | 3.37 | 3.37 | | | | | 73.8 | 73.8 |
| 41a | | 1.31 | 1.31 | | | | | 31.2 | 31.2 |
| 41b | | 1.97 | 1.97 | | | | | | |
| 42a | | 0.97 | 0.97 | | | | | 31.7 | 31.7 |
| 42b | | | | | | | | | |
| 43 | | 0.93 | 0.93 | d | d | 6.5 | 6.5 | 16.8[c] | 16.9[c] |
| 44 | | 1.78 | 1.63 | s | s | | | 15.6 | 12.7 |
| 45 | | 0.98 | 1.00 | | | | | 21.7 | 21.7 |
| 46 | | 1.00 | 1.02 | | | | | 16.7 | 19.1 |
| 47 | | 1.58 | 1.48 | s | s | | | 13.1 | 11.7 |
| 48 | | 1.07 | 1.00 | d | | 6.9 | | 16.2 | 14.6 |
| 49 | | 0.89 | 0.89 | d | d | 6.8 | 6.8 | 14.6[d] | 15.2[d] |
| 50 | | 3.37 | 3.37 | s | s | | | 56.5 | 56.5 |

[a]may be assigned instead to H4a
[b]tentative assignment
[c]the assignment may be interchanged
[d]the assignment may be interchanged Compound 6 exists as a 1:1 mixture of conformers in CDCl$_3$. The data above is for both conformers. Where a dotted line has been drawn across the table it was not possible to determine connectivity between spin systems, hence the assignment of data to a particular conformer is not possible.

EXAMPLE 24

Isolation of Product from Fermentation of *S. hygroscopicus* MG2-10[pSGsetrapKIMLh]

9-Deoxo-27-desmethoxy-rapamycin was obtained by conjugating *S. hygroscopicus* MG2-10 strain with pSGset-KIML$_{his}$ as described in example 1 and isolating the products produced on fermentation. This demonstrated that it was possible to complement the deletion of rapK, rapI, rapM and rapL in the MG2-10 strain with the production of a rapamycin analogue lacking some post-PKS modification.

*S. hygroscopicus* MG2-10 [pSGsetKIML$_{his}$] was fermented (see Materials and Methods), extracted and isolated using the method (B) as outlined in Materials and Methods.

The isocratic solvent system used for preparative HPLC was 75% CH$_3$CN/H$_2$O. 9-Deoxo-27-desmethoxy rapamycin (Compound 16) has the following characteristics:
  Isolated yield: 24 mg
  Molecular weight: 870
  Molecular formula: C$_{50}$H$_{79}$NO$_{11}$
  UV (by diode array detection during HPLC analysis): 268 nm, 278 nm, 288 nm
  Electrospray MS: m/z for MNa$^+$=892, m/z for M−H=868

Table XI below summarises the $^1$H and $^{13}$C NMR data for 9-deoxo-27-desmethoxy rapamycin in CDCl$_3$.

TABLE XI

| Position | $\delta_H$ | multiplicity | coupling | $\delta_C$ |
|---|---|---|---|---|
| 1 | | | | 171.0 |
| 2 | 5.37 | m | | 52.0 |
| 3a | 1.73 | m | | 26.8 |
| 3b | 2.22 | m | | |
| 4a | 1.39 | m | | 20.5 |
| 4b | 1.73 | m | | |
| 5a | 1.56 | m | | 25.1 |
| 5b | 1.77 | m | | |
| 6a | 3.34 | m | | 43.5 |
| 6b | 3.85 | br.d | 12.9 | |
| 8 | | | | 173.4 |
| 9a | 2.43 | d | 14.4 | 38.8 |
| 9b | 2.74 | d | 14.4 | |
| 10 | | | | 98.0 |
| 10-OH | 6.02 | s | | |
| 11 | 1.43 | m | | 39.1 |
| 12a | 1.44 | m | | 27.5 |
| 12b | 1.58 | m | | |
| 13a | 1.28 | m | | 32.2 |
| 13b | 1.45 | m | | |
| 14 | 3.61 | m | | 65.8 |
| 15a | 1.55 | m | | 38.6 |
| 15b | 1.64 | m | | |
| 16 | 3.70 | dd | 10.8, 4.7 | 84.5 |
| 17 | | | | 134.8 |
| 18 | 5.98 | d | 9.2 | 130.8 |
| 19 | 6.34 | m | | 126.9 |
| 20 | 6.32 | m | | 133.1 |
| 21 | 6.11 | dd | 15.3, 9.0 | 130.6 |
| 22 | 5.46 | dd | 15.2, 8.6 | 139.3 |

TABLE XI-continued

| Position | $\delta_H$ | multiplicity | coupling | $\delta_C$ |
|---|---|---|---|---|
| 23 | 2.22 | m | | 35.7 |
| 24a | 1.28 | m | | 40.2 |
| 24b | 1.49 | m | | |
| 25 | 2.58 | m | | 44.8 |
| 26 | | | | 215.0 |
| 27a | 2.65 | m | | 46.2 |
| 27b | 2.65 | m | | |
| 28 | 4.37 | m | | 73.1 |
| 29 | | | | 139.8 |
| 30 | 5.32 | d | 9.9 | 124.5 |
| 31 | 3.38 | m | | 46.3 |
| 32 | | | | 208.9 |
| 33a | 2.59 | m | | 41.4 |
| 33b | 2.59 | m | | |
| 34 | 5.04 | ddd | 5.2, 5.2, 5.2 | 75.7 |
| 35 | 1.97 | m | | 33.4 |
| 36a | 1.11 | m | | 38.6 |
| 36b | 1.26 | m | | |
| 37 | 1.41 | m | | 33.1 |
| 38a ax. | 0.69 | ddd | 12.3, 12.3, 12.3 | 34.1 |
| 38b eq. | 2.11 | m | | |
| 39 | 2.93 | m | | 84.4 |
| 40 | 3.37 | m | | 73.9 |
| 41a | 1.32 | m | | 31.2 |
| 41b | 1.97 | m | | |
| 42a | 1.00 | m | | 31.6 |
| 42b | 1.68 | m | | |
| 43 | 0.88 | d | 6.4 | 16.9 |
| 44 | 3.10 | s | | 55.6 |
| 45 | 1.59 | s | | 9.9 |
| 46 | 1.02 | d | 7.2 | 20.5 |
| 47 | 1.03 | d | 7.1 | 15.7 |
| 48 | 1.67 | s | | 12.2 |
| 49 | 1.12 | d | 6.8 | 16.3 |
| 50 | 0.92 | d | 6.8 | 15.8 |
| 51 | 3.39 | s | | 56.5 |

EXAMPLE 25

Isolation of Product from Fermentation of *S. hygroscopicus* MG2-10[pSGsetKIN/OLh]

9-Deoxo-16-O-desmethyl-27-O-desmethyl-rapamycin was obtained by conjugating *S. hygroscopicus* MG2-10 strain with pSGsetKIN/OL$_{his}$ as described in Example 1 and isolating the products produced on fermentation. This demonstrated that it was possible to complement the deletion of rapK, rapI, rapN/O and rapL in the MG2-10 strain with the production of a rapamycin analogue lacking some post-PKS modification.

*S. hygroscopicus* MG2-10 [pSGsetKIN/OL$_{his}$] was fermented (see Materials and Methods), extracted and isolated using the method (B) as outlined in Materials and Methods.

The isocratic solvent system used for preparative HPLC was 60% CH$_3$CN/H$_2$O. 9-Deoxo-16desmethyl-27-O-desmethylrapamycin (Compound 9) has the following characteristics:

Isolated yield: 77 mg
Molecular weight: 872
Molecular formula: C49H77NO$_{12}$
UV (by diode array detection during HPLC analysis): 268 nm, 278 nm, 288 nm
Electrospray MS: m/z for MNa$^+$=894, m/z for M−H=870

Table XII below summarises the $^1$H and $^{13}$C NMR data for 9-deoxo-16-O-desmethyl-27-O-desmethylrapamycin in CDCl$_3$.

TABLE XII

| Position | $\delta_H$ | multiplicity | coupling | $\delta_C$ |
|---|---|---|---|---|
| 1 | | | | 172.1 |
| 2 | 5.55 | m | | 52.8 |
| 3a | 1.74 | m | | 26.0 |
| 3b | 2.21 | m | | |
| 4a | 1.18 | m | | 21.1 |
| 4b | 1.73 | m | | |
| 5a | 1.44 | m | | 25.2 |
| 5b | 1.73 | m | | |
| 6a | 3.28 | m | | 45.7 |
| 6b | 3.87 | m | | |
| 8 | | | | 171.6 |
| 9a | 2.41 | d | 12.5 | 42.3 |
| 9b | 3.34 | d | 12.5 | |
| 10 | | | | 99.2 |
| 10-OH | 4.15 | m | | |
| 11 | 1.61 | m | | 38.3 |
| 12a | 1.50 | m | | 27.9 |
| 12b | 1.61 | m | | |
| 13a | 1.36 | m | | 31.5 |
| 13b | 1.52 | m | | |
| 14 | 3.99 | m | | 72.5 |
| 15a | 1.45 | m | | 40.9 |
| 15b | 1.70 | m | | |
| 16 | 3.86 | m | | 75.3 |
| 17 | | | | 140.0 |
| 18 | 6.44 | d | 11.4 | 121.9 |
| 19 | 6.33 | dd | 14.4, 11.4 | 128.6 |
| 20 | 6.20 | dd | 14.8, 10.6 | 131.2 |
| 21 | 6.02 | dd | 14.9, 10.6 | 131.2 |
| 22 | 5.25 | m | | 137.4 |
| 23 | 2.26 | m | | 35.3 |
| 24a | 1.21 | m | | 41.1 |
| 24b | 1.21 | m | | |
| 25 | 2.37 | m | | 40.9 |
| 26 | | | | 212.8 |
| 27 | 4.55 | d | 2.3 | 74.9 |
| 28 | 4.20 | | | 77.3 |
| 29 | | | | 135.8 |
| 30 | 5.25 | m | | 124.9 |
| 31 | 3.29 | m | | 44.9 |
| 32 | | | | 208.0 |
| 33a | 2.53 | dd | 18.2, 4.0 | 42.2 |
| 33b | 2.81 | dd | 18.2, 10.6 | |
| 34 | 5.28 | ddd | , 4.0, 4.0 | 75.8 |
| 35 | 1.71 | m | | 31.2 |
| 36a | 0.92 | m | | 36.9 |
| 36b | 1.04 | m | | |
| 37 | 1.23 | m | | 32.6 |
| 38a ax. | 0.28 | ddd | 11.9, 11.9, 11.9 | 34.2 |
| 38b eq. | 1.88 | m | | |
| 39 | 2.85 | | | 84.8 |
| 40 | 3.29 | m | | 74.1 |
| 41a | 1.26 | m | | 31.3 |
| 41b | 1.92 | m | | |
| 42a | 0.88 | m | | 32.3 |
| 42b | 1.57 | m | | |
| 43 | 0.98 | d | 6.2 | 16.6 |
| 44 | 1.59 | s | | 14.6 |
| 45 | 1.01 | d | 6.4 | 21.4 |
| 46 | 0.89 | d | 6.4 | 12.0 |
| 47 | 1.90 | s | | 15.7 |
| 48 | 0.92 | d | 6.4 | 15.6 |
| 49 | 0.84 | d | 6.8 | 17.6 |
| 50 | 3.37 | s | | 57.5 |

EXAMPLE 26

Isolation of Product from Fermentation of *S. hygroscopicus* MG2-10[pSGsetKJLh]

16-O-Desmethyl-27-O-desmethoxy-39-O-desmethyl-rapamycin was obtained by conjugating *S. hygroscopicus* MG2-10 strain with pSGsetKJL$_{his}$ as described in Example 1 and isolating the products produced on fermentation. This demonstrated that it was possible to complement the deletion of rapK, rapJ and rapL in the MG2-10 strain with the production of a rapamycin analogue lacking some post-PKS modification.

S. hygroscopicus MG2-10 [pSGsetKJL$_{his}$] was fermented (see Materials and Methods), extracted and isolated using the method (B) as outlined in Materials and Methods.

The isocratic solvent system used for preparative HPLC was 55% $CH_3CN/H_2O$. 16-O-Desmethyl-27-desmethoxy-39-O-desmethyl rapamycin (Compound 3) has the following characteristics:

Isolated yield: 176 mg (mixture of 2 interconverting isomers)
Molecular weight: 856
Molecular formula: $C_{48}H_{73}NO_{12}$
UV (by diode array detection during HPLC analysis): 268 nm, 278 nm, 288 nm
Electrospray MS: m/z for MNa$^+$=878, m/z for M–H=854
MS fragmentation: The sodiated adduct (m/z 878) was fragmented to provide three fragments: C8-C42, m/z MNa$^+$ 749; C1-C27, m/z MNa $_+$570; C28-C42+C1-C14, m/z MNa$^+$ 628. The fragment ions 628 and 570 were fragmented further to give the same fragment: C1-C14, m/z MNa$^+$ 320. The mass of this C1-C14 fragment is 14 mass units greater than the equivalent fragment from the fragmentation of the sodiated adduct of 9-deoxo-16-O-desmethyl-27-desmethoxy-39-O-desmethyl rapamycin (Compound 1) consistent with oxidation at C9.

EXAMPLE 27

Isolation of Product from Fermentation of S. hygroscopicus MG2-10[pSGsetKMNOLh]

9-Deoxo-27-O-desmethyl-39-O-desmethyl-rapamycin was obtained by conjugating S. hygroscopicus MG2-10 strain with pSGsetKMN/OL$_{his}$ as described in example 1 and isolating the products produced on fermentation. This demonstrated that it was possible to complement the deletion of rapK, rapM, rapN/O and rapL in the MG2-10 strain with the production of a rapamycin analogue lacking some post-PKS modification.

S. hygroscopicus MG2-10 [pSGsetKMN/OL$_{his}$] was fermented (see Materials and Methods), extracted and isolated using the method (B) as outlined in Materials and Methods.

The isocratic solvent system used for preparative HPLC was 60% $CH_3CN/H_2O$. 9Deoxo-27-O-desmethyl-39-O-desmethyl rapamycin (Compound 8) has the following characteristics:

Isolated yield: 6 mg
Molecular weight: 872
Molecular formula: $C_{49}H_{77}NO_{12}$
UV (by diode array detection during HPLC analysis): 268 nm, 278 nm, 288 nm
Electrospray MS: m/z for MNa$^+$=894, m/z for M–H=870
MS fragmentation: The sodiated adduct (m/z 894) was fragmented to provide three fragments: C8-C42, m/z MNa$^+$ 765; C1-27, m/z MNa$^+$ 586; C28-C42+C1-C14, m/z MNa$^+$ 614. The fragment ions 614 and 586 were fragmented further to give the same fragment: C1-C14, m/z MNa$^+$ 306. The C1-C14 is identical to that obtained from fragmentation of the sodiated adduct of 9-deoxo-16-desmethyl-27-desmethoxy-39-O-desmethyl rapamycin; the compound is 9-deoxo. The C1-C27 fragment is 30 mass units greater than the equivalent fragment from 9-deoxo-16-O-desmethyl-27-desmethoxy-39-O-desmethyl rapamycin, consistent with one hydroxylation and one methylation; RapM methylates the hydroxy group at C-16 (see Example 22 for pSGsetKIL$_{his}$ together with Example 23 pSGsetKIML$_{his}$) and RapN in combination with RapO hydroxylates C27 so the data is consistent with the compound being 9-deoxo-27-O-desmethyl-39-O-desmethyl rapamycin (Compound 8).

EXAMPLE 28

Isolation of Product from Fermentation of S. hygroscopicus MG2-10[pSGsetKIJLh]

16-O-desmethyl-27-desmethoxy-rapamycin was obtained by conjugating S. hygroscopicus MG2-10 strain with pSGsetKIJL$_{his}$ as described in Example 1 and isolating the products produced on fermentation. This demonstrated that it was possible to complement the deletion of rapK, rapI, rapJ and rapL in the MG2-10 strain with the production of a rapamycin analogue lacking some post-PKS modification.

S. hygroscopicus MG2-10 [pSGsetKIJL$_{his}$] was fermented (see Materials and Methods), extracted and isolated using the method (B) as outlined in Materials and Methods.

The isocratic solvent system used for preparative HPLC was 60% $CH_3CN/H_2O$. 16-O-Desmethyl-27-desmethoxy rapamycin (Compound 12) has the following characteristics:

Isolated yield: 11 mg
Molecular weight: 870
Molecular formula: $C_{49}H_{75}NO_{12}$
UV (by diode array detection during HPLC analysis): 268 nm, 278 nm, 288 nm
Electrospray MS: m/z for MNa$^+$=892, m/z for M–H=868

EXAMPLE 29

Isolation of Product from Fermentation of S. hygroscopicus MG2-10[pSGsetKL$_{his}$]

9-Deoxo-16-O-desmethyl-27-desmethoxy-39-O-desmethyl-rapamycin was obtained by conjugating S. hygroscopicus MG2-10 strain with pSGsetKL$_{his}$ as described in example 1 and isolating the products produced on fermentation. This demonstrated that it was possible to complement the deletion of rapK and rapL in the MG2-10 strain with the production of a rapamycin analogue lacking post-PKS modification (pre-rapamycin).

S. hygroscopicus MG2-10 [pSGsetKL$_{his}$] was fermented, extracted and isolated using the methods outlined in Materials and Methods.

The isocratic solvent system used for preparative HPLC was 60% $CH_3CN/H_2O$.

9-Deoxo-16-O-desmethyl-27-desmethoxy-39-O-desmethyl rapamycin (Compound 1) has the following characteristics:

Isolated yield: 24 mg
Molecular weight: 842
Molecular formula: $C_{48}H_{75}NO_{11}$
UV (by diode array detection during HPLC analysis): 268 nm, 278 nm, 288 nm
Electrospray MS: m/z for MNa$^+$=864, m/z for M–H=840
MS fragmentation: The sodiated adduct (m/z 864.5) was fragmented to provide four fragments: C8-C42, m/z MNa$^+$ 735; C1-C27, m/z MNa$^+$ 556; C28-C42+C1-C14, m/z MNa$^+$ 614, C1-C14, m/z MNa$^+$ 306. The expected m/z for these fragments were determined by comparison to the reported fragmentation of rapamycin (J. A. Reather, Ph.D. Dissertation, University of Cambridge, 2000). These fragments have the same m/z as the predicted m/z for the fragmentation of 9-deoxo-16-O-desmethyl-27-desmethoxy-39-O-desmethyl rapamycin.

EXAMPLE 30

Isolation of Product from Fermentation of S. hygroscopicus MG2-10 fed with Cyclohexane Carboxylic Acid 9-Deoxo-16-O-desmethyl-27-desmethoxy-39-desmethoxy-rapamycin was obtained on feeding cyclohexane carboxylic acid to S. hygroscopicus MG2-10 and isolating the products produced on fermentation. The resulting mutasynthesis demonstrated that it was possible to chemically complement the deletion of rapK in the MG2-10 strain, in the absence of natural endogenous starter, with the resulting production of a rapamycin analogue lacking post-PKS modification.

S. hygroscopicus MG2-10 was fermented (see Materials and Methods), fed (see Materials and Methods), extracted and isolated using the method (B) as outlined in Materials and Methods.

The isocratic solvent system used for preparative HPLC was 60% $CH_3CN/H_2O$.

9-Deoxo-16-O-desmethyl-27-desmethoxy-39-desmethoxy rapamycin (Compound 47) has the following characteristics:

Isolated yield: 12 mg
Molecular weight: 826
Molecular formula: $C_{48}H_{75}NO_{10}$
UV (by diode array detection during HPLC analysis): 268 nm, 278 nm, 288 nm
Electrospray MS: m/z for $MNa^+$=848.5, m/z for M−H=825

MS fragmentation: The sodiated adduct (m/z 848.5) was fragmented to provide four fragments: C8-C42, m/z $MNa^+$ 719; C1-C27, m/z $MNa^+$ 556; C28-C42+C1-C14, m/z $MNa^+$ 598, C1-C14, m/z MNa+ 306. These data illustrate that the difference between Compound 47 and 9-deoxo-1-desmethyl-27-desmethoxy-39-O-desmethyl rapamycin (Compound 1) is located in the region of C28-C42. This fragment is 16 mass units less for Compound 47 than it is for Compound 1, consistent with Compound 47 being 9-deoxo-16-O-desmethyl-27-desmethoxy-39-desmethoxy rapamycin.

EXAMPLE 31

Isolation of Product from Fermentation of S. hygroscopicus MG2-10[pSGsetKNOLh]

9-Deoxo-16-O-desmethyl-27-O-desmethyl-39-O-desmethyl-rapamycin is obtained by conjugating S. hygroscopicus MG2-10 strain with pSGsetKN/$OL_{his}$ as described in Example 1 and isolating the products produced on fermentation. This demonstrates that it is possible to complement the deletion of rapK, rapN/O and rapL in the MG2-10 strain with the production of a rapamycin analogue lacking some post-PKS modification.

S. hygroscopicus MG2-10 [pSGsetKN/$OL_{his}$] is fermented (see Materials and Methods), extracted and isolated using the method (B) as outlined in Materials and Methods.

The isocratic solvent system used for preparative HPLC is 60% $CH_3CN/H_2O$.

9Deoxo-16-O-desmethyl-27-O-desmethyl-39-O-desmethyl rapamycin (Compound 2) has the following characteristics:

Molecular weight: 858
Molecular formula: $C_{48}H_{75}NO_{12}$
UV (by diode array detection during HPLC analysis): 268 nm, 278 nm, 288 nm
Electrospray MS: m/z for $MK^+$=896, m/z for M−H=856

EXAMPLE 32

Identification of Product from Fermentation of S. hygroscopicus MG2-10[pSGsetKJNOLh]

16-O-Desmethyl-27-O-desmethyl-39-O-desmethyl-rapamycin was obtained by conjugating S. hygroscopicus MG2-10 strain with pSGsetKJN/$OL_{his}$ as described in example 1 and analysing the products produced on fermentation. This demonstrated that it was possible to complement the deletion of rapK, rapJ, rapN/O and rapL in the MG2-10 strain with the production of a rapamycin analogue lacking some post-PKS modification.

The fermentation broth (1 mL) was treated as described in the extraction, isolation and analysis Method (B) described in Materials and Methods. The HPLC chromatogram (280 nm) contained a peak that had the characteristic rapamycin triene (268 nm, 278 nm, 288 nm). This peak was not observed in the chromatogram of the control sample extracted from S. hygroscopicus MG2-10 in the absence of the cassette. LCMS (see Materials and Methods, Method B) of the novel rapamycin analogue peak gave ions m/z 895 ($MNa^+$) and 871 (M−H). These ions confirm that the molecular weight of the novel rapamycin analogue is 872, 30 mass units greater than 9-deoxo-16-O-desmethyl-27-desmethoxy-39-O-desmethyl rapamycin (Compound 1), consistent with oxidation at C9 (rapJ) and hydroxylation at C27 (rapN/O). These data are consistent with the compound being 16-O-desmethyl-27-O-desmethyl-39-O-desmethyl rapamycin (Compound 7).

EXAMPLE 33

Isolation of Product from Fermentation of S. hygroscopicus MG2-10[pSGsetKJNOLh]

16-O-Desmethyl-27-O-desmethyl-39-O-desmethyl-rapamycin is obtained by conjugating S. hygroscopicus MG2-10 strain with pSGsetKJN/$OL_{his}$ as described in Example 1 and isolating the products produced on fermentation. This demonstrates that it is possible to complement the deletion of rapK, rapJ, rapN/O and rapL in the MG2-10 strain with the production of a rapamycin analogue lacking some post-PKS modification.

S. hygroscopicus MG2-10 [pSGsetKJN/$OL_{his}$] is fermented (see Materials and Methods), extracted and isolated using the method (B) as outlined in Materials and Methods.

The isocratic solvent system used for preparative HPLC is 60% $CH_3CN/H_2O$.

16-O-Desmethyl-27-O-desmethyl-39-O-desmethyl rapamycin (Compound 7) has the following characteristics:

Molecular weight: 872
Molecular formula: $C_{48}H_{73}NO_{13}$
UV (by diode array detection during HPLC analysis): 268 nm, 278 nm, 288 nm
Electrospray MS: m/z for $MNa^+$=895, m/z for M−H=871

EXAMPLE 34

Identification of Product from Fermentation of *S. hygroscopicus* MG2-10 [pSGsetKIJNOQLh]

16-O-Desmethyl-rapamycin was obtained by conjugating *S. hygroscopicus* MG2-10 strain with pSGsetKIJN/OQL$_{his}$ as described in example 1 and analysing the products produced on fermentation. This demonstrated that it was possible to complement the deletion of rapK, rapI, rapJ, rapN/O, rapQ and rapL in the MG2-10 strain with the production of a rapamycin analogue lacking methylation at C16-OH. In addition, it clearly identified RapQ as the SAM-dependent O-methyltransferase responsible for methylation of C27-OH.

*S. hygroscopicus* MG2-10 [pSGsetKIJN/OQL$_{his}$] was fermented (see Materials and Methods), extracted and analysed using the method (B) as outlined in Materials and Methods.

The fermentation broth (1 mL) was treated as described in Materials and Methods. The HPLC chromatogram (280 nm) contained a peak that had the characteristic rapamycin triene (268 nm, 278 nm, 288 nm). This peak was not observed in the chromatogram of the control sample extracted from *S. hygroscopicus* MG2-10 in the absence of the cassette. LCMS (see Materials and Methods) of the novel rapamycin analogue peak gave ions m/z 923 (MNa$^+$) and 899 (M–H).

These ions confirm that the molecular weight of the novel rapamycin analogue is 900, 14 mass units less than rapamycin. It has already been established that the only post-PKS gene not included in the cassette, rapM, acts to methylate the C16-OH, hence the novel rapamycin analogue is 16-O-desmethyl rapamycin (Compound 20) and rapQ is shown to be functional and acting to O-methylate at C27.

EXAMPLE 35

Bioassay of Rapamycin Analogues (1)=9-deoxo-16-O-desmethyl-27-desmethoxy-39-O-desmethyl-rapamycin (pre-rapamycin)
(6)=9-deoxo-16-O-desmethyl-27-desmethoxy-rapamycin
(16)=9-deoxo-27-desmethoxy-rapamycin,
(3)=16-O-desmethyl-27-desmethoxy-39-O-desmethyl-rapamycin
(9)=9-deoxo16-O-desmethyl-27-O-desmethyl-rapamycin
(8)=9-deoxo27-desmethyl-39-O-desmethyl-rapamycin.

Cancer Cell Lines:

Growth inhibition of adherent human tumour cell lines of solid malignancies HT29 (colon) and MCF-7 (breast) was tested in vitro using an MTT (3-(4,5-dimethylthiazol-2-yl)-2,5-diphenyltetrazolium bromide) assay using micro-titre plates (Sieuwerts, A. M., et al., 1995). All cell lines were obtained from either the ATCC (American Type Culture Collection) or ECACC (European Collection of Cell Cultures). All cell lines were grown from frozen stocks and passaged at least once prior to use in RPMI 1640. Cells were harvested from sub-confluent cultures using minimal trypsinization. Cells were diluted to the appropriate density for each cell line (dependent on cell doubling time) in RPMI 1640, and seeded in 60 wells of a 96 well plate in a volume of 100 μl per well (i.e. outside wells of the plate were not used). Plates were incubated at 37° C. overnight Following this incubation, log scale dilutions of reference and test substances were added in 100 μl per well, 6 replicates were used to test all test compounds, reference compounds and medium controls. Plates were incubated for a further 72 h prior to analysis. MTT (5 mg/ml) was added to each well and plates were re-incubated for 3-4 h. Unreacted MTT was removed from the wells and formazan crystals formed from the MTT were dissolved in DMSO and characteristic absorbance read at 570 nm. The concentration (nM) of each test compound and reference compound, which resulted in 50% of maximum inhibition (IC$_{50}$), was calculated for each cell line and quoted along with the maximum percentage of inhibition observed (I$_m$), see Table XIII. For reference, rapamycin has an IC$_{50}$ of 200 nM and an I$_m$ of 40% in the HT-29 cell line and an IC$_{50}$ of 0.03 nM and an I$_m$ of 56% in the MCF-7 cell line.

TABLE XIII

| | Assay | | | | | | | | | | | |
|---|---|---|---|---|---|---|---|---|---|---|---|---|
| | 1 | | 6 | | 16 | | 3 | | 9 | | 8 | |
| | IC$_{50}$ | I$_m$ | IC$_{50}$ | I$_m$ | IC$_{50}$ | I$_m$ | IC$_{50}$ | I$_m$ | IC$_{50}$ | I$_m$ | IC$_{50}$ | I$_m$ |
| HT29 rIC$_{50}$ | 50.1 | 38 | 25 | 38 | 15.8 | 25 | 63.1 | 37 | 12.6 | 35 | 63 | 30 |
| MCF-7 rIC$_{50}$ | 3.2 | 38 | 126 | 48 | 2 | 32 | 20 | 38 | 17.8 | 40 | 20 | 38 |

Mixed Lymphocyte Reaction (MLR):

Originally developed to assess tissue compatibility prior to allografts, MLR offers an established model for immune reaction in vitro (SOUILLOU, J. P., et al. (1975); T. Meo. "Immunological Methods", L. Lefkovits and B. Pernis, Eds., Academic Press, N.Y. pp. 227-239 (1979). MLR was performed by mixing splenic lymphocytes isolated from C57BL/6 mice (5×10$^5$ cells) with inhibited splenic lymphocytes from CBA mice (2.5×10$^5$ cells). The inhibited CBA lymphocytes induced a proliferative response in C57BL/6 lymphoctes and this was determined by [$^3$H] thymidine incorporation into DNA as a measure of proliferation of splenic lymphocytes isolated from C57BL/6 mice. The anti-proliferative effect was assayed for in the presence of log scale dilutions of reference compounds, test compounds and media controls over a 72 h period at 37° C. The concentration of each test compound and reference compound, which inhibited lymphocyte proliferation by 50% (IC$_{50}$), compared to control proliferation, was calculated for each cell line and quoted as a ratio of the concentration of rapamycin required to inhibit lymphocyte proliferation by 50% (rIC$_{50}$), see Table XIV.

TABLE XIV

| | \multicolumn{6}{c}{Assay} | | | | | |
|---|---|---|---|---|---|---|
| | 1 | 6 | 16 | 3 | 9 | 8 |
| MLR rIC$_{50}$ | 9.4 | 8.8 | >14.7 | 7.9 | 6.5 | 4.1 |

Anti-fungal Assay:

The comparative anti-fungal activities of reference and test compounds were determined against pathogenic fungi *Candida albicans* DSM 5816, *Candida albicans* DSM 1386 and *Candida glabrata* DSM 11226. This was achieved using a microtitre plate adaption of the NCCLS Reference Method for Broth Dilution Antifungal Susceptibility Testing for Yeasts: Approved Standard (M27-A, vol. 17 No. 9. (1997)). Yeast strains were inoculated (10$^4$ cfu/ml) to RPMI 1640 media containing 0.165 mM MOPS, pH 7. Growth was determined in the presence of log scale dilutions of reference compounds, test compounds and media controls after incubation with shaking at 37° C., 24 h. Minimum inhibitory concentration (MIC) and minimum fungicidal activity (MFC) were determined for test compounds and expressed as a ratio of the rapamycin minimum inhibitory concentration (rMIC respectively), see Table XV.

TABLE XV

| | Assay | | | | | |
|---|---|---|---|---|---|---|
| | 1 | 6 | 16 | 3 | 9 | 8 |
| *C. albicans* DSM 5816 rMIC | 1 | 1 | 1 | 1 | 1 | 1 |
| *C. albicans* DSM 1386 rMIC | 5 | 5 | 5 | 1 | 1 | 1 |
| *C. glabrata* DSM 11226 rMIC | 5 | 5 | 5 | 1 | 1 | 1 |

REFERENCES

Alarcon, C. M., Heitman, J., and Cardenas, M. E. (1999) Protein kinase activity and identification of a toxic effector domain of the target of rapamycin TOR proteins in yeast. *Molecular Biology of the Cell* 10: 2531-2546.

Aparicio, J. F., Molnár, I., Schwecke, T., König, A., Haydock, S. F., Khaw, L. E., Staunton, J., and Leadlay, P. F. (1996) Organization of the biosynthetic gene cluster for rapamycin in *Streptomyces hygroscopicus*: analysis of the enzymatic domains in the modular polyketide synthase. *Gene* 169: 916.

Baker, H., Sidorowicz, A., Sehgal, S. N., and Vézina, C. (1978) Rapamycin (AY-22,989), a new antifungal antibiotic. III. In vitro and in vivo evaluation. *Journal of Antibiotics* 31: 539-545.

Bierman, M., Logan, R., O'Brien, K, Seno, E. T., Nagaraja Rao, R., and Schoner, B. E. (1992) Plasmid cloning vectors for the conjugal transfer of DNA from *Escherichia coli* to *Streptomyces* spp. *Gene* 116: 4349.

Blanc, V., Lagneaux, D., Didier, P., Gil, P., Lacroix, P., and Crouzet, J. (1995) Cloning and analysis of structural genes from *Streptomyces pristinaespiralis* encoding enzymes involved in the conversion of pristinamycin II$_B$ to pristinamycin II$_A$ (PII$_A$): PII$_A$ synthase and NADH: riboflavin 5'-phosphate oxidoreductase. *Journal of Bacteriology* 177: 5206-5214.

Blanc, V., Gil, P., Bamas-Jacques, N., Lorenzon, S., Zagorec, M., Schleuniger, J., Bisch, D., Blanche, F., Debussche, L., Crouzet, J., and Thibaut, D. (1997) Identification and analysis of genes from *Streptomyces pristinaespiralis* encoding enzymes involved in the biosynthesis of the 4-dimethylamino-L-phenylalanine precursor of pristinamycin I. *Molecular Microbiology* 23: 191-202.

Box, S. J., Shelley, P. R., Tyler, J. W., Verrall, M. S., Warr, S. R. C., Badger, A. M., Levy, M. A., and Banks, R. M. (1995) 27-O-Demethylrapamycin, an immunosuppressant compound produced by a new strain of *Streptomyces hygroscopicus*. *Journal of Antibiotics* 48: 1347-1349.

Brown, E. J., Albers, M. W., Shin, T. B., Ichikawa, K., Keith, C. T., Lane, W. S., and Schreiber, S. L. (1994) A mammalian protein targeted by G1-arresting rapamycin-receptor complex. *Nature* 369: 756-758.

Brunn, G. J., Williams, J., Sabers, C., Wiederrecht, G., Lawrence, J. C., and Abraham, R. T. (1996) Direct inhibition of the signaling functions of the mammalian target of rapamycin by the phosphoinositide 3-kinase inhibitors, wortmannin and LY294002. *EMBO Journal* 15: 5256-5267.

Cao, W., Mohacsi, P., Shorthouse, R., Pratt, R. and Morris, R. E. (1995). Effects of rapamycin on growth factor-stimulated vascular smooth muscle cell DNA synthesis. Inhibition of basic fibroblast growth factor and platelet-derived growth factor action and antagonism of rapamycin by FK506. *Transplantation* 59(3): 390-395.

Carlson, R. P., Hartman, D. A., Tomchek, L. A., Walter, T. L., Lugay, J. R., Calhoun, W., Sehgal, S. N., Chang, J. Y. (1993). Rapamycin, a potential disease-modifying antiarthritic drug. J. Pharmacol. Exp. Ther. 266(2):1125-38.

Chambraud, B., Radanyi, C., Camonis, J. H., Shazand, K, Rajkowski, K, and Baulieu, E. E. (1996) FAP48, a new protein that forms specific complexes both immunophilins FKBP59 and FKBP12. Prevention by the immunosuppressant drugs FK506 and rapamycin. *Journal of Biological Chemistry* 271: 32923-32929.

Chang, J. Y., Sehgal, S. N., and Bansbach, C. C. (1991) FK506 and rapamycin: novel pharmacological probes of the immune response. *Trends in Pharmacological Sciences* 12: 218-223.

Chen, J., Zheng, X. F., Brown, E. J., and Schreiber, S. L. (1995) Identification of an 11-kDa FKBP12-rapamycin-binding domain within the 289-kDa FKBP12-rapamycin-associated protein and characterization of a critical serine residue. *Proceedings of the National Academy of Sciences of the United States of America* 92: 4947-4951.

Chini, M., Crotti, P., Gardelli, C., and Macchia, F., (1992), *Tetrahedron*, 48, 3805-3812

Choi, J. W., Chen, J., Schreiber, S. L., and Clardy, J. (1996) Structure of the FKBP12-rapamycin complex interacting with the binding domain of human FRAP. *Science* 273: 239-242.

Chung, L., Liu, L., Patel, S., Carney, J. R., and Reeves, C. D. (2001) Deletion of rapQNML from the rapamycin gene cluster of *Streptomyces hygroscopicus* gives production of the 16-O-desmethyl-27-desmethoxy analog. *Journal of Antibiotics* 54: 250-256.

Corey, E. J. and Huang, H., (1989) *Tetrahedron Lett.*, 30, 5235-5238

DiLella, A. G., and Craig, R. J. (1991) Exon organization of the human FKBP-12 gene: correlation with structural and functional protein domains. *Biochemistry* 30: 8512-8517.

Du, L. C., Sánchez, C., Chen, M., Edwards, D. J., and Shen, B. (2000) The biosynthetic gene cluster for the antitumor drug bleomycin from *Streptomyces verticillus*

ATCC15003 supporting functional interactions between nonribosomal peptide synthetases and a polyketide synthase. *Chemistry & Biology* 7: 623-642.

Dudkin, L., Dilling, M. B., Cheshire, P. J., Hanwood, F. C., Hollingshead, M., Arbuck, S. G., Travis, R., Sausville, E. A., Houghton, P. J. (2001). Biochemical correlates of mTOR inhibition by the rapamycin ester CCI-779 and tumor growth inhibition. Clin. Cancer Res. 7(6):1758-64

Fehr, T., Sanglier, J-J., Schuler, W., Gschwind, L., Ponelle, M., Schilling, W., Wioland, C. (1996). Antascomicinc A, B, C, D and E: Novel FKBP12 binding compounds from a *Micromonospora* strain. *J. Antibiot.* 49(3): 230-233.

Ferrari, S., Pearson, R. B., Siegmann, M., Kozma, S. C., and Thomas, G. (1993) The immunosuppressant rapamycin induces inactivation of $p70^{s6k}$ through dephosphorylation of a novel set of sites. *Journal of Biological Chemistry* 268: 16091-16094.

Findlay J. A, and Radics, L. (1980) *Canadian Journal of Chemistry* 58:579.

Fishbein, T. M., Florman, S., Gondolesi, G., Schiano, T., LeLeiko, N., Tschemia, A., Kaufman, S. (2002). Intestinal transplantation before and after the introduction of sirolimus. Transplantation. 73(10): 1538-42.

Foey, A., Green, P., Foxwell, B., Feldmann, M., Brennan, F. (2002). Cytokine-stimulated T cells induce macrophage IL-10 production dependent on phosphatidylinositol 3-kinase and p70S6K: implications for rheumatoid arthritis. Arthritis Res. 4(1):64-70. Epub 2001 Oct. 10.

Gaisser, S., Reather, J., Wirtz, G., Kellenberger, L., Staunton, J., and Leadlay, P. F. (2000) A defined system for hybrid macrolide biosynthesis in *Saccharopolyspora erythraea*. *Molecular Microbiology* 36: 391-401.

Gaisser, S., Lill, R., Staunton, J., Mendez, C., Salas, J., Leadlay, P F. (2002) Parallel pathways for oxidation of 14-membered polyketide macrolactones in *Saccharopolyspora erythraea*. Mol Microbiol 44:771-81.

Galat, A. (2000) Sequence diversification of the FK506-binding proteins in several different genomes. *European Journal of Biochemistry* 267: 4945-4959.

Gregory, C. R., Huie, P., Billingham, M. E. and Morris, R. E. (1993). Rapamycin inhibits arterial intimal thickening caused by both alloimmune and mechanical injury. Its effect on cellular, growth factor and cytokine response in injured vessels. *Transplantation* 55(6):1409-1418.

Gregory M A, Till R, Smith, M C M. (in Press) Integration site for *Streptomyces* phage φBT1 and the development of site-specific integrating vectors. *J Bacteriol*.

Guba, M., von Breitenbuch, P., Steinbauer, M., Koehl, G., Flegel, S., Hornung, M., Bruns, C. J., Zuelke, C., Farkas, S., Anthuber, M., Jauch, K. W., and Geissler, E. K (2002) Rapamycin inhibits primary and metastatic tumor growth by antiangiogenesis: involvement of vascular endothelial growth factor. *Nature Medicine* 8: 128-135.

Hamilton, G. S., and Steiner, J. P. (1998) Immunophilins: Beyond immunosuppression. *Journal of Medicinal Chemistry* 41: 5119-5143.

Hara, K., Yonezawa, K., Kozlowski, M. T., Sugimoto, T., Andrabi, K., Weng, Q. P., Kasuga, M., Nishimoto, I., and Avruch, J. (1997) Regulation of eIF-4E BP1 phosphorylation by mTOR. *Journal of Biological Chemistry* 272: 26457-26463.

Hardwick, J. S., Kuruvilla, F. G., Tong, J. K, Shamji, A. F., and Schreiber, S. L. (1999) Rapamycin-modulated transcription defines the subset of nutrient-sensitive signaling pathways directly controlled by the Tor proteins. *Proceedings of the National Academy of Sciences of the United States of America* 96: 14866-14870.

Hatanaka, H., Kino, T., Miyata, S., Inamura, N., Kuroda, A, Goto, T., Tanaka, H., Okuhara, M. (1988). FR-900520 and FR-900523, novel immunosuppressants isolated from a *Streptomyces*. II. Fermentation, isolation and physicochemical and biological characteristics. *J. Antibiot.* (Tokyo). 41(11):1592-601.

Hatanaka H, Kino T, Asano M, Goto T, Tanaka H, Okuhara M. (1989). FK-506 related compounds produced by *Streptomyces tsukubaensis* No. 9993. *J. Antibiot.* (Tokyo). 42(4):620-2.

Hendrickson, B. A., Zhang, W., Craig, R. J., Jin, Y. J., Bierer, B. E., Burakoff, S., and DiLella, A. G. (1993) Structural organization of the genes encoding human and murine FK506-binding protein (FKBP)13 and comparison to FKBP1. *Gene* 134: 271-275.

Hentges, K. E., Sirry, B., Gingeras, A. C., Sarbassov, D., Sonenberg, N., Sabatini, D., and Peterson, A. S. (2001) FRAP/mTOR is required for proliferation and patterning during embryonic development in the mouse. *Proceedings of the National Academy of Sciences of the United States of America* 98: 13796-13801.

Hopwood, D. A. (1997) Genetic contributions to understanding polyketide synthases. *Chemical Reviews* 97: 2465-2497.

Hosted, T. J., and Baltz, R. H. (1997) Use of rpsL for dominance selection and gene replacement in *Streptomyces roseosporus*. *Journal of Bacteriology* 179: 180-186.

Hung, D. T., and Schreiber, S. L. (1992) cDNA cloning of a human 25 kDa FK506 and rapamycin binding protein. *Biochemical and Biophysical Research Communications* 184: 733-738.

Hung, D. T., Jamison, T. F., and Schreiber, S. L. (1996) Understanding and controlling the cell cycle with natural products. *Chemistry & Biology* 3: 623-639.

Jain, S., Bicknell, G. R., Whiting, P. H., Nicholson, M. L. (2001). Rapamycin reduces expression of fibrosis-associated genes in an experimental model of renal ischaemia reperfusion injury. Transplant Proc. 33(1-2):556-8.

Jin, Y. J., Burakoff, S. J., and Bierer, B. E. (1992) Molecular cloning of a 25-kDa high affinity rapamycin binding protein, FKBP25. *Journal of Biological Chemistry* 267: 10942-10945.

Kahan, B. D., Chang, J. Y., and Sehgal, S. N. (1991) Preclinical evaluation of a new potent immunosuppressive agent, rapamycin. *Transplantation* 52: 185-191.

Kahan, B. D., and Camardo, J. S. (2001) Rapamycin: Clinical results and future opportunities. *Transplantation* 72:1181-1193.

Kallen, J. A., Sedrani, R., and Cottens S. (1996) X-ray crystal structure of 28-O-methylrapamycin complexed with FKBP12: Is the cyclohexyl moiety part of the effector domain of rapamycin? *Journal of the American Chemical Society* 118: 5857-5861.

Kawasome, H., Papst, P., Webb, S., Keller, G. M., Johnson, G. L., Gelfand, E. W., and Terada, N. (1998) Targeted disruption of $p70^{s6k}$ defines its role in protein synthesis and rapamycin sensitivity. *Proceedings of the National Academy of Sciences of the United States of America* 95: 5033-5038.

Khaw, L. E., Böhm, G. A., Metcalfe, S., Staunton, J., and Leadlay, P. F. (1998) Mutational biosynthesis of novel rapamycins by a strain of *Streptomyces hygroscopicus* NRRL 5491 disrupted in rapL, encoding a putative lysine cyclodeaminase. *Journal of Bacteriology* 180: 809-814.

Kieser, T., Bibb, M. J., Buttner, M. J., Chater, K. F., and Hopwood, D. A. (2000) Practical *Streptomyces* Genetics, John Innes Foundation, Norwich.

Kirby, B., and Griffiths, C. E. M. (2001) Psoriasis: the future. *British Journal of Dermatology* 144:37-43.

Kirchner, G. I., Winkler, M., Mueller L., Vidal, C., Jacobsen, W., Franzke, A., Wagner, S., Blick, S., Manns M. P., and Sewing K.-F.(2000) Pharmacokinetics of SDZ RAD and cyclosporin including their metabolites in seven kidney graft patients after the first dose of SDZ RAD. British Journal of Clinical Pharmacology 50:449-454.

König, A., Schwecke, T., Molnár, I., Böhm, G., Lowden, P. A. S., Staunton, J., and Leadlay, P. F. (1997) The pipecolate-incorporating enzyme for the biosynthesis of the immunosuppressant rapamycin. Nucleotide sequence analysis, disruption and heterologus expression of rapP from *Streptomyces hygroscopicus*. *European Journal of Biochemistry* 247: 526-534.

Kunz, J., Loeschmann, A., Deuter-Reinhard, M., and Hall, M. N. (2000) FAP1, a homologue of human transcription factor NF-X1, competes with rapamycin for binding to FKBP12 in yeast. *Molecular Microbiology* 37: 1480-1493.

Kuo, C. J., Chung, J. K., Fiorentino, D. F., Flanagan, W. M., Blenis, J., and Crabtree, G. R. (1992) Rapamycin selectively inhibits interleukin-2 activation of p70 S6 kinase. *Nature* 358: 70-73.

Lee, M. H. Pascopella, L., Jacobs, W. R., Jr and Hatfull, G. F (1991). Site specific integration of mycobacteriophage L5: integration-proficient vectors for *Mycobacterium smegmatis, Mycobacterium tuberculosis* and Bacille Calmette-Guerin. *Proc. Natl. Acad. Sci. USA,* 88:3111-3115.

Lee M H, Pascopella L, Jacobs W R Jr, Hatfull G F. (1991), Site-specific integration of mycobacteriophage L5: integration-proficient vectors for *Mycobacterium smegmatis, Mycobacterium tuberculosis*, and bacille Calmette-Guerin. *Proc Natl Acad Sci USA.;* 88:3111-5.

Liang, J., Choi, J., and Clardy, J. (1999) Refined structure of the FKBP12-rapamycin-FRB ternary complex at 2.2 Å resolution. *Acta Crystallographica Section D-Biological Crystallography* 55: 736-744.

Lomovsgkaya, N., Fonstein, L., Ruan, X., Stassi, D., Katz, L., and Hutchinson, C. R. (1997) Gene-disruption and replacement-in the rapamycin-producing *Streptomyces hygroscopicus* strain ATCC 29253. *Microbiology-Uk* 143: 875-883.

Lowden, P. A. S., Böhm, G., Staunton, J., and Leadlay, P. F. (1996) The nature of the starter unit for the rapamycin polyketide sythase. *Angewandte Chemie* 35: 2249-2251.

Lowden, P. A. S., (1997) Ph.D. Dissertation, University of Cambridge. "Studies on the biosynthesis of rapamycin".

Lowden, P. A. S, Wilkinson, B., Böhm, G. A., Handa, S., Floss, H. G., Leadlay, P. F., and Staunton, J. (2001) Origin and true nature of the starter unit for the rapamycin polyketide synthase. *Angewandte Chemie-International Edition* 40: 777-779.

Luengo, J. I., Yamashita, D. S., Dunnington, D., Beck, A. K., Rozamus, L. W., Yen, H. K, Bossard, M. J., Levy, M. A., Hand, A., Newmantarr, T., Badger, A., Faucette, L, Johnson, R. K., Dalessio, K, Porter, T., Shu, A. Y. L, Heys, R., Choi, J. W., Kongsaeree, P., Clardy, J., and Holt, D. A. (1995) Structure-Activity Studies of Rapamycin Analogs—Evidence That the C-7 Methoxy Group Is Part of the Effector Domain and Positioned at the Fkbp12-Frap Interface. *Chemistry & Biology* 2: 471-481.

Lyons, W. E., George, E. B., Dawson, T. M., Steiner, J. P., and Snyder, S. H. (1994) Immunosuppressant FK506 promotes neurite outgrowth in cultures of PC12 cells and sensory ganglia. *Proceedings of the National Academy of Sciences of the United States of America* 91:3191-3195.

MacNeil, D. J., Gewain, K. M., Ruby, C. L., Dezeny, G., Gibbons, P. H., and MacNeil, T. (1992) Analysis of *Streptomyces avermitilis* genes required for avermectin biosynthesis utilizing a novel integration vector. *Gene* 111: 61-68.

Marahiel, M. A., Stachelhaus, T., and Mootz, H. D. (1997) Modular peptide synthetases involved in nonribosomal peptide synthesis. *Chemical Reviews* 97: 2651-2673.

Matsuura, M., Noguchi, T., Yamaguchi, D., Aida, T., Asayama, M., Takahashi, H. and Shirai, M. (1996). The sre gene (ORF469) encodes a site-specific recombinase responsible for integration of the R4 phage genome. *J Bact.* 178(11):3374-3376.

McAlpine, J. B,. Swanson S. J., Jackson, M., Whittern, D. N. (1991). Revised NMR assignments for rapamycin. *Journal of Antibiotics* 44: 688-690.

Meo, T. in "Immunological Methods", L. Lefkovits and B. Pernis, Eds., Academic Press, N.Y. pp. 227-239 (1979).

Molnár, I., Aparicio, J. F., Haydock, S. F., Khaw, L. E., Schwecke, T., König, A., Staunton, J., and Leadlay, P. F. (1996) Organisation of the biosynthetic gene cluster for rapamycin in *Streptomyces hygroscopicus*: analysis of genes flanking the polyketide synthase. *Gene* 169: 1-7.

Morice, M. C., Serruys, P. W., Sousa, J. E., Fajadet, J., Ban Hayashi, E., Perin, M., Colombo, A., Schuler, G., Barragan, P., Guagliumi, G., Molnar, F., Falotico, R. (2002). RAVEL Study Group. Randomized Study with the Sirolimus-Coated Bx Velocity Balloon-Expandable Stent in the Treatment of Patients with de Novo Native Coronary Artery Lesions. A randomized comparison of a sirolimus-eluting stent with a standard stent for coronary revascularization. *N. Eng.l J. Med.* 346(23):1773-80.

Motamedi, H., Shafiee, A., Cai, S. J., Streicher, S. L., Arison, B. H., and Miller, R. R. (1996) Characterization of methyltransferase and hydroxylase genes involved in the biosynthesis of the immunosuppressants FK506 and FK520. *Journal of Bacteriology* 178: 5243-5248.

Motamedi, H., Cai, S. J., Shafiee, A., and Elliston, K. O. (1997) Structural organization of a multifunctional polyketide synthase involved in the biosynthesis of the macrolide immunosuppressant FK506. *European Journal of Biochemistry* 244: 74-80.

Motamedi, H., and Shafiee, A. (1998) The biosynthetic gene cluster for the macrolactone ring of the immunosuppressant FK506. *European Journal of Biochemistry* 256: 528-534.

Myckatyn, T. M., Ellis, R. A., Grand, A. G., Sen, S. K., Lowe, J. B. 3rd, Hunter, D. A., Mackinnon, S. E. (2002). The effects of rapamycin in murine peripheral nerve isografts and allografts. Plast. Reconstr. Surg. 109(7): 2405-17.

Navé, B. T., Ouwens, D. M., Withers, D. J., Alessi, D. R., and Sheperd, P. R. (1999) Mammalian target of rapamycin is a direct target for protein kinase B: identification of a convergence point for opposing effects of insulin and amino-acid deficiency on protein translation. *Biochemical Journal* 344:427-431.

Navia, M. A. (1996) Protein-drug complexes important for immunoregulation and organ transplantation. *Current Opinion in Structural Biology* 6: 838-847.

NCCLS Reference Method for Broth Dilution Antifungal Susceptibility Testing for Yeasts: Approved Standard M27-A, vol. 17 No. 9. (1997).

Nishida, H., Sakakibara, T., Aoki, F., Saito, T., Ichikawa, K., Inagaki, T., Kojima, Y., Yamauchi, Y., Huang, L. H., Guadliana, M. A., Kaneko, T., and Kojima, N. (1995)

Generation of novel rapamycin structures by microbial manipulations. *Journal of Antibiotics* 48: 657-666.

Nielsen, J. B., Hsu, M. J., Byrne, K. M., and Kaplan, L. (1991) Biosynthesis of the immunosuppressant immunomycin: the enzymology of pipecolate incorporation. *Biochemistry* 30: 5789-5796.

Paget, M. S. B., Chamberlin, L., Atrih, A., Foster, S. J., and Buttner, M. J. (1999) Evidence that the extracytoplasmic function sigma factor $\sigma^E$ is required for normal cell wall structure in *Streptomyces coelicolor* A3(2). *Journal of Bacteriology* 181: 204-211)

Paiva, N. L., Demain, A. L., and Roberts, M. F. (1991) Incorporation of acetate, propionate, and methionine into rapamycin By *Streptomyces hygroscopicus*. *Journal of Natural Products* 54: 167-177.

Paiva, N. L., Demain, A. L., and Roberts, M. F. (1993) The immediate precursor of the nitrogen-containing ring of rapamycin is free pipecolic acid. *Enzyme and Microbial Technology* 15: 581-585.

Patterson, C. E., Schaub, T., Coleman, E. J., and Davies E. C. (2000) Developmental regulation of FKBP65. An ER-localized extracellular matrix binding-protein. *Molecular Biology of the Cell* 11:3925-3935.

Pfeifer, B. A., Admiraal, S. J., Gramajo, H., Cane, D. E., and Khosla, C. (2001) Biosynthesis of complex polyketides in a metabolically engineered strain of *E. coli*. *Science* 291: 1790-1792.

Powell, N., Till, S., Bungre, J., Corrigan, C. (2001). The immunomodulatory drugs cyclosporin A, mycophenolate mofetil, and sirolimus (rapamycin) inhibit allergen-induced proliferation and IL-5 production by PBMCs from atopic asthmatic patients. J. Allergy Clin. Immunol. 108 (6):915-7

Rabinovitch, A., Suarez-Pinzon, W. L., Shapiro, A. M., Rajotte, R. V., Power, R. (2002). Combination therapy with sirolimus and interleukin-2 prevents spontaneous and recurrent autoimmune diabetes in NOD mice. Diabetes. 51(3):638-45.

Raught, B., Gingras, A. C., and Sonenberg, N. (2001) The target of rapamycin (TOR) proteins. *Proceedings of the National Academy of Sciences of the United States of America* 98: 7037-7044.

Rawlings, B. J. (2001) Type I polyketide biosynthesis in bacteria (Part A). *Natural Product Reports* 18: 190-227.

Reather, J. A., (2000), Ph.D. Dissertation, University of Cambridge. "Late steps in the biosynthesis of macrocyclic lactones".

Reitamo, S., Spuls, P., Sassolas, B., Lahfa, M., Claudy, A., Griffiths, C. E.; Sirolimus European Psoriasis Study Group. (2001). Efficacy of sirolimus (rapamycin) administered concomitantly with a subtherapeutic dose of cyclosporin in the treatment of severe psoriasis: a randomized controlled trial. Br. J. Dermatol. 145(3):438-45.

Rosen, M. K., and Schreiber, S. L. (1992) Natural products as probes of cellular function: studies of immunophilins. *Angewandte Chemie-International Edition in English* 31: 384-400.

Roymans, D., and Slegers, H. (2001) Phosphaditbdylinositol 3-kinases in tumor progression. *European Journal of Biochemistry* 268:487-498.

Ruan, X. A, Stass, D., Lax, S. A., and Katz, L. (1997) A second type-I PKS gene cluster isolated from *Streptomyces hygroscopicus* ATCC 29253, a rapamycin-producing strain. *Gene* 203: 1-9.

Salituro, G. M., Zink, D. L., Dahl, A, Nielsen, J., Wu, E., Huang, L., Kastner C., Dumont, F. (1995) Meridamycin: a novel nonimmunosuppressive FKBP12 ligand from *Streptomyces hygroscopicus*. *Tetrahydron letters* 36: 997-1000.

Schwarzer, D., and Marahiel, M. A. (2001) Multimodular biocatalysts for natural product assembly. *Naturwissenschaften* 88: 93-101.

Sambrook, J., Fritsch, E. F., and Maniatis, T. (1989) Molecular cloning: a laboratory manual, 2nd ed. Cold Spring Harbor Laboratory Press, N.Y.

Schreiber, S. L., and Crabtree, G. R. (1992) The mechanism of action of cyclosporine A and FK506. *Immunology Today* 13:136-142.

Schwecke, T., Aparicio, J. F., Molnár, I., König, A., Khaw, L. E., Haydock, S. F., Oliynyk, M., Caffrey, P., Cortés, J., Lester, J. B., Böhm, G. A., Staunton, J., and Leadlay, P. F. (1995) The biosynthetic gene cluster for the polyketide immunosuppressant rapamycin. *Proceedings of the National Academy of Sciences of the United States of America* 92: 7839-7843.

Sedrani, R., Cottens, S., Kallen, J., and Schuler, W. (1998) Chemical modifications of rapamycin: the discovery of SDZ RAD. *Transplantation Proceedings* 30: 2192-2194.

Sehgal, S. N., Baker, H., and Vézina, C. (1975) Rapamycin (AY-22,989), a new antifungal antibiotic II. Fermentation, isolation and characterization. *The Journal of Antibiotics* 28: 727-733.

Shepherd, P. R, Withers, D. J., and Siddle K. (1998) Phosphoinositde 3-kinase: the key switch mechanism in insulin signalling. *Biochemical Journal* 333: 471-490.

Shima, J., Hesketh, A., Okamoto, S., Kawamoto, S., and Ochi, K. (1996) Induction of actinorhodin production by rpsL (encoding ribosomal protein S12) mutations that confer streptomycin resistance in *Streptomyces lividans* and *Streptomyces coelicolor* A3(2). *Journal of Bacteriology* 178: 7276-7284.

Sigal, N. H., and Dumont, F. J. (1992) Cyclosporine A, FK-506, and rapamycin: pharmacological probes of lymphocyte signal transduction. *Annual Review of Immunology* 10: 519-560.

Sieuwerts, A. M., Klijn, J. G., Peters, H. A., Foekens, J. A. (1995). The MTT tetrazolium salt assay scrutinized: how to use this assay reliably to measure metabolic activity of cell cultures in vitro for the assessment of growth characteristics, IC50values and cell survival. Eur. J Clin. Chem. Clin. Biochem. 33(11):813-23.

Smovkina, T., Mazodier, P., Boccard, F., Thompson, C. J. and Guerineau, M. (1990) Contstruction of a series of pSAM2-based integrative vectors for use in actinomycetes. *Gene* 94: 53-59.

SOULILLOU, J. P., CARPENTER, C. B., LUNDIN, A. P. and STROM, T. B. (1975) Augmentation of proliferation and in vitro production of cytotoxic cells by 2-ME in the rat. J Immunol. 115(6):156671.

Staunton, J., and Weissman, K. J. (2001) Polyketide biosynthesis: a millennium review. *Natural Product Reports* 18: 380-416.

Steiner, J. P., Hamilton, G. S., Ross, D. T., Valentine, H. L., Guo, H., Connolly, M. A., Liang, S., Ramsey, C., Li, J.-H. J., Huang, W., Howorth, P., Soni, R., Fuller, M., Sauer, H., Nowotnik, A. C., and Suzdak, P. D. (1997) Neutrophic immunophilin ligands stimulate structural and functional recovery in neurodegenerative animal models. *Proceedings of the National Academy of Sciences of the United States of America* 94:2019-2024.

Tang, S. J., Reis, G., Kang, H., Gingras, A.-C., Sonenberg, N., and Schuman, E. M. (2002) A rapamycin-sensitive signaling pathway contributes to long-term synaptic plasticity in the hippocampus. *Proceedings of the National Academy of Sciences of the United States of America* 1:467-472.

Van Duyne, G. D., Standaert, R. F., Karplus, P. A., Schreiber, S. L., and Clardy, J. (1993) Atomic structures of the human immunophilin FKBP-12 complexes with FK508 and rapamycin. *Journal of Molecular Biology* 229: 105-124.

Van Mellaert, L., Mei, L., Lammertyn, E., Schacht, S., and Anné, J. (1998) Site-specific integration of bacteriophage VWB genome into *Streptomyces venezuelae* and construction of a VWB-based integrative vector. *Microbiology* 144:3351-3358.

Vézina, C., Kudelski, A., and Sehgal, S. N. (1975) Rapamycin (AY-22,989), a new antifungal antibiotic. I. Taxonomy of the producing streptomycete and isolation of the active principle. *The Journal of Antibiotics* 28: 721-726.

Vilella-Bach, M., Nuzzi, P., Fang, Y. M., and Chen, J. (1999) The FKBP12-rapamycin-binding domain is required for FKBP12-rapamycin-associated protein kinase activity and $G_1$ progression. *Journal of Biological Chemistry* 274: 4266-4272.

Waller, J. R., and Nicholson, M. L. (2001) Molecular mechanisms of renal allograft fibrosis. *British Journal of Surgery* 88:1429-1441.

Warner, L. M., Adams, L. M., Chang, J. Y., Sehgal, S. N. (1992). A modification of the in vivo mixed lymphocyte reaction and rapamycin's effect in this model. Clin. Immunol. Immunopathol. 64(3):242-7.

Weber, T., and Marahiel, M. A. (2001) Exploring the domain structure of modular nonribosomal peptide synthetases. *Structure* 9: R3-R9

Welch, J. T. and Seper, K., W., (1988), *J. Org. Chem.,* 53, 2991-2999

Wilkinson, B., Foster, G., Rudd, B. A. M., Taylor, N. L., Blackaby, A. P., Sidebottom, P. J., Cooper, D. J., Dawson, M. J., Buss, A. D., Gaisser, S., Böhm, I. U., Rowe, C. J., Cortés, J., Leadlay, P. F. and Staunton, J. (2000). Novel octaketide macrolides related to 6-deoxoerythronolide B provide evidence for iterative operation of the erythromycin polyketide synthase. *Chemistry & Biology* 7: 111-117.

Wong, G. K., Griffith, S., Kojima, I., and Demain, A. L. (1998) Antifungal activities of rapamycin and its derivatives, prolylrapamycin, 32-desmethylrapamycin, and 32-desmethoxyrapamycin. *Journal of Antibiotics* 51: 487-491.

Wu, K, Chung, L., Revill, W. P., Katz, L., and Reeves, C. D. (2000) The FK520 gene cluster of *Streptomyces hygroscopicus* var. *ascomyceticus* (ATCC 14891) contains genes for biosynthesis of unusual polyketide extender units. *Gene* 251: 81-90.

Yem, A. W., Tomasselli, A. G., Heinrikson, R. L., Zurcher-Neely, H., Ruff, V. A., Johnson, R. A., and Deibel, M. R. (1992) The Hsp56 component of steroid receptor complexes binds to immobilized FK506 and shows homology to FKBP-12 and FKBP-13. *Journal of Biological Chemistry* 267: 2868-2871.

Yu, K., Toral-Barza, L., Discafani, C., Zhang, W. G., Skotnicki, J., Frost, P., Gibbons, J. J. (2001) mTOR, a novel target in breast cancer: the effect of CCI-779, an mTOR inhibitor, in preclinical models of breast cancer. Endocrine-Related Cancer 8:249-258.

Zhu, J., Wu J., Frizell, E., Liu, S. L., Bashey, R., Rubin, R., Norton, P., Zern, M. A. (1999). Rapamycin inhibits hepatic stellate cell proliferation in-vitro and limits fibrogenesis in an in vivo model of liver fibrosis. Gastroenterology. 117(5):1198-204.

---

The invention claimed is:

1. A compound of the formula:

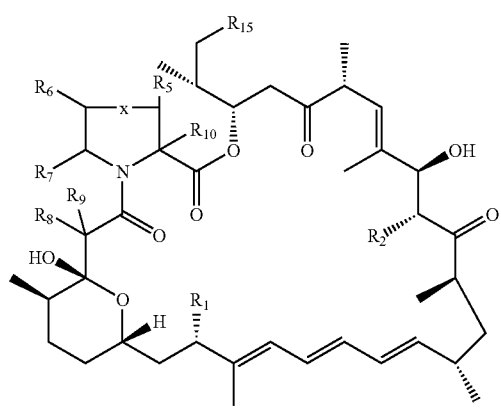

where:

x = bond or $CH_2$, or —$CHR_6$-x-$CHR_5$— is

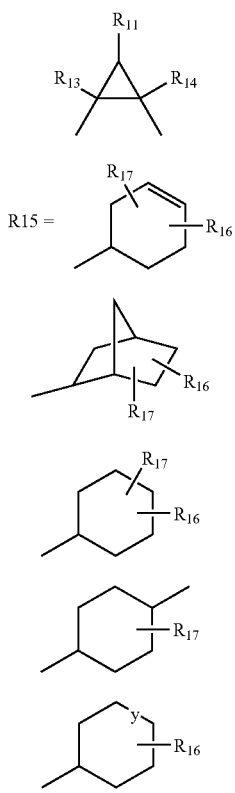

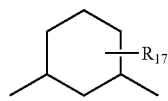

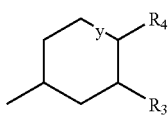

$R_1$=OH, $OCH_3$
$R_2$=H, OH
$R_{16}$=OH
$R_{17}$=H, Cl, F
$R_5$=H, OH
$R_6$=H, OH
$R_8$ and $F_9$ together are =O or H,H; and
y=bond, $CH_2$.

2. A compound of the formula:

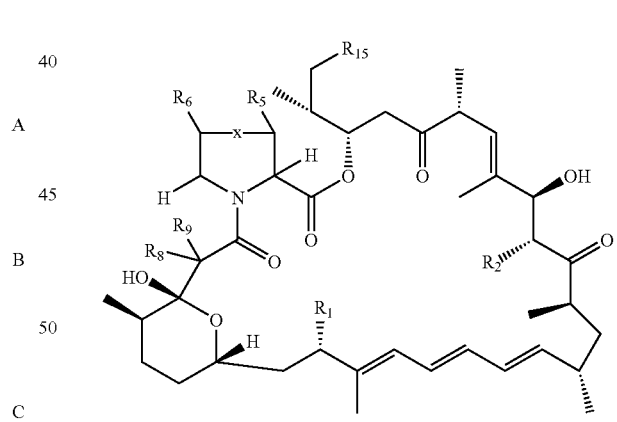

where:
x=bond or $CH_2$, or —$CHR_6$-x-$CHR_5$— is

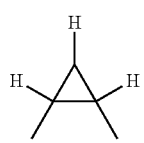

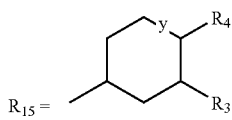

$R_1$=OH, OCH$_3$
$R_2$=H, OH, OCH$_3$
$R_3$=H, OH, CH$_3$, OCR$_3$
$R_4$=H
$R_5$=H
$R_6$=H, OH
$R_8$ and $R_9$ together are =O or H,H; and
y=bond, CH$_2$.

3. A compound according to claim 1 which is selected from the group consisting of: 9-deoxo-16-O-desmethyl-27-desmethoxy-39-desmethoxy-rapamycin, 9-deoxo-16-O-desmethyl-27-O-desmethyl-39-desmethoxy-rapamycin, 16O-desmethyl27-desmethoxy-39-desmethoxy-rapamycin, 9-deoxo-27-desmethoxy-39-desmethoxy-rapamycin, 16-O-desmethyl-27-O-desmethyl-39desmethoxy-rapamycin, 9-deoxo27-O-desmethyl-39-desmethoxy-rapamycin, 27desmethoxy39-desmethoxy-rapamycin, 27-O-desmethyl-39-desmethoxy-rapamycin, 9-deoxo-39-desmethoxy-rapamycin, 8-deoxo-15-O-desmethyl-26-desmethoxy-38desmethoxy-prolylrapamycin, 8deoxo-15-O-desmethyl-26-O-desmethyl-38-desmethoxy-prolylrapamycin, 15-O-desmethyl-26-desmethoxy-38-desmethoxy-prolylrapamycin, 8-deoxo-26-desmethoxy-38-desmethoxy-prolylrapamycin, 15-O-desmethyl-26-O-desmethyl-38-desmethoxy-prolylrapamycin, 8-deoxo-26-O-desmethyl-38-desmethoxy-prolylrapamycin, 26-desmethoxy-38-desmethoxy-prolylrapamycin, 26-O-desmethyl-38-desmethoxy-prolYlrapamycin, 9-deoxo-16-O-desmethyl-27-desmethoxy-36-de(3-cis-methoxy-4-trans-hydroxycyclohexyl)-36-(hydroxycyclohexenyl) rapamycin, 9-deoxo-16-O-desmethyl-27-desmethoxy-36-de(3-cis-methoxy-4-trans-hydroxycyclohexyl)-36-(hydroxynorbornyl) rapamycin, 9-deoxo-16-O-desmethyl-27-desmethoxy-36-de(3-cis-methoxy-4-trans-hydroxycyclohexyl)-36-(3-methyl-4-hydroxycyclohexyl) rapamycin, 9deoxo-16-O-desmethyl-27-desmethoxy-36de(3-cis-methoxy-4-trans-hydroxycyclohexyl)-36-(4-methyl hydroxycyclohexyl) rapamycin, 9-deoxo-16-O-desmethyl-27-desmethoxy-36-de(3-cis-methoxy-4-trans-hydroxycyclohexyl)-36-(3-fluoro-4-hydroxycyclohexyl) rapamycin, 9-deoxo-16-O-desmethyl-27-desmethoxy-36-de(3-cis-methoxy-4-trans-hydroxycyclohexyl)-36-(3-hydroxy-4-fluorocyclohexyl) rapamycin, 9-deoxo16-O-desmethyl-27desmethoxy36-de(3-cis-methoxy-4-trans-hydroxycyclohexyl)-36-(3-chloro-4-hydroxycyclohexyl) rapamycin, 9-deoxo-16-O-desmethyl-27-desmethoxy-36-de(3-cis-methoxy-4-trans-hydroxycyclohexyl)-36-(3-hydroxy-4-chlorocyclohexyl) rapamycin, 9-deoxo-16-O-desmethyl-27O-desmethyl-36-de(3-cis-methoxy4-trans-hydroxycyclohexyl)-36-(hydroxycyclohexenyl) rapamycin, 9-deoxo-16-O-desmethyl-27-O-desmethyl-36-de(3cis-methoxy-4-trans-hydroxycyclohexyl)-36-(hydroxynorbornyl) rapamycin, and 9-deoxo-16-O-desmethyl-27-O-desmethyl-36-de(3-cis-methoxy-4-trans-hydroxycyclohexyl)-36-(4-methyl hydroxycyclohexyl) rapamycin.

4. A method for the treatment of a fungal infection in a patient in need of said treatment, comprising administration of a medicament comprising the compound of claim 1.

5. A compound of the formula:

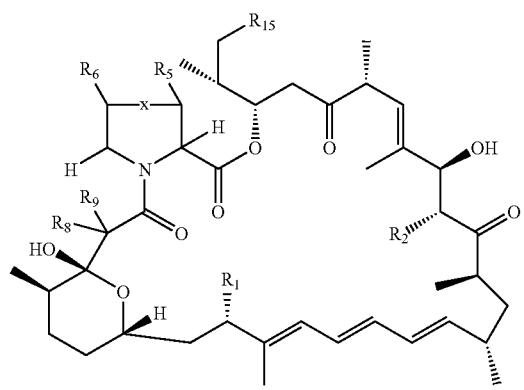

where:
x=bond or CH$_2$, or —CHR$_6$-x-CHR$_5$— is

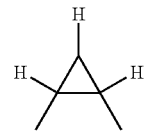

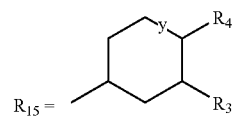

$R_1$=OH, OCH$_3$
$R_2$=H, OH, OCH$_3$
$R_3$=F, Cl
$R_4$=H, OH, CH$_3$, F, Cl
$R_5$=H, OH
$R_6$=H, OH
$R_8$ and $R_9$ together are =O or H,H; and
y=bond, CH$_2$.

6. A compound of the formula:

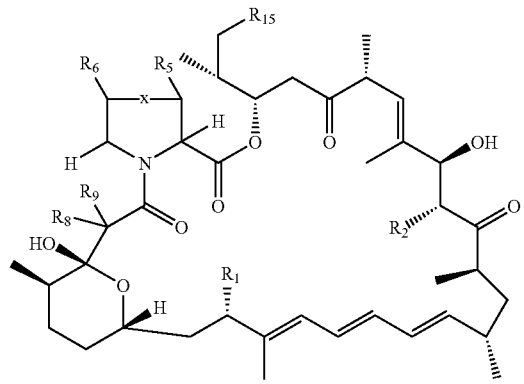

where:

x=bond or $CH_2$, or —$CHR_6$-x-$CHR_5$— is

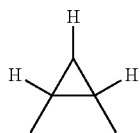

$R_{15}$ = 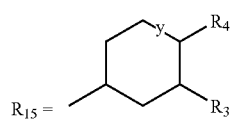

$R_1$=OH, $OCH_3$
$R_2$=H, OH, $OCH_3$
$R_3$=H, OH, $CH_3$, F, Cl, $OCH_3$
$R_4$=$CH_3$
$R_5$=H, OH
$R_6$=H, OH
$R_8$ and $R_9$ together are =O or H,H; and
y=bond, $CH_2$.

7. A method for the treatment of a fungal infection in a patient in need of said treatment, comprising administration of a medicament comprising the compound of claim 5.

8. A method for the treatment of a fungal infection in a patient in need of said treatment, comprising administration of a medicament comprising the compound of claim 6.

9. A method for the treatment of a fungal infection in a patient in need of said treatment, comprising administration of a medicament comprising the compound of claim 2.

* * * * *

UNITED STATES PATENT AND TRADEMARK OFFICE
CERTIFICATE OF CORRECTION

PATENT NO. : 7,300,942 B2
APPLICATION NO. : 10/497135
DATED : November 27, 2007
INVENTOR(S) : Matthew Alan Gregory et al.

It is certified that error appears in the above-identified patent and that said Letters Patent is hereby corrected as shown below:

Column 167, line 11
Please delete "$OCR_3$" and insert therefor --$OCH_3$--.

Signed and Sealed this

Eighth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,300,942 B2  Page 1 of 1
APPLICATION NO. : 10/497135
DATED : November 27, 2007
INVENTOR(S) : Matthew Alan Gregory et al.

It is certified that error appears in the above-identified patent and that said Letters Patent is hereby corrected as shown below:

Column 165, line 60

Please delete the formula 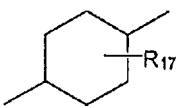 and insert therefor 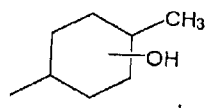

Column 166, line 15

Please delete the formula 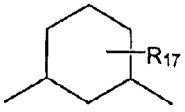 and insert therefor 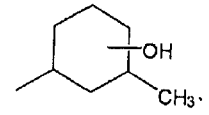

Column 166, line 21

Please delete "G".

Column 166, line 25

Please delete the formula 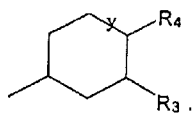

Signed and Sealed this

Twenty-fourth Day of June, 2008

JON W. DUDAS
*Director of the United States Patent and Trademark Office*

SEQUENCE LISTING

<160> NUMBER OF SEQ ID NOS: 63

<210> SEQ ID NO 1
<211> LENGTH: 646
<212> TYPE: DNA
<213> ORGANISM: Streptomyces hygroscopicus

<400> SEQUENCE: 1

```
gcgacccgag cagatcgttg gtgtcctgct tgcggcgttc cgcgatcagc tcggagaggt      60
agaggtagag cgactggccg gccgccatca cgacttcctg tgagtaggcg ccgttcgaga     120
gcatctggtc cgaccaggtc cggaacttgg tctggtcctc gatcggcacg cccagcagct     180
cacagatcat gatgatcggc agaggcaggg cgaagtcctc catcagatcg gcggggcgc      240 ccttggccag cattttgtcg atcagatcgt cggcgacctc ctgggtgcgc ggacgcaggg     300
cctccatccg gcggctggtc agcgccttgg tcgccaaccg gcgcagccgg gtgtgttccg     360
gagggtccat cagcatgatg acgggctggt cctggatcgc cgggaggacc cggggcacgt     420
ccttgccgag cgtcgcgctg cggctgaacc gcgggtccac gaacaccttg gcgacgtcct     480
cccagctggt ggccagccag gtctcccgc cgtacggcat caggacccgg ccgagctcac      540
cggcgtcccg cagccggttg tactcggggt ggatctcgag tcgctccatt tcggcgaaag     600
gataagggca ggcctttccg gtctcaccct gatcggtcgt cgacat                    646
```

-continued

```
<210> SEQ ID NO 2
<211> LENGTH: 646
<212> TYPE: DNA
<213> ORGANISM: Streptomyces hygroscopicus

<400> SEQUENCE: 2
gcgacccgag cagatcgttg gtgtcctgct tgcgacgttc cgcgatcagc tcggagaggt      60
agaggtagag cgactggccg gccgccatca cgacttcctg tgagtaggcg ccgttcgaga     120
gcatctggtc cgaccaggtc cggaacttgg tctggtcctc gatcggcacg cccagcagct     180
cacagatcat gatgatcggc agaggcaggg cgaagtcctc catcagatcg gcggggggcgc    240 ccttggccag cattttgtcg atcagatcgt cggcgacctc ctgggtgcgc ggacgcaggg     300
cctccatccg gcggctggtc agcgccttgg tcgccacccg gcgcagccgg gtgtgttccg     360
gagggtccat cagcatgatg acgggctggt cctggatcgc cgggaggacc cggggcacgt     420
ccttgccgag cgtcgcgctg cggctgaacc gcgggtccac gaacaccttg cgacgtcct     480 cccagctggc ggccagccag gcctcccggc cgtccaacat caggacccgg ccgagctcac     540
cggcgtcccg cagccggttg tactcggggt ggatctcgag tcgctccatt tcggcgaaag     600
gataagggca ggcctttccg gtctcaccct gatcggtcgt cgacat                    646

<210> SEQ ID NO 3
<211> LENGTH: 404
<212> TYPE: PRT
<213> ORGANISM: Streptomyces hygroscopicus

<400> SEQUENCE: 3

Met Ser Thr Thr Asp Gln Gly Glu Thr Gly Lys Ala Cys Pro Tyr Pro
1               5                   10                  15

Phe Ala Glu Met Glu Arg Leu Glu Ile His Pro Glu Tyr Asn Arg Leu
                20                  25                  30

Arg Asp Ala Gly Glu Leu Gly Arg Val Leu Met Pro Tyr Gly Gly Glu
            35                  40                  45

Thr Trp Leu Ala Thr Ser Trp Glu Asp Val Ala Lys Val Phe Val Asp
    50                  55                  60

Pro Arg Phe Ser Arg Ser Ala Thr Leu Gly Lys Asp Val Pro Arg Val
65                  70                  75                  80

Leu Pro Ala Ile Gln Asp Gln Pro Val Ile Met Leu Met Asp Pro Pro
                85                  90                  95

Glu His Thr Arg Leu Arg Arg Leu Ala Thr Lys Ala Leu Thr Ser Arg
                100                 105                 110

Arg Met Glu Ala Leu Arg Pro Arg Thr Gln Glu Val Ala Asp Asp Leu
            115                 120                 125

Ile Asp Lys Met Leu Ala Lys Gly Ala Pro Ala Asp Leu Met Glu Asp
    130                 135                 140

Phe Ala Leu Pro Leu Pro Ile Ile Met Ile Cys Glu Leu Leu Gly Val
145                 150                 155                 160

Pro Ile Glu Asp Gln Thr Lys Phe Arg Thr Trp Ser Asp Gln Met Leu
                165                 170                 175

Ser Asn Gly Ala Tyr Ser Gln Glu Val Val Met Ala Ala Gly Gln Ser
            180                 185                 190

Leu Tyr Leu Tyr Leu Ser Glu Leu Ile Ala Glu Arg Arg Lys Gln Asp
    195                 200                 205

Thr Asn Asp Leu Leu Gly Ser Leu Val Arg Ala Arg Asp Lys Asp Asp
210                 215                 220
```

```
Arg Leu Ser Glu Thr Glu Leu Val Gly Phe Ala Val Thr Leu Leu Ile
225                 230                 235                 240

Ala Gly Tyr Glu Thr Thr Ala Asn Ala Ile Gly Asn Ser Val Tyr Thr
            245                 250                 255

Leu Leu Thr His Pro Glu Lys Leu Ala Glu Leu Arg Lys Asp Leu Ser
                260                 265                 270

Leu Ile Pro Lys Ala Val Asp Glu Leu Leu Arg Ile Ile Pro Ile Ala
            275                 280                 285

Lys Gln Ala Ser Trp Val Arg Met Ala Val Glu Asp Val Glu Leu Ser
290                 295                 300

Gly Thr Ile Val Lys Ala Gly Glu Ala Val Ala Ile Gln Thr His Ser
305                 310                 315                 320

Ala Asn Thr Asp Pro Lys Val Tyr Asp His Pro Glu Glu Ile Asp Phe
                325                 330                 335

His Arg Thr Ser Asn Pro His Met Ser Leu Gly His Gly Ala His His
                340                 345                 350

Cys Met Gly Ala Gln Leu Val Arg Val Glu Met Gln Thr Ala Leu Gly
            355                 360                 365

Ser Leu Ile Ser Arg Ile Pro Ala Leu Arg Phe Ala Val Pro Glu Pro
370                 375                 380

Arg Ile Lys Phe Leu Arg Gly Arg Leu Val Pro Ser Leu Glu Ala Leu
385                 390                 395                 400

Pro Leu Thr Trp

<210> SEQ ID NO 4
<211> LENGTH: 404
<212> TYPE: PRT
<213> ORGANISM: Streptomyces hygroscopicus

<400> SEQUENCE: 4

Met Ser Thr Thr Asp Gln Gly Glu Thr Gly Lys Ala Cys Pro Tyr Pro
1               5                   10                  15

Phe Ala Glu Met Glu Arg Leu Glu Ile His Pro Glu Tyr Asn Arg Leu
                20                  25                  30

Arg Asp Ala Gly Glu Leu Gly Arg Val Leu Met Leu Asp Gly Arg Glu
            35                  40                  45

Ala Trp Leu Ala Ala Ser Trp Glu Asp Val Ala Lys Val Phe Val Asp
    50                  55                  60

Pro Arg Phe Ser Arg Ser Ala Thr Leu Gly Lys Asp Val Pro Arg Val
65                  70                  75                  80

Leu Pro Ala Ile Gln Asp Gln Pro Val Ile Met Leu Met Asp Pro Pro
                85                  90                  95

Glu His Thr Arg Leu Arg Arg Val Ala Thr Lys Ala Leu Thr Ser Arg
                100                 105                 110

Arg Met Glu Ala Leu Arg Pro Arg Thr Gln Glu Val Ala Asp Asp Leu
            115                 120                 125

Ile Asp Lys Met Leu Ala Lys Gly Ala Pro Ala Asp Leu Met Glu Asp
130                 135                 140

Phe Ala Leu Pro Leu Pro Ile Ile Met Ile Cys Glu Leu Leu Gly Val
145                 150                 155                 160

Pro Ile Glu Asp Gln Thr Lys Phe Arg Thr Trp Ser Asp Gln Met Leu
                165                 170                 175

Ser Asn Gly Ala Tyr Ser Gln Glu Val Val Met Ala Ala Gly Gln Ser
                180                 185                 190
```

```
Leu Tyr Leu Tyr Leu Ser Glu Leu Ile Ala Glu Arg Arg Lys Gln Asp
            195                 200                 205

Thr Asn Asp Leu Leu Gly Ser Leu Val Arg Ala Arg Asp Lys Asp Asp
        210                 215                 220

Arg Leu Ser Glu Thr Glu Leu Val Gly Phe Ala Val Thr Leu Leu Ile
225                 230                 235                 240

Ala Gly Tyr Glu Thr Thr Ala Asn Ala Ile Gly Asn Ser Val Tyr Thr
                245                 250                 255

Leu Leu Thr His Pro Glu Lys Leu Ala Glu Leu Arg Lys Asp Leu Ser
            260                 265                 270

Leu Ile Pro Lys Ala Val Asp Glu Leu Leu Arg Ile Ile Pro Ile Ala
        275                 280                 285

Lys Gln Ala Ser Trp Val Arg Met Ala Val Glu Asp Val Glu Leu Ser
290                 295                 300

Gly Thr Ile Val Lys Ala Gly Glu Ala Val Ala Ile Gln Thr His Ser
305                 310                 315                 320

Ala Asn Thr Asp Pro Lys Val Tyr Asp His Pro Glu Glu Ile Asp Phe
                325                 330                 335

His Arg Thr Ser Asn Pro His Met Ser Leu Gly His Gly Ala His His
            340                 345                 350

Cys Met Gly Ala Gln Leu Val Arg Val Glu Met Gln Thr Ala Leu Gly
        355                 360                 365

Ser Leu Ile Ser Arg Ile Pro Ala Leu Arg Phe Ala Val Pro Glu Pro
370                 375                 380

Arg Ile Lys Phe Leu Arg Gly Arg Leu Val Pro Ser Leu Glu Ala Leu
385                 390                 395                 400

Pro Leu Thr Trp

<210> SEQ ID NO 5
<211> LENGTH: 758
<212> TYPE: DNA
<213> ORGANISM: Streptomyces hygroscopicus

<400> SEQUENCE: 5
cggaggtgac tgtccggggc catccgccgg cgcaccgcgg cacggacttg atcggagatg      60
tcgtgatcgc tgacccactt cagttcgggt atttccgttg tgatccgacg catcgcctca     120
aggcgctgcc gcgtgaacac gtcgatgtgc gaaagggcgc cacccgggcg cagcacgcgc     180
gcggcctccc gcaggaaacg tcccagattg gggtaggtgt gcgagctctc gatgttgacg     240
agcacatcca ccgaggagtc ctcgaagggc agttcctcgg cgtcgccctg gacgaaccgc     300
agggtatcgc cgcgggacag cgtggcgtg gcgctggcga tcgccttcgg cgccaggtcc     360
agcccggtca tccgggcggt ggggacgagg cgggacagga agttgagccc ctcccccatt     420
ccgcagccga cctccaggac cgtccggccg tcgcagctct ccaagccctt cggaaggtcg     480
cgcagggcca ggtagtagag ctgctcgctg aatccgtcgg tgccgtactc ggtgaatccg     540
ggcagcctgg cctcgatctc ggcgacgaac tcggaatcgt gcacacccca gttccacagc     600 tggcccttg ccgacatgct ggcggcgagg tcgtagatgg aggagctggc ggacttgaag     660
gtggcggcct tcgtctccgc ctgcggggtg ccggattcgt cgagattgat gtcggcgaca     720
ccgctggtga aggcggtcac gacgtcgggt tggatcat                             758

<210> SEQ ID NO 6
<211> LENGTH: 755
```

-continued

```
<212> TYPE: DNA
<213> ORGANISM: Streptomyces hygroscopicus

<400> SEQUENCE: 6
cggaggtgac tgtccggggg catccgccgg cgcaccgcgg cacggacttg atcggagatg    60
tcgtgatcgc tgacccactt cagttcgggt atttccgttg tgatccgacg catcgcctca   120
aggcgctgcc gcgtgaacac gtcgatgtgc gaaagggcgc cacccggcg cagcgcgcgc    180 gcggcctccc gcaggaaacg tcccagattg gggtaggtgt gcgagctctc gatgttgacg   240
agcacatcca ccgaggagtc ctcgaagggc agttcctcgg cgtcgccctg gacgaaccgc   300
agggtatcgc cgcgggacag cgtggcggtg gcgctggcga tcgccttcgg cgccaggtcc   360
agcccggtca tccgggcggt ggggacgagg cgggacagga agttgagccc ctcccccatt   420
ccgcagccga cctccaggac cgtccggccg tcgcagctct ccaagccctt cggaaggtcg   480
cgcagggcca ggtagtagag ctgctcgctg aatccgtcgg tgccgtactc ggtgaatccg   540
ggcagcctgg cctcgatctc ggcgacgaac tcggaatcgt gcacacccca gttccacagc   600
tggccctttg ccgacatgct ggcggcgagg tcgtagatgg aggagctggc ggacttgaag   660
gtggcggcct tcgtctccgc ctgcggggtg ccgggttcgt cgagattgat gtcgcgaacc   720
gctgtgaagg cggtcacgac gtcgggttgg atcat                              755

<210> SEQ ID NO 7
<211> LENGTH: 318
<212> TYPE: PRT
<213> ORGANISM: Streptomyces hygroscopicus

<400> SEQUENCE: 7

Met Ile Gln Pro Asp Val Val Thr Ala Phe Thr Ser Gly Val Ala Asp
1               5                   10                  15

Ile Asn Leu Asp Glu Ser Gly Thr Pro Gln Ala Glu Thr Lys Ala Ala
            20                  25                  30

Thr Phe Lys Ser Ala Ser Ser Ile Tyr Asp Leu Ala Ala Ser Met
        35                  40                  45

Ser Ala Lys Gly Gln Leu Trp Asn Trp Gly Val His Asp Ser Glu Phe
    50                  55                  60

Val Ala Glu Ile Glu Ala Arg Leu Pro Gly Phe Thr Glu Tyr Gly Thr
65                  70                  75                  80

Asp Gly Phe Ser Glu Gln Leu Tyr Tyr Leu Ala Leu Arg Asp Leu Pro
                85                  90                  95

Lys Gly Leu Glu Ser Cys Asp Gly Arg Thr Val Leu Glu Val Gly Cys
            100                 105                 110

Gly Met Gly Glu Gly Leu Asn Phe Leu Ser Arg Leu Val Pro Thr Ala
        115                 120                 125

Arg Met Thr Gly Leu Asp Leu Ala Pro Lys Ala Ile Ala Ser Ala Thr
    130                 135                 140

Ala Thr Leu Ser Arg Gly Asp Thr Leu Arg Phe Val Gln Gly Asp Ala
145                 150                 155                 160

Glu Glu Leu Pro Phe Glu Asp Ser Ser Val Asp Val Leu Val Asn Ile
                165                 170                 175

Glu Ser Ser His Thr Tyr Pro Asn Leu Gly Arg Phe Leu Arg Glu Ala
            180                 185                 190

Ala Arg Val Leu Arg Pro Gly Gly Ala Leu Ser His Ile Asp Val Phe
        195                 200                 205

Thr Arg Gln Arg Leu Glu Ala Met Arg Arg Ile Thr Thr Glu Ile Pro
```

```
            210                 215                 220
Glu Leu Lys Trp Val Ser Asp His Asp Ile Ser Asp Gln Val Arg Ala
225                 230                 235                 240

Ala Val Arg Arg Met Ala Pro Asp Ser His Leu Arg Ser Thr Leu
                245                 250                 255

Asn Lys Gln Arg Met Asn Arg Leu Ala Arg Thr Leu Ala Leu His Ser
                260                 265                 270

Gln Ile Thr Val Phe Gly Gly Thr Phe Ala Asp Tyr Gln Pro Pro Ala
                275                 280                 285

Ser Val Lys Met Leu Ser Arg Leu Gly Leu Val Pro Pro Met Asp Ser
                290                 295                 300

Leu Pro Met Glu Thr Tyr Arg His Gln Ile Ala Val Arg Val
305                 310                 315

<210> SEQ ID NO 8
<211> LENGTH: 317
<212> TYPE: PRT
<213> ORGANISM: Streptomyces hygroscopicus

<400> SEQUENCE: 8

Met Ile Gln Pro Asp Val Val Thr Ala Phe Thr Ala Val Arg Asp Ile
1               5                   10                  15

Asn Leu Asp Glu Pro Gly Thr Pro Gln Ala Glu Thr Lys Ala Ala Thr
                20                  25                  30

Phe Lys Ser Ala Ser Ser Ile Tyr Asp Leu Ala Ala Ser Met Ser
                35                  40                  45

Ala Lys Gly Gln Leu Trp Asn Trp Gly Val His Asp Ser Glu Phe Val
50                  55                  60

Ala Glu Ile Glu Ala Arg Leu Pro Gly Phe Thr Glu Tyr Gly Thr Asp
65                  70                  75                  80

Gly Phe Ser Glu Gln Leu Tyr Tyr Leu Ala Leu Arg Asp Leu Pro Lys
                85                  90                  95

Gly Leu Glu Ser Cys Asp Gly Arg Thr Val Leu Glu Val Gly Cys Gly
                100                 105                 110

Met Gly Glu Gly Leu Asn Phe Leu Ser Arg Leu Val Pro Thr Ala Arg
                115                 120                 125

Met Thr Gly Leu Asp Leu Ala Pro Lys Ala Ile Ala Ser Ala Thr Ala
                130                 135                 140

Thr Leu Ser Arg Gly Asp Thr Leu Arg Phe Val Gln Gly Asp Ala Glu
145                 150                 155                 160

Glu Leu Pro Phe Glu Asp Ser Ser Val Asp Val Leu Val Asn Ile Glu
                165                 170                 175

Ser Ser His Thr Tyr Pro Asn Leu Gly Arg Phe Leu Arg Glu Ala Ala
                180                 185                 190

Arg Ala Leu Arg Arg Gly Gly Ala Leu Ser His Ile Asp Val Phe Thr
                195                 200                 205

Arg Gln Arg Leu Glu Ala Met Arg Arg Ile Thr Thr Glu Ile Pro Glu
                210                 215                 220

Leu Lys Trp Val Ser Asp His Asp Ile Ser Asp Gln Val Arg Ala Ala
225                 230                 235                 240

Val Arg Arg Arg Met Pro Pro Asp Ser His Leu Arg Ser Thr Leu Asn
                245                 250                 255

Lys Gln Arg Met Asn Arg Leu Ala Arg Thr Leu Ala Leu His Ser Gln
                260                 265                 270
```

```
Ile Thr Val Phe Gly Gly Thr Phe Ala Asp Tyr Gln Pro Pro Ala Ser
        275                 280                 285

Val Lys Met Leu Ser Arg Leu Gly Leu Val Pro Pro Met Asp Ser Leu
        290                 295                 300

Pro Met Glu Thr Tyr Arg His Gln Ile Ala Val Arg Val
305                 310                 315
```

```
<210> SEQ ID NO 9
<211> LENGTH: 300
<212> TYPE: DNA
<213> ORGANISM: Streptomyces hygroscopicus

<400> SEQUENCE: 9
gatcagggcg agggtggtgc tccccggccg ggcgagcagc cgggtggcga cggccgcgac    60
cgcgccggtc cgcatggcgg tgatggtggc cgcgtcggcg agcgcgacca tgcttccgct   120
gtcgtcgtcg agccgcgaca cggtcccgac gatggtgggc aggttgaagc gctcgaagtt   180
ctgcggactg tagctgaccg tcttcatcgt cacaccgatg cccgacgcgc ggtgcggcat   240
gaactcgatg acgcccggaa cgtcgccgcc gcgggcaaag ccggtacgcg gtggcggctc   300
```

```
<210> SEQ ID NO 10
<211> LENGTH: 300
<212> TYPE: DNA
<213> ORGANISM: Streptomyces hygroscopicus

<400> SEQUENCE: 10
gatcagggcg agggtggtgc tccccggccg ggcgagcagc cgggtggtga cggacgcgac    60
cgcgccggtc cgcatcgcgg tgatggtggc cgcgtcggcg agcgcgacca tgcttccgct   120
gtcgtcgccg agccgcgaca cggtccccac gatggtgggc aggttgaagc gctcgaagtt   180
ctccggactg tagctgaccg tcttcatcga gcacccgatg cccgacgcgc ggtgcggcat   240
gaactcgatg acgcccggaa cgtcgccgcc gcgggcaaag ccgggacgcg gtggcggctc   300
```

```
<210> SEQ ID NO 11
<211> LENGTH: 343
<212> TYPE: PRT
<213> ORGANISM: Streptomyces hygroscopicus

<400> SEQUENCE: 11

Met Gln Thr Lys Val Leu Cys Gln Arg Asp Ile Lys Arg Ile Leu Ser
1               5                   10                  15

Val Val Gly Arg Asp Val Met Met Asp Arg Leu Ile Ser Glu Val His
            20                  25                  30

Ala Gly Phe Ala Arg Leu Gly Arg Gly Glu Thr Asp Glu Pro Pro Pro
        35                  40                  45

Arg Thr Gly Phe Ala Arg Gly Gly Asp Val Pro Gly Val Ile Glu Phe
    50                  55                  60

Met Pro His Arg Ala Ser Gly Ile Gly Val Thr Met Lys Thr Val Ser
65                  70                  75                  80

Tyr Ser Pro Gln Asn Phe Glu Arg Phe Asn Leu Pro Thr Ile Val Gly
                85                  90                  95

Thr Val Ser Arg Leu Asp Asp Asp Ser Gly Ser Met Val Ala Leu Ala
            100                 105                 110

Asp Ala Ala Thr Ile Thr Ala Met Arg Thr Gly Ala Val Ala Ala Val
        115                 120                 125

Ala Thr Arg Leu Leu Ala Arg Pro Gly Ser Thr Thr Leu Ala Leu Ile
    130                 135                 140
```

-continued

Gly Ala Gly Ala Gln Ala Val Thr Gln Ala His Ala Leu Ser Arg Val
145                 150                 155                 160

Leu Pro Leu Glu Arg Ile Leu Ile Ser Asp Ile Lys Ala Glu His Ala
            165                 170                 175

Glu Ser Phe Ala Gly Arg Val Ala Phe Leu Glu Leu Pro Val Glu Val
        180                 185                 190

Thr Asp Ala Ala Thr Ala Met Ala Thr Ala Asp Val Leu Cys Thr Val
    195                 200                 205

Thr Ser Val Pro Val Gly Gly Pro Val Pro Ala Glu Pro Arg
210                 215                 220

Gln Ala His Leu His Val Asn Gly Ile Gly Ala Asp Glu Gln Gly Lys
225                 230                 235                 240

Thr Glu Leu Pro Lys Ala Leu Leu Asp Asp Ala Phe Ile Cys Val Asp
                245                 250                 255

His Pro Gly Gln Ala Arg Ala Glu Gly Glu Phe Gln Gln Leu Pro Asp
            260                 265                 270

Arg Glu Leu Gly Pro Ser Leu Ala Asp Leu Cys Ala Ala Pro Glu Ile
        275                 280                 285

Ala Ala Pro His Pro Glu Arg Leu Ser Val Phe Asp Ser Thr Gly Ser
    290                 295                 300

Ala Phe Ala Asp His Ile Ala Leu Asp Val Leu Leu Gly Phe Ala Asp
305                 310                 315                 320

Glu Leu Gly Leu Gly His Lys Met Ser Ile Glu Ser Thr Pro Glu Asp
                325                 330                 335

Val Leu Asp Pro Tyr Ser Leu
            340

<210> SEQ ID NO 12
<211> LENGTH: 343
<212> TYPE: PRT
<213> ORGANISM: Streptomyces hygroscopicus

<400> SEQUENCE: 12

Met Gln Thr Lys Val Leu Cys Gln Arg Asp Ile Lys Arg Ile Leu Ser
1               5                   10                  15

Val Val Gly Arg Asp Val Met Met Asp Arg Leu Ile Ser Glu Val His
            20                  25                  30

Ala Gly Phe Ala Arg Leu Gly Arg Gly Glu Thr Asp Glu Pro Pro Pro
        35                  40                  45

Arg Pro Gly Phe Ala Arg Gly Gly Asp Val Pro Gly Val Ile Glu Phe
    50                  55                  60

Met Pro His Arg Ala Ser Gly Ile Gly Cys Ser Met Lys Thr Val Ser
65                  70                  75                  80

Tyr Ser Pro Glu Asn Phe Glu Arg Phe Asn Leu Pro Thr Ile Val Gly
                85                  90                  95

Thr Val Ser Arg Leu Gly Asp Asp Ser Gly Ser Met Val Ala Leu Ala
            100                 105                 110

Asp Ala Ala Thr Ile Thr Ala Met Arg Thr Gly Ala Val Ala Ser Val
        115                 120                 125

Thr Thr Arg Leu Leu Ala Arg Pro Gly Ser Thr Thr Leu Ala Leu Ile
    130                 135                 140

Gly Ala Gly Ala Gln Ala Val Thr Gln Ala His Ala Leu Ser Arg Val
145                 150                 155                 160

Leu Pro Leu Glu Arg Ile Leu Ile Ser Asp Ile Lys Ala Glu His Ala

```
                165                 170                 175
Glu Ser Phe Ala Gly Arg Val Ala Phe Leu Glu Leu Pro Val Glu Val
            180                 185                 190

Thr Asp Ala Ala Thr Ala Met Ala Thr Ala Asp Val Leu Cys Thr Val
            195                 200                 205

Thr Ser Val Pro Val Gly Gly Pro Val Val Pro Ala Glu Pro Arg
            210                 215                 220

Gln Ala His Leu His Val Asn Gly Ile Gly Ala Asp Glu Gln Gly Lys
225                 230                 235                 240

Thr Glu Leu Pro Lys Ala Leu Leu Asp Asp Ala Phe Ile Cys Val Asp
                245                 250                 255

His Pro Gly Gln Ala Arg Ala Glu Gly Glu Phe Gln Gln Leu Pro Asp
            260                 265                 270

Arg Glu Leu Gly Pro Ser Leu Ala Asp Leu Cys Ala Ala Pro Glu Ile
            275                 280                 285

Ala Ala Pro His Pro Glu Arg Leu Ser Val Phe Asp Ser Thr Gly Ser
290                 295                 300

Ala Phe Ala Asp His Ile Ala Leu Asp Val Leu Leu Gly Phe Ala Asp
305                 310                 315                 320

Glu Leu Gly Leu Gly His Lys Met Ser Ile Glu Ser Thr Pro Glu Asp
                325                 330                 335

Val Leu Asp Pro Tyr Ser Leu
            340

<210> SEQ ID NO 13
<211> LENGTH: 550
<212> TYPE: DNA
<213> ORGANISM: Streptomyces hygroscopicus

<400> SEQUENCE: 13
gcacgcggag gggccgaagg agtcgggcag ccatgatggc gtcgcctggg ctcggacacc      60
tgactacctc ttcggtgtcg cgcgggtgcc cgagggcggc cggtacgcgg ccggcaccgc     120
ggccgtctac accggaatct tcgacctgat cgggacgctg gggtacccca gtctggcccg     180
cacctggaac tacgtcagcg gaatcaacac gccgaacgcc gatggcctcg aggtctaccg     240
ggacttctgt gtgggccgcg ccgaggcgct ggacgcccgt gggatcgacc cggcgaccat     300
gccggcggcg accggcatcg cgcccacgg cggcggcatc acgtgctact tcatcgccgc     360
acgcgccggt gaccgggtca acatggagaa cccggccgtg ctcacggctc accgctaccc     420
gcagcggtac ggcccccgcc cgccggtctt ctcccgggcc acctggctct cgccgccggg     480
ggcggacgac ggccggctct tcgtctccgc gaccgccggc atcgtcggtc acgagacggt     540
gcaccacggc                                                           550

<210> SEQ ID NO 14
<211> LENGTH: 541
<212> TYPE: DNA
<213> ORGANISM: Streptomyces hygroscopicus

<400> SEQUENCE: 14
gcacgcggag gggccgaagg agtcgtcgag gcatgatggc gtcgcctggg ctcggacacc      60
tgactacctc ttcggtgtcg cgcgggtgcc cgagggcggc cggtacgcgg ccggcaccgc     120
ggccgtctac accggaatct tcgacctgat cgggacgctg gggtacccca gtctggcccg     180
cacctggaac tacgtcagcg gaatcaacac gccgaacgcc gatggcctcg aggtctaccg     240
```

```
ggacttctgt gtgggccgcg ccgaggcgct ggacgcccgt gggatcgacc cggcgaccat    300
gccggcggcg accggcatcg gcgcccacgg cgcgcgcatc acgtgctact tcatcgccgc    360
acgcgccggt gaccgggtca acatggagaa cccggccgtg ctcacggctc accgctaccc    420
gcagcggtac ggccccccgcc cgccggtctt ctccggccac ctggctctcg ccgccggggg    480
cggacggctc ttcgtctccg cgaccgccgg catcgtcggt caggagacgg tgcaccacgg    540
c                                                                   541
```

<210> SEQ ID NO 15
<211> LENGTH: 337
<212> TYPE: PRT
<213> ORGANISM: Streptomyces hygroscopicus

<400> SEQUENCE: 15

```
Val Arg Gln Leu Thr Pro Pro Val Thr Ala Pro Tyr Cys Arg Phe Glu
1               5                   10                  15

Lys Leu Gly Ala Ser Asp Leu Asp Gly Asp Glu Thr Leu Leu Gly Val
            20                  25                  30

Ile Glu His Arg Thr Gly His Thr Gly Val Ser Leu Ala Glu Gly Cys
        35                  40                  45

Pro Arg Thr Ala Val His Thr Thr Arg Glu Asp Glu Ser Phe Ala
    50                  55                  60

Glu Ala Trp His Ala Glu Gly Pro Lys Glu Ser Gly Ser His Asp Gly
65                  70                  75                  80

Val Ala Trp Ala Arg Thr Pro Asp Tyr Leu Phe Gly Val Ala Arg Val
                85                  90                  95

Pro Glu Gly Gly Arg Tyr Ala Ala Gly Thr Ala Ala Val Tyr Thr Gly
            100                 105                 110

Ile Phe Asp Leu Ile Gly Thr Leu Gly Tyr Pro Ser Leu Ala Arg Thr
        115                 120                 125

Trp Asn Tyr Val Ser Gly Ile Asn Thr Pro Asn Ala Asp Gly Leu Glu
    130                 135                 140

Val Tyr Arg Asp Phe Cys Val Gly Arg Ala Glu Ala Leu Asp Ala Arg
145                 150                 155                 160

Gly Ile Asp Pro Ala Thr Met Pro Ala Ala Thr Gly Ile Gly Ala His
                165                 170                 175

Gly Gly Gly Ile Thr Cys Tyr Phe Ile Ala Ala Arg Ala Gly Asp Arg
            180                 185                 190

Val Asn Met Glu Asn Pro Ala Val Leu Thr Ala His Arg Tyr Pro Gln
        195                 200                 205

Arg Tyr Gly Pro Arg Pro Pro Val Phe Ser Arg Ala Thr Trp Leu Ser
    210                 215                 220

Pro Pro Gly Ala Asp Asp Gly Arg Leu Phe Val Ser Ala Thr Ala Gly
225                 230                 235                 240

Ile Val Gly His Glu Thr Val His Gly Asp Val Ala Ala Gln Cys
                245                 250                 255

Glu Val Ser Leu Glu Asn Ile Ala Arg Val Ile Gly Ala Glu Asn Leu
            260                 265                 270

Gly Arg His Gly Leu Arg Arg Gly Tyr Ala Leu Ala Asp Val Asp His
        275                 280                 285

Leu Lys Val Tyr Val Arg His Arg Glu Asp Ile Ser Thr Val Arg Arg
    290                 295                 300

Ile Cys Ala Glu Arg Leu Ser Arg Glu Ala Thr Val Ala Val Leu His
305                 310                 315                 320
```

-continued

```
Thr Asp Ile Ala Arg Thr Asp Leu Leu Val Glu Ile Glu Gly Val Val
            325                 330                 335
Ala

<210> SEQ ID NO 16
<211> LENGTH: 334
<212> TYPE: PRT
<213> ORGANISM: Streptomyces hygroscopicus

<400> SEQUENCE: 16

Val Arg Gln Leu Thr Pro Pro Val Thr Ala Pro Tyr Cys Arg Phe Glu
1               5                   10                  15

Lys Leu Gly Ala Ser Asp Leu Asp Gly Asp Glu Thr Leu Leu Gly Val
            20                  25                  30

Ile Glu His Arg Thr Gly His Thr Gly Val Ser Leu Ala Glu Gly Cys
        35                  40                  45

Pro Arg Thr Ala Val His Thr Thr Thr Arg Glu Asp Glu Ser Phe Ala
    50                  55                  60

Glu Ala Trp His Ala Glu Gly Pro Lys Glu Ser Ser Arg His Asp Gly
65                  70                  75                  80

Val Ala Trp Ala Arg Thr Pro Asp Tyr Leu Phe Gly Val Ala Arg Val
                85                  90                  95

Pro Glu Gly Gly Arg Tyr Ala Ala Gly Thr Ala Ala Val Tyr Thr Gly
            100                 105                 110

Ile Phe Asp Leu Ile Gly Thr Leu Gly Tyr Pro Ser Leu Ala Arg Thr
        115                 120                 125

Trp Asn Tyr Val Ser Gly Ile Asn Thr Pro Asn Ala Asp Gly Leu Glu
    130                 135                 140

Val Tyr Arg Asp Phe Cys Val Gly Arg Ala Glu Ala Leu Asp Ala Arg
145                 150                 155                 160

Gly Ile Asp Pro Ala Thr Met Pro Ala Ala Thr Gly Ile Gly Ala His
                165                 170                 175

Gly Ala Arg Ile Thr Cys Tyr Phe Ile Ala Ala Arg Ala Gly Asp Arg
            180                 185                 190

Val Asn Met Glu Asn Pro Ala Val Leu Thr Ala His Arg Tyr Pro Gln
        195                 200                 205

Arg Tyr Gly Pro Arg Pro Val Phe Ser Gly His Leu Ala Leu Ala
    210                 215                 220

Ala Gly Gly Gly Arg Leu Phe Val Ser Ala Thr Ala Gly Ile Val Gly
225                 230                 235                 240

Gln Glu Thr Val His His Gly Asp Val Ala Ala Gln Cys Glu Val Ser
                245                 250                 255

Leu Glu Asn Ile Ala Arg Val Ile Gly Ala Glu Asn Leu Gly Arg His
            260                 265                 270

Gly Leu Arg Arg Gly Tyr Ala Leu Ala Asp Val Asp His Leu Lys Val
        275                 280                 285

Tyr Val Arg His Arg Glu Asp Ile Ser Thr Val Arg Arg Ile Cys Ala
    290                 295                 300

Glu Arg Leu Ser Arg Glu Ala Thr Val Ala Val Leu His Thr Asp Ile
305                 310                 315                 320

Ala Arg Thr Asp Leu Leu Val Glu Ile Glu Gly Val Val Ala
                325                 330

<210> SEQ ID NO 17
```

<211> LENGTH: 767
<212> TYPE: DNA
<213> ORGANISM: Streptomyces hygroscopicus

<400> SEQUENCE: 17

```
agcgcctggc gtccctggcc atccacgacc tctacggcct gaatgaggag gaggggcccg      60
tactcgaggg ccagatgcgg gccatggagg cggcaccga catggagagc atcaagaggc      120
tgaccgacga attcttcggt cacgtcctgg cgctggtgcg tgccaagcgg gagcaggcgg      180
gcgacaggct tctgcaccgg ctggccgagt ccggcgagga cgagatcctg ctcagcgacg      240
aggaggcgac cggggtgttc gccactctgc tgttcgccgg gcacgactcg atgcagcaga      300
tggtcggcta ctgtctgtac gcgctgctct cccatcccga gcagcgggcg cgctgcgggc      360
agaacccgga cctgatcgac ggcgcggtcg aggagctgct gcgcttcctg ccgctcaacc      420
agctcggcgt gccgcgggtc tgtgtcgagg acgtcgagct gcacggccag accatcagcg      480
ccggcgacaa cgtgatcccg ctctactcga cggccaaccg cgaccccggc gtcttcgccg      540
acccccgacac gttcgacatc acgcgtaagc ccgaacacaa cttcgctttc gggtacggca      600
tccacaagtg cccggggcag cacctcgccc gcgtgttgat caaggtcgcc acgctgcgcc      660
tgttcgagcg cttcccggat gtgcgactgg cgggcgacgt gccgatgaac gagggtctgg      720
gcctgttcag cccggccgag ctccgggtca cctggggagc ggagtga              767
```

<210> SEQ ID NO 18
<211> LENGTH: 761
<212> TYPE: DNA
<213> ORGANISM: Streptomyces hygroscopicus

<400> SEQUENCE: 18

```
agcgcctggc gtccctggcc atccacgacc tctacggcct gaatgaggag gggcccgtac      60
tcgagggcca gatgcgggcc atggagggcg caccgacat ggagagcatc aagaggctga      120
ccgacgaatt cggtcacgtc ctggcgctgg tgcgtgccaa gcgggacgag gcgggcgaca      180
ggcttctgca ccggctggcc gagtccggca ggacgagat cctgctcagc gacgaggagg      240
cgaccggggt gttcgccact ctgctgttcg ccgggcacga ctcgatgcag cagatggtcg      300
gctacagtct gtacgcgctg ctctcccatc ccgagcagcg ggcggcgctg cgggagaacc      360
cggacctgat cgacggcgcg gtcgaggagc tgctgcgctt cctgccgctc aaccagctcg      420
gcgtgccgcg ggtctgtgtc gaggacgtcg agctgcacgg ccagaccatc agcgccggcg      480
acaacgtgat cccgctctac tcgacggcca accgcgaccc cggcgtcttc gccgaccccg      540
acacgttcga catcacgcgt aagcccgaac acaacttcgc tttcgggtac ggcatccacg      600
gctgcccggg gcagcacctc gcccgcgtgt tgatcaaggt cgccaccgtg cgcctgttcg      660
agcgcttccc ggatgtgcga ctggcgggcg acgtgccgat gaacgagggt ctgggcctgt      720
tcagcccggc cgagctccgg gtcacctggg gagcggagtg a              761
```

<210> SEQ ID NO 19
<211> LENGTH: 388
<212> TYPE: PRT
<213> ORGANISM: Streptomyces hygroscopicus

<400> SEQUENCE: 19

```
Met Ser Thr Glu Ala Gln Gln Glu Ser Thr Pro Thr Ala Arg Cys Pro
1               5                   10                  15

Phe Ser Ile Gln Asp Gly His Arg Thr Ile Leu Glu Thr Gly Thr Val
            20                  25                  30
```

```
Gly Ala His Glu Leu Phe Gly Val Lys Gln Trp Leu Val Ala Ala
         35                  40                  45

Glu Asp Val Lys Leu Val Thr Asn Asp Pro Arg Phe Ser Ser Ala Ala
 50                  55                  60

Pro Ser Gly Ile Leu Gly Asp Arg Arg Pro Gly Trp Phe Ser Gly Met
 65                  70                  75                  80

Asp Ser Pro Glu His Asn Arg Tyr Arg Gln Lys Ile Ala Arg Asp Phe
                 85                  90                  95

Thr Leu Arg Ala Ala Arg Lys Gln Glu Phe Ile Val Arg Ala Ala
             100                 105                 110

Asp Ser Cys Leu Asp Asp Ile Glu Ala Ser Gly Pro Gly Thr Asp Leu
             115                 120                 125

Val Pro Gly Tyr Ala Lys Arg Leu Ala Ser Leu Ala Ile His Asp Leu
             130                 135                 140

Tyr Gly Leu Asn Glu Glu Gly Pro Val Leu Glu Gly Gln Met Arg
145                 150                 155                 160

Ala Met Glu Gly Gly Thr Asp Met Glu Ser Ile Lys Arg Leu Thr Asp
                 165                 170                 175

Glu Phe Phe Gly His Val Leu Ala Leu Val Arg Ala Lys Arg Glu Gln
                 180                 185                 190

Ala Gly Asp Arg Leu Leu His Arg Leu Ala Glu Ser Gly Glu Asp Glu
             195                 200                 205

Ile Leu Leu Ser Asp Glu Glu Ala Thr Gly Val Phe Ala Thr Leu Leu
210                 215                 220

Phe Ala Gly His Asp Ser Met Gln Gln Met Val Gly Tyr Cys Leu Tyr
225                 230                 235                 240

Ala Leu Leu Ser His Pro Glu Gln Arg Ala Ala Leu Arg Glu Asn Pro
                 245                 250                 255

Asp Leu Ile Asp Gly Ala Val Glu Glu Leu Leu Arg Phe Leu Pro Leu
             260                 265                 270

Asn Gln Leu Gly Val Pro Arg Val Cys Val Glu Asp Val Glu Leu His
275                 280                 285

Gly Gln Thr Ile Ser Ala Gly Asp Asn Val Ile Pro Leu Tyr Ser Thr
         290                 295                 300

Ala Asn Arg Asp Pro Gly Val Phe Ala Asp Pro Asp Thr Phe Asp Ile
305                 310                 315                 320

Thr Arg Lys Pro Glu His Asn Phe Ala Phe Gly Tyr Gly Ile His Lys
                 325                 330                 335

Cys Pro Gly Gln His Leu Ala Arg Val Leu Ile Lys Val Ala Thr Leu
             340                 345                 350

Arg Leu Phe Glu Arg Phe Pro Asp Val Arg Leu Ala Gly Asp Val Pro
         355                 360                 365

Met Asn Glu Gly Leu Gly Leu Phe Ser Pro Ala Glu Leu Arg Val Thr
     370                 375                 380

Trp Gly Ala Glu
385

<210> SEQ ID NO 20
<211> LENGTH: 386
<212> TYPE: PRT
<213> ORGANISM: Streptomyces hygroscopicus

<400> SEQUENCE: 20

Met Ser Thr Glu Ala Gln Gln Glu Ser Thr Pro Thr Ala Arg Cys Pro
```

```
                1               5                    10                    15
        Phe Ser Ile Gln Asp Gly His Arg Thr Ile Leu Glu Thr Gly Thr Val
                            20                    25                    30

Gly Ala His Glu Leu Phe Gly Val Lys Gln Trp Leu Val Ala Ala Ala
                        35                    40                    45

Glu Asp Val Lys Leu Val Thr Asn Asp Pro Arg Phe Ser Ser Ala Ala
                    50                    55                    60

Pro Ser Gly Ile Leu Gly Asp Arg Arg Pro Gly Trp Phe Ser Gly Met
        65                    70                    75                    80

Asp Ser Pro Glu His Asn Arg Tyr Arg Gln Lys Ile Ala Arg Asp Phe
                            85                    90                    95

Thr Leu Arg Ala Ala Arg Lys Gln Glu Glu Phe Ile Val Arg Ala Ala
                        100                   105                   110

Asp Ser Cys Leu Asp Asp Ile Glu Ala Ser Gly Pro Gly Thr Asp Leu
                    115                   120                   125

Val Pro Gly Tyr Ala Lys Arg Leu Ala Ser Leu Ala Ile His Asp Leu
                    130                   135                   140

Tyr Gly Leu Asn Glu Glu Gly Pro Val Leu Glu Gly Gln Met Arg Ala
        145                   150                   155                   160

Met Glu Gly Gly Thr Asp Met Glu Ser Ile Lys Arg Leu Thr Asp Glu
                            165                   170                   175

Phe Gly His Val Leu Ala Leu Val Arg Ala Lys Arg Asp Glu Ala Gly
                        180                   185                   190

Asp Arg Leu Leu His Arg Leu Ala Glu Ser Gly Glu Asp Glu Ile Leu
                    195                   200                   205

Leu Ser Asp Glu Glu Ala Thr Gly Val Phe Ala Thr Leu Leu Phe Ala
                    210                   215                   220

Gly His Asp Ser Met Gln Gln Met Val Gly Tyr Ser Leu Tyr Ala Leu
        225                   230                   235                   240

Leu Ser His Pro Glu Gln Arg Ala Ala Leu Arg Glu Asn Pro Asp Leu
                            245                   250                   255

Ile Asp Gly Ala Val Glu Glu Leu Leu Arg Phe Leu Pro Leu Asn Gln
                        260                   265                   270

Leu Gly Val Pro Arg Val Cys Val Glu Asp Val Glu Leu His Gly Gln
                    275                   280                   285

Thr Ile Ser Ala Gly Asp Asn Val Ile Pro Leu Tyr Ser Thr Ala Asn
                    290                   295                   300

Arg Asp Pro Gly Val Phe Ala Asp Pro Asp Thr Phe Asp Ile Thr Arg
        305                   310                   315                   320

Lys Pro Glu His Asn Phe Ala Phe Gly Tyr Gly Ile His Gly Cys Pro
                            325                   330                   335

Gly Gln His Leu Ala Arg Val Leu Ile Lys Val Ala Thr Val Arg Leu
                        340                   345                   350

Phe Glu Arg Phe Pro Asp Val Arg Leu Ala Gly Asp Val Pro Met Asn
                    355                   360                   365

Glu Gly Leu Gly Leu Phe Ser Pro Ala Glu Leu Arg Val Thr Trp Gly
                    370                   375                   380

Ala Glu
        385

<210> SEQ ID NO 21
<211> LENGTH: 649
<212> TYPE: DNA
<213> ORGANISM: Streptomyces hygroscopicus
```

<400> SEQUENCE: 21

```
gtgagcgcgt ccgtgcagac catcaagctg ccgaacggca agaccgtcgc ccacgtcaac      60
ccgggcgagg cgcagttcct ctaccaggag atcttcgccg agcggtgcta cttgcggcgc     120
ggccttgagc tgcgagcggg tgacgtggtc ttcgacgtcg gcgcgaacat cggcatgttc     180
tcgctcttcg cccacctgga gtgccccgat gtcacggtgc acgccttcga gccggcgccg     240
gtgccgtacg ccgcgctcag ggccaatgcc gagcggtacg gcatcgcggg ccggttcgag     300
cagtgcgcgt tctcggacgt ggccggccgc ggcaagatga cgttctacac ggataccacg     360
atgatgtcgg gcttccaccc ggatccggcg acccgcgcgg agctgctgcg caggctcgcc     420
atcaacggcg ggtacagtgc cgaggccgcc gaccggatgc tggccgagct gccggacacc     480
agccaggtga tcgagacgtc cgtcgtacgc ctctccgacg tcatcgcgga gcggggcatc     540
acctcgatcg gactgctcaa gatcgatgtg gagaagaacg agcggcatgt gatggccggg     600
atcgacgcgg ccgactggcc gcgcatccgc caggtcgtca ccgaggtgc                 649
```

<210> SEQ ID NO 22
<211> LENGTH: 649
<212> TYPE: DNA
<213> ORGANISM: Streptomyces hygroscopicus

<400> SEQUENCE: 22

```
gtgagcgcgt ccgtgcagac catcaagctg ccgtacggca gaccgtcggc ccacgtcaac      60
ccgggcgagg cgcagttcct ctaccaggag atcttcgccg agcggtgcta cttgcggcgc     120
ggccttgagc tgcgagcggg tgacgtggtc ttcgacgtcg gcgcgaacat cggcatgttc     180
tcgctcttcg cccacctgga gtgccccgat gtcacggtgc acgccttcga gccggcgccg     240
gtgccgtacg ccgcgctcag ggccaatgcc gagcggtacg ccatcgcggg ccggttcgag     300
cagtgcgcgt tctcggacgt ggccggccgc ggcaagatga cgttctacac ggataccacg     360
atgatgtcgg gcttccaccc ggatccggcg acccgcgcgg agctgctgcg caggctcgcc     420
atcaacggcg ggtacagtgc cgaggccgcc gaccggatgc tggccgagct gccggacacc     480
agccaggtga tcgagacgtc cgtcgtacgc ctctccgacg tcatcgcgga gcggggcatc     540
acctcgatcg gactgctcaa gatcgatgtg gagaagaacg agcggcatgt gatggccggg     600
atcgacgcgg cgactggcc gcgcatccgc caggtcgtca ccgaggtgc                  649
```

<210> SEQ ID NO 23
<211> LENGTH: 260
<212> TYPE: PRT
<213> ORGANISM: Streptomyces hygroscopicus

<400> SEQUENCE: 23

```
Val Ser Ala Ser Val Gln Thr Ile Lys Leu Pro Asn Gly Lys Thr Val
 1               5                  10                  15

Ala His Val Asn Pro Gly Glu Ala Gln Phe Leu Tyr Gln Glu Ile Phe
                20                  25                  30

Ala Glu Arg Cys Tyr Leu Arg Arg Gly Leu Glu Leu Arg Ala Gly Asp
            35                  40                  45

Val Val Phe Asp Val Gly Ala Asn Ile Gly Met Phe Ser Leu Phe Ala
        50                  55                  60

His Leu Glu Cys Pro Asp Val Thr Val His Ala Phe Glu Pro Ala Pro
    65                  70                  75                  80

Val Pro Tyr Ala Ala Leu Arg Ala Asn Ala Glu Arg Tyr Gly Ile Ala
```

```
                    85                  90                  95
Gly Arg Phe Glu Gln Cys Ala Val Ser Asp Val Ala Gly Arg Gly Lys
                100                 105                 110
Met Thr Phe Tyr Thr Asp Thr Met Met Ser Gly Phe His Pro Asp
                115                 120                 125
Pro Ala Thr Arg Ala Glu Leu Leu Arg Arg Leu Ala Ile Asn Gly Gly
        130                 135                 140
Tyr Ser Ala Glu Ala Ala Asp Arg Met Leu Ala Glu Leu Pro Asp Thr
145                 150                 155                 160
Ser Gln Val Ile Glu Thr Ser Val Val Arg Leu Ser Asp Val Ile Ala
                165                 170                 175
Glu Arg Gly Ile Thr Ser Ile Gly Leu Leu Lys Ile Asp Val Glu Lys
            180                 185                 190
Asn Glu Arg His Val Met Ala Gly Ile Asp Ala Ala Asp Trp Pro Arg
            195                 200                 205
Ile Arg Gln Val Val Thr Glu Val His Asp Ile Asp Gly Arg Leu Asp
        210                 215                 220
Glu Val Leu Thr Leu Leu Arg Gly Gln Gly Phe Thr Val Leu Ser Glu
225                 230                 235                 240
Gln Glu Pro Leu Phe Ala Gly Thr Asp Ile Tyr Gln Val Val Ala Arg
                245                 250                 255
Arg Gly Asp Ala
        260

<210> SEQ ID NO 24
<211> LENGTH: 260
<212> TYPE: PRT
<213> ORGANISM: Streptomyces hygroscopicus

<400> SEQUENCE: 24

Val Ser Ala Ser Val Gln Thr Ile Lys Leu Pro Tyr Gly Arg Pro Ser
1               5                   10                  15
Ala His Val Asn Pro Gly Glu Ala Gln Phe Leu Tyr Gln Glu Ile Phe
            20                  25                  30
Ala Glu Arg Cys Tyr Leu Arg Arg Gly Leu Glu Leu Arg Ala Gly Asp
        35                  40                  45
Val Val Phe Asp Val Gly Ala Asn Ile Gly Met Phe Ser Leu Phe Ala
    50                  55                  60
His Leu Glu Cys Pro Asp Val Thr Val His Ala Phe Glu Pro Ala Pro
65                  70                  75                  80
Val Pro Tyr Ala Ala Leu Arg Ala Asn Ala Glu Arg Tyr Ala Ile Ala
                85                  90                  95
Gly Arg Phe Glu Gln Cys Ala Val Ser Asp Val Ala Gly Arg Gly Lys
                100                 105                 110
Met Thr Phe Tyr Thr Asp Thr Met Met Ser Gly Phe His Pro Asp
                115                 120                 125
Pro Ala Thr Arg Ala Glu Leu Leu Arg Arg Leu Ala Ile Asn Gly Gly
        130                 135                 140
Tyr Ser Ala Glu Ala Ala Asp Arg Met Leu Ala Glu Leu Pro Asp Thr
145                 150                 155                 160
Ser Gln Val Ile Glu Thr Ser Val Val Arg Leu Ser Asp Val Ile Ala
                165                 170                 175
Glu Arg Gly Ile Thr Ser Ile Gly Leu Leu Lys Ile Asp Val Glu Lys
            180                 185                 190
```

```
Asn Glu Arg His Val Met Ala Gly Ile Asp Ala Gly Asp Trp Pro Arg
            195                 200                 205

Ile Arg Gln Val Val Thr Glu Val His Asp Ile Asp Gly Arg Leu Asp
        210                 215                 220

Glu Val Leu Thr Leu Leu Arg Gly Gln Gly Phe Thr Val Leu Ser Glu
225                 230                 235                 240

Gln Glu Pro Leu Phe Ala Gly Thr Asp Ile Tyr Gln Val Val Ala Arg
                245                 250                 255

Arg Gly Asp Ala
            260

<210> SEQ ID NO 25
<211> LENGTH: 100
<212> TYPE: DNA
<213> ORGANISM: Streptomyces hygroscopicus

<400> SEQUENCE: 25
ggccacctcc atcgatctgt cacccgaact gaccgcggta ggccgccgca agttggcctc    60
gcgggggatc gataacgtca ccctggtcga gggtgacgtt                         100

<210> SEQ ID NO 26
<211> LENGTH: 100
<212> TYPE: DNA
<213> ORGANISM: Streptomyces hygroscopicus

<400> SEQUENCE: 26
ggccacctcc atcgatctgt cacccgaact gaccgcggta ggccccccaca agttggcctc   60 gcgggggatc gataacgtca ccctggtcga gggtgacgtt                         100

<210> SEQ ID NO 27
<211> LENGTH: 210
<212> TYPE: PRT
<213> ORGANISM: Streptomyces hygroscopicus

<400> SEQUENCE: 27

Met Leu Glu Leu Gly Thr Arg Leu Lys Phe Arg Phe Thr Gly Pro Leu
1               5                   10                  15

Leu Glu Ala Val Asn Pro Arg Leu Gln Gly His Pro Tyr Asp Val Leu
            20                  25                  30

Met Arg Leu Leu Glu Gly Gly Arg Ile Glu Asn Val Leu Glu Leu Cys
        35                  40                  45

Gly Gly Thr Gly Phe Ala Ser Arg Met Leu Ala Glu Arg His Ser Lys
    50                  55                  60

Val Gln Ala Thr Ser Ile Asp Leu Ser Pro Glu Leu Thr Ala Val Gly
65                  70                  75                  80

Arg Arg Lys Leu Ala Ser Arg Gly Ile Asp Asn Val Thr Leu Val Glu
                85                  90                  95

Gly Asp Val Ser Thr Leu Pro Tyr Pro Asp Asp Ser Phe Asp Thr Val
            100                 105                 110

Met Ser Ala Phe Gly Leu His Glu Val Pro Thr Ala Gly Arg Leu Ser
        115                 120                 125

Ala Ile Arg Glu Ser Val Arg Val Leu Lys Pro Gly Gly Arg Phe Val
    130                 135                 140

Ile Val Asp Leu Asp Arg Arg Thr Lys Tyr Gly Trp Thr Met Asp Leu
145                 150                 155                 160

Phe Met Lys Val Met Glu Pro Lys Phe Ala Pro Glu Val Phe Gly Thr
                165                 170                 175
```

-continued

```
Gly Leu Val Asp Arg Leu Lys Glu Asn Gly Phe Thr Ile Asp His His
            180                 185                 190
Glu Ser Ala Gly Pro Asn Gly Trp Thr Gln Ser Ile Val Ala Thr Leu
        195                 200                 205
Glu Ala
    210

<210> SEQ ID NO 28
<211> LENGTH: 210
<212> TYPE: PRT
<213> ORGANISM: Streptomyces hygroscopicus

<400> SEQUENCE: 28

Met Leu Glu Leu Gly Thr Arg Leu Lys Phe Arg Phe Thr Gly Pro Leu
1               5                   10                  15
Leu Glu Ala Val Asn Pro Arg Leu Gln Gly His Pro Tyr Asp Val Leu
            20                  25                  30
Met Arg Leu Leu Glu Gly Gly Arg Ile Glu Asn Val Leu Glu Leu Cys
        35                  40                  45
Gly Gly Thr Gly Phe Ala Ser Arg Met Leu Ala Glu Arg His Ser Lys
    50                  55                  60
Val Gln Ala Thr Ser Ile Asp Leu Ser Pro Glu Leu Thr Ala Val Gly
65                  70                  75                  80
Pro His Lys Leu Ala Ser Arg Gly Ile Asp Asn Val Thr Leu Val Glu
                85                  90                  95
Gly Asp Val Ser Thr Leu Pro Tyr Pro Asp Asp Ser Phe Asp Thr Val
            100                 105                 110
Met Ser Ala Phe Gly Leu His Glu Val Pro Thr Ala Gly Arg Leu Ser
        115                 120                 125
Ala Ile Arg Glu Ser Val Arg Val Leu Lys Pro Gly Gly Arg Phe Val
    130                 135                 140
Ile Val Asp Leu Asp Arg Arg Thr Lys Tyr Gly Trp Thr Met Asp Leu
145                 150                 155                 160
Phe Met Lys Val Met Glu Pro Lys Phe Ala Pro Glu Val Phe Gly Thr
                165                 170                 175
Gly Leu Val Asp Arg Leu Lys Glu Asn Gly Phe Thr Ile Asp His His
            180                 185                 190
Glu Ser Ala Gly Pro Asn Gly Trp Thr Gln Ser Ile Val Ala Thr Leu
        195                 200                 205
Glu Ala
    210

<210> SEQ ID NO 29
<211> LENGTH: 33
<212> TYPE: DNA
<213> ORGANISM: Artificial sequence
<220> FEATURE:
<223> OTHER INFORMATION: primer

<400> SEQUENCE: 29
gcaagcttgg taccgacacg ctcgccgaac agg                                33

<210> SEQ ID NO 30
<211> LENGTH: 31
<212> TYPE: DNA
<213> ORGANISM: Artificial sequence
<220> FEATURE:
<223> OTHER INFORMATION: Primer
```

```
<400> SEQUENCE: 30
gcgcatgccc tagggtgtac attacttctc c                              31

<210> SEQ ID NO 31
<211> LENGTH: 28
<212> TYPE: DNA
<213> ORGANISM: Artificial sequence
<220> FEATURE:
<223> OTHER INFORMATION: primer

<400> SEQUENCE: 31
tatctagact tcgcacgtgc ctgggaca                                  28

<210> SEQ ID NO 32
<211> LENGTH: 28
<212> TYPE: DNA
<213> ORGANISM: Artificial sequence
<220> FEATURE:
<223> OTHER INFORMATION: primer

<400> SEQUENCE: 32
agaagcttac ccaattccaa catcacct                                  28

<210> SEQ ID NO 33
<211> LENGTH: 28
<212> TYPE: DNA
<213> ORGANISM: Artificial sequence
<220> FEATURE:
<223> OTHER INFORMATION: primer

<400> SEQUENCE: 33
ggaagctttg accacacgcc gcccgttc                                  28

<210> SEQ ID NO 34
<211> LENGTH: 28
<212> TYPE: DNA
<213> ORGANISM: Artificial sequence
<220> FEATURE:
<223> OTHER INFORMATION: primer

<400> SEQUENCE: 34
atgcatgccc gccgcaaccc gctggcct                                  28

<210> SEQ ID NO 35
<211> LENGTH: 58
<212> TYPE: DNA
<213> ORGANISM: Artificial sequence
<220> FEATURE:
<223> OTHER INFORMATION: primer

<400> SEQUENCE: 35
taaactagtc catctgagag tttcatatgg ccctattctg cccagccgct ctagaaat  58

<210> SEQ ID NO 36
<211> LENGTH: 58
<212> TYPE: DNA
<213> ORGANISM: Artificial sequence
<220> FEATURE:
<223> OTHER INFORMATION: primer

<400> SEQUENCE: 36
atttctagag cggctgggca gaatagggcc atatgaaact ctcagatgga ctagttta  58

<210> SEQ ID NO 37
```

```
<211> LENGTH: 46
<212> TYPE: DNA
<213> ORGANISM: Artificial sequence
<220> FEATURE:
<223> OTHER INFORMATION: primer

<400> SEQUENCE: 37
gggcatatga ggcaattgac tccgccggtc acggcaccgt actgcc        46

<210> SEQ ID NO 38
<211> LENGTH: 40
<212> TYPE: DNA
<213> ORGANISM: Artificial sequence
<220> FEATURE:
<223> OTHER INFORMATION: primer

<400> SEQUENCE: 38
ggggtctaga ggtcacgcca ccacaccctc gatctcgacc                40

<210> SEQ ID NO 39
<211> LENGTH: 44
<212> TYPE: DNA
<213> ORGANISM: Artificial sequence
<220> FEATURE:
<223> OTHER INFORMATION: primer

<400> SEQUENCE: 39
gggcatatgt cgacgaccga tcagggtgag accggaaagg cctg           44

<210> SEQ ID NO 40
<211> LENGTH: 48
<212> TYPE: DNA
<213> ORGANISM: Artificial sequence
<220> FEATURE:
<223> OTHER INFORMATION: primer

<400> SEQUENCE: 40
ggggtctaga ggtcagtcct ggggttcgag aagctcgccg gtctcctt       48

<210> SEQ ID NO 41
<211> LENGTH: 43
<212> TYPE: DNA
<213> ORGANISM: Artificial sequence
<220> FEATURE:
<223> OTHER INFORMATION: primer

<400> SEQUENCE: 41
gggcatatga tccaacccga cgtcgtgacc gccttcacag cgg            43

<210> SEQ ID NO 42
<211> LENGTH: 44
<212> TYPE: DNA
<213> ORGANISM: Artificial sequence
<220> FEATURE:
<223> OTHER INFORMATION: primer

<400> SEQUENCE: 42
ggggtctaga ggtcacacgc ggacggcgat ctggtgccga tagg           44

<210> SEQ ID NO 43
<211> LENGTH: 42
<212> TYPE: DNA
<213> ORGANISM: Artificial sequence
<220> FEATURE:
<223> OTHER INFORMATION: primer

<400> SEQUENCE: 43
```

```
gggcatatgc agaccaaggt tctgtgccag cgtgacatca ag                         42

<210> SEQ ID NO 44
<211> LENGTH: 50
<212> TYPE: DNA
<213> ORGANISM: Artificial sequence
<220> FEATURE:
<223> OTHER INFORMATION: primer

<400> SEQUENCE: 44
ggggtctaga ggtcactaca gcgagtacgg atcgaggacg tcctcgggcg                 50

<210> SEQ ID NO 45
<211> LENGTH: 40
<212> TYPE: DNA
<213> ORGANISM: Artificial sequence
<220> FEATURE:
<223> OTHER INFORMATION: primer

<400> SEQUENCE: 45
ggagatctca gcgagtacgg atcgaggacg tcctcgggcg                            40

<210> SEQ ID NO 46
<211> LENGTH: 49
<212> TYPE: DNA
<213> ORGANISM: Artificial sequence
<220> FEATURE:
<223> OTHER INFORMATION: primer

<400> SEQUENCE: 46
gggcatatga gcaccgaagc tcagcaagag agcacgccca ccgcacgct                  49

<210> SEQ ID NO 47
<211> LENGTH: 45
<212> TYPE: DNA
<213> ORGANISM: Artificial sequence
<220> FEATURE:
<223> OTHER INFORMATION: primer

<400> SEQUENCE: 47
ggggtctaga ggtcactccg ctccccaggt gacccggagc tcggc                      45

<210> SEQ ID NO 48
<211> LENGTH: 38
<212> TYPE: DNA
<213> ORGANISM: Artificial sequence
<220> FEATURE:
<223> OTHER INFORMATION: primer

<400> SEQUENCE: 48
gggcatatga gcgcgtccgt gcagaccatc aagctgcc                              38

<210> SEQ ID NO 49
<211> LENGTH: 41
<212> TYPE: DNA
<213> ORGANISM: Artificial sequence
<220> FEATURE:
<223> OTHER INFORMATION: primer

<400> SEQUENCE: 49
ggggtctaga ggtcaggcgt ccccgcggcg ggcgacgacc t                          41

<210> SEQ ID NO 50
<211> LENGTH: 27
<212> TYPE: DNA
```

```
<213> ORGANISM: Artificial sequence
<220> FEATURE:
<223> OTHER INFORMATION: primer

<400> SEQUENCE: 50
catatgttgg aattgggtac ccgcctg                                          27

<210> SEQ ID NO 51
<211> LENGTH: 25
<212> TYPE: DNA
<213> ORGANISM: Artificial sequence
<220> FEATURE:
<223> OTHER INFORMATION: primer

<400> SEQUENCE: 51
tctagacgct cacgcctcca gggtg                                            25

<210> SEQ ID NO 52
<211> LENGTH: 72
<212> TYPE: DNA
<213> ORGANISM: Artificial sequence
<220> FEATURE:
<223> OTHER INFORMATION: primer

<400> SEQUENCE: 52
ggggaattca gatctggtct agaggtcagc cggcgtggcg gcgcgtgagt tcctccagtc      60
gcgggacgat ct                                                          72

<210> SEQ ID NO 53
<211> LENGTH: 47
<212> TYPE: DNA
<213> ORGANISM: Artificial sequence
<220> FEATURE:
<223> OTHER INFORMATION: primer

<400> SEQUENCE: 53
gggtctagat ccggacgaac gcatcgatta attaaggagg acacata                    47

<210> SEQ ID NO 54
<211> LENGTH: 26
<212> TYPE: DNA
<213> ORGANISM: Artificial sequence
<220> FEATURE:
<223> OTHER INFORMATION: primer

<400> SEQUENCE: 54
gggcatatga ccgatgccgg acgcca                                           26

<210> SEQ ID NO 55
<211> LENGTH: 30
<212> TYPE: DNA
<213> ORGANISM: Artificial sequence
<220> FEATURE:
<223> OTHER INFORMATION: primer

<400> SEQUENCE: 55
ggggtctaga tcacgccacc atgccttcga                                       30

<210> SEQ ID NO 56
<211> LENGTH: 29
<212> TYPE: DNA
<213> ORGANISM: Artificial sequence
<220> FEATURE:
<223> OTHER INFORMATION: Primer

<400> SEQUENCE: 56
```

```
caaagcttcc tggcgcggtt cggccggca                              29

<210> SEQ ID NO 57
<211> LENGTH: 29
<212> TYPE: DNA
<213> ORGANISM: Artificial sequence
<220> FEATURE:
<223> OTHER INFORMATION: Primer

<400> SEQUENCE: 57
tggcatgccc ttccccgccg ttccctggc                              29

<210> SEQ ID NO 58
<211> LENGTH: 29
<212> TYPE: DNA
<213> ORGANISM: Artificial sequence
<220> FEATURE:
<223> OTHER INFORMATION: Primer

<400> SEQUENCE: 58
tggcatgccc ccgccgagct gacctggaa                              29

<210> SEQ ID NO 59
<211> LENGTH: 29
<212> TYPE: DNA
<213> ORGANISM: artificial sequence
<220> FEATURE:
<223> OTHER INFORMATION: primer

<400> SEQUENCE: 59
gttctagagc ttacgcgtga tgtcgaacg                              29

<210> SEQ ID NO 60
<211> LENGTH: 29
<212> TYPE: DNA
<213> ORGANISM: Artificial sequence
<220> FEATURE:
<223> OTHER INFORMATION: Pimer

<400> SEQUENCE: 60
gctctagagc ccgcggctcg ccggacacg                              29

<210> SEQ ID NO 61
<211> LENGTH: 30
<212> TYPE: DNA
<213> ORGANISM: Artificial sequence
<220> FEATURE:
<223> OTHER INFORMATION: Primer

<400> SEQUENCE: 61
cccctgcagg cgtccggcat cggtcatcag                             30

<210> SEQ ID NO 62
<211> LENGTH: 31
<212> TYPE: DNA
<213> ORGANISM: Artificial sequence
<220> FEATURE:
<223> OTHER INFORMATION: Primer

<400> SEQUENCE: 62
cgcctgcagg gatacggtcc gccgggtctg c                           31

<210> SEQ ID NO 63
<211> LENGTH: 30
<212> TYPE: DNA
```

-continued

```
<213> ORGANISM: Artificial sequence
<220> FEATURE:
<223> OTHER INFORMATION: Primer

<400> SEQUENCE: 63
ccaagcttgt acggttcgcc acgggcgtgc                              30
```